(12) United States Patent
Fell et al.

(10) Patent No.: US 12,351,581 B2
(45) Date of Patent: Jul. 8, 2025

(54) COMPOUNDS FOR FGFR INHIBITION

(71) Applicant: Cogent Biosciences, Inc., Waltham, MA (US)

(72) Inventors: Jay Bradford Fell, Boulder, CO (US); John E. Robinson, Boulder, CO (US); John P. Fischer, Boulder, CO (US); Logan E. Vine, Boulder, CO (US); Martha E. Rodriguez, Boulder, CO (US); Jennifer Fulton, Boulder, CO (US); Tanna Bettendorf, Boulder, CO (US); Bradley J. Newhouse, Boulder, CO (US); Robert A. Rieger, Boulder, CO (US); Cori A. Malinky, Boulder, CO (US); Aaron Christopher Smith, Boulder, CO (US); Ravi Kumar Jalluri, Boulder, CO (US); Mark Joseph Chicarelli, Boulder, CO (US); Leah J. Salituro, Boulder, CO (US); Macedonio J. Mejia, Boulder, CO (US)

(73) Assignee: Cogent Biosciences, Inc., Waltham, MA (US)

( * ) Notice: Subject to any disclaimer, the term of this patent is extended or adjusted under 35 U.S.C. 154(b) by 0 days.

(21) Appl. No.: 18/808,641

(22) Filed: Aug. 19, 2024

(65) Prior Publication Data

US 2025/0066352 A1 Feb. 27, 2025

Related U.S. Application Data

(63) Continuation of application No. PCT/US2024/041350, filed on Aug. 7, 2024.

(60) Provisional application No. 63/614,476, filed on Dec. 22, 2023, provisional application No. 63/590,177, filed on Oct. 13, 2023, provisional application No. 63/517,996, filed on Aug. 7, 2023.

(51) Int. Cl.
| | | |
|---|---|---|
| *C07D 471/04* | (2006.01) | |
| *A61K 31/444* | (2006.01) | |
| *A61K 31/4545* | (2006.01) | |
| *A61K 31/496* | (2006.01) | |
| *A61K 31/5377* | (2006.01) | |
| *A61P 35/00* | (2006.01) | |

(52) U.S. Cl.
CPC .......... *C07D 471/04* (2013.01); *A61K 31/444* (2013.01); *A61K 31/4545* (2013.01); *A61K 31/496* (2013.01); *A61K 31/5377* (2013.01); *A61P 35/00* (2018.01)

(58) Field of Classification Search
CPC .................................................... C07D 471/04
USPC ................................................... 514/233.2
See application file for complete search history.

(56) References Cited

U.S. PATENT DOCUMENTS

| | | |
|---|---|---|
| 8,648,087 B2 | 2/2014 | Lyssikatos et al. |
| 2011/0207711 A1 | 8/2011 | Katz et al. |
| 2017/0240552 A1 | 8/2017 | Brown et al. |
| 2018/0148447 A1 | 5/2018 | Hudkins et al. |
| 2018/0186790 A1 | 7/2018 | Andrews et al. |
| 2022/0081438 A1 | 3/2022 | Blake et al. |
| 2023/0159523 A1 | 5/2023 | Cheng et al. |
| 2023/0322769 A1 | 10/2023 | Zhu et al. |
| 2024/0027074 A1 | 1/2024 | Bartelick et al. |

FOREIGN PATENT DOCUMENTS

| | | | |
|---|---|---|---|
| WO | WO-2010017047 A1 | 2/2010 | |
| WO | WO-2015017610 A1 | 2/2015 | |
| WO | 2020131627 | * 6/2020 | |
| WO | WO-2020131627 A1 | * 6/2020 | .............. A61P 35/00 |
| WO | WO-2021156178 A1 | 8/2021 | |
| WO | WO-2021156180 A1 | 8/2021 | |
| WO | WO-2022003575 A1 | 1/2022 | |
| WO | WO-2022187443 A1 | 9/2022 | |
| WO | WO-2023212535 A1 | 11/2023 | |
| WO | WO-2024054808 A1 | 3/2024 | |
| WO | WO-2024083111 A1 | 4/2024 | |
| WO | WO-2024114680 A1 | 6/2024 | |

(Continued)

OTHER PUBLICATIONS

International Search Report and Written Opinion for PCT/US2024/010888 dated Jan. 9, 2024.
Davies et. al. "Binding affinity and biological activity of oxygen and sulfur isosteres at melatonin receptors as a function of their hydrogen bonding capability", Bioorganic Chemistry, 2004, 32 (1), pp. 1-12.
CAS Registry No. 3004850-92-1, STN Entry Date: Nov. 17, 2023; chemical name: Pyrazolo[1,5-a]pyridine-3-carbonitrile, 6-[1-(hexahydro-1H-azepin-4-yl)-3-methyl-1H-pyrazol-4-yl]-4-[(1R)-1-(2-pyridinyl)ethoxy]-.

(Continued)

*Primary Examiner* — Niloofar Rahmani
(74) *Attorney, Agent, or Firm* — Goodwin Procter LLP

(57) ABSTRACT

A compound having the following structure of Formula (IV):

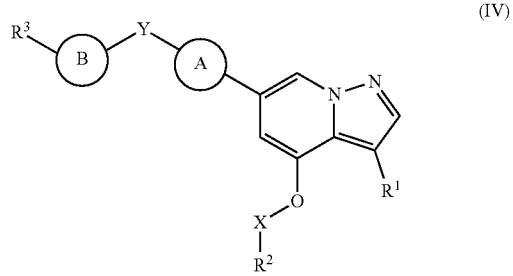

or a stereoisomer, salt, or tautomer thereof, wherein $R^1$, $R^2$, $R^3$, A, B, X, and Y are as defined herein. Pharmaceutical composition comprising the compounds, and their use in methods of treating diseases are also described.

30 Claims, 5 Drawing Sheets

(56) References Cited

FOREIGN PATENT DOCUMENTS

| WO | WO-2024137587 A1 | 6/2024 |
|---|---|---|
| WO | WO-2024151638 A2 | 7/2024 |

OTHER PUBLICATIONS

CAS Registry No. 3004850-90-9, STN Entry Date: Nov. 17, 2023; chemical name: Pyrazolo[1,5-a]pyridine-3-carbonitrile, 6-[1-(hexahydro-1H-azepin-4-yl)-5-methyl-1H-pyrazol-4-yl]-4-[(1R)-1-(2-pyridinyl)ethoxy.

CAS Registry No. 3004850-88-5, STN Entry Date: Nov. 17, 2023; chemical name: Pyrazolo[1,5-a]pyridine-3-carbonitrile, 6-[1-(2-azaspiro[3.3]hept-6-yl)-5-methyl-1H-pyrazol-4-yl]-4-[(1R)-1-(2-pyridinyl)ethoxy.

CAS Registry No. 2833716-20-2, STN Entry Date:Sep. 30, 2022; chemical name: Pyrazolo[1,5-a]pyridine-3-carbonitrile, 6-[5-methyl-1-(4-piperidinyl)-1H-pyrazol-4-yl]-4-[(1R)-1-(1-methyl-1H-pyrazol-3-yl)ethoxy]-.

CAS Registry No. 2833714-81-9, STN Entry Date: Sep. 30, 2022; chemical name: Pyrazolo[1,5-a]pyridine-3-carbonitrile, 6-[5-methyl-1-(4-piperidinyl)-1H-pyrazol-4-yl]-4-[1-methyl-1-(2-pyridinyl)ethoxy]-.

CAS Registry No. 2833714-37-5, STN Entry Date: Sep. 30, 2022; chemical name: Pyrazolo[1,5-a]pyridine-3-carbonitrile, 6-[5-methyl-1-(4-piperidinyl)-1H-pyrazol-4-yl]-4-[(1R)-1-(1-methyl-1H-pyrazol-5-yl)ethoxy]-.

CAS Registry No. 2833714-35-3, STN Entry Date: Sep. 30, 2022; chemical name: Pyrazolo[1,5-a]pyridine-3-carbonitrile, 4-[(1R)-1-(3-fluoro-2-pyridinyl)ethoxy]-6-[5-methyl-1-(4-piperidinyl)-1H-pyrazol-4-yl]-.

CAS Registry No. 2833714-33-1, STN Entry Date: Sep. 30, 2022; chemical name: Pyrazolo[1,5-a]pyridine-3-carbonitrile, 4-[(3-fluoro-2-pyridinyl)methoxy]-6-[5-methyl-1-(4-piperidinyl)-1H-pyrazol-4-yl]-.

CAS Registry No. 2833714-27-3, STN Entry Date: Sep. 30, 2022; chemical name: Pyrazolo[1,5-a]pyridine-3-carbonitrile, 6-[5-methyl-1-[1-(3R)-3-pyrrolidinyl-3-azetidinyl]-1H--pyrazol-4-yl]-4-[(1R)-1-(2-pyridinyl)ethoxy]-.

CAS Registry No. 2833714-25-1, STN Entry Date: Sep. 30, 2022; chemical name: Pyrazolo[1,5-a]pyridine-3-carbonitrile, 6-[5-methyl-1-[1-(3S)-3-pyrrolidinyl-3-azetidinyl]-1H-pyrazol-4-yl]-4-[(1R)-1-(2-pyridinyl)ethoxy]-.

CAS Registry No. 2833714-23-9, STN Entry Date: Sep. 30, 2022; chemical name: Pyrazolo[1,5-a]pyridine-3-carbonitrile, 6-[5-methyl-1-(4-piperidinyl)-1H-pyrazol-4-yl]-4-[(1S)-1-(2-pyridinyl)ethoxy]-.

CAS Registry No. 2833714-15-9, STN Entry Date:Sep. 30, 2022; chemical name: Pyrazolo[1,5-a]pyridine-3-carbonitrile, 6-[1-(3-azetidinyl)-5-methyl-1H-pyrazol-4-yl]-4-[(1R)-1-(2-pyridinyl)ethoxy]-.

CAS Registry No. 2833712-56-2, STN Entry Date: Sep. 30, 2022; chemical name: Pyrazolo[1,5-a]pyridine-3-carbonitrile, 6-[5-methyl-1-(4-piperidinyl)-1H-pyrazol-4-yl]-4-[(1R)-1-(2-pyridinyl)propoxy]-.

CAS Registry No. 2833712-54-0, STN Entry Date: Sep. 30, 2022; chemical name: Pyrazolo[1,5-a]pyridine-3-carbonitrile, 6-[5-methyl-1-(4-piperidinyl)-1H-pyrazol-4-yl]-4-[(1R)-1-(2-pyrazinyl)ethoxy]-.

CAS Registry No. 2833711-65-0, STN Entry Date: Sep. 30, 2022; chemical name: Pyrazolo[1,5-a]pyridine-3-carbonitrile, 4-[1-(5-fluoro-2-pyridinyl)-2-hydroxyethoxy]-6-[5-methyl-1-(4-piperidinyl)-1H-pyrazol-4-yl]-.

CAS Registry No. 1650543-70-6, STN Entry Date: Feb. 24, 2015; chemical name: 2-Pyrrolidinone, 4-[(1R)-1-[6-[5-(4-acetyl-1-piperazinyl)-2-pyridinyl]-3-chloropyrazolo[1,5-a]pyridin-4-ylloxylethyl]-, (4R)-.

CAS Registry No. 1650543-68-2, STN Entry Date: Feb. 24, 2015; chemical name: 2-Pyrrolidinone, 4-[(1R)-1-[[3-chloro-6-[5-[4-(methylsulfonyl)-1-piperazinyl]-2-pyridinyl]pyrazolo[1,5-a]pyridin-4-ylloxylethyl]-, (4R)-.

CAS Registry No. 1650543-62-6, STN Entry Date: Feb. 24, 2015; chemical name: 2-Pyrrolidinone, 4-[(1R)-1-[3-chloro-6-[1-(tetrahydro-2H-pyran-4-yl)-1H-pyrazol-4-yl]pyrazolo[1,5-a]pyridin-4-ylloxylethyl]-, (4R)-.

CAS Registry No. 1650543-56-8, STN Entry Date: Feb. 24, 2015; chemical name: 2-Pyrrolidinone, 4-[(1R)-1-[[3-chloro-6-[1-(1,1-dimethylethyl)-1 H-pyrazol-4-yl]pyrazolo[1,5-a]pyridin-4-yl]oxylethyl]-, (4R)-.

CAS Registry No. 1650543-46-6, STN Entry Date: Feb. 24, 2015; chemical name: 2-Pyrrolidinone, 4-[(1R)-1-[[6-[1-(1,1-dimethylethyl)-1H-pyrazol-4-yl]-3-methylpyrazolo[1,5-a]pyridin-4-yl]oxylethyl]-, (4R)-.

International Search Report and Written Opinion for PCT/US2024/041350 dated Nov. 29, 2024.

Miyake et al., "Identification of novel lysine demethylase 5-selective inhibitors by inhibitor-based fragment merging strategy." Bioorg Med Chem. Mar. 15, 2019;27(6):1119-1129.

Yang et al., "Host Kinase CSNK2 is a Target for Inhibition of Pathogenic SARS-like β- Coronaviruses," ACS Chem Biol. Jul. 15, 2022;17(7):1937-1950.

Shi et al., "One-step Synthesis of Cyanated Pyrazolo[I, 5-a]pyridines Utilizing N-Aminopyridines as 1,3-Dipole and Nitrogen Source," Organic Chemistry Frontiers (2023), pp. S1-S16.

\* cited by examiner

COMPOUNDS FOR FGFR INHIBITION

RELATED APPLICATIONS

The present application is a continuation of International Patent Application No. PCT/US2024/041350, filed on Aug. 7, 2024, which claims the benefit of, and priority to, U.S. Provisional Patent Applications 63/517,996, filed Aug. 7, 2023, 63/590,177, filed Oct. 13, 2023, and 63/614,476, filed Dec. 22, 2023, the contents of each of which are hereby incorporated by reference in their entirety for all purposes.

TECHNICAL FIELD

The disclosure relates to substituted pyrazolo pyridine compounds that act as fibroblast growth factor receptor tyrosine kinase (FGFR) inhibitors. The disclosure also provides compounds of formula (I), (IA), (IB)-(IB-3), (IC-a)-(II-a), (IC-b)-(II-b), (III-a)-(III-h), (IV) or (IV-a) and pharmaceutically acceptable salts thereof and uses of the compounds for the treatment of abnormal cell growth, such as cancer, in a subject.

BACKGROUND

Fibroblast growth factors (FGF's) and their receptors (FGFRs) regulate a wide range of physiologic cellular processes, such as embryonic development, differentiation, proliferation, survival, migration, and angiogenesis. There are five FGFRs, of which four (FGFRs 1-4) are highly conserved single-pass transmembrane tyrosine kinase receptors. The binding of an FGF to an FGFR leads to receptor dimerization and transphosphorylation of tyrosine kinase domains. Dysregulation of the FGF signaling system underlies a range of diseases associated with the increased FGF expression.

There remains a need to discover FGFR inhibitors having enhanced activity profiles which may be useful for the treatment of FGFR mutation cancers or other proliferative diseases or conditions.

BRIEF SUMMARY

In brief, the present disclosure provides compounds, including stereoisomers, pharmaceutically acceptable salts, or tautomers thereof, which can be used alone or in combination with other therapeutic agents.

In one aspect, provided herein, are compounds having the following structure of Formula (IV):

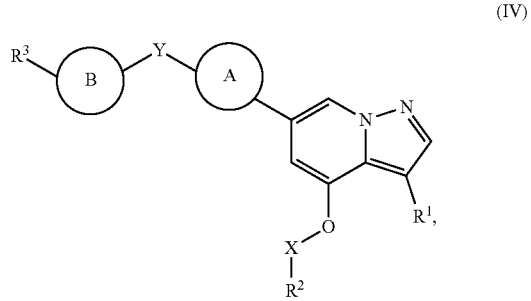

(IV)

or stereoisomers, salts, or tautomers thereof, wherein $R^1$, $R^2$, $R^3$, A, B, X, and Y are as defined herein.

In certain embodiments, provided herein as compounds having the following structure of Formula (IV-a):

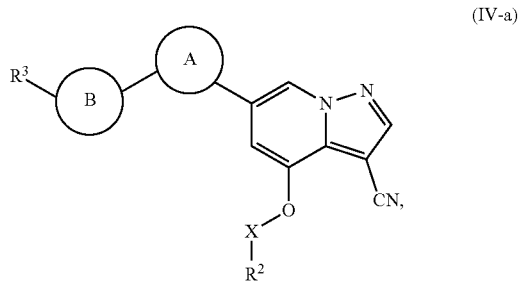

(IV-a)

or stereoisomers, salts, or tautomers thereof, wherein $R^2$, $R^3$, A, B and X are as defined herein.

Pharmaceutical compositions comprising one or more of the foregoing compounds of Formula (IV) or (IV-a) and a therapeutic agent are also provided.

In other embodiments, methods of treatment by administering the foregoing compounds of Formula (IV) or (IV-a) or the pharmaceutical compositions comprising a compound of Formula (IV) or (IV-a) to a subject in need thereof to treat a disease are provided. In some embodiments, the disease is associated with mutations in FGFR2 or FGFR3. In some embodiments, the disease associated with mutations in FGFR2 is a cancer or craniosynostoic syndrome.

In other embodiments, methods of treatment by administering the foregoing compounds of Formula (IV) or (IV-a) or the pharmaceutical compositions comprising a compound of Formula (IV) or (IV-a) to a subject in need thereof to treat a disease are provided, wherein the compound or pharmaceutical composition is highly selective for FGFR2 over FGR1.

Various aspects and embodiments now will be described more fully hereinafter. Such aspects and embodiments make take many different forms and the exemplary ones disclosed herein should not be construed as limiting; rather, these embodiments are provided so that this disclosure will be thorough and complete, and will fully convey its scope to those skilled in the art.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

I. Definitions

Figure 1:
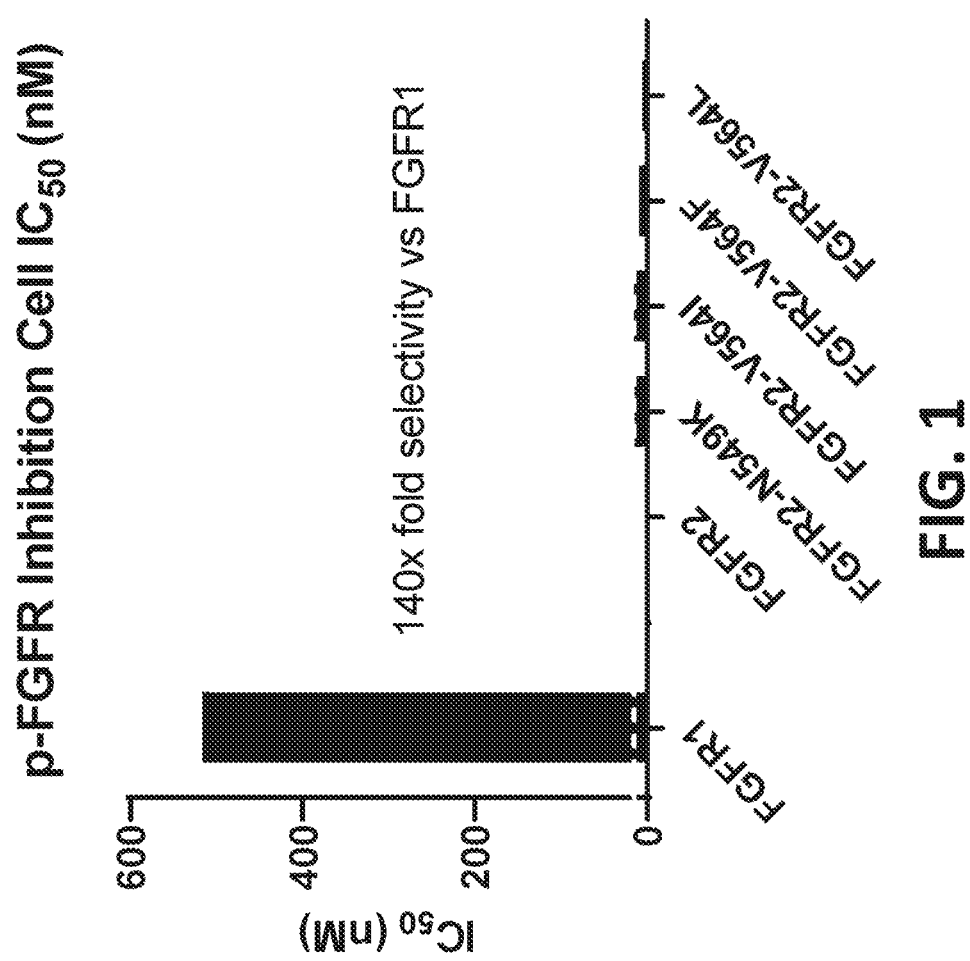
FIG. 1 shows p-FGFR inhibition cell $IC_{50}$ data and fold shift from FGFR2 WT IC50.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The term "about," particularly in reference to a given quantity, is meant to encompass deviations of plus or minus five percent.

The compositions of the present disclosure can comprise, consist essentially of, or consist of, the components disclosed.

All percentages, parts and ratios are based upon the total weight of the compositions and all measurements made are at about 25° C., unless otherwise specified.

As used in the specification and appended claims, unless specified to the contrary, the following terms have the meaning indicated:

"Amino" refers to the $-NH_2$, $-NHR$, or $-NR_2$ radical.
"Cyano" refers to the $-CN$ radical.
"Hydroxyl" refers to the $-OH$ radical.
"Imino" refers to the $=NH$ or $=NR$ substituent.
"Nitro" refers to the $-NO_2$ radical.
"Oxo" refers to the $=O$ substituent.
"Thio" refers to the $=S$ substituent.
"Trifluoromethyl" refers to the $-CF_3$ radical.
Hydrazido or hydrazino refers to $N-N$ substituent.
  wherein each R is a compatible substituent as described in this disclosure. Where an R group is chiral, isomers are contemplated and included herein.

"Alkyl" refers to a linear, saturated, acyclic, monovalent hydrocarbon radical or branched, saturated, acyclic, monovalent hydrocarbon radical, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. An optionally substituted alkyl radical is an alkyl radical that is optionally substituted, valence permitting, by one, two, three, four, or five substituents independently selected from the group consisting of halo, cyano, nitro, aryl, cycloalkyl, heterocyclyl, heteroaryl, oxo, trimethylsilanyl, $-OR'$, $-OC(O)-R'$, $-N(R')_2$, $-C(O)R''$, $-C(O)OR'$, $-C(O)N(R')_2$, $-N(R')C(O)OR'''$, $-N(R')C(O)R'''$, $-N(R')S(O)_tR'''$ (where t is 1 or 2), $-S(O)_tOR'''$ (where t is 1 or 2), $-S(O)_pR'''$ (where p is 0, 1, or 2) and $-S(O)_tN(R')_2$ (where t is 1 or 2), where each R' is independently hydrogen, alkyl, haloalkyl, cycloalkyl, cycloalkylalkyl, aryl, aralkyl, heterocyclyl, or heteroaryl; each R'' is independently hydrogen, cycloalkyl, aryl, heterocyclyl, or heteroaryl; and each R''' is independently alkyl, haloalkyl, cycloalkyl, aryl, heterocyclyl, or heteroaryl.

"Alkylene" is a divalent radical of an alkyl group.

"Alkylalcohol" or "alkyl alcohol" refers to an alkyl group substituted with an alcohol ($-OH$) group.

"Alkoxy" refers to a radical of the formula $-OR_a$ where $R_a$ is an alkyl radical as defined above containing one to twelve carbon atoms. The alkyl part of the optionally substituted alkoxy radical is optionally substituted as defined above for an alkyl radical.

"Alkoxyalkyl" refers to a radical of the formula $-R_a-O-R_b$ where $R_a$ is alkylene and $R_b$ is alkyl as defined above. Alkyl and alkylene parts of the optionally substituted alkoxyalkyl radical are optionally substituted as defined above for an alkyl radical and alkylene chain, respectively.

"Aralkyl" refers to a radical of the formula $-R_a-R_b$, where $R_a$ is alkylene and $R_b$ is aryl as described herein. Alkylene and aryl portions of optionally substituted aralkyl are optionally substituted as described herein for alkylene and aryl, respectively.

"Aryl" refers to an aromatic monocyclic or multicyclic hydrocarbon ring system radical containing from 6 to 18 carbon atoms, where the multicyclic aryl ring system is a bicyclic, tricyclic, or tetracyclic ring system. Aryl radicals include, but are not limited to, groups such as fluorenyl, phenyl and naphthyl. An optionally substituted aryl is an aryl radical that is optionally substituted by one, two, three, four, or five substituents independently selected from the group consisting of alkyl, akenyl, halo, haloalkyl, haloalkenyl, cyano, nitro, aryl, heteroaryl, heteroarylalkyl, $-R''-OR'$, $-R''-OC(O)-R'$, $-R''-N(R')_2$, $-R''-C(O)R'$, $-R''-C(O)OR'$, $-R''-C(O)N(R')_2$, $-R''-N(R')C(O)OR'''$, $-R''-N(R')C(O)R'''$, $-R''-N(R')S(O)_tR'''$ (where t is 1 or 2), $-R''-S(O)_tOR'''$ (where t is 1 or 2), $-R''-S(O)_pR'''$ (where p is 0, 1, or 2), and $-R''-S(O)_tN(R')_2$ (where t is 1 or 2), where each R' is independently hydrogen, alkyl, haloalkyl, cycloalkyl, aryl, heterocyclyl, or heteroaryl; each R'' is independently a direct bond or a linear or branched alkylene or alkenylene chain; and each R''' is independently alkyl, haloalkyl, cycloalkyl, cycloalkylalkyl, aryl, heterocyclyl, or heteroaryl.

"Arylalkoxy" refers to a group of formula $-O-R$, where R is aralkyl. An optionally substituted arylalkoxy is an arylalkoxy that is optionally substituted as described herein for aralkyl. In some embodiments, arylalkoxy is benzyloxy.

"Bicyclic" refers to a ring system that features two joined rings with at least two common atoms. Bicyclic compounds include, but are not limited to, groups such as bicyclic aryl, bicyclic heteroaryl, bicyclic cycloalkyl, and bicyclic heterocycloalkyl. Bicyclic compounds may be, for example, fused (i.e., fused bicyclic), bridged (i.e., bridged bicyclic), or spirocyclic.

"Cycloalkyl" refers to a stable non-aromatic monocyclic or polycyclic hydrocarbon radical having from three to fifteen carbon atoms, preferably having from three to ten carbon atoms, and which is saturated or unsaturated, and which attaches to the rest of the molecule by a single bond. A polycyclic hydrocarbon radical is bicyclic, tricyclic, or tetracyclic ring system. An unsaturated cycloalkyl contains one, two, or three carbon-carbon double bonds and/or one carbon-carbon triple bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, and the like. An optionally substituted cycloalkyl is a cycloalkyl radical that is optionally substituted by one, two, three, four, or five substituents independently selected from the group consisting of alkyl, alkenyl, halo, haloalkyl, haloalkenyl, cyano, nitro, oxo, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2) and —R"—S(O)$_t$N(R')$_2$ (where t is 1 or 2) where each R' is independently hydrogen, alkyl, haloalkyl, cycloalkyl, aryl, heterocyclyl, or heteroaryl; each R" is independently a direct bond or a linear or branched alkylene or alkenylene chain; and each R''' is independently alkyl, haloalkyl, cycloalkyl, cycloalkylalkyl, aryl, aralkyl, heterocyclyl, or heteroaryl.

"Cycloalkylene" is a divalent radical of a cycloalkyl group.

"Deuterated compounds" are compounds where one of more hydrogen atoms have been replaced with a deuterium atom. Deuterated drugs may be derivatives of an active compound. Deuterated drugs may be prodrugs. Deuteration may alter the physical properties, metabolic properties, activity or safety of a drug.

"Derivatives" are related chemical species that can be derived from a similar compound via chemical reactions. They may encompass slight chemical modifications, substitution of atoms with deuterated atoms, substitution of atoms with stable or radioactive isotopes or other modifications that imbue a compound with desirable properties.

"Fused" refers to any ring system described herein which is fused to an existing ring structure in the compounds of the invention (e.g., fused bicyclic, fused heterocyclic). When the fused ring system is a heterocyclyl or a heteroaryl, any carbon atom on the existing ring structure which becomes part of the fused ring system may be replaced with a nitrogen atom.

"Halo" refers to the halogen substituents: bromo, chloro, fluoro, and iodo.

"Haloalkyl" refers to an alkyl radical, as defined above, that is further substituted by one or more halogen substituents. The number of halo substituents included in haloalkyl is from one and up to the total number of the hydrogen atoms available for replacement with the halo substituents (e.g., perfluoroalkyl). Non-limiting examples of haloalkyl include trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl and the like. For an optionally substituted haloalkyl, the hydrogen atoms bonded to the carbon atoms of the alkyl part of the haloalkyl radical may be optionally replaced with substituents as defined above for an optionally substituted alkyl.

"Haloalkenyl" refers to an alkenyl radical, as defined above, that is further substituted by one or more halo substituents. The number of halo substituents included in haloalkenyl is from one and up to the total number of the hydrogen atoms available for replacement with the halo substituents (e.g., perfluoroalkenyl). Non-limiting examples of haloalkenyl include 2,2-difluoroethenyl, 3-chloroprop-1-enyl, and the like. For an optionally substituted haloalkenyl, the hydrogen atoms bonded to the carbon atoms of the alkenyl part of the haloalkenyl radical may be optionally replaced with substituents as defined above for an optionally substituted alkenyl group.

"Haloalkynyl" refers to an alkynyl radical, as defined above, that is further substituted by one or more halo substituents. The number of halo substituents included in haloalkynyl is from one and up to the total number of the hydrogen atoms available for replacement with the halo substituents (e.g., perfluoroalkenyl). Non-limiting examples of haloalkynyl include 3-chloroprop-1-ynyl and the like. The alkynyl part of the haloalkynyl radical may be additionally optionally substituted as defined above for an alkynyl group.

"Heteroalkyl" refers to a linear, saturated, acyclic, monovalent hydrocarbon radical or branched, saturated, acyclic, monovalent hydrocarbon radical, having from one to twelve carbon atoms containing a total of one to six heteroatoms independently selected from the group consisting of nitrogen, oxygen, phosphorus, and sulfur. Heteroalkyl is optionally substituted as described herein for alkyl.

"Heteroarylalkyl" refers to a radical of the formula —R$_a$—R$_b$, where R$_a$ is alkylene and R$_b$ is heteroaryl as described herein. Alkylene and heteroaryl portions of optionally substituted heteroarylalkyl are optionally substituted as described herein for alkylene and heteroaryl, respectively.

"Heterocycloalkyl" refers to 3- to 18-membered saturated ring system radical having the carbon count of two to twelve and containing a total of one to six heteroatoms independently selected from the group consisting of nitrogen, oxygen, phosphorus, and sulfur. A heterocycloalkyl radical is a monocyclic, bicyclic, tricyclic, or tetracyclic ring system. A bicyclic, tricyclic, or tetracyclic heterocycloalkyl is a fused, spiro, and/or bridged ring system.

"Heterocycloalkylene" is a divalent radical of a heterocycloalkyl group.

"Heterocyclyl" or "heterocyclic" refers to a stable 3- to 18-membered non-aromatic ring system radical having the carbon count of two to twelve and containing a total of one to six heteroatoms independently selected from the group consisting of nitrogen, oxygen, phosphorus, and sulfur. A heterocyclyl radical is a monocyclic, bicyclic, tricyclic, or tetracyclic ring system. A bicyclic, tricyclic, or tetracyclic heterocyclyl is a fused, spiro, and/or bridged ring system. The heterocyclyl radical may be saturated or unsaturated. An unsaturated heterocyclyl contains one, two, or three carbon-carbon double bonds and/or one carbon-carbon triple bond. An optionally substituted heterocyclyl is a heterocyclyl radical that is optionally substituted by one, two, three, four, or five substituents independently selected from the group consisting of alkyl, alkenyl, halo, haloalkyl, haloalkenyl, cyano, oxo, thioxo, nitro, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2), and —R"—S(O)$_t$N(R')$_2$ (where t is 1 or 2), where each R' is independently hydrogen, alkyl, alkenyl, haloalkyl, cycloalkyl, aryl, heterocyclyl, or heteroaryl; each R" is independently a direct bond or a linear or branched alkylene or alkenylene chain; and each R''' is independently alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom); the nitrogen atom may be optionally quaternized (when the substituent is alkyl, alkenyl, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R'" (where p is 0, 1, or 2), and —R"—S(O)$_t$N(R')$_2$ (where t is 1 or 2), where R" is a linear or branched alkylene or alkenylene chain, and R' and R'" are as defined above). Examples of optionally substituted heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heterocyclylene" refers to a heterocyclyl in which one hydrogen atom is replaced with a valency. An optionally substituted heterocyclylene is optionally substituted as described herein for heterocyclyl.

"Heteroaryl" refers to a 5- to 18-membered ring system radical containing at least one aromatic ring, having the carbon count of one to seventeen carbon atoms, and containing a total of one to ten heteroatoms independently selected from the group consisting of nitrogen, oxygen, and sulfur. The heteroaryl radical is a monocyclic, bicyclic, tricyclic, or tetracyclic ring system. The bicyclic, tricyclic, or tetracyclic heteroaryl radical is a fused and/or bridged ring system. An optionally substituted heteroaryl is a heteroaryl radical that is optionally substituted by one, two, three, four, or five substituents independently selected from the group consisting of alkyl, alkenyl, alkoxy, halo, haloalkyl, haloalkenyl, cyano, oxo, thioxo, nitro, oxo, aryl, aralkyl, cycloalkyl, heterocyclyl, heteroaryl, or heteroarylalkyl, —R"—OR', —R"—OC(O)—R', —R"—N(R')$_2$, —R"—C(O)R', —R"—C(O)OR', —R"—C(O)N(R')$_2$, —R"—N(R') C(O)OR'", —R"—N(R')C(O)R'", —R"—N(R')S(O)$_t$R'" (where t is 1 or 2), —R"—S(O)$_t$OR'" (where t is 1 or 2), —R"—S(O)$_p$R'" (where p is 0, 1, or 2), and —R"—S(O)$_t$N (R')$_2$ (where t is 1 or 2), where each R' is independently hydrogen, alkyl, alkenyl, haloalkyl, cycloalkyl, aryl, heterocyclyl, or heteroaryl; each R" is independently a direct bond or a linear or branched alkylene or alkenylene chain; and each R'" is alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom), provided that at least one ring in heteroaryl remains aromatic; the nitrogen atom may be optionally quaternized (when the substituent is alkyl, alkenyl, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR'", —R"—N(R')C (O)R'", —R"—N(R')S(O)$_t$R'" (where t is 1 or 2), —R"—S (O)$_t$OR'" (where t is 1 or 2), —R"—S(O)$_p$R'" (where p is 0, 1, or 2), and —R"—S(O)$_t$N(R')$_2$ (where t is 1 or 2), where R" is a linear or branched alkylene or alkenylene chain, and R' and R'" are as defined above), provided that at least one ring in heteroaryl remains aromatic. Examples of optionally substituted heteroaryl radicals include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a] pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl).

"Heteroarylene" is a divalent radical of a heteroaryl group.

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

"Prodrugs" are compounds that after administration are metabolized or otherwise chemically transformed into an active moiety. Prodrugs may be derivatives of an active compound. Prodrugs may or may not be active prior to conversion into an active form in vivo.

The term "treating" is used herein, for instance, in reference, for example, to methods of treating inflammatory diseases or to a gastrointestinal disease, and generally includes the administration of a compound or composition which reduces the frequency of, or delays the onset of, symptoms of a medical condition (e.g., autoimmune disease, inflammatory disorder, gastrointestinal disorder) in a subject relative to a subject not receiving the compound or composition. This can include reversing, reducing, or arresting the symptoms, clinical signs, and underlying pathology of a condition in a manner to improve or stabilize a subject's condition (e.g., regression of symptoms of an autoimmune or inflammatory disease such as improvement in the MAYO score in the treatment of ulcerative colitis).

The embodiments disclosed herein encompass all pharmaceutically acceptable compounds of the compound of (I), (IA), (IB)-(IB-3), (IC-a)-(II-a), (IC-b)-(II-b), (III-a)-(III-h), (IV) or (IV-a) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labelled compounds of (I), (IA), (IB)-(IB-3), (IC-a)-(II-a), (IC-b)-(II-b), (III-a)-(III-h), (IV) or (IV-a), for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of (I), (IA), (IB)-(IB-3), (IC-a)-(II-a), (IC-b)-(II-b), (III-a)-(III-h), (IV) or (IV-a) can generally be prepared by conventional techniques known to those skilled in the art or by processes analogous to those described in the Preparations and Examples as set out below using an appropriate isotopically-labeled reagent in place of the non-labeled reagent previously employed.

The embodiments disclosed herein encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid (TFA), undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents and excipients therefore.

"Effective amount" or "therapeutically effective amount" refers to that amount of a compound of the disclosure which, when administered to a mammal, preferably a human, is sufficient to effect treatment in the mammal, preferably a human. The amount of a compound which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. The present disclosure also contemplates "diastereomers", which refers to non-mirror image of non-identical stereoisomers. Diastereomers occur when two or more stereoisomers of a compound have different configurations at one or more of the equivalent stereocenters and are not mirror images of each other.

A "tautomer" refers to a proton shift from one atom of a molecule to another atom of the same molecule. The present disclosure includes tautomers of any said compounds.

"Abnormal cell growth", as used herein, unless otherwise indicated, means cell growth that is independent of normal regulatory mechanisms (e.g., loss of contact inhibition). Abnormal cell growth may be benign (not cancerous) or malignant (cancerous).

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

II. Compounds

The compounds described herein are FGFR inhibitors.

In one aspect, provided herein is a compound having the following structure of Formula (IV):

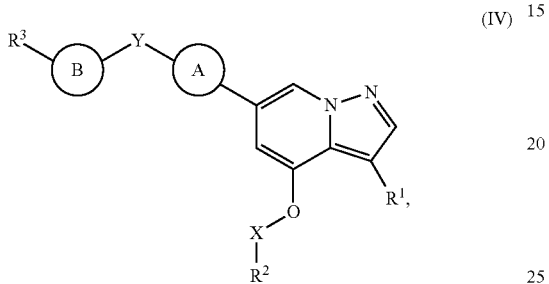

or a stereoisomer of the compound, salt, tautomer, or prodrug of the compound thereof, wherein:
- $R^1$ is selected from the group consisting of —CN, —Cl, —Br, —CH$_3$, —CF$_2$H, and —CF$_3$;
- $R^2$ is 5-6 membered heteroaryl optionally substituted with 1 or 2 substituents each independently selected from the group consisting of halo, C$_1$-C$_6$ alkyl, and C$_1$-C$_6$ haloalkyl;
- $R^3$ is selected from the group consisting of H, —OH, halo, C$_1$-C$_6$ alkyl, C$_1$-C$_6$ heteroalkyl, —C(=O)R$^4$, —OC(=O)R$^4$, —NR$^5$R$^6$, —NR$^5$C(=O)R$^4$, —NR$^5$C(=O)OR$^4$, —CH$_2$C(=O)NR$^5$N$^6$, —NR$^5$R$^6$CH$_2$C(=O)NR$^5$N$^6$, —CH$_2$NR$^5$C(=O)R$^4$, —S(O)$_2$—CH$_3$, oxo, phosphate, and CN, wherein the C$_1$-C$_6$ alkyl is optionally substituted with one or more —OH;
- $R^4$ is selected from the group consisting of —C$_1$-C$_6$ alkyl, C$_1$-C$_6$ heteroalkyl, C$_4$-C$_6$ cycloalkyl, and C$_4$-C$_6$ heterocycloalkyl, wherein the C$_1$-C$_6$ alkyl or C$_4$-C$_6$ cycloalkyl is optionally substituted with one or more —OH or —NR$^5$R$^6$;
- $R^5$ and $R^6$ are, each independently, selected from the group consisting of H, C$_1$-C$_6$ alkyl, C$_1$-C$_6$ alkyl alcohol, —S(O)$_2$—CH$_3$, and C$_3$-C$_6$ cycloalkyl;
- X is selected from the group consisting of —(CH$_2$)$_n$—, —(CH$_2$)$_n$O—, —(CHCH$_3$)$_n$—, —(CHCH$_3$)$_n$—(CH$_2$)$_m$—, —(CHCH$_3$)$_n$—(CH$_2$)$_m$O—, —(CHCF$_3$)$_n$—, —(CHCH$_2$OH)$_n$—, —(CHCH$_2$CH$_3$)$_n$—, and a direct bond;
- Y is selected from the group consisting of —CH$_2$—, —CHCH$_3$—, —C(CH$_3$)$_2$—, —(CH$_2$) PC(=O)—, —NCH$_3$—, and a direct bond;
- n is an integer between 1 and 4;
- m is an integer between 1 and 4;
- p is an integer between 0 and 4;
- A is i) 5-6 membered heteroarylene having at most of two nitrogen atoms, wherein the 5-6 membered heteroarylene is optionally substituted with one or more substituents each independently selected from the group consisting of C$_1$-C$_6$ alkyl, halo, —CN, —NH$_2$, and —(C$_1$-C$_6$ alkylene)-(C$_1$-C$_6$ alkoxy), or ii)

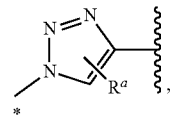

wherein § indicates a location of a bond to the pyrazolopyrimidine core and * indicates a location of a bond to Y, wherein $R^a$ is selected from H, C$_1$-C$_6$ alkyl and —NH$_2$;
- B is selected from the group consisting of C$_3$-C$_8$ cycloalkylene, 5-6 membered heterocycloalkylene, and —CH$_2$—, wherein the C$_3$-C$_8$ cycloalkylene or 5-6 membered heterocycloalkylene is optionally substituted with one or more substituents each independently selected from the group consisting of C$_1$-C$_6$ alkyl, —OH, oxo, C$_1$-C$_6$ alkoxy, halo, C$_1$-C$_6$ haloalkyl, and C$_1$-C$_6$ alkyl alcohol;

wherein, when B is

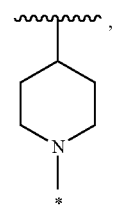

wherein § indicates a location of a bond to Y, * indicates a location of a bond to R$^3$, R$^3$ is H or —CN, and A is pyrazolylene, the pyrazolylene is optionally substituted with one or more halo, —CN, —NH$_2$, or —(C$_1$-C$_6$ alkylene)-(C$_1$-C$_6$ alkoxy); or two C$_1$-C$_6$ alkyl; and wherein, when B is

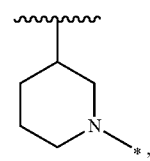

wherein § indicates a location of a bond to Y, * indicates a location of a bond to R$^3$, and A is pyrazolylene, R$^2$ is 5-6 membered heteroaryl substituted with halo, C$_1$-C$_6$ alkyl, or C$_1$-C$_6$ haloalkyl.

In another aspect, provided herein is a compound having the following structure of Formula (IV):

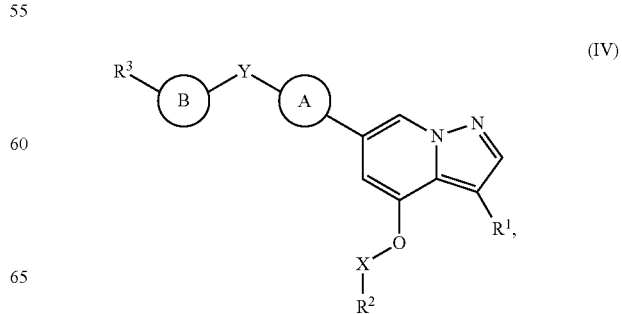

or a stereoisomer of the compound, salt or tautomer of the compound thereof, wherein:

R¹ is selected from the group consisting of —CN, —Cl, —Br, —CH₃, —CF₂H, and —CF₃;

R² is 5-6 membered heteroaryl optionally substituted with 1 or 2 substituents each independently selected from the group consisting of halo, $C_1$-$C_6$ alkyl, and $C_1$-$C_6$ haloalkyl;

R³ is selected from the group consisting of H, —OH, halo, $C_1$-$C_6$ alkyl, $C_1$-$C_6$ heteroalkyl, —C(=O)R⁴, —OC(=O)R⁴, —NR⁵R⁶, —NR⁵C(=O)R⁴, —NR⁵C(=O)OR⁴, —CH₂C(=O)NR⁵N⁶, —NR⁵R⁶CH₂C(=O)NR⁵N⁶, —CH₂NR⁵C(=O)R⁴, —S(O)₂—CH₃, oxo, phosphate, and CN, wherein the $C_1$-$C_6$ alkyl is optionally substituted with one or more —OH;

R⁴ is selected from the group consisting of —$C_1$-$C_6$ alkyl, $C_1$-$C_6$ heteroalkyl, $C_4$-$C_6$ cycloalkyl, and $C_4$-$C_6$ heterocycloalkyl, wherein the $C_1$-$C_6$ alkyl or $C_4$-$C_6$ cycloalkyl is optionally substituted with one or more —OH or —NR⁵R⁶;

R⁵ and R⁶ are, each independently, selected from the group consisting of H, $C_1$-$C_6$ alkyl, $C_1$-$C_6$ alkyl alcohol, —S(O)₂—CH₃, and $C_3$-$C_6$ cycloalkyl;

X is selected from the group consisting of —(CH₂)$_n$—, —(CH₂)$_n$O—, —(CHCH₃)$_n$—, —(CHCH₃)$_n$(CH₂)$_m$—, —(CHCH₃)$_n$—(CH₂)$_m$O—, —(CHCF₃)$_n$—, —(CHCH₂OH)$_n$—, —(CHCH₂CH₃)$_n$—, and a direct bond;

Y is selected from the group consisting of —CH₂—, —CHCH₃—, —C(CH₃)₂—, —(CH₂)$_p$C(=O)—, —NCH₃—, and a direct bond;

n is an integer between 1 and 4;

m is an integer between 1 and 4;

p is an integer between 0 and 4;

A is i) 5-6 membered heteroarylene having at most of two nitrogen atoms, wherein the 5-6 membered heteroarylene is optionally substituted with one or more substituents each independently selected from the group consisting of $C_1$-$C_6$ alkyl, halo, —CN, —NH₂, and —($C_1$-$C_6$ alkylene)-($C_1$-$C_6$ alkoxy), or ii)

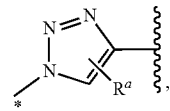

wherein ⸮ indicates a location of a bond to the pyrazolopyrimidine core and * indicates a location of a bond to Y, wherein R$^a$ is selected from H, $C_1$-$C_6$ alkyl and —NH₂;

B is selected from the group consisting of $C_3$-$C_8$ cycloalkylene, 5-6 membered heterocycloalkylene, and —CH₂—, wherein the $C_3$-$C_8$ cycloalkylene or 5-6 membered heterocycloalkylene is optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol;

wherein, when B is

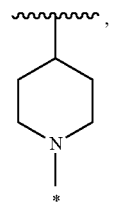 [SMILES: *C1CCN(C)CC1]

wherein ⸮ indicates a location of a bond to Y, * indicates a location of a bond to R³, R³ is H or —CN, and A is pyrazolylene, the pyrazolylene is optionally substituted with one or more halo, —CN, —NH₂, or —($C_1$-$C_6$ alkylene)-($C_1$-$C_6$ alkoxy); or two $C_1$-$C_6$ alkyl; and wherein, when B is

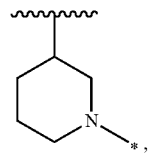

wherein ⸮ indicates a location of a bond to Y, * indicates a location of a bond to R³, and A is pyrazolylene, R² is 5-6 membered heteroaryl substituted with halo, $C_1$-$C_6$ alkyl, or $C_1$-$C_6$ haloalkyl.

In some embodiments, R¹ is —CN.

In some embodiments, R² is 5-6 membered heteroaryl optionally substituted with halo. In some embodiments, R² is 5-6 membered heteroaryl optionally substituted with F.

In some embodiments, R² is pyridinyl optionally substituted with halo.

In some embodiments, R² is pyridinyl optionally substituted with F.

In some embodiments, R² is selected from the group consisting of:

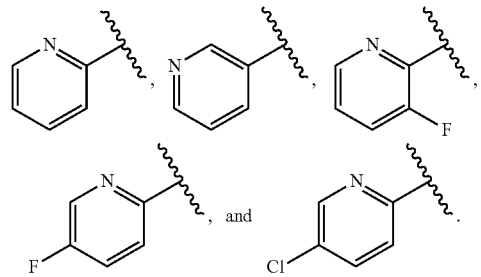

In some embodiments, R³ is selected from the group consisting of H, —OH, halo, $C_1$-$C_6$ alkyl, $C_1$-$C_6$ heteroalkyl, —C(=O)R⁴, —OC(=O)R⁴, =NR⁵, —NR⁵R⁶, —NR⁵C(=O)R⁴, —NR⁵C(=O)OR⁴, —CH₂C(=O)NR⁵N⁶, —NR⁵R⁶CH₂C(=O)NR⁵N⁶, —CH₂NR⁵C(=O)R⁴, —S(O)₂—CH₃, oxo, and phosphate, wherein the $C_1$-$C_6$ alkyl is optionally substituted with one or more —OH. In some embodiments, R³ is selected from the group consisting of —OH, halo, $C_1$-$C_6$ alkyl, $C_1$-$C_6$ heteroalkyl, —C(=O)R⁴, —OC(=O)R⁴, =NR⁵, —NR⁵R⁶, —NR⁵C(=O)R⁴, —NR⁵C(=O)OR⁴, —CH₂C(=O)NR⁵N⁶, —NR⁵R⁶CH₂C(=O)NR⁵N°, —CH—NR⁵C(=O)R⁴, —S(O)₂—CH₃, oxo, and phosphate, wherein the $C_1$-$C_6$ alkyl is optionally substituted with one or more —OH.

In some embodiments, $R^3$ is selected from the group consisting of: —H, —OH, halo, $C_1$-$C_6$ alkyl, —C(=O)$R^4$, =$NR^5$, —$NR^5R^6$, —$NR^5$C(=O)$R^4$, oxo, and CN, wherein the $C_1$-$C_6$ alkyl is optionally substituted with one or more —OH. In some embodiments, $R^3$ is selected from the group consisting of: —H, —OH, halo, $C_1$-$C_6$ alkyl, —C(=O)$R^4$, =$NR^5$, —$NR^5R^6$, —$NR^5$C(=O)$R^4$, and oxo, wherein the $C_1$-$C_6$ alkyl is optionally substituted with one or more —OH. In some embodiments, $R^3$ is selected from the group consisting of: —OH, halo, $C_1$-$C_6$ alkyl, —C(=O)$R^4$, =$NR^5$, —$NR^5R^6$, —$NR^5$C(=O)$R^4$, and oxo, wherein the $C_1$-$C_6$ alkyl is optionally substituted with one or more —OH.

In some embodiments, $R^3$ is selected from the group consisting of: H, —OH, $C_1$-$C_6$ alkyl, and —C(=O)$R^4$, wherein the $C_1$-$C_6$ alkyl is optionally substituted with one or more —OH. In some embodiments, $R^3$ is selected from the group consisting of: —OH, $C_1$-$C_6$ alkyl, and —C(=O)$R^4$, wherein the $C_1$-$C_6$ alkyl is optionally substituted with one or more —OH.

In some embodiments, the $C_1$-$C_6$ alkyl at $R^3$ is optionally substituted with 1, 2, or 3 —OH.

In some embodiments, $R^4$ is selected from the group consisting of —CH$_3$, —CH$_2$OH, —CH(CH$_3$)OH, —C(CH$_3$)$_2$OH, —CH(CH(CH$_3$)$_2$)NH$_2$, $C_1$-$C_6$ heteroalkyl, $C_4$-$C_6$ cycloalkyl, and $C_4$-$C_6$ heterocycloalkyl, wherein the $C_4$-$C_6$ cycloalkyl is optionally substituted with one or more —OH or —$NR^5R^6$.

In some embodiments, $R^4$ is selected from the group consisting of —CH$_3$, —CH$_2$OH, —CH(CH$_3$)OH, —C(CH$_3$)$_2$OH, —CH(CH(CH$_3$)$_2$) NH$_2$, and $C_4$-$C_6$ cycloalkyl, wherein the $C_4$-$C_6$ cycloalkyl is optionally substituted with —OH or —$NR^5R^6$.

In some embodiments, $R^4$ is —CH$_3$ or —CH(CH$_3$)OH.

In some embodiments, $R^5$ and $R^6$ are, each independently, H or $C_1$-$C_6$ alkyl.

In some embodiments, $R^5$ and $R^6$ are H.

In some embodiments, X is selected from the group consisting of —(CHCH$_3$)$_n$—, —(CHCF$_3$)$_n$—, —(CHCH$_2$OH)$_n$— and —(CHCH$_2$CH$_3$)$_n$—.

In some embodiments, X is —(CHCH$_3$)$_n$—.

In some embodiments, Y is a direct bond.

In some embodiments, n is 1.

In some embodiments, A is 5-6 membered heteroarylene having at most of two nitrogen atoms wherein the 5-6 membered heteroarylene is optionally substituted with one or more substituents each independently selected from the group consisting of $C_1$-$C_6$ alkyl, halo, —CN, —NH$_2$, and —($C_1$-$C_6$ alkylene)-($C_1$-$C_6$ alkoxy).

In some embodiments, A is 5-6 membered heteroarylene having at most of two nitrogen atoms wherein the 5-6 membered heteroarylene is optionally substituted with 1, 2, or 3 substituents each independently selected from $C_1$-$C_6$ alkyl and —NH$_2$.

In some embodiments, the 5-6 membered heteroarylene is selected from the group consisting of:

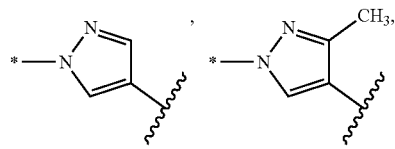

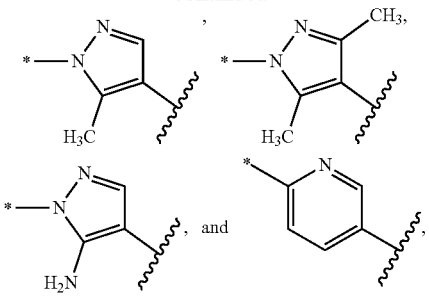

wherein * indicates a location of a bond to Y, and ⨎ indicates a location of a bond to the pyrazolopyrimidine core.

In some embodiments, A is

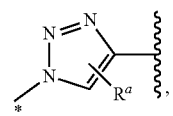

wherein * indicates a location of a bond to Y, and ⨎ indicates a location of a bond to the pyrazolopyrimidine core, wherein $R^a$ is selected from the group consisting of H, $C_1$-$C_6$ alkyl, and —NH$_2$.

In some embodiments, $R^a$ is selected from —CH$_3$ and —NH$_2$.

In some embodiments, B is $C_3$-$C_8$ cycloalkylene, wherein the $C_3$-$C_8$ cycloalkylene is optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol.

In some embodiments, B is $C_3$-$C_8$ cycloalkylene, wherein the $C_3$-$C_8$ cycloalkylene is optionally substituted with $C_1$-$C_6$ alkyl or —OH.

In some embodiments, B is 5-6 membered heterocycloalkylene, wherein the 5-6 membered heterocycloalkylene is optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol.

In some embodiments, B is 5-6 membered heterocycloalkylene, wherein the 5-6 membered heterocycloalkylene is optionally substituted with $C_1$-$C_6$ alkyl or —OH.

In some embodiments, B is —CH$_2$—.

In some embodiments, the compound is a compound having the following structure of Formula (IV-a):

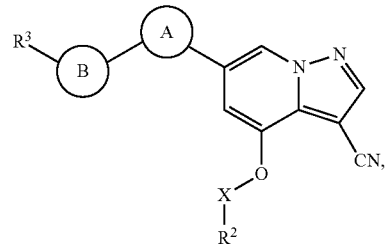

(IV-a)

or a stereoisomer of the compound, salt or tautomer of the compound thereof, wherein:

$R^2$ is 5-6 membered heteroaryl optionally substituted with halo;

$R^3$ is H, —OH, halo, $C_1$-$C_6$ alkyl, —C(=O)$R^4$, =$NR^5$, —$NR^5R^6$, —$NR^5$C(=O)$R^4$, oxo, and CN, wherein the $C_1$-$C_6$ alkyl is optionally substituted with one or more —OH;

$R^4$ is selected from the group consisting of —$C_1$-$C_6$ alkyl, $C_1$-$C_6$ heteroalkyl, $C_4$-$C_6$ cycloalkyl, and $C_4$-$C_6$ heterocycloalkyl, wherein the $C_1$-$C_6$ alkyl or $C_4$-$C_6$ cycloalkyl is optionally substituted with one or more —OH or —$NR^5R^6$;

$R^5$ and $R^6$ are, each independently, H, or $C_1$-$C_6$ alkyl;

X is —(CHCH$_3$)$_n$—, —(CHCF$_3$)$_n$—, —(CHCH$_2$OH)$_n$— and —(CHCH$_2$CH$_3$)$_n$—;

n is an integer between 1 and 4;

A is pyrazolylene optionally substituted with one or more $C_1$-$C_6$ alkyl, halo, —CN, —NH$_2$, or —($C_1$-$C_6$ alkylene)-($C_1$-$C_6$ alkoxy); and B is selected from the group consisting of $C_3$-$C_8$ cycloalkylene, 5-6 membered heterocycloalkylene, and —CH$_2$—, wherein the $C_3$-$C_8$ cycloalkylene or 5-6 membered heterocycloalkylene is optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol, wherein, when B is

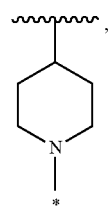 [SMILES: *C1CCN(C)CC1]

wherein ⚡ indicates a location of a bond to Y, * indicates a location of a bond to $R^3$, $R^3$ is H or —CN, and A is pyrazolylene, the pyrazolylene is optionally substituted with one or more halo, —CN, —NH$_2$, or —($C_1$-$C_6$ alkylene)-($C_1$-$C_6$ alkoxy); or two $C_1$-$C_6$ alkyl; and wherein, when B is

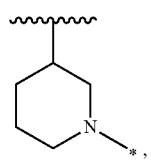

wherein ⚡ indicates a location of a bond to Y, * indicates a location of a bond to $R^3$, and A is pyrazolylene, $R^2$ is 5-6 membered heteroaryl substituted with halo, $C_1$-$C_6$ alkyl, or $C_1$-$C_6$ haloalkyl.

In some embodiments, $R^2$ is pyridinyl optionally substituted with halo.

In some embodiments, $R^2$ is pyridinyl optionally substituted with F.

In some embodiments, $R^2$ is selected from the group consisting of:

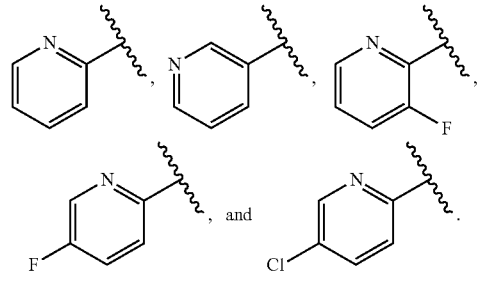

In some embodiments, $R^3$ is selected from the group consisting of: H, —OH, halo, $C_1$-$C_6$ alkyl, —C(=O)$R^4$, =$NR^5$, —$NR^5R^6$, —$NR^5$C(=O)$R^4$, and oxo, wherein the $C_1$-$C_6$ alkyl is optionally substituted with one or more —OH. In some embodiments, $R^3$ is selected from the group consisting of: —OH, halo, $C_1$-$C_6$ alkyl, —C(=O)$R^4$, =$NR^5$, —$NR^5R^6$, —$NR^5$C(=O)$R^4$, and oxo, wherein the $C_1$-$C_6$ alkyl is optionally substituted with one or more —OH.

In some embodiments, $R^3$ is selected from the group consisting of: H, OH, $C_1$-$C_6$ alkyl, and —C(=O)$R^4$, wherein the $C_1$-$C_6$ alkyl is optionally substituted with one or more —OH. In some embodiments, $R^3$ is selected from the group consisting of: OH, $C_1$-$C_6$ alkyl, and —C(=O)$R^4$, wherein the $C_1$-$C_6$ alkyl is optionally substituted with one or more —OH.

In some embodiments, the $C_1$-$C_6$ alkyl at $R^3$ is optionally substituted with 1, 2, or 3 —OH.

In some embodiments, $R^4$ is —CH$_3$, —CH$_2$OH, —CH(CH$_3$)OH, —C(CH$_3$)$_2$OH, —CH(CH(CH$_3$)$_2$)NH$_2$, and $C_4$-$C_6$ cycloalkyl, wherein the $C_4$-$C_6$ cycloalkyl is optionally substituted with —OH or —$NR^5R^6$.

In some embodiments, $R^4$ is —CH$_3$ or —CH(CH$_3$)OH.

In some embodiments, $R^5$ and $R^6$ are, each independently, H or —CH$_3$.

In some embodiments, $R^5$ and $R^6$ are H.

In some embodiments, X is —(CHCH$_3$)$_n$—.

In some embodiments, n is 1.

In some embodiments, A is 5-6 membered heteroarylene is selected from the group consisting of:

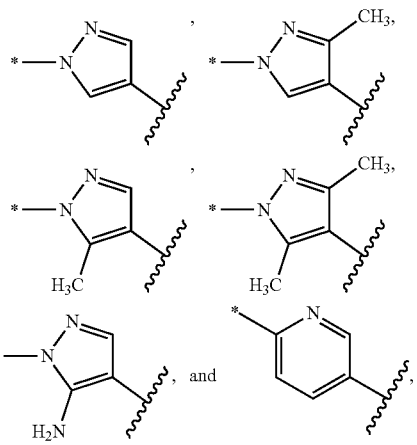

wherein * indicates a location of a bond to B, and ⚡ indicates a location of a bond to the pyrazolopyrimidine core.

In some embodiments, B is $C_3$-$C_8$ cycloalkylene, wherein the $C_3$-$C_8$ cycloalkylene is optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol.

In some embodiments, B is $C_3$-$C_8$ cycloalkylene, wherein the $C_3$-$C_8$ cycloalkylene is optionally substituted with $C_1$-$C_6$ alkyl or —OH.

In some embodiments, B is 5-6 membered heterocycloalkylene, wherein the 5-6 membered heterocycloalkylene is optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol.

In some embodiments, B is 5-6 membered heterocycloalkylene, wherein the 5-6 membered heterocycloalkylene is optionally substituted with $C_1$-$C_6$ alkyl or —OH.

In some embodiments, the compound has one of the following structures:

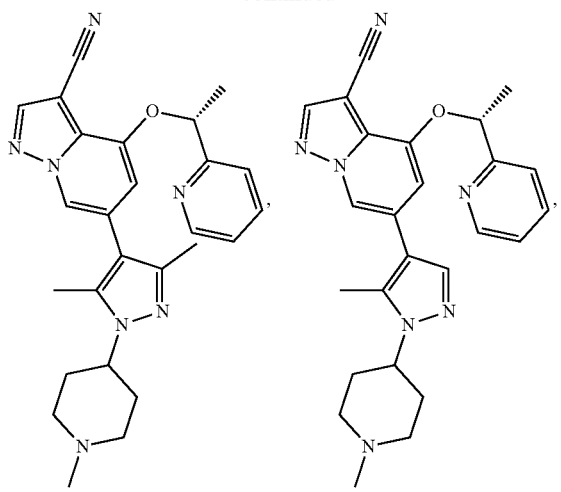

-continued

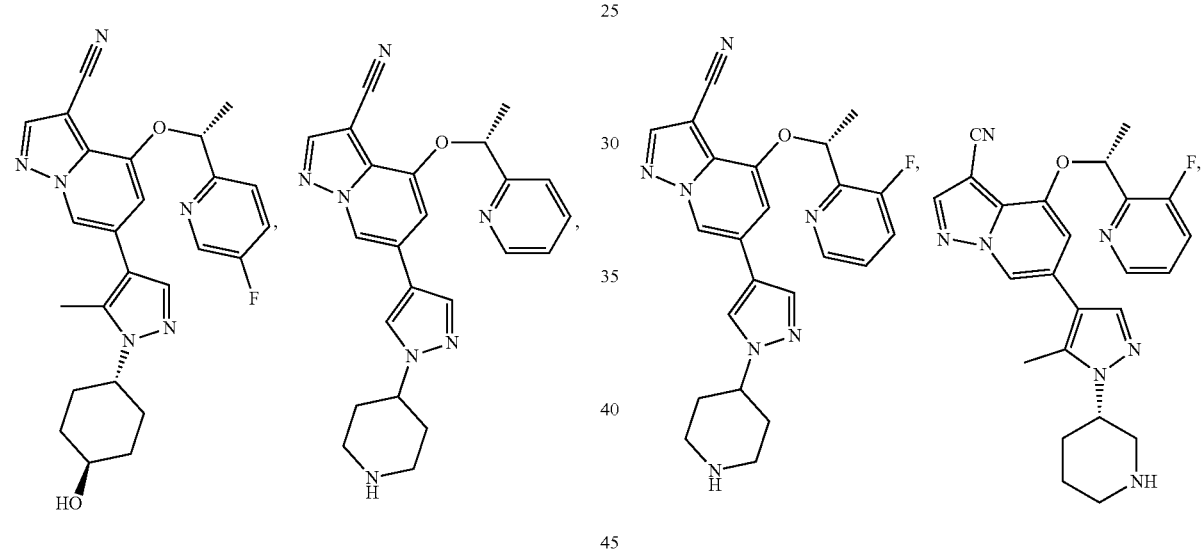

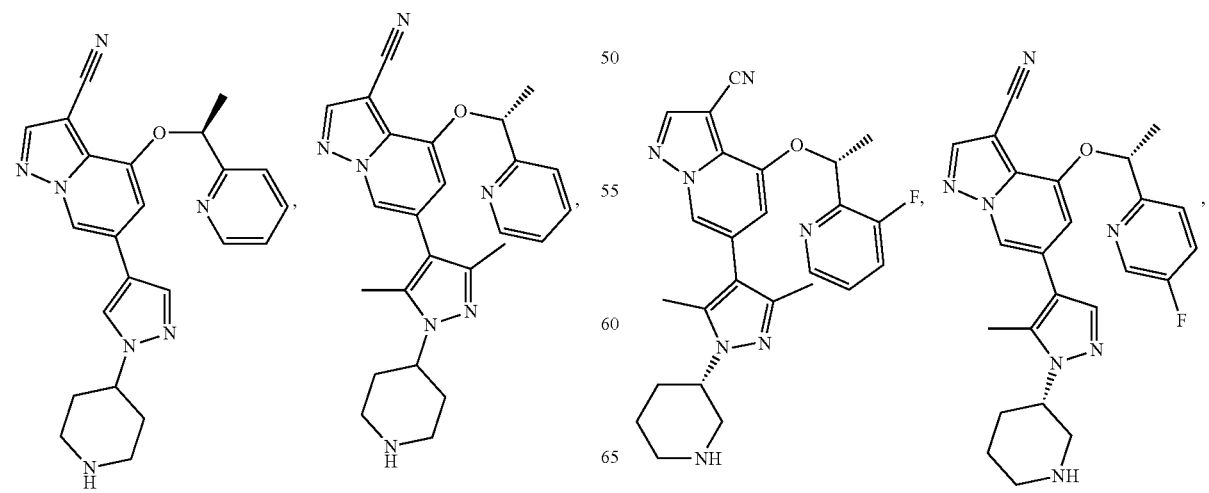

-continued
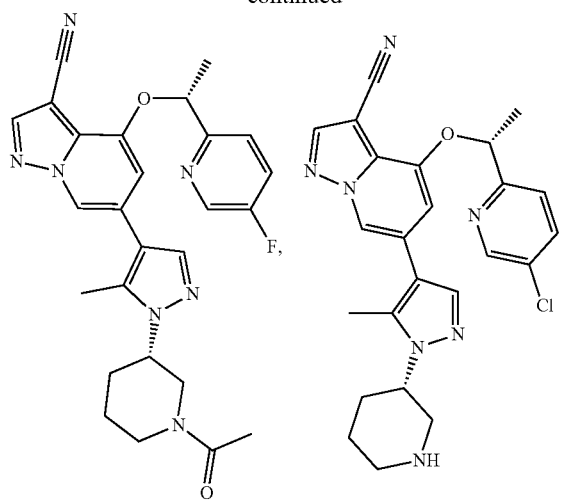
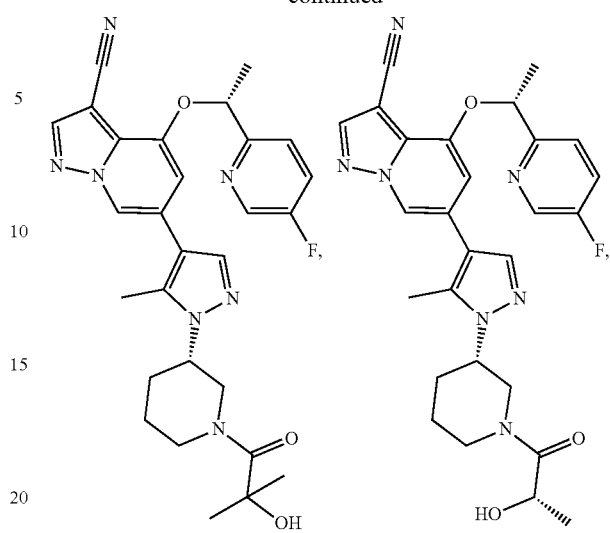
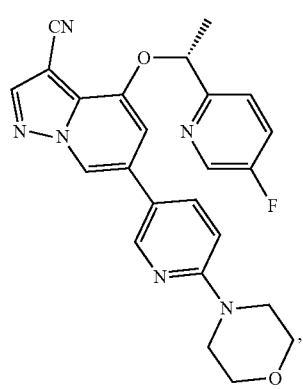
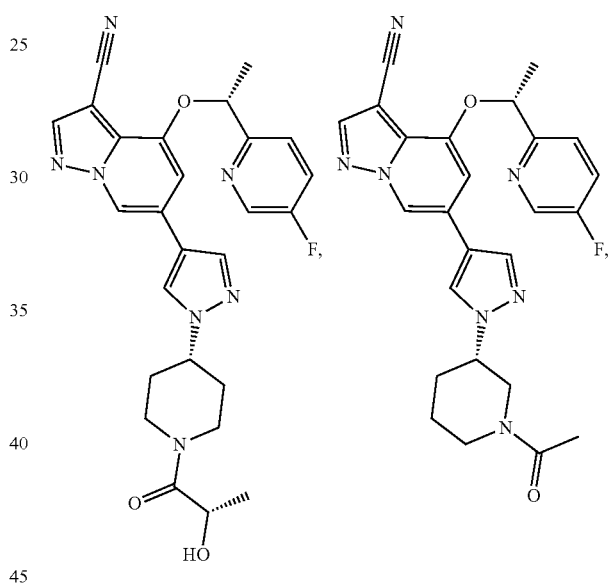
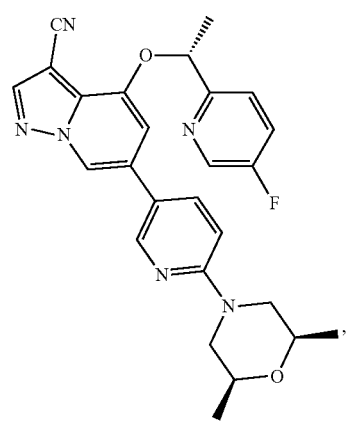
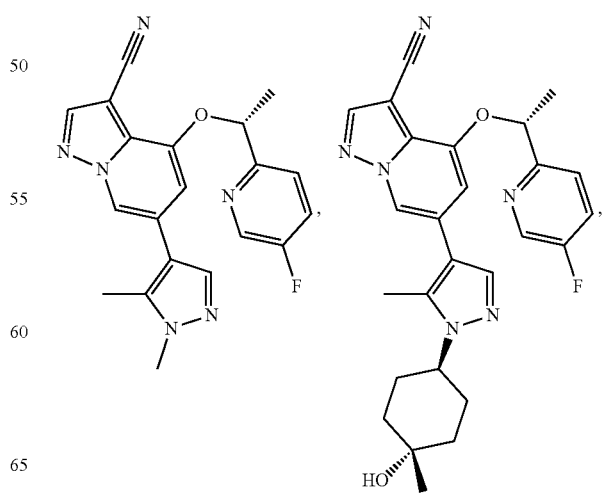

23
-continued
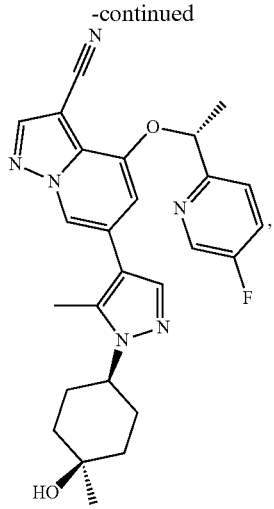
24
-continued
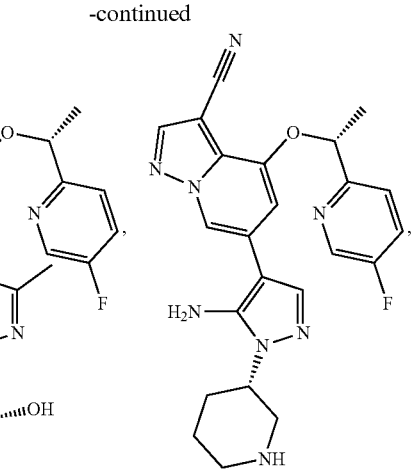
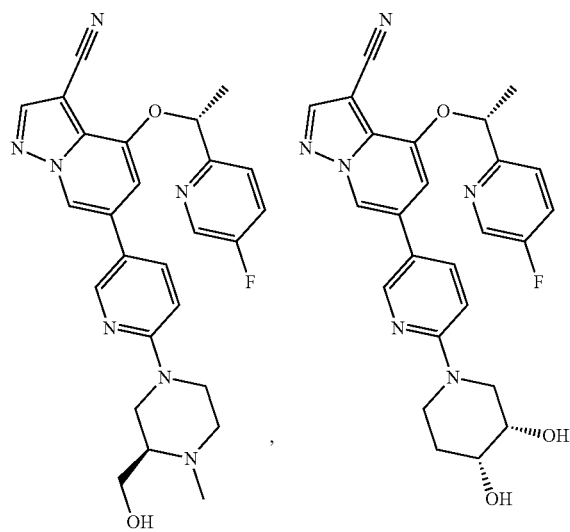
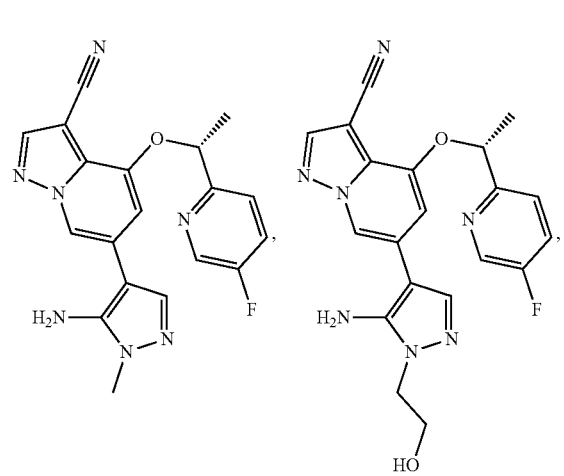
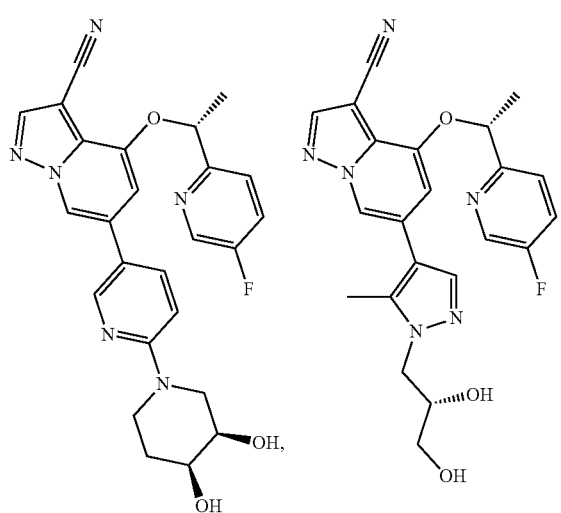
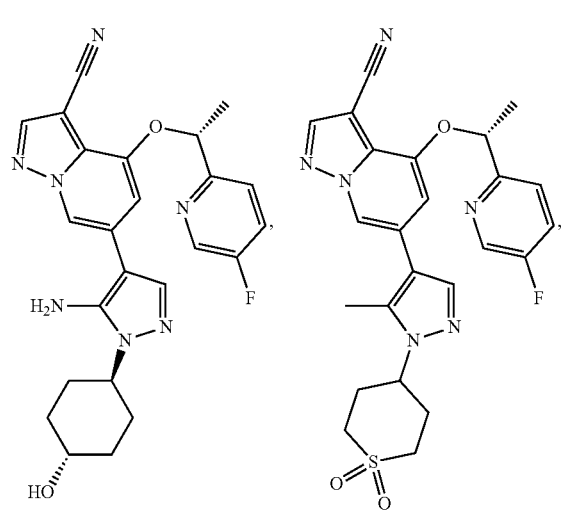

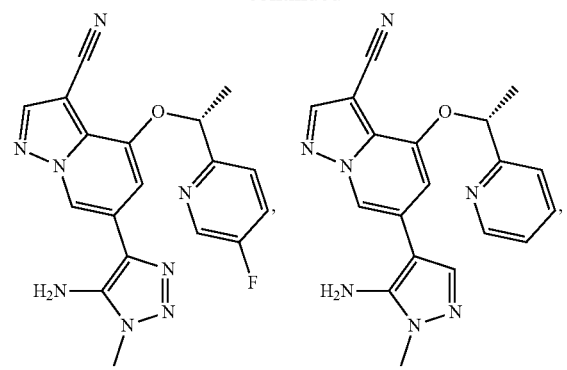
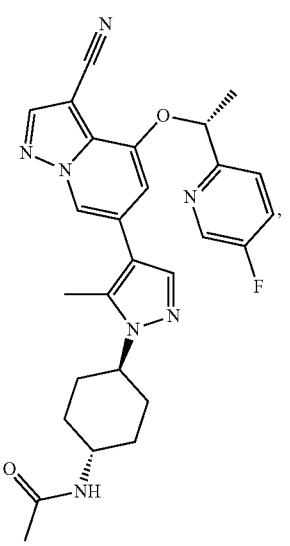
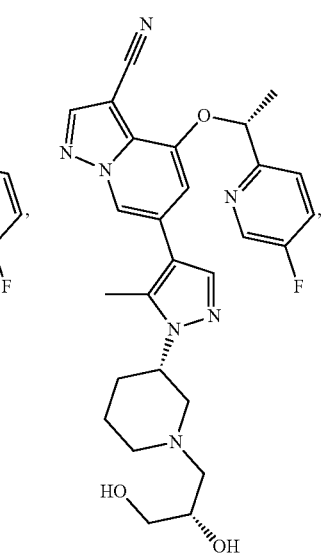
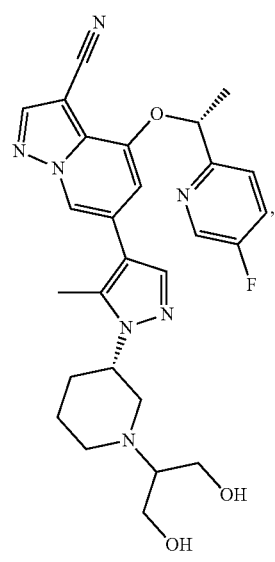
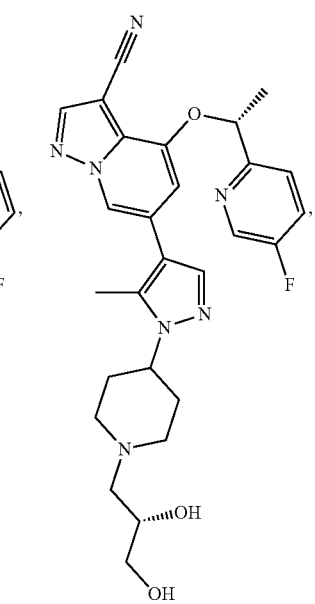
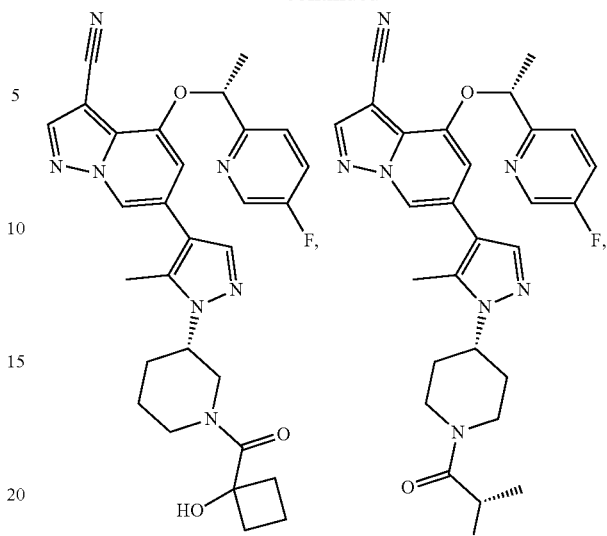
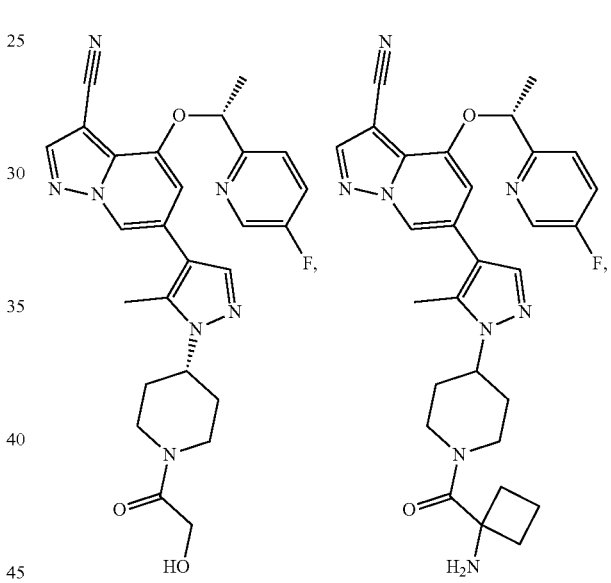
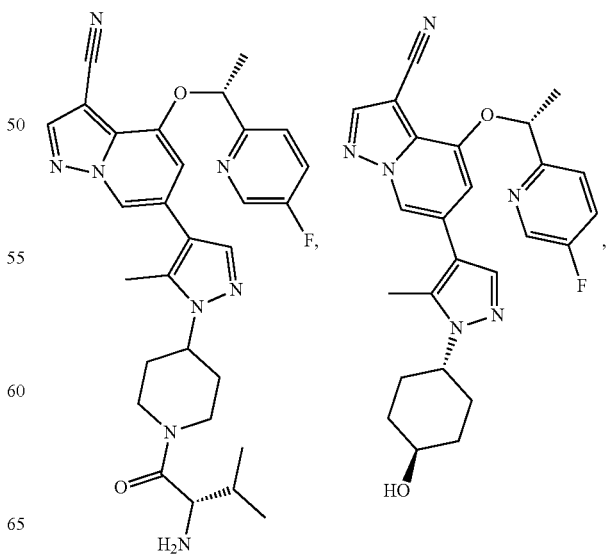

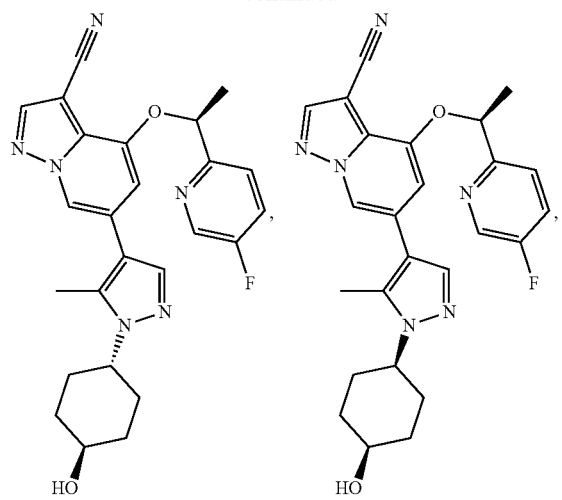
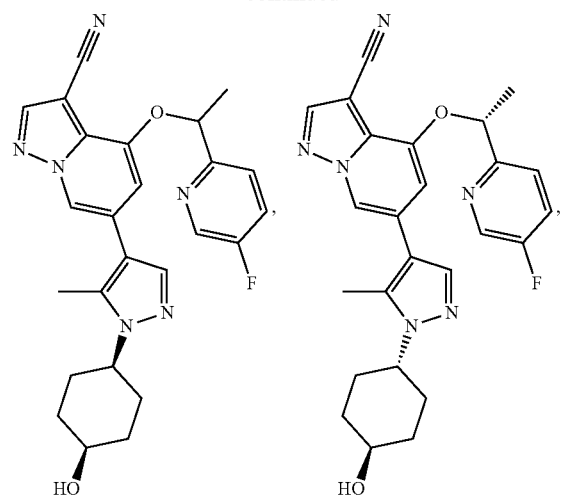
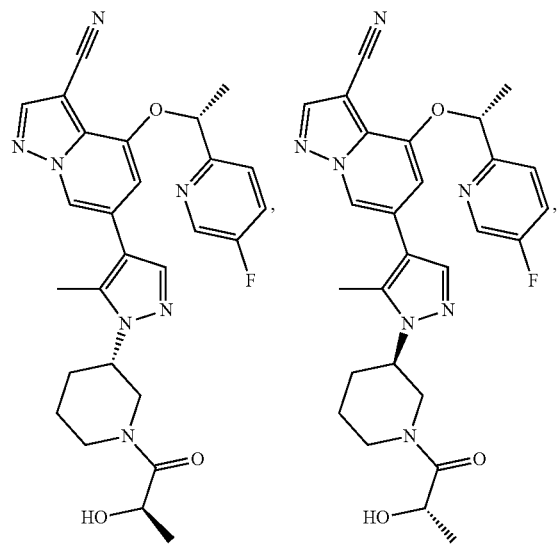
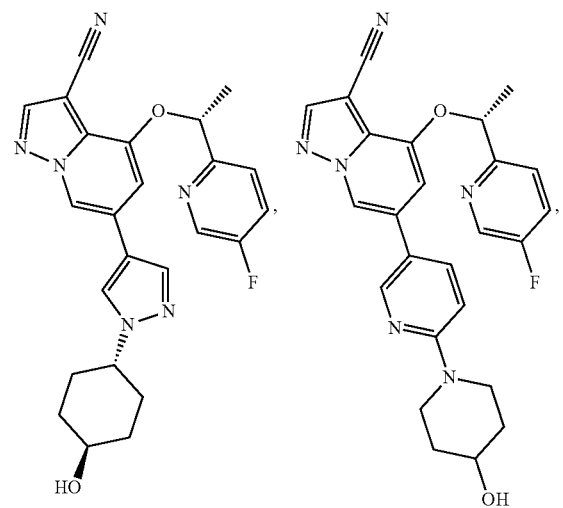
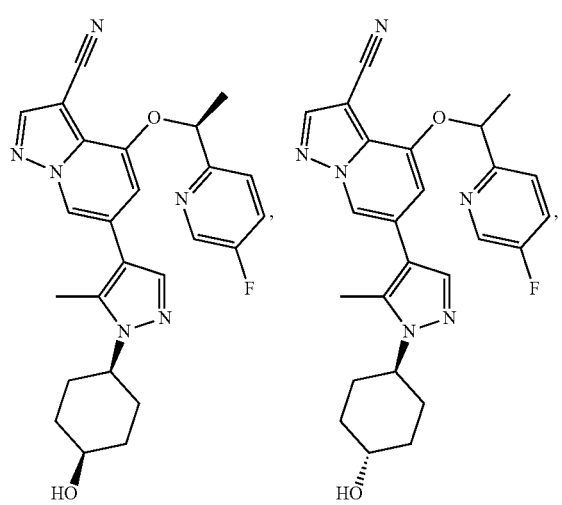
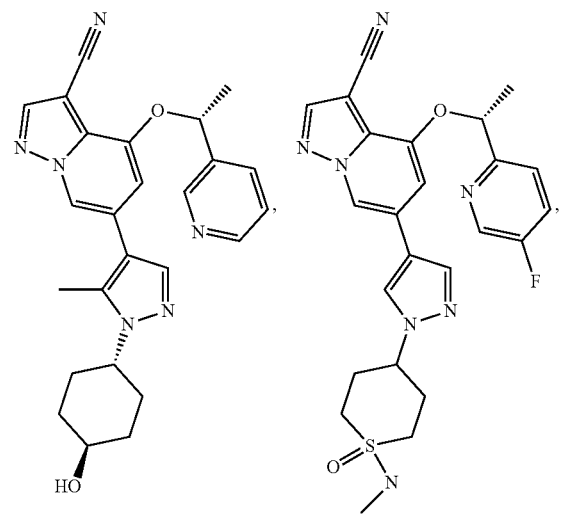

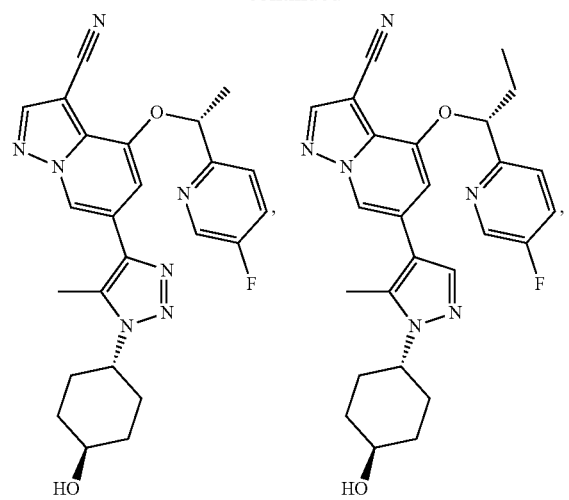
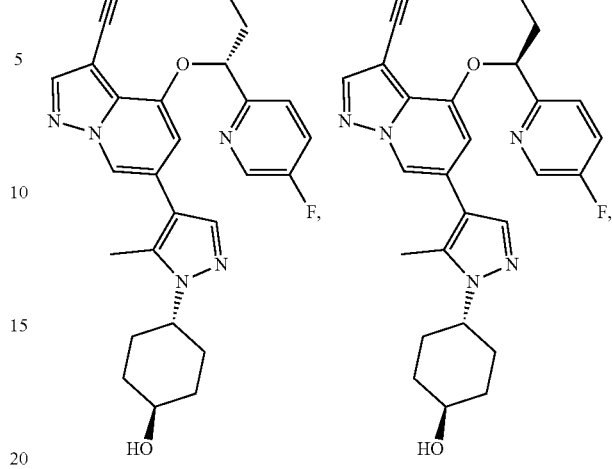
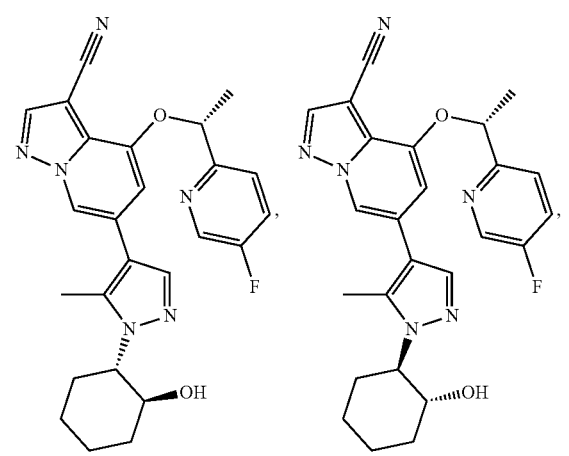
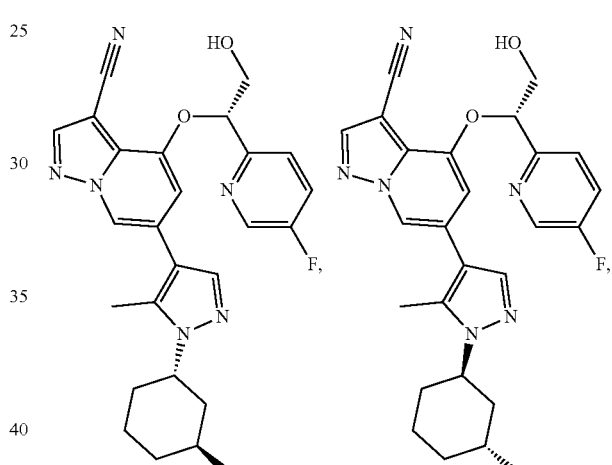
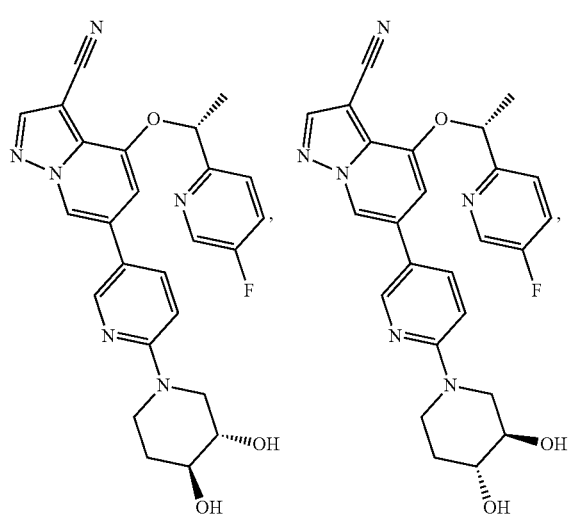
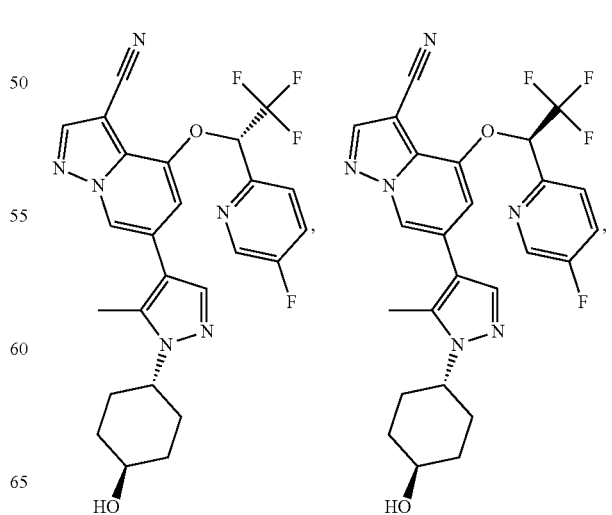

-continued

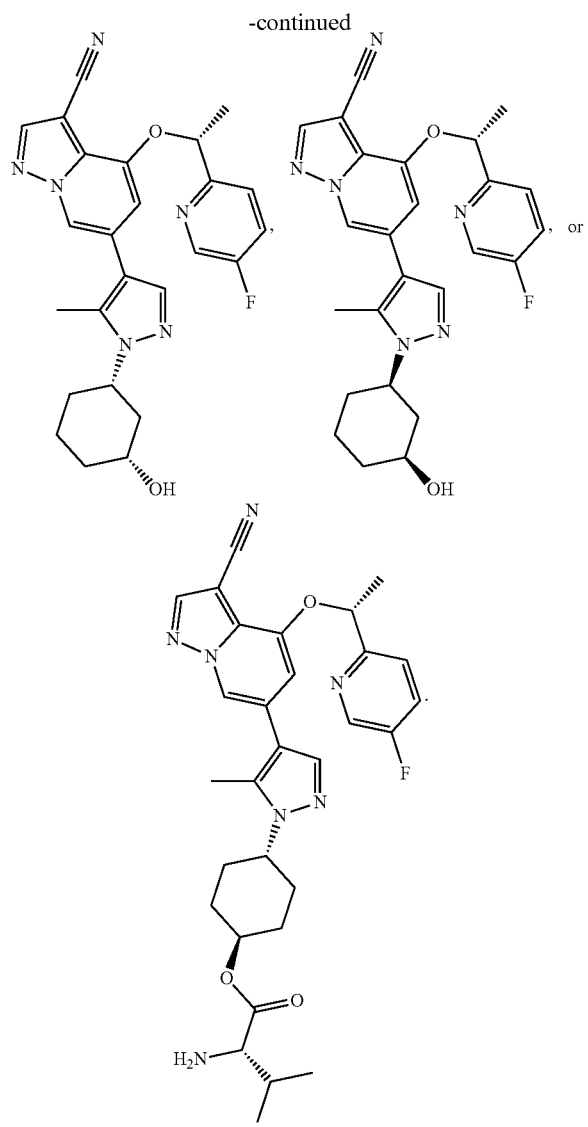

In some embodiments, the salt is a pharmaceutically acceptable salt.

In another aspect, a compound having a structure of Formula (I) is provided:

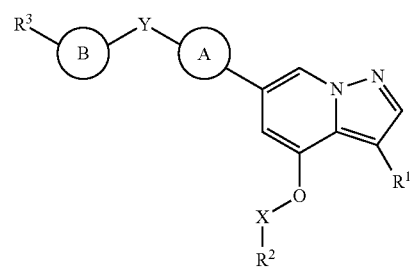

$R^1$ is —CN, —Cl, —Br, —CH$_3$, —CF$_2$H, or —CF$_3$; $R^2$ is aryl, heteroaryl, a fused bicyclic, C$_3$-C$_8$ cycloalkyl, or C$_3$-C$_8$ heterocycloalkyl; $R^3$ is —H, —OH, —F, C$_1$-C$_6$ alkyl, C$_1$-C$_6$ heteroalkyl, a 5-6 membered heteroaryl, C$_3$-C$_8$ heterocycloalkyl, —C(=O)R$^4$, —OC(=O)R$^4$, —NR$^5$R$^6$, —NR$^5$C(=O)R$^4$, —NR$^5$C(=O)OR$^4$, —CH$_2$C(=O)NR$^5$N$^6$, —NR$^5$R$^6$CH$_2$C(=O)NR$^5$N$^6$, —CH$_2$NR$^5$C(=O)R$^4$, sulfonylmethane, oxo, phosphate, or a combination thereof, provided that R$^3$ is not —CN; $R^4$ is —CH$_3$, —CH$_2$OH, —CH(CH$_3$)OH, —C(CH$_3$)$_2$OH, C$_1$-C$_6$ heteroalkyl, C$_4$-C$_6$ cycloalkyl, or C$_4$-C$_6$ heterocycloalkyl; $R^5$ and $R^6$ are, each independently, H, C$_1$-C$_6$ alkyl, C$_1$-C$_6$ alkyl alcohol, sulfonylmethane, C$_3$-C$_6$ cycloalkyl, or 5-6 membered heteroaryl; X is —(CH$_2$)$_n$—, —(CH$_2$)$_n$O—, —(CHCH$_3$)$_n$—, —(CHCH$_3$)$_n$—, —(CH$_2$)$_m$—, —(CHCH$_3$)$_n$—, —(CH$_2$)$_m$O—, —(CHCF$_3$)$_n$—, —(CHCH$_2$OH)$_n$—, —(CHCH$_2$CH$_3$)$_n$—, or a direct bond; Y is —CH$_2$—, —CHCH$_3$—, —C(CH$_3$)$_2$—, —(CH$_2$)$_p$C(=O)—, —NCH$_3$—, or a direct bond; n is an integer between 1 and 4; m is an integer between 1 and 4; p is an integer between 0 and 4; A is an aryl, a 5-6 membered heteroaryl, a halo, or a fused heterocyclic; and B is C$_3$-C$_8$ cycloalkyl, C$_3$-C$_8$ heterocycloalkyl, a fused bicyclic, a bridged bicyclic, a spirocyclic, or absent, or a stereoisomer of the compound, salt or tautomer of the compound thereof.

In one embodiment, $R^1$ is —CN, —Cl, —Br, —CF$_2$H, or —CF$_3$. In some embodiments, $R^1$ has one of the following structures:

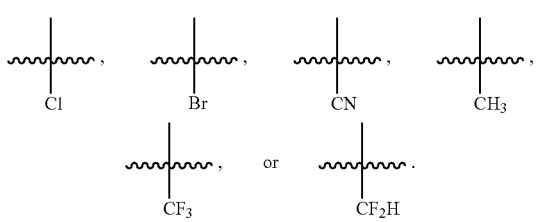

In some embodiments, $R^1$ is

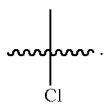

In some embodiments, $R^1$ is

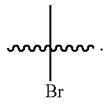

In some embodiments, $R^1$ is

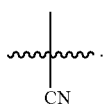

In some embodiments, $R^1$ is

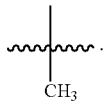

In some embodiments, $R^1$ is

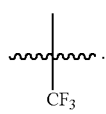

In some embodiments, $R^1$ is

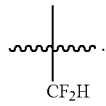

In one embodiment, the compound has the following structure of Formula (IA):

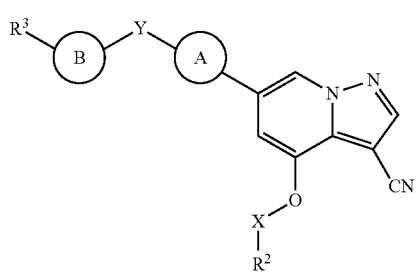

or a stereoisomer, salt or tautomer thereof.

In one embodiment, X is $-(CH_2)_n-$, $-(CH_2)_nO-$, $-(CHCH_3)_n-$, $-(CHCH_3)_n-(CH_2)_m-$, $-(CHCH_3)_n-(CH_2)_mO-$, $-(CHCF_3)_n-$, $-(CHCH_2OH)_n-$, $-(CHCH_2CH_3)_n-$, or a direct bond. In some embodiments, X is $-(CH_2)_n-$. In some embodiments, X is $-(CH_2)_nO-$. In some embodiments, X is $-(CHCH_3)_n-$. In some embodiments, X is $-(CHCH_3)_n-(CH_2)_m-$. In some embodiments, X is $-(CHCH_3)_n-(CH_2)_mO-$. In some embodiments, X is $-(CHCF_3)_n-$. In some embodiments, X is $-(CHCH_2OH)_n-$. In some embodiments, X is $-(CHCH_2CH_3)_n-$. In some embodiments, X is a direct bond.

In one embodiment, n is an integer between 1 and 4. In some embodiments, n is an integer between 1 and 2. In some embodiments, n is an integer of 1 or 2. In some embodiments, n is an integer of 1. In some embodiments, n is an integer of 2.

In one embodiment, m is an integer between 1 and 4. In some embodiments, m is an integer between 1 and 2. In some embodiments, m is an integer of 1 or 2. In some embodiments, m is an integer of 1. In some embodiments, m is an integer of 2. In some embodiments, X is $-(CHCH_3)_n-$ and n is 1. In some embodiments, X is $-(CHCF_3)_n-$ and n is 1. In some embodiments, X is $-(CHCH_2OH)_n-$ and n is 1. In some embodiments, X is $-(CHCH_2CH_3)_n-$ and n is 1.

In one embodiment, the compound has the following structure of Formula (IB):

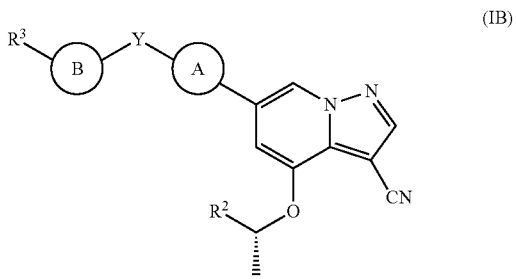

or a stereoisomer, salt or tautomer thereof.

In some embodiments, the compound has the following structure of Formula (IB-1):

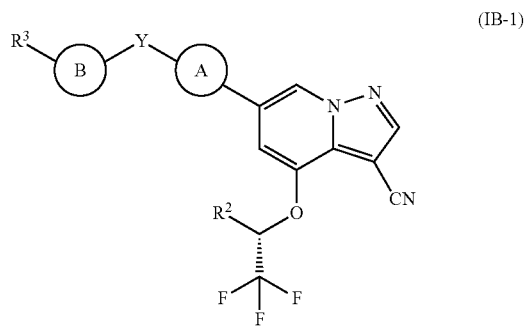

or a stereoisomer, salt or tautomer thereof.

In some embodiments, the compound has the following structure of Formula (IB-2):

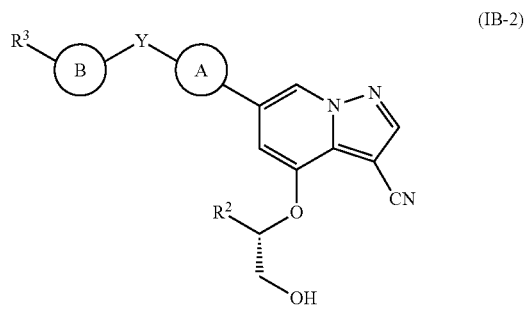

or a stereoisomer, salt or tautomer thereof.

In some embodiments, the compound has the following structure of Formula (IB-3):

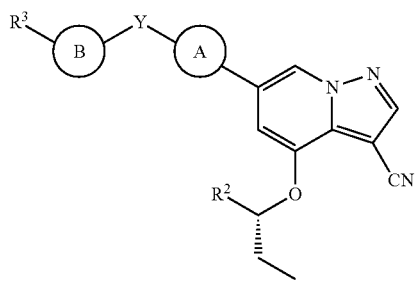

(IB-3)

or a stereoisomer, salt or tautomer thereof.

In one embodiment, A is a 5-6 membered heteroaryl. In some embodiments, the 5-6 membered heteroaryl of A is a 5 membered heteroaryl. In certain embodiments, the 5 membered heteroaryl is pyrazole or triazole. In some embodiments, the 5-6 membered heteroaryl of A is a 6 membered heteroaryl. In certain embodiments, the 6 membered heteroaryl is pyridine. In some embodiments, the 5-6 membered heteroaryl of A is optionally substituted with $C_1$-$C_4$ alkyl, $C_1$-$C_4$ heteroalkyl, or halo. In some embodiments, the 5-6 membered heteroaryl of A is optionally substituted with methyl ($C_1$ alkyl), cyano ($C_1$ heteroalkyl), methoxylethyl ($C_3$ heteroalkyl), fluoro (halo), or chloro (halo). In some certain embodiments, the 5-6 membered heteroaryl is 5-methylpyrazole.

In one embodiment, A has one of the following structures:

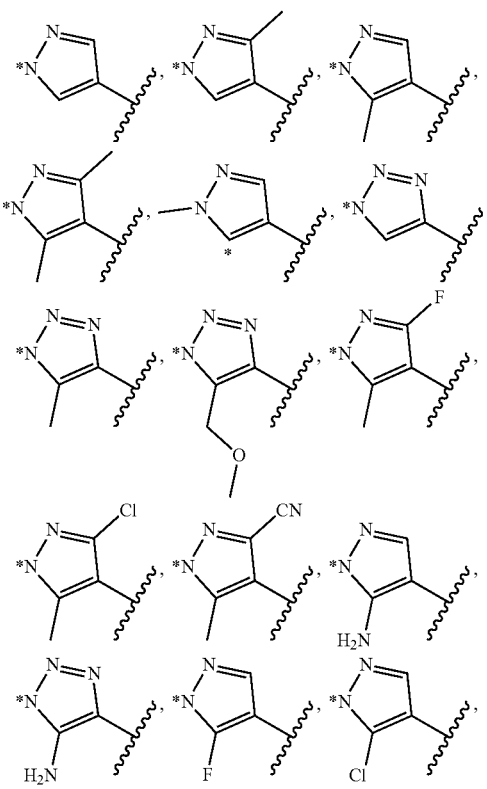

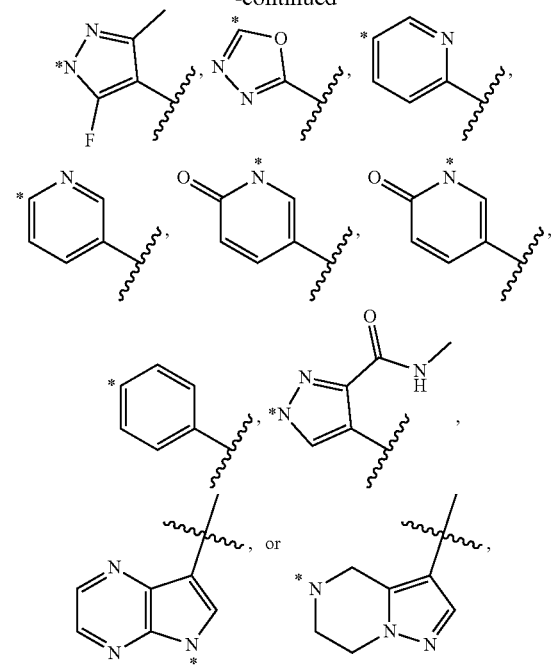

wherein * indicates a location of a bond to Y. In some embodiments, A is

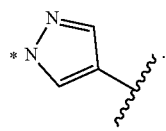 [SMILES: *c1cn[nH]c1]

In some embodiments, A is

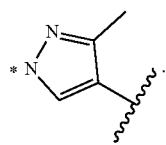 [SMILES: *c1c[nH]nc1C]

In some embodiments, A is

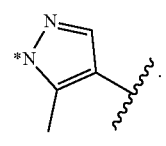

In some embodiments, A is

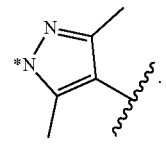

In some embodiments, A is
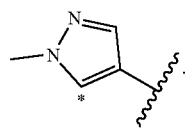 [SMILES: *c1cnn(C)c1]
In some embodiments, A is
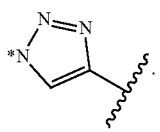
In some embodiments, A is
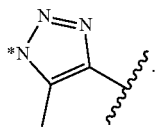
In some embodiments, A is
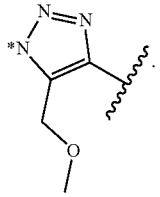
In some embodiments, A is
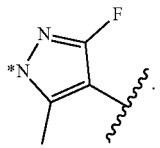
In some embodiments, A is
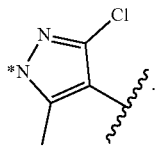
In some embodiments, A is
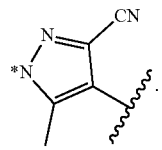
In some embodiments, A is
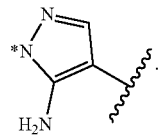
In some embodiments, A is
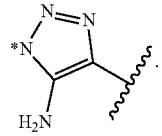
In some embodiments, A is
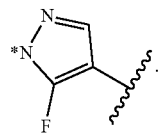
In some embodiments, A is
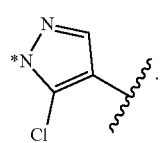
In some embodiments, A is
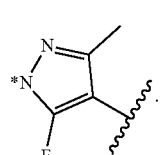
In some embodiments, A is
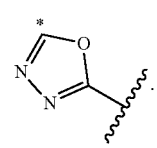

In some embodiments, A is

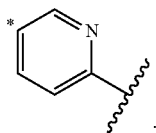

In some embodiments, A is

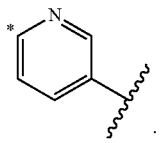

In some embodiments, A is

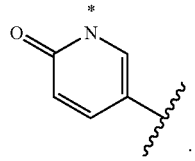 [SMILES: *c1ccc(=O)[nH]c1]

In some embodiments, A is

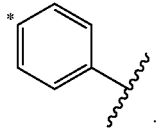

In some embodiments, A is

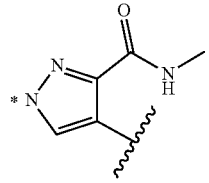

In some embodiments, A is

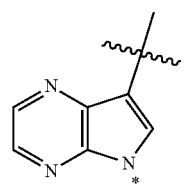

In some embodiments, A is

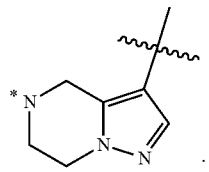 [SMILES: *c1cnn2c1CNCC2]

In some embodiments, A has one of the following structures:

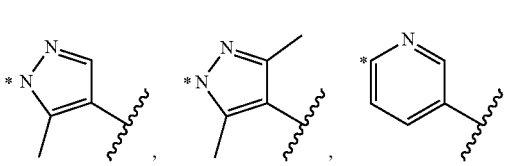

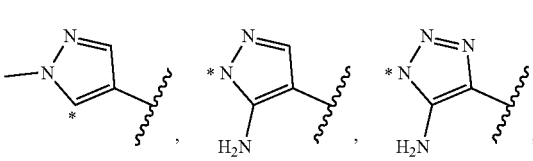

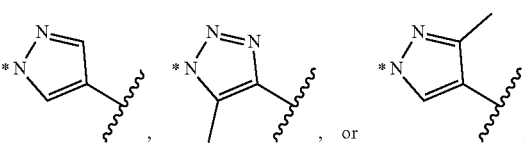

wherein * indicates a location of a bond to Y.

In one embodiment. A is a 5-6 membered heteroaryl and the compound has one of the following structures of Formula (IC-a)-(II-a):

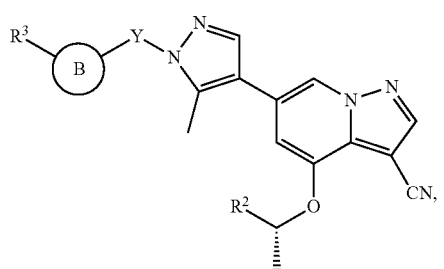

(IC-a)

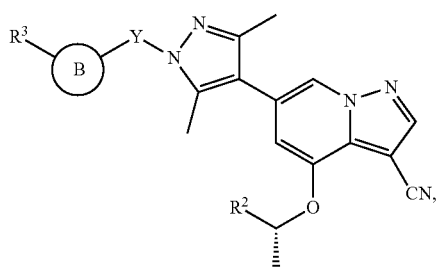

(ID-a)

-continued
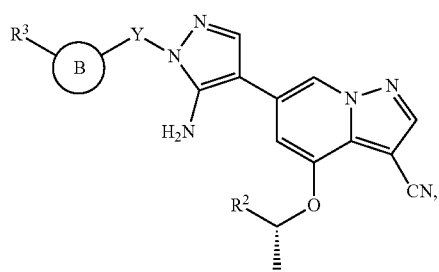
(IE-a)
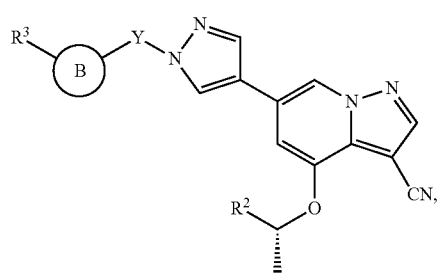
(IF-a)
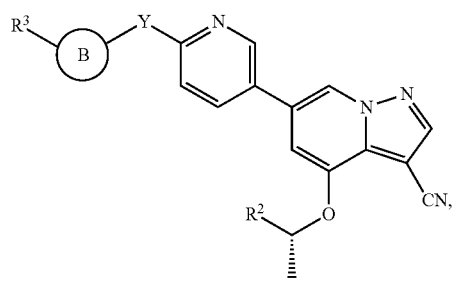
(IG-a)
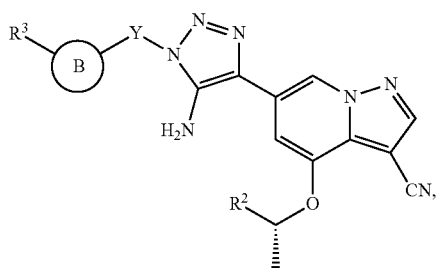
(IH-a)
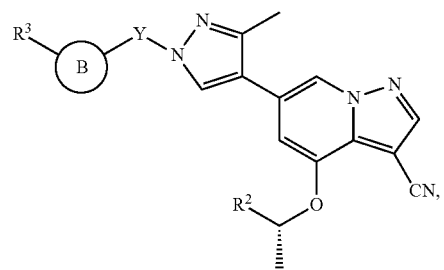
(II-a)
or a stereoisomer, salt or tautomer thereof. In some embodiments, the compound has the structure of Formula (IC-a):
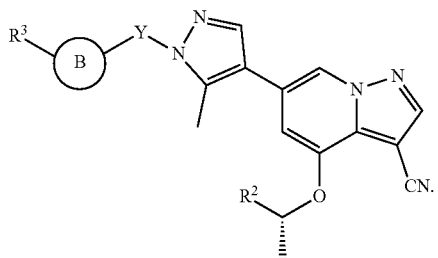
In some embodiments, the compound has the structure of Formula (ID-a):
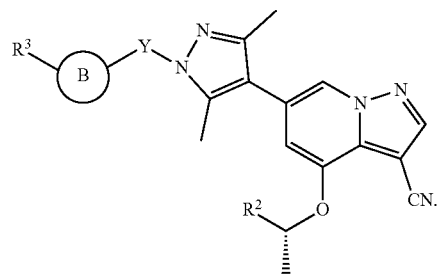
In some embodiments, the compound has the structure of Formula (IE-a):
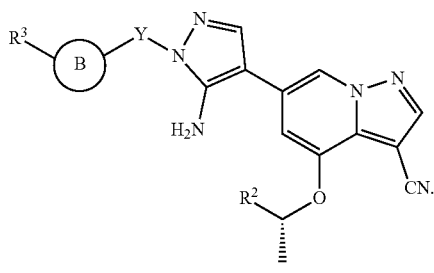
In some embodiments, the compound has the structure of Formula (IF-a):
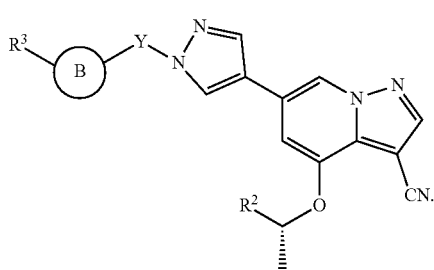

In some embodiments, the compound has the structure of Formula (IG-a):

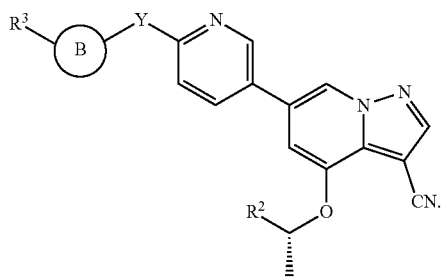

In some embodiments, the compound has the structure of Formula (IH-a):

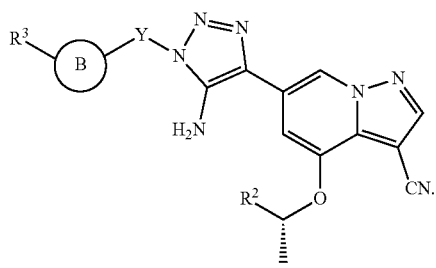

In some embodiments, the compound has the structure of Formula (II-a):

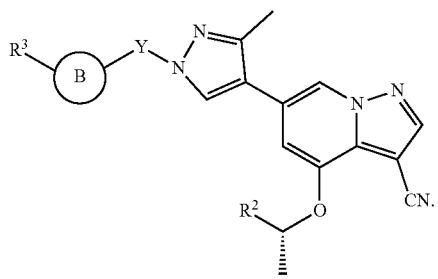

In one embodiment, Y is —CH₂—, —CHCH₃—, —C(CH₃)₂—, or a direct bond. In some embodiments, Y is —CH₂—. In some embodiments, Y is —CHCH₃—. In some embodiments, Y is C(CH₃)₂. In some embodiments, Y is —(CH₂)ₚC(═O)—, wherein p is an integer between 0 and 2. In some embodiments, the compound of any one of claims 1-26, wherein Y is —NCH₃—. In some embodiments, Y is a direct bond.

In one embodiment, Y is a direct bond and the compound has one of the following structures of Formula (IC-b)-(II-b):

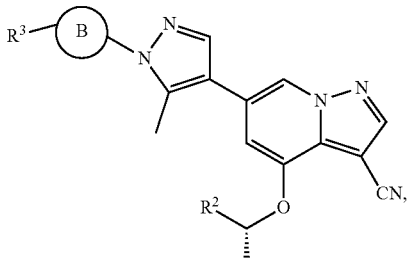

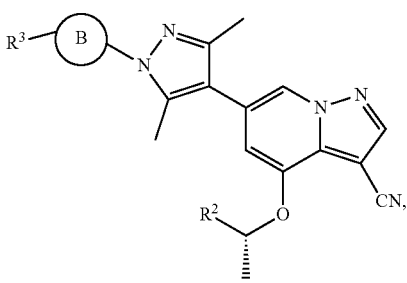

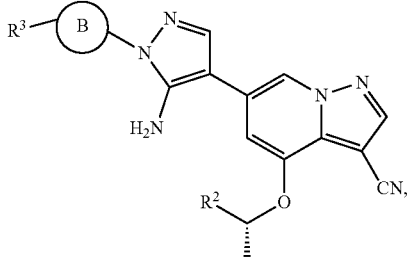

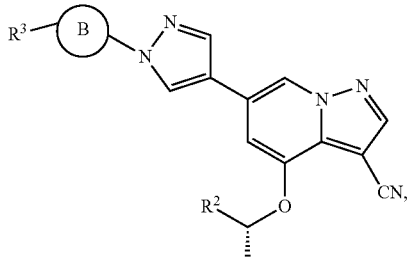

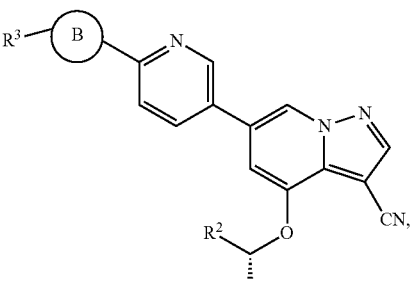

-continued (IH-b)

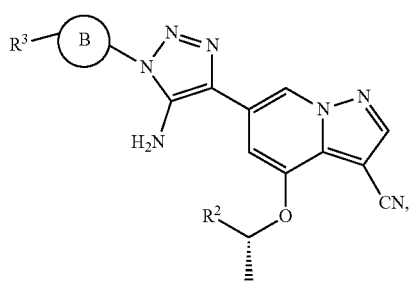

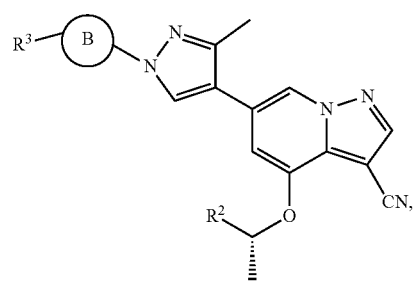

(II-b)

or a stereoisomer, salt or tautomer thereof. In some embodiments, the compound has the structure of Formula (IC-b):

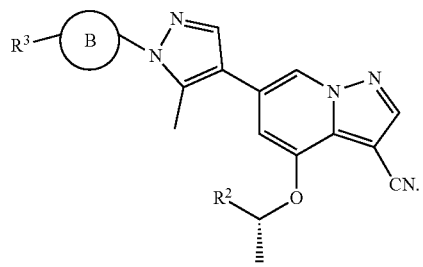

In some embodiments, the compound has the structure of Formula (ID-b):

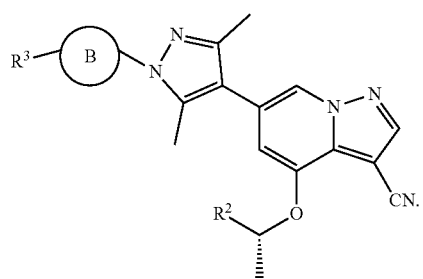

In some embodiments, the compound has the structure of Formula (IE-b):

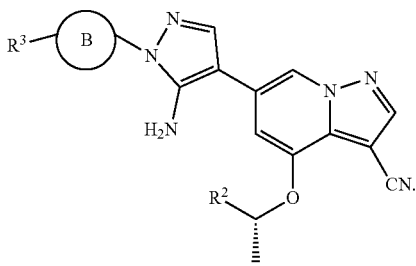

In some embodiments, the compound has the structure of Formula (IF-b):

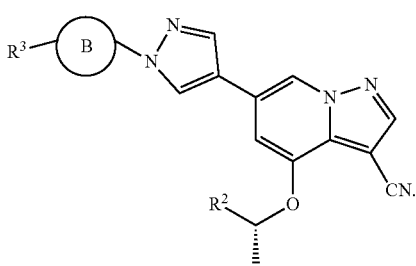

In some embodiments, the compound has the structure of Formula (IG-b):

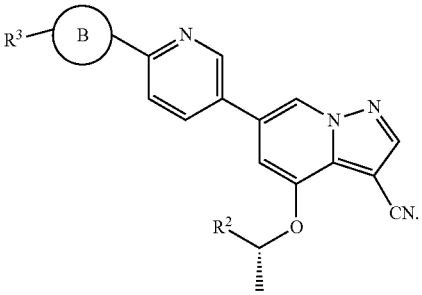

In some embodiments, the compound has the structure of Formula (IH-b):

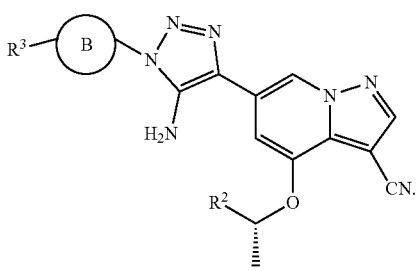

In some embodiments, the compound has the structure of Formula (II-b):

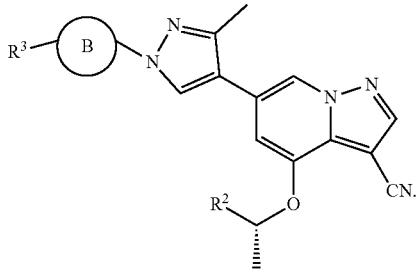
(II-b)

In one embodiment, Y is a direct bond and B is C₃-C₈ cycloalkyl, C₃-C₈ heterocycloalkyl, or absent. In some certain embodiments, the compound has one of the following structures of Formula (III-a)-(III-h):

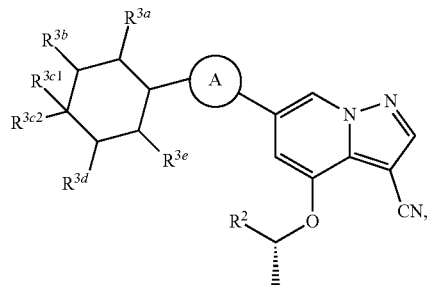
(III-a)

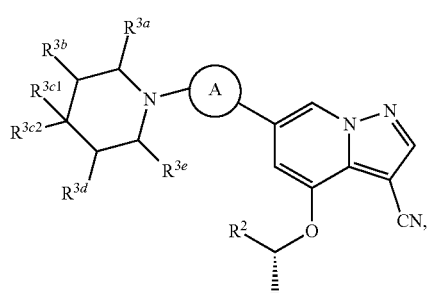
(III-b)

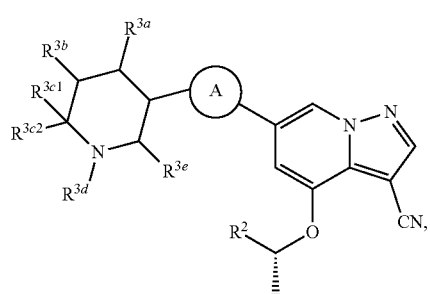
(III-c)

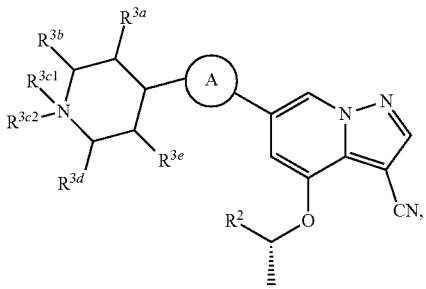
(III-d)

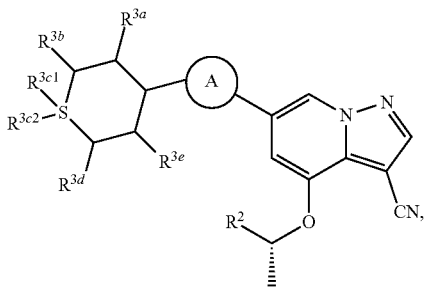
(III-e)

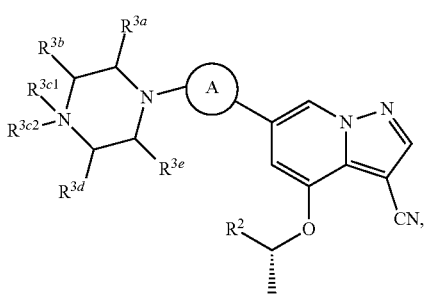
(III-f)

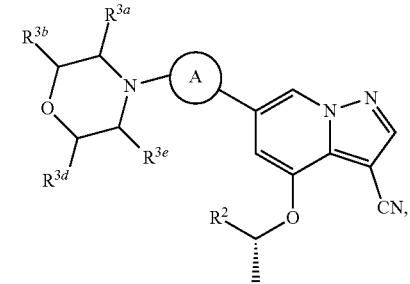
(III-g)

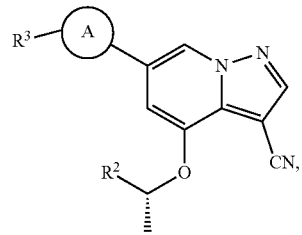
(III-h)

or a stereoisomer of the compound, salt or tautomer of the compound thereof, wherein $R^3$, $R^{3a}$, $R^{3b}$, $R^{3c1}$, $R^{3c2}$, $R^{3d}$, and $R^{3e}$ are, each independently, —H, —OH, —F, $C_1$-$C_6$ alkyl, $C_1$-$C_6$ heteroalkyl, a 5-6 membered heteroaryl, $C_3$-$C_8$ heterocycloalkyl, —C(=O)R⁴, —OC(=O)R⁴, —NR⁵R⁶, —NR⁵C(=O)R⁴, —NR⁵C(=O)OR⁴, —CH₂C(=O)NR⁵N⁶, —NR⁵R⁶CH₂C(=O)NR⁵N⁶, —CH₂NR⁵C(=O)R⁴, sulfonylmethane, oxo, or phosphate. $R^3$, $R^{3a}$, $R^{3b}$, $R^{3c1}$, $R^{3c2}$, $R^{3d}$, or $R^{3e}$ of Formula (III-a)-(III-h) is not —CN. In some embodiments, the compound has the structure of Formula (III-a):

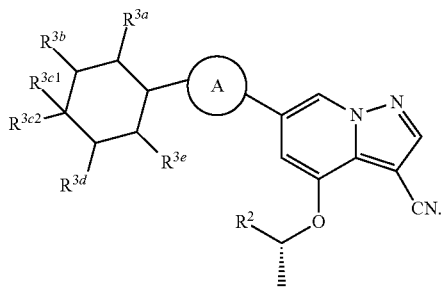

In some embodiments, the compound has the structure of Formula (III-b):

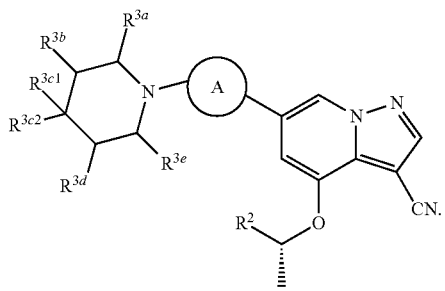

In some embodiments, the compound has the structure of Formula (III-c):

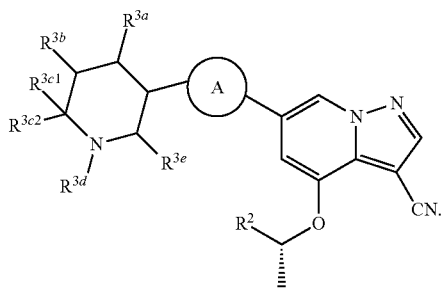

In some embodiments, the compound has the structure of Formula (III-d):

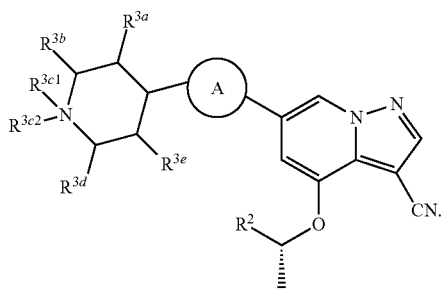

In some embodiments, the compound has the structure of Formula (III-e):

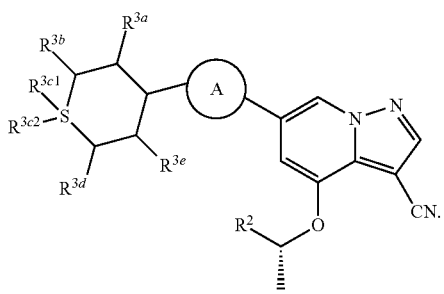

In some embodiments, the compound has the structure of Formula (III-f):

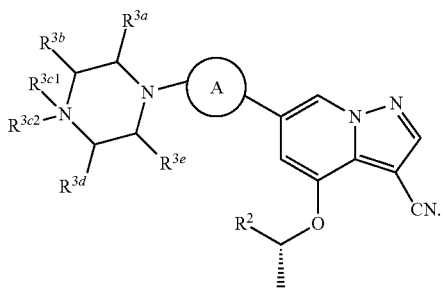

In some embodiments, the compound has the structure of Formula (III-g):

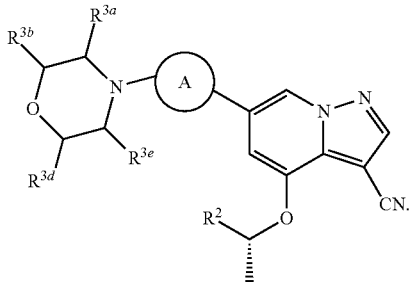

In some embodiments, the compound has the structure of Formula (III-h):

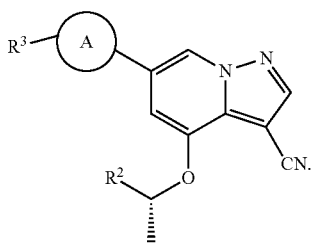

In one embodiment, $R^2$ is $C_1$-$C_6$ alkyl, $C_1$-$C_6$ heteroalkyl, aryl, heteroaryl, a fused bicyclic, $C_3$-$C_8$ cycloalkyl, $C_3$-$C_8$ heterocycloalkyl, or —$NR^3R^4$. In some embodiments, the aryl, heteroaryl, or fused bicyclic of $R^2$ is further substituted with fluoro, chloro, cyano, methyl, amine, —$CF_2H$, —$CF_3$, $C_1$-$C_3$ alkylalcohol, $C_1$-$C_3$ alkoxyl, or a combination thereof. In some embodiments, the aryl, heteroaryl, or fused bicyclic of $R^2$ is mono-, di-, or tri-substituted with fluoro, chloro, cyano, methyl, amine, —$CF_2H$, —$CF_3$, $C_1$-$C_3$ alkylalcohol, $C_1$-$C_3$ alkoxyl, or a combination thereof. In some embodiments, for example, the aryl, heteroaryl, or fused bicyclic of $R^2$ is substituted with two fluoro substituents. In some embodiments, for example, the aryl, heteroaryl, or fused bicyclic of $R^2$ is substituted with two fluoro substituents and one methyl substituent. In some embodiments, for example, the aryl, heteroaryl, or fused bicyclic of $R^2$ is substituted with one fluoro substituent and one cyano substituent. In some embodiments, for example, the aryl, heteroaryl, or fused bicyclic of $R^2$ is substituted with one methyl, one cyano, and one fluoro substituents. In some embodiments, for example, the aryl, heteroaryl, or fused bicyclic of $R^2$ is substituted with one fluoro substituent and one methyl substituent. In some embodiments, for example, the aryl, heteroaryl, or fused bicyclic of $R^2$ is substituted with one chloro substituent and one cyano substituent. In some embodiments, for example, the aryl, heteroaryl, or fused bicyclic of $R^2$ is substituted with two methyl substituents. In some embodiments, for example, the aryl, heteroaryl, or fused bicyclic of $R^2$ is substituted with one fluoro substituent and one amino substituent. In some embodiments, for example, the aryl, heteroaryl, or fused bicyclic of $R^2$ is substituted with one fluoro substituent and one deuterium substituent. In some embodiments, for example, the aryl, heteroaryl, or fused bicyclic of $R^2$ is substituted with one fluoro substituent and one methoxy substituent. In some embodiments, for example, the aryl, heteroaryl, or fused bicyclic of $R^2$ is substituted with two fluoro substituents and one methoxy substituent. In some embodiments, for example, the aryl, heteroaryl, or fused bicyclic of $R^2$ is substituted with one fluoro, one chloro, and one methyl substituent. In some embodiments, for example, the aryl, heteroaryl, or fused bicyclic of $R^2$ is substituted with two methyl and one fluoro substituents. In some embodiments, for example, the aryl, heteroaryl, or fused bicyclic of $R^2$ is substituted with one fluoro, one methoxyl, and one methyl substituent. In some embodiments, for example, the aryl, heteroaryl, or fused bicyclic of $R^2$ is substituted with one cyano substituent and one methoxy substituent. In some embodiments, for example, the aryl, heteroaryl, or fused bicyclic of $R^2$ is substituted with one cyano, one methoxyl, and one methyl substituents.

In one embodiment, the fused bicyclic of $R^2$ has one of the following structures:

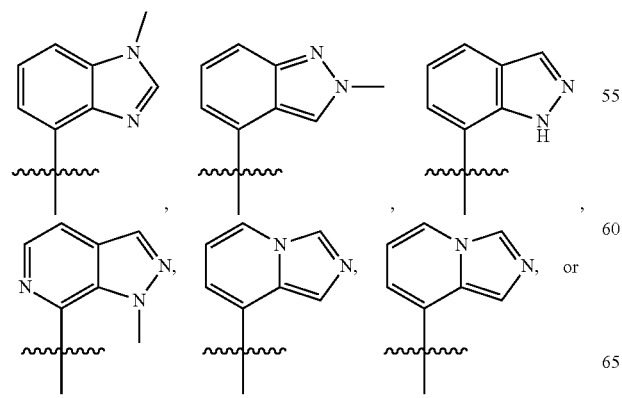

In some embodiments, the fused bicyclic of $R^2$ has one of the following structures:

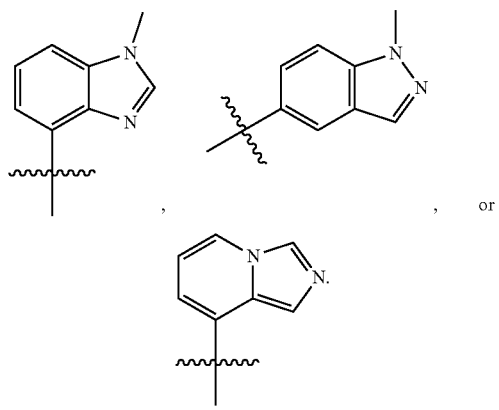

In some embodiments, the fused bicyclic of $R^2$ is

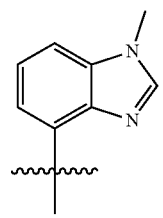

In some embodiments, the fused bicyclic of $R^2$ is

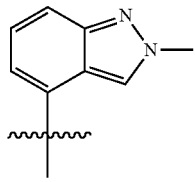

In some embodiments, the fused bicyclic of $R^2$ is

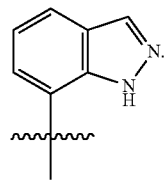 [SMILES: *c1cccc2cn[nH]c12]

In some embodiments, the fused bicyclic of R² is
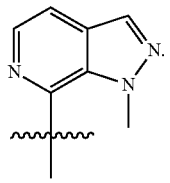
In some embodiments, the fused bicyclic of R² is
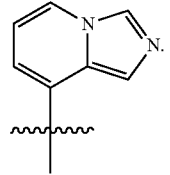 [SMILES: *c1cccn2cncc12]
In some embodiments, the fused bicyclic of R² is
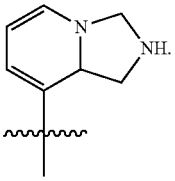 [SMILES: *C1=CC=CN2CNCC12]
In some embodiments, the fused bicyclic of R² is
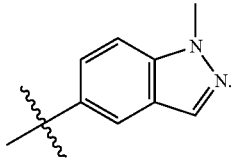 [SMILES: *c1ccc2c(cnn2C)c1]
In one embodiment, the aryl of R² has one of the following structures:
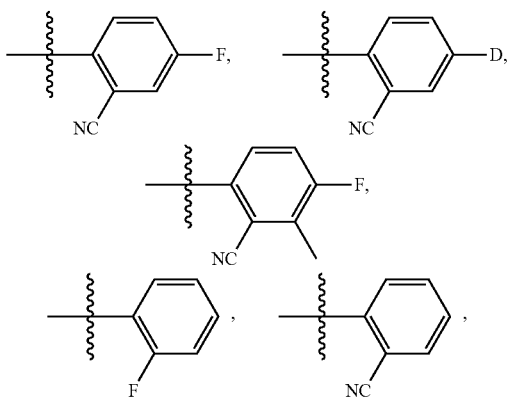
-continued
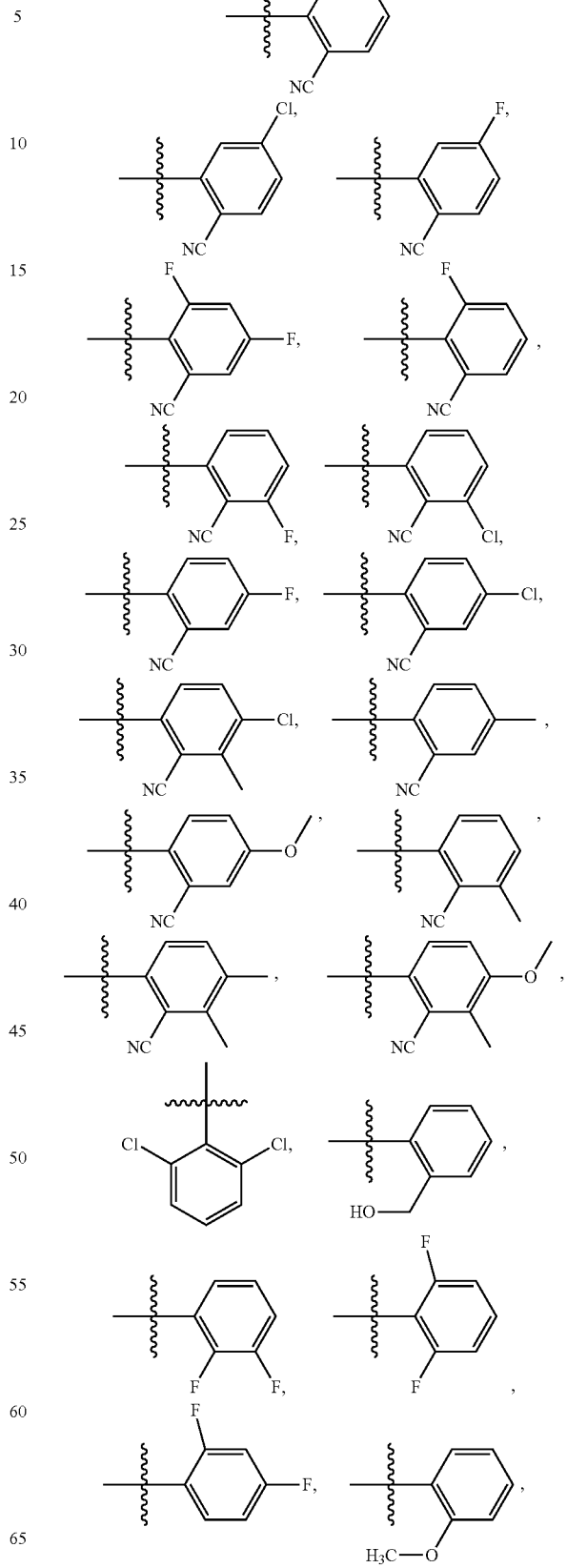

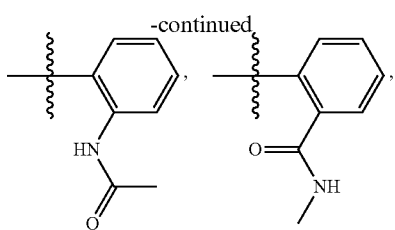

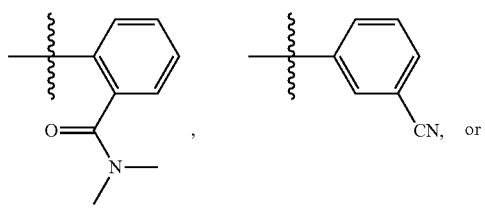

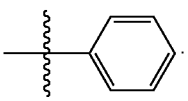

In some embodiments, the aryl of $R^2$ is

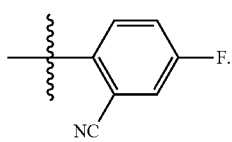

In some embodiments, the aryl of $R^2$ is

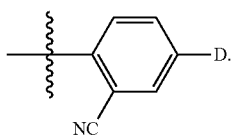

In some embodiments, the aryl of $R^2$ is

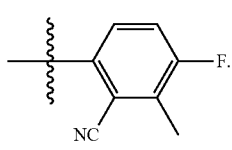 [SMILES: *c1ccc(F)c(C)c1C#N]

In some embodiments, the aryl of $R^2$ is

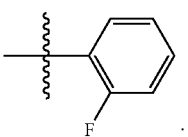 [SMILES: *c1ccccc1F]

In some embodiments, the aryl of $R^2$ is

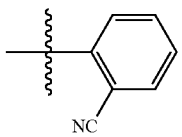

In some embodiments, the aryl of $R^2$ is

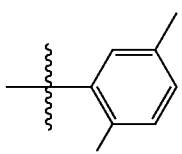

In some embodiments, the aryl of $R^2$ is

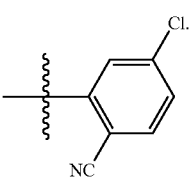

In some embodiments, the aryl of $R^2$ is

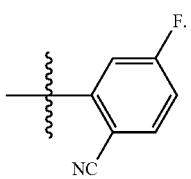 [SMILES: *c1cc(F)ccc1C#N]

In some embodiments, the aryl of $R^2$ is

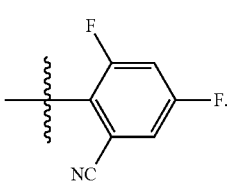 [SMILES: *c1c(F)cc(F)cc1C#N]

In some embodiments, the aryl of $R^2$ is

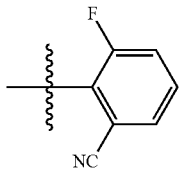

In some embodiments, the aryl of R² is

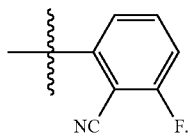

In some embodiments, the aryl of R² is

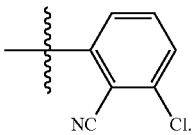 [SMILES: *c1cccc(Cl)c1C#N]

In some embodiments, the aryl of R² is

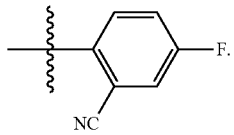

In some embodiments, the aryl of R² is

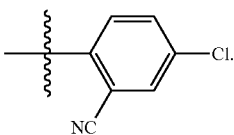 [SMILES: *c1ccc(Cl)cc1C#N]

In some embodiments, the aryl of R² is

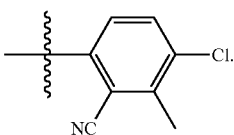 [SMILES: *c1ccc(Cl)c(C)c1C#N]

In some embodiments, the aryl of R² is

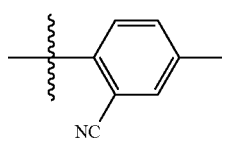

In some embodiments, the aryl of R² is

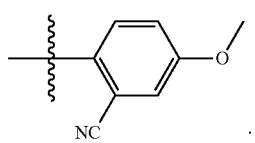 [SMILES: *c1ccc(OC)cc1C#N]

In some embodiments, the aryl of R² is

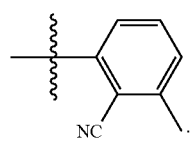 [SMILES: *c1cccc(C)c1C#N]

In some embodiments, the aryl of R² is

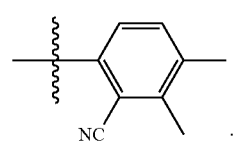 [SMILES: *c1ccc(C)c(C)c1C#N]

In some embodiments, the aryl of R² is

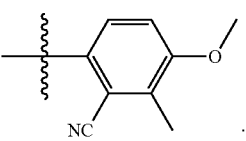

In some embodiments, the aryl of R² is

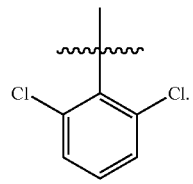

In some embodiments, the aryl of R² is

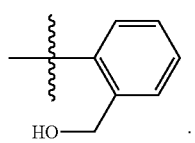 [SMILES: *c1ccccc1CO]

In some embodiments, the aryl of R² is

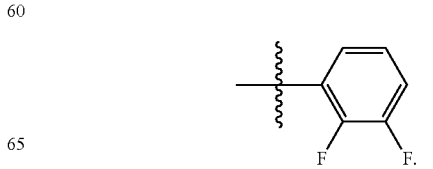

In some embodiments, the aryl of R² is

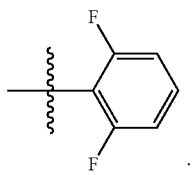 [SMILES: *c1c(F)cccc1F]

In some embodiments, the aryl of R² is

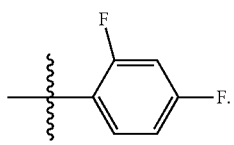 [SMILES: *c1ccc(F)cc1F]

In some embodiments, the aryl of R² is

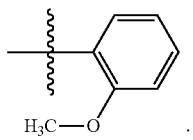

In some embodiments, the aryl of R² is

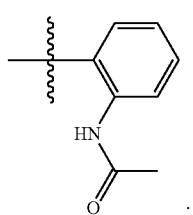 [SMILES: *c1ccccc1NC(C)=O]

In some embodiments, the aryl of R² is

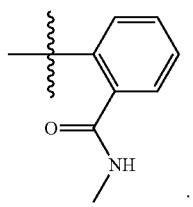 [SMILES: *c1ccccc1C(=O)NC]

In some embodiments, the aryl of R² is

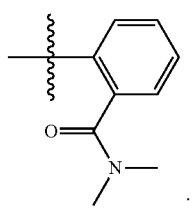 [SMILES: *c1ccccc1C(=O)N(C)C]

In some embodiments, the aryl of R² is

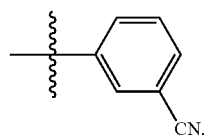

In some embodiments, the aryl of R² is

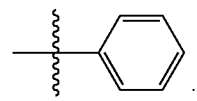

In one embodiment, the heteroaryl of R² has one of the following structures:

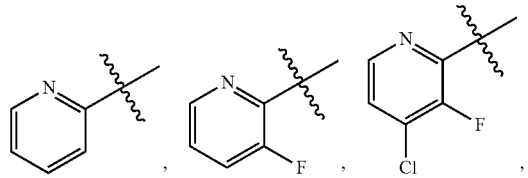

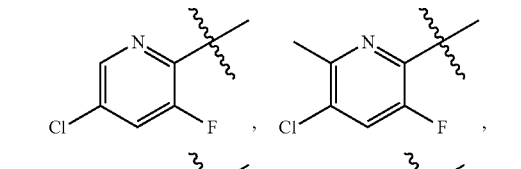

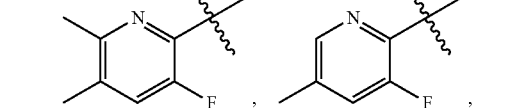

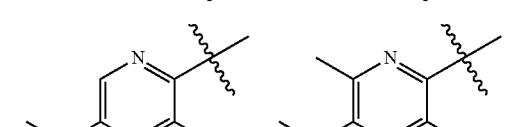

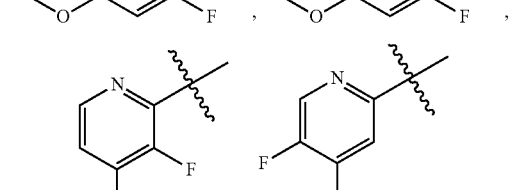

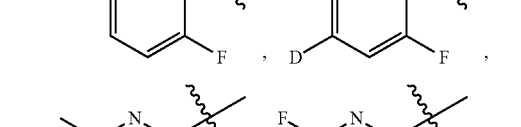

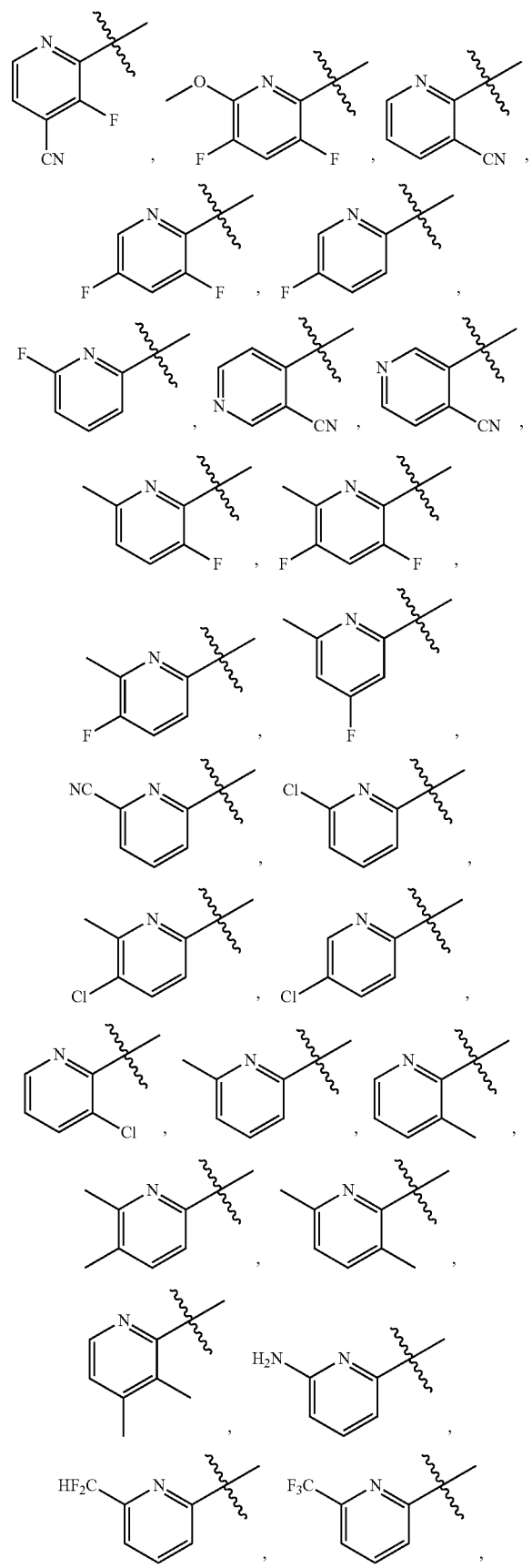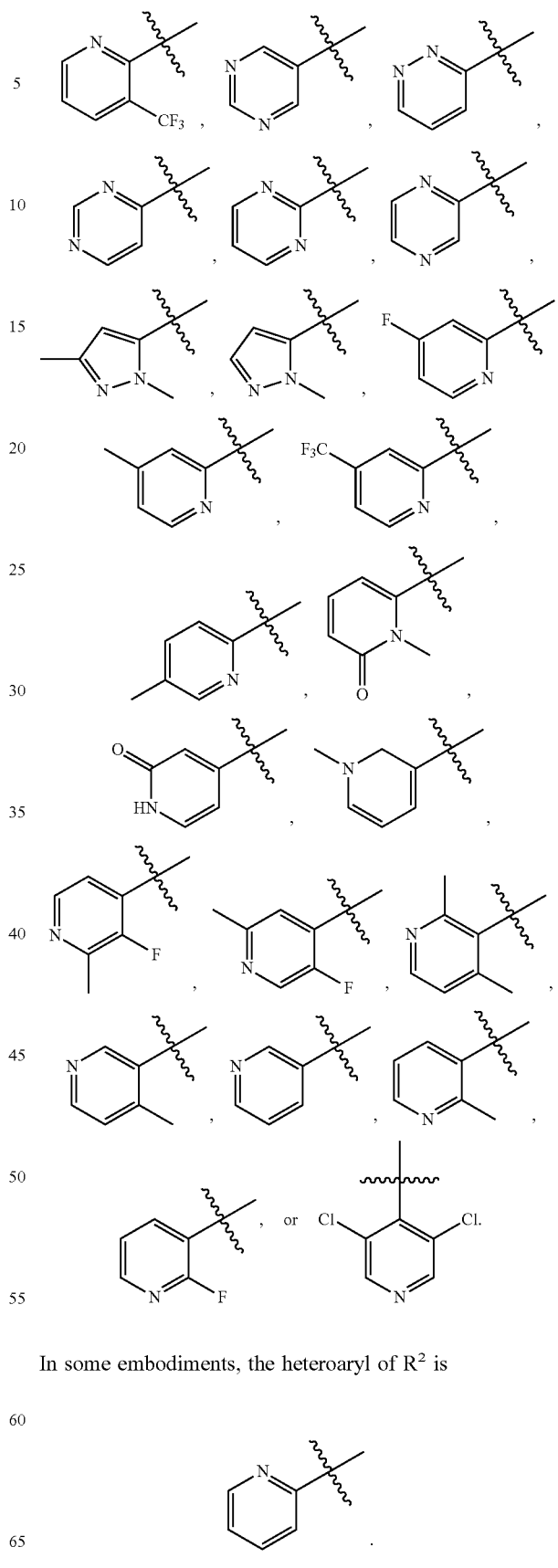
In some embodiments, the heteroaryl of $R^2$ is
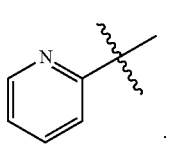 [SMILES: *c1ccccn1]

In some embodiments, the heteroaryl of R² is

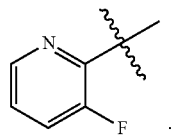 [SMILES: *c1ncccc1F]

In some embodiments, the heteroaryl of R² is

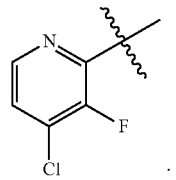 [SMILES: *c1nccc(Cl)c1F]

In some embodiments, the heteroaryl of R² is

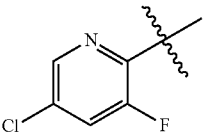

In some embodiments, the heteroaryl of R² is

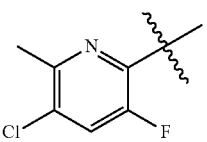

In some embodiments, the heteroaryl of R² is

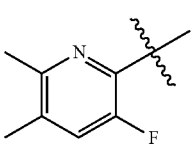

In some embodiments, the heteroaryl of R² is

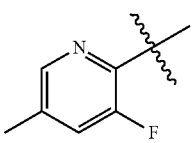

In some embodiments, the heteroaryl of R² is

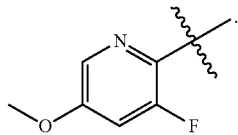 [SMILES: *c1ncc(OC)cc1F]

In some embodiments, the heteroaryl of R² is

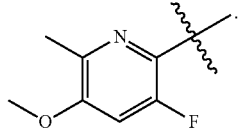 [SMILES: *c1nc(C)c(OC)cc1F]

In some embodiments, the heteroaryl of R² is

In some embodiments, the heteroaryl of R² is

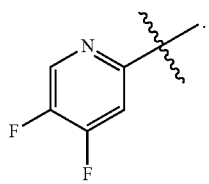 [SMILES: *c1cc(F)c(F)cn1]

In some embodiments, the heteroaryl of R² is

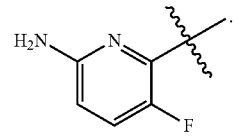 [SMILES: *c1nc(N)ccc1F]

In some embodiments, the heteroaryl of R² is

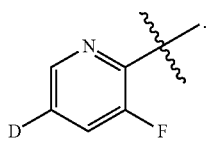

In some embodiments, the heteroaryl of R² is

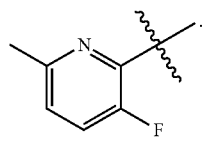 [SMILES: *c1nc(C)ccc1F]

In some embodiments, the heteroaryl of R² is

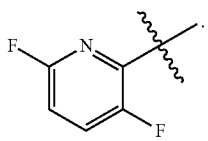 [SMILES: *c1nc(F)ccc1F]

In some embodiments, the heteroaryl of R² is

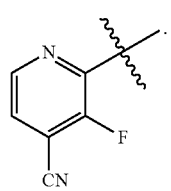 [SMILES: *c1nccc(C#N)c1F]

In some embodiments, the heteroaryl of R² is

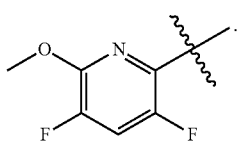 [SMILES: *c1nc(OC)c(F)cc1F]

In some embodiments, the heteroaryl of R² is

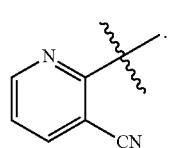 [SMILES: *c1ncccc1C#N]

In some embodiments, the heteroaryl of R² is

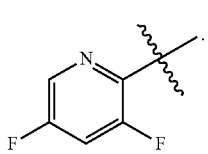 [SMILES: *c1ncc(F)cc1F]

In some embodiments, the heteroaryl of R² is

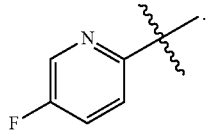

In some embodiments, the heteroaryl of R² is

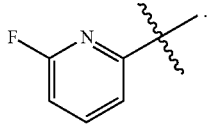

In some embodiments, the heteroaryl of R² is

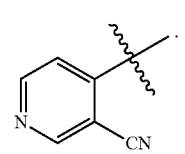 [SMILES: *c1ccncc1C#N]

In some embodiments, the heteroaryl of R² is

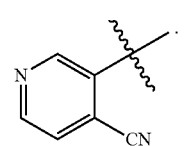

In some embodiments, the heteroaryl of R² is

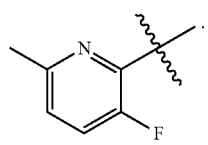 [SMILES: *c1nc(C)ccc1F]

In some embodiments, the heteroaryl of R² is

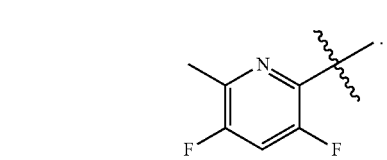

In some embodiments, the heteroaryl of R² is

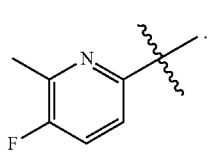

In some embodiments, the heteroaryl of R² is

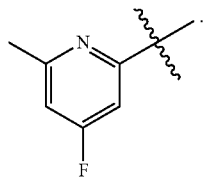 [SMILES: *c1cc(F)cc(C)n1]

In some embodiments, the heteroaryl of R² is

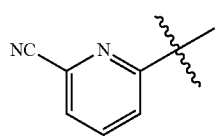

In some embodiments, the heteroaryl of R² is

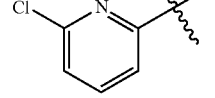

In some embodiments, the heteroaryl of R² is

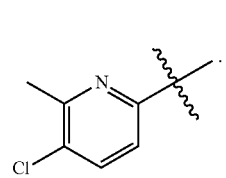 [SMILES: *c1ccc(Cl)c(C)n1]

In some embodiments, the heteroaryl of R² is

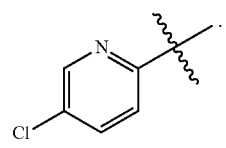 [SMILES: *c1ccc(Cl)cn1]

In some embodiments, the heteroaryl of R² is

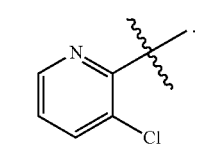 [SMILES: *c1ncccc1Cl]

In some embodiments, the heteroaryl of R² is

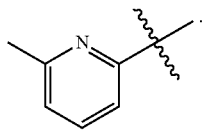 [SMILES: *c1cccc(C)n1]

In some embodiments, the heteroaryl of R² is

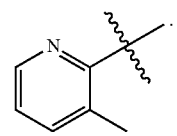 [SMILES: *c1ncccc1C]

In some embodiments, the heteroaryl of R² is

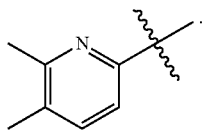 [SMILES: *c1ccc(C)c(C)n1]

In some embodiments, the heteroaryl of R² is

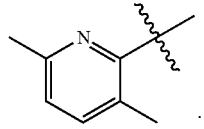 [SMILES: *c1nc(C)ccc1C]

In some embodiments, the heteroaryl of R² is

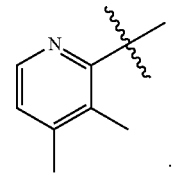 [SMILES: *c1nccc(C)c1C]

In some embodiments, the heteroaryl of R² is

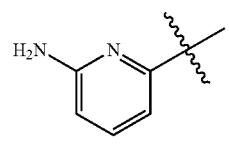

In some embodiments, the heteroaryl of R² is

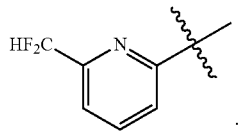

In some embodiments, the heteroaryl of R² is

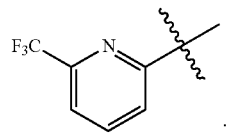

In some embodiments, the heteroaryl of R² is

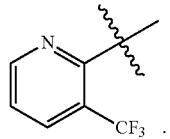

In some embodiments, the heteroaryl of R² is

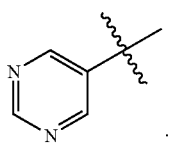 [SMILES: *c1cncnc1]

In some embodiments, the heteroaryl of R² is

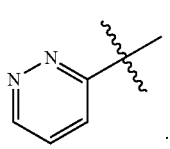

In some embodiments, the heteroaryl of R² is

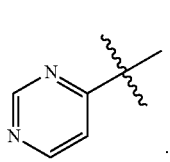 [SMILES: *c1ccncn1]

In some embodiments, the heteroaryl of R² is

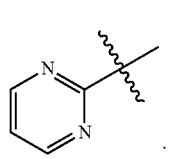 [SMILES: *c1ncccn1]

In some embodiments, the heteroaryl of R² is

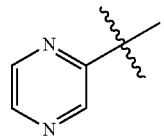

In some embodiments, the heteroaryl of R² is

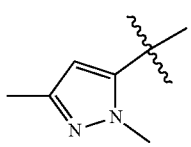

In some embodiments, the heteroaryl of R² is

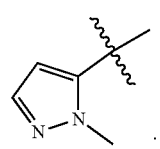 [SMILES: *c1ccnn1C]

In some embodiments, the heteroaryl of R² is

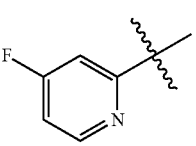

In some embodiments, the heteroaryl of R² is

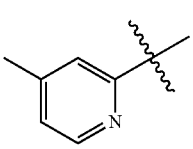

In some embodiments, the heteroaryl of R² is

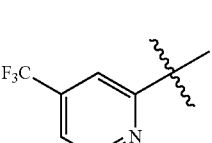

In some embodiments, the heteroaryl of R² is

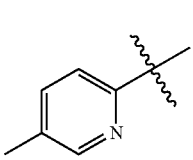

In some embodiments, the heteroaryl of $R^2$ is

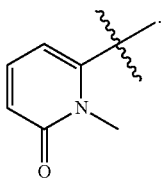 [SMILES: *c1cccc(=O)n1C]

In some embodiments, the heteroaryl of $R^2$ is

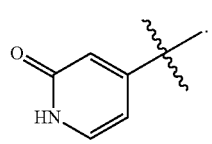

In some embodiments, the heteroaryl of $R^2$ is

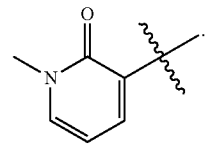 [SMILES: *c1cccn(C)c1=O]

In some embodiments, the heteroaryl of $R^2$ is

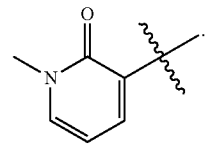 [SMILES: *c1cccn(C)c1=O]

In some embodiments, the heteroaryl of $R^2$ is

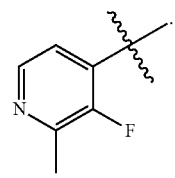

In some embodiments, the heteroaryl of $R^2$ is

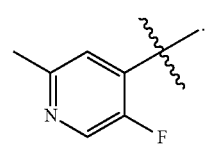 [SMILES: *c1cc(C)ncc1F]

In some embodiments, the heteroaryl of $R^2$ is

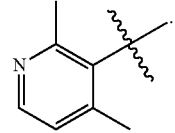 [SMILES: *c1c(C)ccnc1C]

In some embodiments, the heteroaryl of $R^2$ is

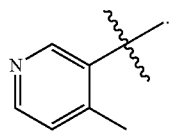

In some embodiments, the heteroaryl of $R^2$ is

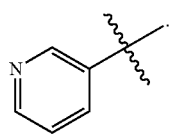

In some embodiments, the heteroaryl of $R^2$ is

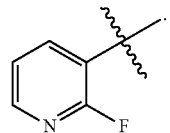 [SMILES: *c1cccnc1F]

In some embodiments, the heteroaryl of $R^2$ is

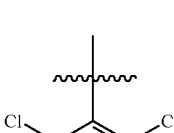

In some embodiments, the heteroaryl of $R^2$ is

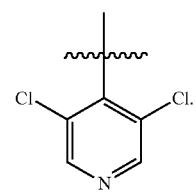

In one embodiment, the $C_3$-$C_8$ cycloalkyl or $C_3$-$C_8$ heterocycloalkyl of $R^2$ has one of the following structures:

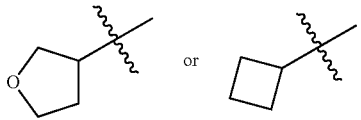

In some embodiments, the $C_3$-$C_8$ cycloalkyl or $C_3$-$C_8$ heterocycloalkyl of $R^2$ is
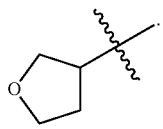 [SMILES: *C1CCOC1]
In some embodiments, the $C_3$-$C_8$ cycloalkyl or $C_3$-$C_8$ heterocycloalkyl of $R^2$ is
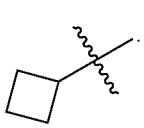 [SMILES: *C1CCC1]
In one embodiment, $R^2$ has one of the following structures:
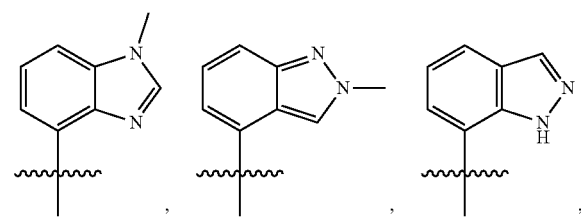
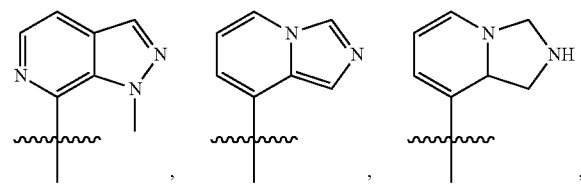
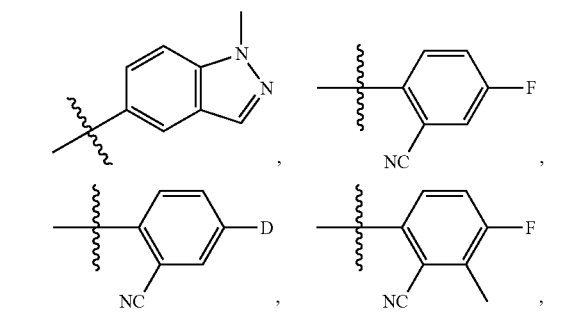
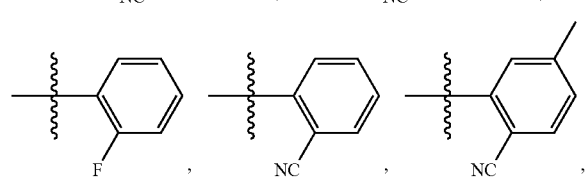
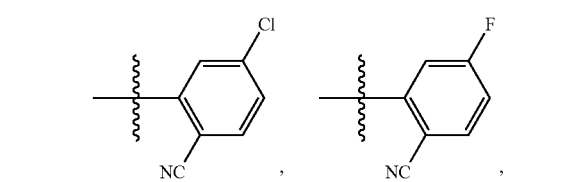
-continued
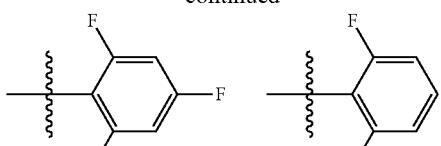
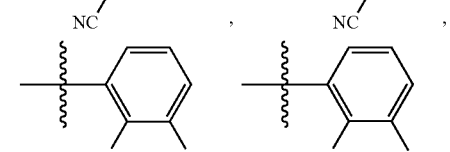
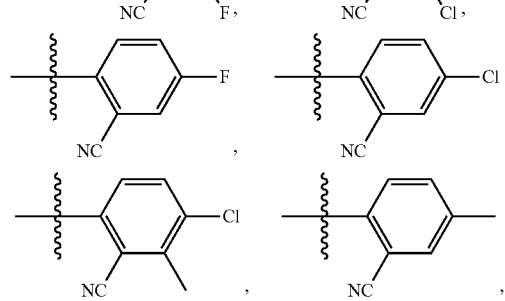
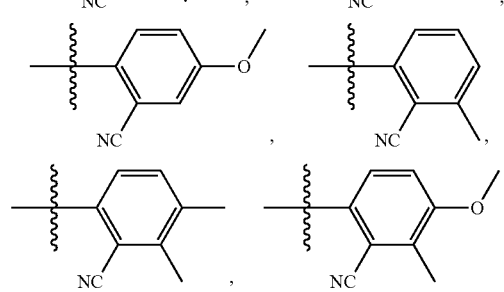
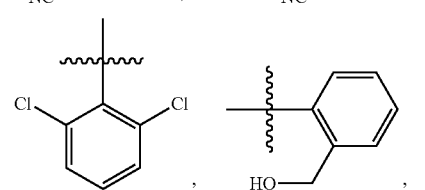
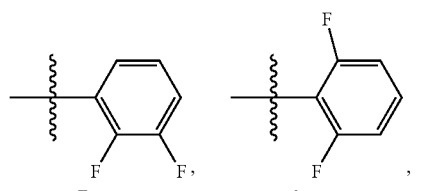
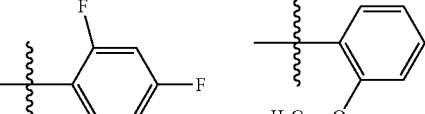
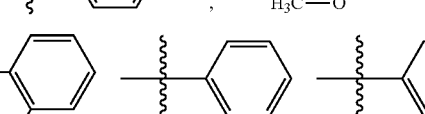
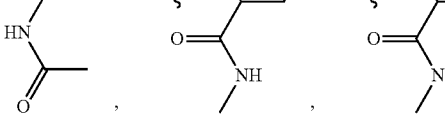
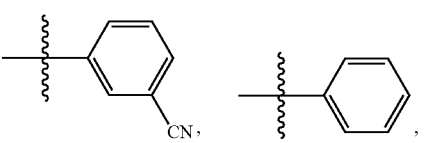

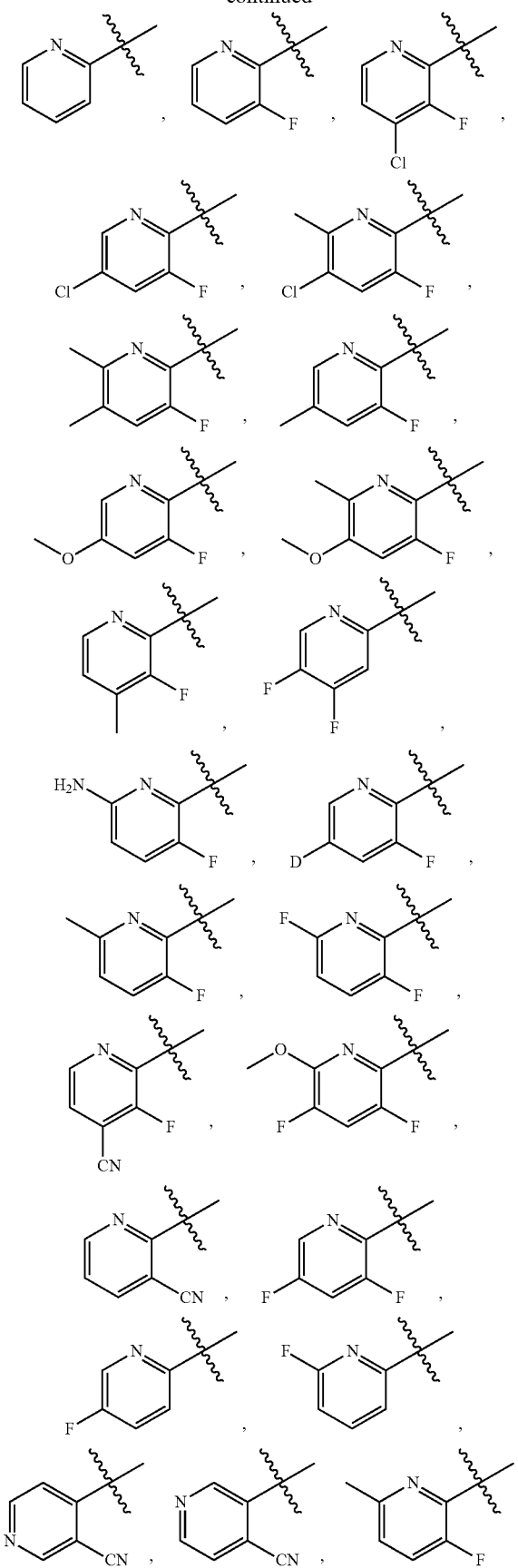
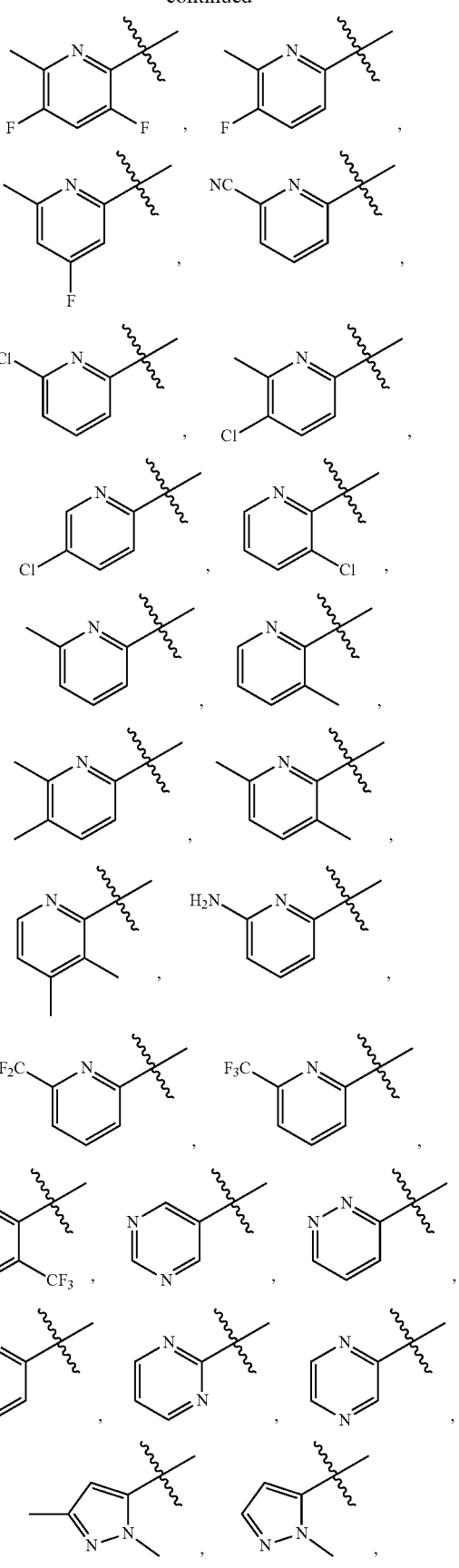

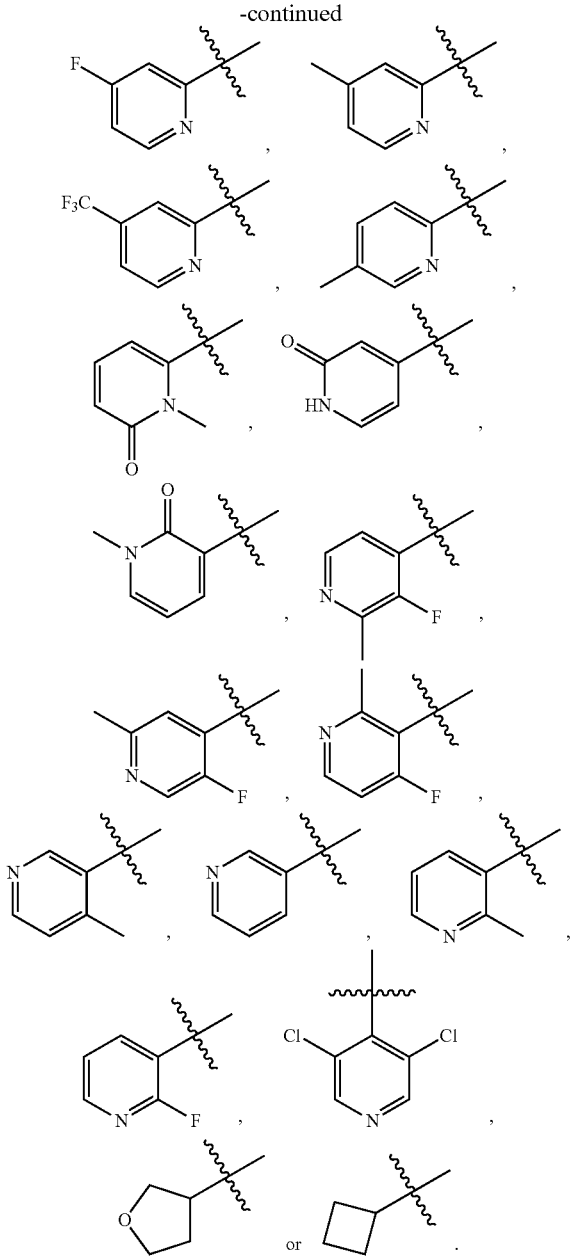

In one embodiment, R³ and R⁴ are, each independently, H or $C_1$-$C_4$ alkyl. In some embodiments, R³ and R⁴ are, each independently, H or $C_1$ alkyl. In some embodiments, R³ and R⁴ each are H. In some embodiments, R³ and R⁴ each are $C_1$ alkyl. In some embodiments, one of R³ or R⁴ is H and the other one of R³ or R⁴ is $C_1$ alkyl. In some embodiments, $C_1$ alkyl of R³ and R⁴ is methyl (—CH₃).

In one embodiment, B is $C_3$-$C_8$ cycloalkyl, $C_3$-$C_8$ heterocycloalkyl, a fused bicyclic, a bridged bicyclic, a spirocyclic, or absent. In some embodiments, the $C_3$-$C_8$ cycloalkyl, $C_3$-$C_8$ heterocycloalkyl, a fused bicyclic, a bridged bicyclic, or a spirocyclic of B is further substituted with fluoro (—F), —OH, or methyl (—CH₃). In some embodiments, the $C_3$-$C_8$ cycloalkyl, $C_3$-$C_8$ heterocycloalkyl, a fused bicyclic, a bridged bicyclic, or a spirocyclic of B is mono-, di-, or tri-substituted with fluoro (—F), —OH, or methyl (—CH₃). For example, the $C_3$-$C_8$ cycloalkyl, $C_3$-$C_8$ heterocycloalkyl, a fused bicyclic, a bridged bicyclic, or a spirocyclic of B is disubstituted with —OH. In some certain embodiments, the $C_3$-$C_8$ heterocycloalkyl of B is sulfoximine or sulfone. In some certain embodiments, the $C_3$-$C_8$ heterocycloalkyl of B is

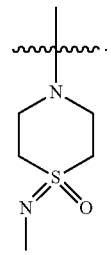 [SMILES: *N1CCS(=O)(=NC)CC1]

In some certain embodiments, the $C_3$-$C_8$ heterocycloalkyl of B is

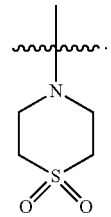 [SMILES: *N1CCS(=O)(=O)CC1]

In some embodiments, B is $C_6$-$C_7$ cycloalkyl, $C_4$-$C_6$ heterocycloalkyl, a fused bicyclic, a bridged bicyclic, or a spirocyclic. In some specific embodiments, B is $C_6$ cycloalkyl, $C_4$-$C_5$ heterocycloalkyl, a fused bicyclic, a bridged bicyclic, or a spirocyclic. In some embodiments, the fused bicyclic of B is octahydrocyclopenta[c]pyrrole, 3-azabicyclo[3.2.0]heptane, or 3-azabicyclo[3.1.0]hexane. In some embodiments, the bridged bicyclic of B is 3-azabicyclo[3.2.1]octane, 8-azabicyclo[3.2.1]octane, or 2-azabicyclo[2.2.1]heptane. In some embodiments, the spirocyclic of B is 1-azaspiro[4.5]decane, 2-azaspiro[4.5]decane, 3-azaspiro[5.5]undecane, 2-azaspiro[3.5]nonane, 2-azaspiro[3.3]heptane, 7-azaspiro[3.5]nonane, 1-azaspiro[3.3]heptane, or spiro[3.3]heptane. In some embodiments, B has one of the following structures:

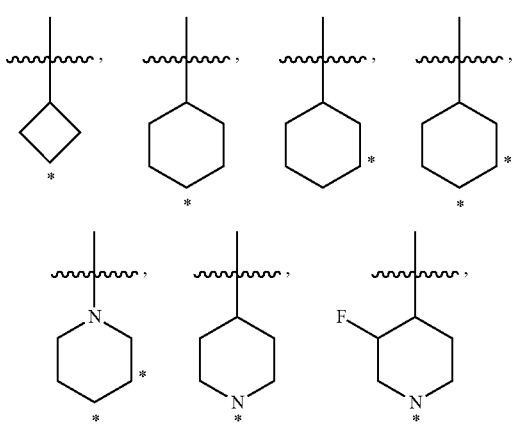

-continued
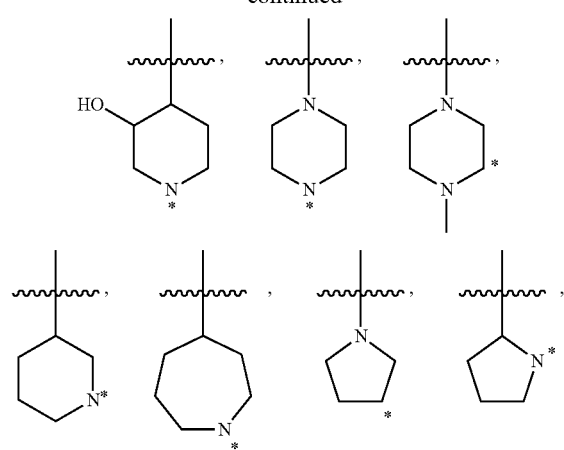
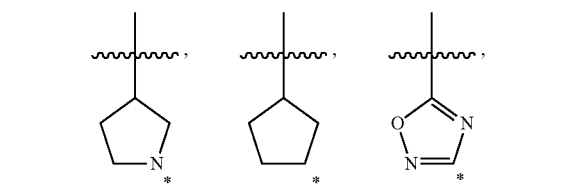
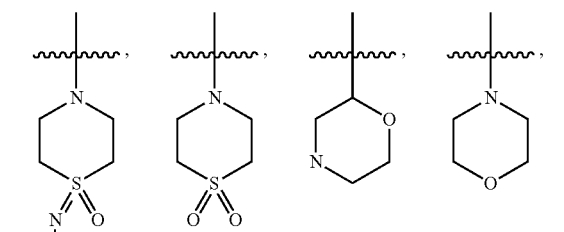
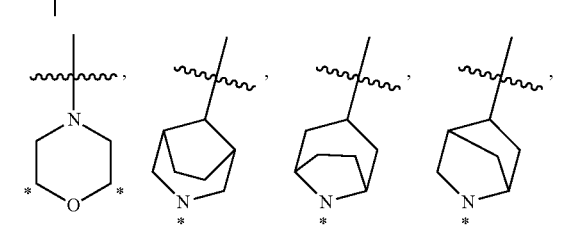
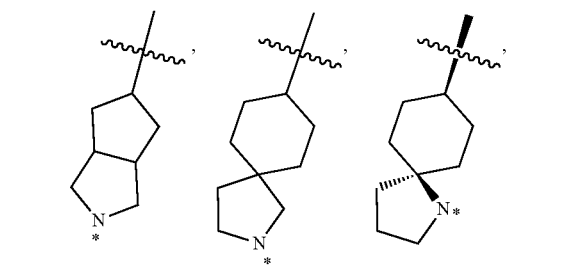
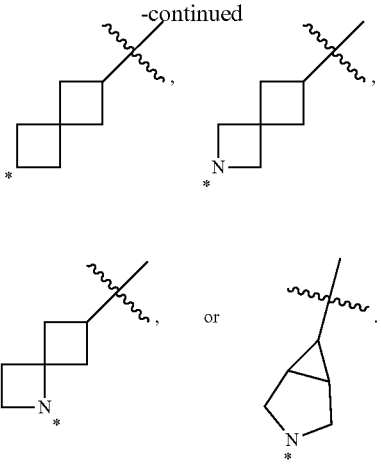
wherein * indicates the location of a bond to R³. In some embodiments, B is
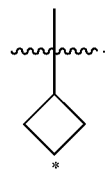 [SMILES: *C1CCC1]
In some embodiments, B is
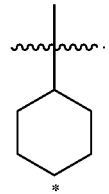
In some embodiments, B is
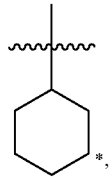
In some embodiments, B is
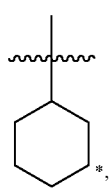

In some embodiments, B is
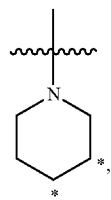
In some embodiments, B is
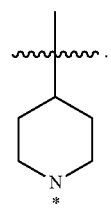
In some embodiments, B is
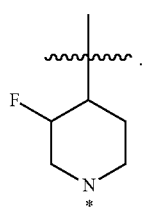
In some embodiments, B is
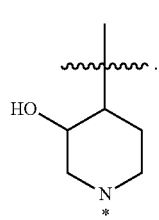
In some embodiments, B is
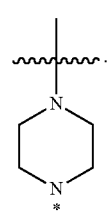
In some embodiments, B is
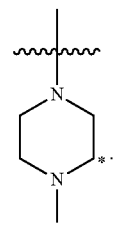
In some embodiments, B is
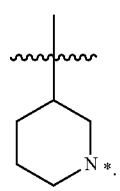
In some embodiments, B is
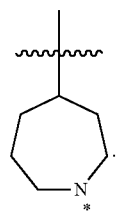
In some embodiments, B is
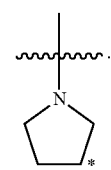 [SMILES: *N1CCCC1]
In some embodiments, B is
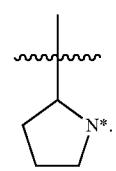

In some embodiments, B is
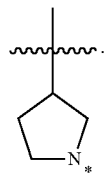 [SMILES: *C1CCNC1]
In some embodiments, B is
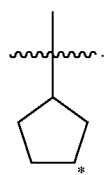
In some embodiments, B is
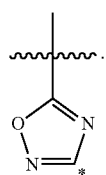
In some embodiments, B is
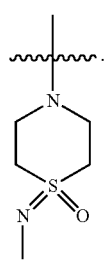
In some embodiments, B is
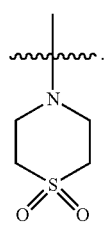
In some embodiments, B is
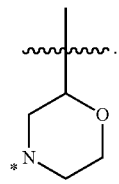
In some embodiments, B is
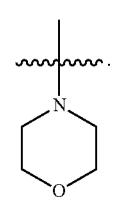 [SMILES: *N1CCOCC1]
In some embodiments, B is
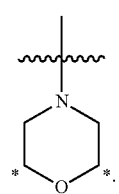
In some embodiments, B is
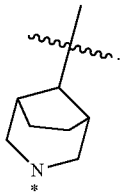 [SMILES: *C1C2CCC1CNC2]
In some embodiments, B is
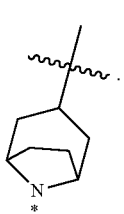 [SMILES: *C1CC2CCC(C1)N2]

In some embodiments, B is

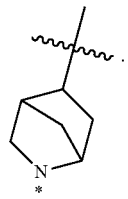

In some embodiments, B is

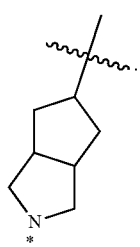 [SMILES: *C1CC2CNCC2C1]

In some embodiments, B is

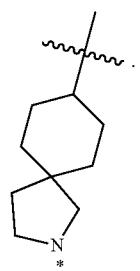 [SMILES: *C1CCC2(CCNC2)CC1]

In some embodiments, B is

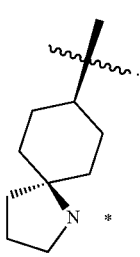

In some embodiments, B is

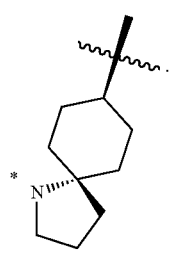

In some embodiments, B is

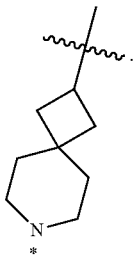

In some embodiments, B is

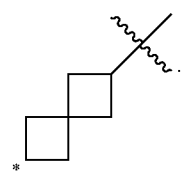

In some embodiments, B is

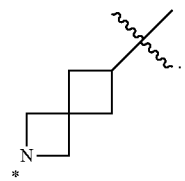

In some embodiments, B is

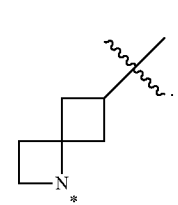 [SMILES: *C1CC2(CCN2)C1]

In some embodiments, B is

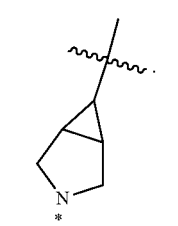 [SMILES: *C1C2CNCC12]

In some embodiments, B is substituted with one or more $R^3$. In some embodiments, B is substituted with one, two, three, four, five, six, or more $R^3$. For example, the compound of Formula (III-a)-(III-h) has $R^{3a}$, $R^{3b}$, $R^{3c1}$, $R^{3c2}$, $R^{3d}$, and $R^{3e}$. In this regard, B is substituted with $R^{3a}$, $R^{3b}$, $R^{3c1}$, $R^{3c2}$, $R^{3d}$, and $R^{3e}$.

In some embodiments, B is absent. When B is absent, Y is directly attached to $R^3$. When B is absent and Y is a direct bond, A is attached to $R^3$ such as the structure of Formula) III-h). In some embodiments, $R^3$, $R^{3a}$, $R^{3b}$, $R^{3c1}$, $R^{3c2}$, $R^{3d}$, and $R^{3e}$ are, each independently, —H, —OH, —F, $C_1$-$C_4$ alkyl $C_1$-$C_4$ heteroalkyl, 6 membered heteroaryl, $C_4$-$C_6$ heterocycloalkyl, —C(=O)$R^4$, —OC(=O)$R^4$, —CH$_2$C(=O)O$R^4$, —N$R^5R^6$, —N$R^5$C(=O)$R^4$, —N$R^5$C(=O)O$R^4$, —CH$_2$C(=O)N$R^5N^6$, —N$R^5R^6$CH$_2$C(=O)N$R^5N^6$, —CH$_2$N$R^5$C(=O)$R^4$, sulfonylmethane, oxo, or phosphate. In some embodiments, the $C_1$-$C_6$ alkyl or $C_1$-$C_6$ heteroalkyl of $R^3$, $R^{3a}$, $R^{3b}$, $R^{3c1}$, $R^{3c2}$, $R^{3d}$, and $R^{3e}$ is substituted with

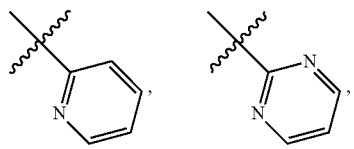 [SMILES: *c1ccccn1 ; *c1ncccn1]

or —OH. In some embodiments, the $C_1$-$C_6$ heteroalkyl of $R^3$, $R^{3a}$, $R^{3b}$, $R^{3c1}$, $R^{3c2}$, $R^{3d}$, and $R^{3e}$ is $C_1$-$C_6$ deutro-alkyl.

In some certain embodiments, the $C_4$-$C_6$ heterocycloalkyl of $R^4$ is pyrrolidine or 1-methyl pyrrolidine. In some embodiments, $R^4$ is $C_1$-$C_3$ alkyl, $C_1$-$C_4$ heteroalkyl, or $C_4$-$C_5$ heterocycloalkyl. In some embodiments, the $C_1$-$C_4$ heteroalkyl of $R^4$ is $C_1$-$C_4$ fluoroalkyl. In some embodiments, the $C_4$-$C_6$ heterocycloalkyl of $R^4$ is substituted with

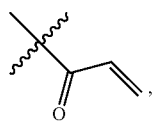

halo, or —OH. In some certain embodiments, the $C_4$-$C_6$ heterocycloalkyl of $R^4$ is substituted with

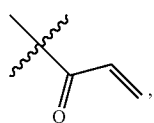

—F, or —OH. In some embodiments, the $C_4$-$C_6$ heterocycloalkyl of $R^4$ substituted with

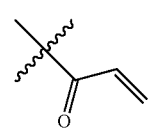 [SMILES: *C(=O)C=C]

is

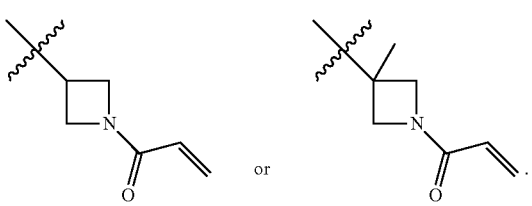

In some certain embodiments, the $C_4$-$C_6$ heterocycloalkyl of $R^4$ substituted with —F is

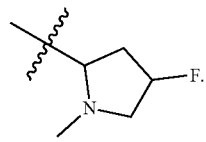 [SMILES: *C1CC(F)CN1C]

In some certain embodiments, the $C_4$-$C_6$ heterocycloalkyl of $R^4$ substituted with —OH is

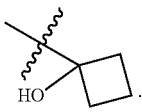

In some embodiments, the $C_4$-$C_6$ cycloalkyl of $R^4$ is substituted with —NH$_2$. In some certain embodiments, the $C_4$-$C_6$ cycloalkyl of $R^4$ substituted with —NH$_2$ is

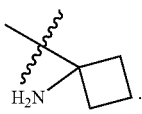

In some other embodiments, the $C_1$-$C_6$ heteroalkyl of $R^4$ is

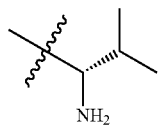

In some certain embodiments, the 5-6 membered heteroaryl of $R^3$, $R^{3a}$, $R^{3b}$, $R^{3c1}$, $R^{3c2}$, $R^{3d}$, and $R^{3e}$ are

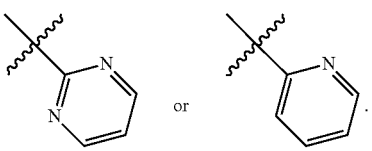 [SMILES: *c1ncccn1 ; *c1ccccn1]

In some certain embodiments, the $C_3$-$C_8$ heterocycloalkyl of $R^3$, $R^{3a}$, $R^{3b}$, $R^{3c1}$, $R^{3c2}$, $R^{3d}$, and $R^{3e}$ are

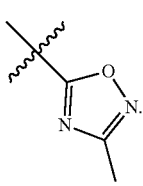

In some embodiments, the oxo of $R^3$, $R^{3a}$, $R^{3b}$, $R^{3c1}$, $R^{3c2}$, $R^{3d}$, and $R^{3e}$ are

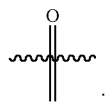

In some certain embodiments, the phosphate of $R^3$, $R^{3a}$, $R^{3b}$, $R^{3c1}$, $R^{3c2}$, $R^{3d}$, and $R^{3e}$ are

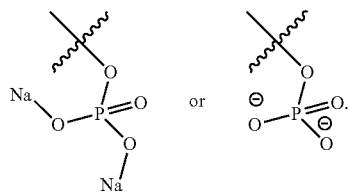

In some embodiments, the $C_1$-$C_6$ alkyl or $C_3$-$C_6$ cycloalkyl of $R^5$ or $R^6$ is substituted with —F, $C_3$-$C_6$ cycloalkyl, or 5-6 membered heteroaryl. In some embodiments, $R^5$ and $R^6$ are, each independently, H, $C_1$-$C_3$ alkyl, $C_1$-$C_3$ alkyl alcohol, sulfonylmethane, $C_3$-$C_4$ cycloalkyl, or 6 membered heteroaryl. In some other embodiments, the $C_1$-$C_3$ alkyl or $C_3$-$C_4$ cycloalkyl is substituted with —F or $C_3$-$C_4$ cycloalkyl.

In some embodiments, $R^3$, $R^{3a}$, $R^{3b}$, $R^{3c1}$, $R^{3c2}$, $R^{3d}$, and $R^{3e}$, each independently, have one of the following structures:

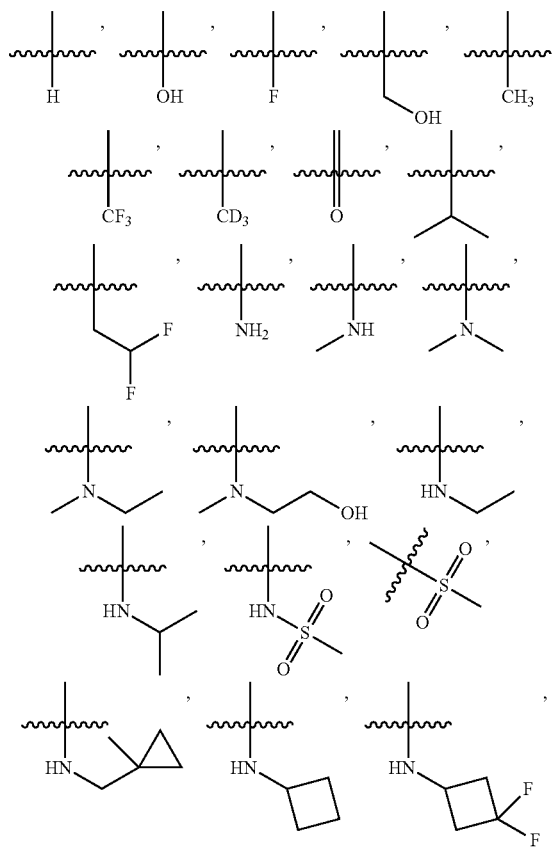

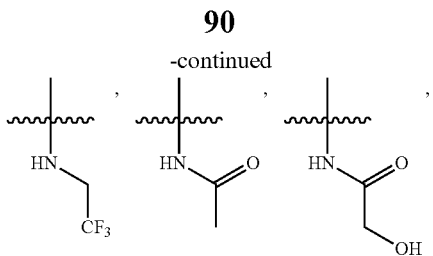

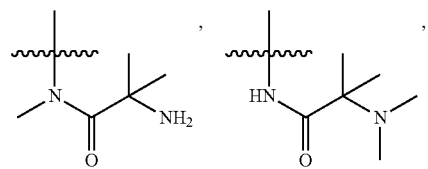

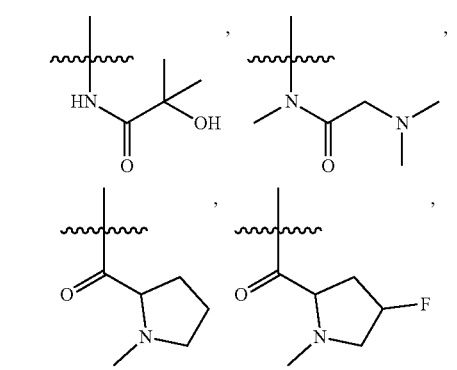

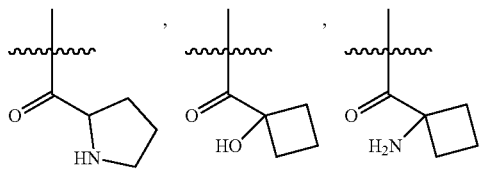

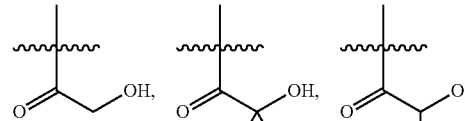

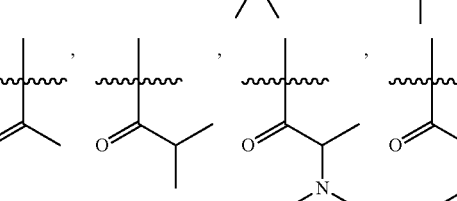

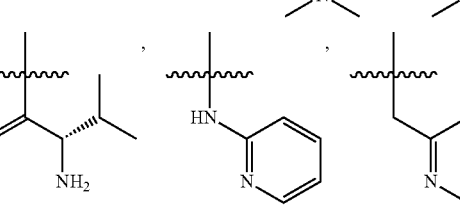

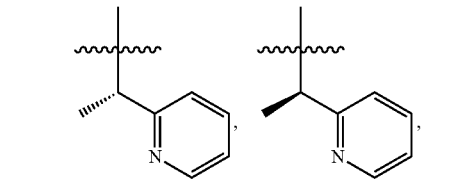

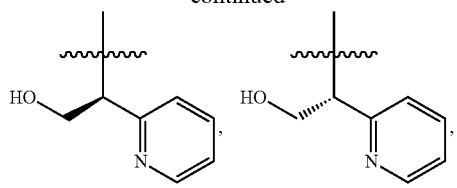
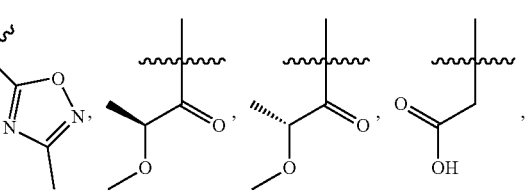
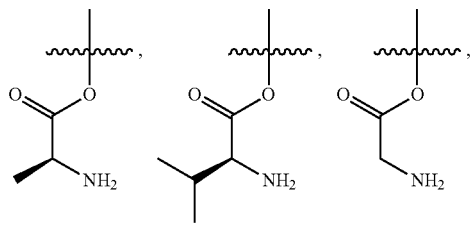
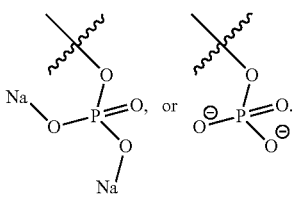
In some embodiments, R³, R³ᵃ, R³ᵇ, R³ᶜ¹, R³ᶜ², R³ᵈ, or R³ᵉ is
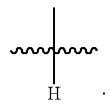
In some embodiments, R³, R³ᵃ, R³ᵇ, R³ᶜ¹, R³ᶜ², R³ᵈ, or R³ᵉ is
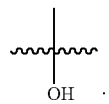
In some embodiments, R³, R³ᵃ, R³ᵇ, R³ᶜ¹, R³ᶜ², R³ᵈ, or R³ᵉ is
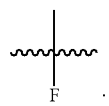

In some embodiments, $R^3$, $R^{3a}$, $R^{3b}$, $R^{3c1}$, $R^{3c2}$, $R^{3d}$, or $R^{3e}$ is

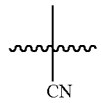

In some embodiments, $R^3$, $R^{3a}$, $R^{3b}$, $R^{3c1}$, $R^{3c2}$, $R^{3d}$, or $R^{3e}$ is

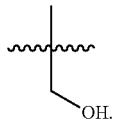

In some embodiments, $R^3$, $R^{3a}$, $R^{3b}$, $R^{3c1}$, $R^{3c2}$, $R^{3d}$, or $R^{3e}$ is

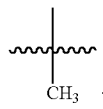

In some embodiments, $R^3$, $R^{3a}$, $R^{3b}$, $R^{3c1}$, $R^{3c2}$, $R^{3d}$, or $R^{3e}$ is

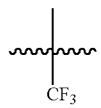

In some embodiments, $R^3$, $R^{3a}$, $R^{3b}$, $R^{3c1}$, $R^{3c2}$, $R^{3d}$, or $R^{3e}$ is

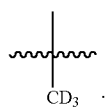

In some embodiments, $R^3$, $R^{3a}$, $R^{3b}$, $R^{3c1}$, $R^{3c2}$, $R^{3d}$, or $R^{3e}$ is

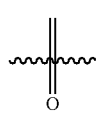

In some embodiments, $R^3$, $R^{3a}$, $R^{3b}$, $R^{3c1}$, $R^{3c2}$, $R^{3d}$, or $R^{3e}$ is

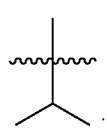

In some embodiments, $R^3$, $R^{3a}$, $R^{3b}$, $R^{3c1}$, $R^{3c2}$, $R^{3d}$, or $R^{3e}$ is

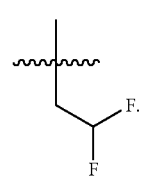

In some embodiments, $R^3$, $R^{3a}$, $R^{3b}$, $R^{3c1}$, $R^{3c2}$, $R^{3d}$, or $R^{3e}$ is

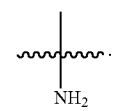

In some embodiments, $R^3$, $R^{3a}$, $R^{3b}$, $R^{3c1}$, $R^{3c2}$, $R^{3d}$, or $R^{3e}$ is

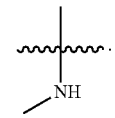

In some embodiments, $R^3$, $R^{3a}$, $R^{3b}$, $R^{3c1}$, $R^{3c2}$, $R^{3d}$, or $R^{3e}$ is In some embodiments, $R^3$, $R^{3a}$, $R^{3b}$, $R^{3c1}$, $R^{3c2}$, $R^{3d}$, or $R^{3e}$ is

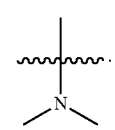

In some embodiments, R³, R³ᵃ, R³ᵇ, R³ᶜ¹, R³ᶜ², R³ᵈ, or R³ᵉ is

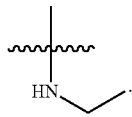

In some embodiments, R³, R³ᵃ, R³ᵇ, R³ᶜ¹, R³ᶜ², R³ᵈ, or R³ᵉ is

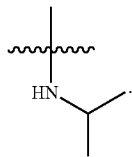 [SMILES: *NC(C)C]

In some embodiments, R³, R³ᵃ, R³ᵇ, R³ᶜ¹, R³ᶜ², R³ᵈ, or R³ᵉ is

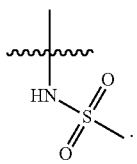 [SMILES: *NS(C)(=O)=O]

In some embodiments, R³, R³ᵃ, R³ᵇ, R³ᶜ¹, R³ᶜ², R³ᵈ, or R³ᵉ is

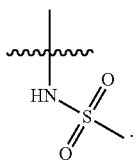

In some embodiments, R³, R³ᵃ, R³ᵇ, R³ᶜ¹, R³ᶜ², R³ᵈ, or R³ᵉ is

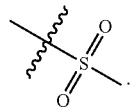

In some embodiments, R³, R³ᵃ, R³ᵇ, R³ᶜ¹, R³ᶜ², R³ᵈ, or R³ᵉ is

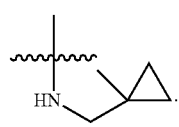

In some embodiments, R³, R³ᵃ, R³ᵇ, R³ᶜ¹, R³ᶜ², R³ᵈ, or R³ᵉ is

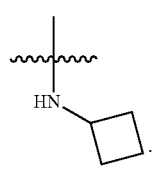 [SMILES: *NC1CCC1]

In some embodiments, R³, R³ᵃ, R³ᵇ, R³ᶜ¹, R³ᶜ², R³ᵈ, or R³ᵉ is

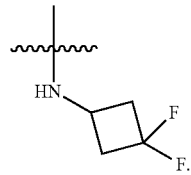 [SMILES: *NC1CC(F)(F)C1]

In some embodiments, R³, R³ᵃ, R³ᵇ, R³ᶜ¹, R³ᶜ², R³ᵈ, or R³ᵉ is

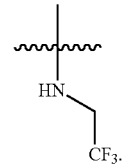

In some embodiments, R³, R³ᵃ, R³ᵇ, R³ᶜ¹, R³ᶜ², R³ᵈ, or R³ᵉ is

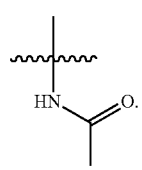

In some embodiments, R³, R³ᵃ, R³ᵇ, R³ᶜ¹, R³ᶜ², R³ᵈ, or R³ᵉ is

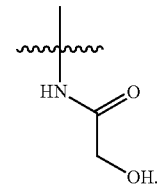 [SMILES: *NC(=O)CO]

In some embodiments, R³, R³ᵃ, R³ᵇ, R³ᶜ¹, R³ᶜ², R³ᵈ, or R³ᵉ is

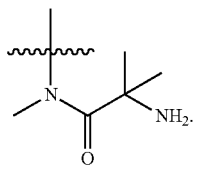 [SMILES: *N(C)C(=O)C(C)(C)N]

In some embodiments, R³, R³ᵃ, R³ᵇ, R³ᶜ¹, R³ᶜ², R³ᵈ, or R³ᵉ is

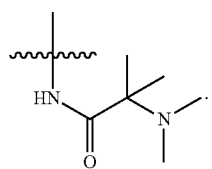 [SMILES: *NC(=O)C(C)(C)N(C)C]

In some embodiments, R³, R³ᵃ, R³ᵇ, R³ᶜ¹, R³ᶜ², R³ᵈ, or R³ᵉ is

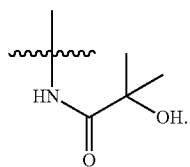 [SMILES: *NC(=O)C(C)(C)O]

In some embodiments, R³, R³ᵃ, R³ᵇ, R³ᶜ¹, R³ᶜ², R³ᵈ, or R³ᵉ is

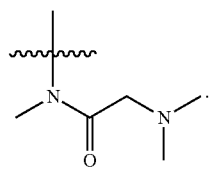

In some embodiments, R³, R³ᵃ, R³ᵇ, R³ᶜ¹, R³ᶜ², R³ᵈ, or R³ᵉ is

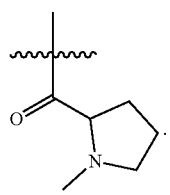 [SMILES: *C(=O)C1CCCN1C]

In some embodiments, R³, R³ᵃ, R³ᵇ, R³ᶜ¹, R³ᶜ², R³ᵈ, or R³ᵉ is

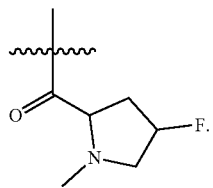 [SMILES: *C(=O)C1CC(F)CN1C]

In some embodiments, R³, R³ᵃ, R³ᵇ, R³ᶜ¹, R³ᶜ², R³ᵈ, or R³ᵉ is

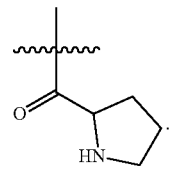 [SMILES: *C(=O)C1CCCN1]

In some embodiments, R³, R³ᵃ, R³ᵇ, R³ᶜ¹, R³ᶜ², R³ᵈ, or R³ᵉ is

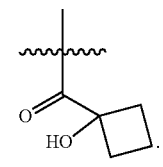 [SMILES: *C(=O)C1(O)CCC1]

In some embodiments, R³, R³ᵃ, R³ᵇ, R³ᶜ¹, R³ᶜ², R³ᵈ, or R³ᵉ is

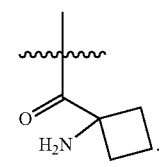

In some embodiments, R³, R³ᵃ, R³ᵇ, R³ᶜ¹, R³ᶜ², R³ᵈ, or R³ᵉ is

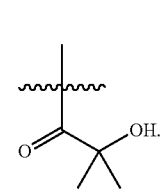 [SMILES: *C(=O)C(C)(C)O]

In some embodiments, R³, R³ᵃ, R³ᵇ, R³ᶜ¹, R³ᶜ², R³ᵈ, or R³ᵉ is

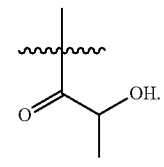 [SMILES: *C(=O)C(C)O]

In some embodiments, $R^3$, $R^{3a}$, $R^{3b}$, $R^{3c1}$, $R^{3c2}$, $R^{3d}$, or $R^{3e}$ is

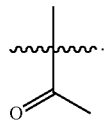

In some embodiments, $R^3$, $R^{3a}$, $R^{3b}$, $R^{3c1}$, $R^{3c2}$, $R^{3d}$, or $R^{3e}$ is

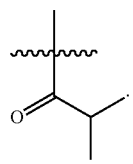

In some embodiments, $R^3$, $R^{3a}$, $R^{3b}$, $R^{3c1}$, $R^{3c2}$, $R^{3d}$, or $R^{3e}$ is

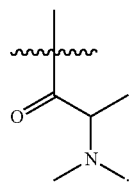

In some embodiments, $R^3$, $R^{3a}$, $R^{3b}$, $R^{3c1}$, $R^{3c2}$, $R^{3d}$, or $R^{3e}$ is

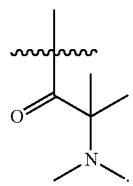

In some embodiments, $R^3$, $R^{3a}$, $R^{3b}$, $R^{3c1}$, $R^{3c2}$, $R^{3d}$, or $R^{3e}$ is

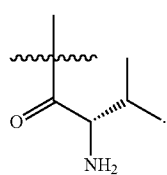

In some embodiments, $R^3$, $R^{3a}$, $R^{3b}$, $R^{3c1}$, $R^{3c2}$, $R^{3d}$, or $R^{3e}$ is

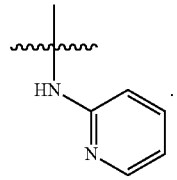 [SMILES: *Nc1ccccn1]

In some embodiments, $R^3$, $R^{3a}$, $R^{3b}$, $R^{3c1}$, $R^{3c2}$, $R^{3d}$, or $R^{3e}$ is

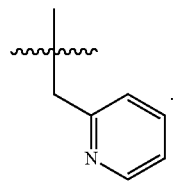 [SMILES: *Cc1ccccn1]

In some embodiments, $R^3$, $R^{3a}$, $R^{3b}$, $R^{3c1}$, $R^{3c2}$, $R^{3d}$, or $R^{3e}$ is

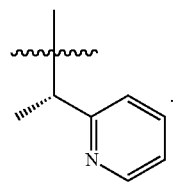 [SMILES: *[C@@H](C)c1ccccn1]

In some embodiments, $R^3$, $R^{3a}$, $R^{3b}$, $R^{3c1}$, $R^{3c2}$, $R^{3d}$, or $R^{3e}$ is

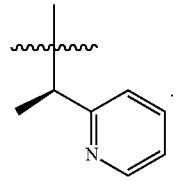 [SMILES: *[C@H](C)c1ccccn1]

In some embodiments, $R^3$, $R^{3a}$, $R^{3b}$, $R^{3c1}$, $R^{3c2}$, $R^{3d}$, or $R^{3e}$ is

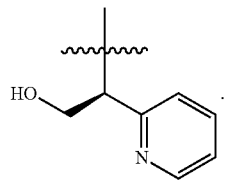 [SMILES: *[C@H](CO)c1ccccn1]

In some embodiments, $R^3$, $R^{3a}$, $R^{3b}$, $R^{3c1}$, $R^{3c2}$, $R^{3d}$, or $R^{3e}$ is

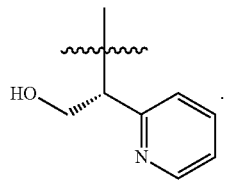 [SMILES: *[C@@H](CO)c1ccccn1]

In some embodiments, $R^3$, $R^{3a}$, $R^{3b}$, $R^{3c1}$, $R^{3c2}$, $R^{3d}$, or $R^{3e}$ is

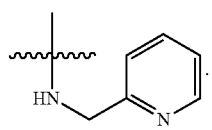 [SMILES: *NCc1ccccn1]

In some embodiments, $R^3$, $R^{3a}$, $R^{3b}$, $R^{3c1}$, $R^{3c2}$, $R^{3d}$, or $R^{3e}$ is

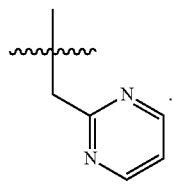 [SMILES: *Cc1ncccn1]

In some embodiments, $R^3$, $R^{3a}$, $R^{3b}$, $R^{3c1}$, $R^{3c2}$, $R^{3d}$, or $R^{3e}$ is

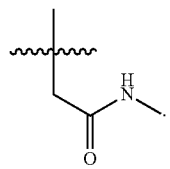

In some embodiments, $R^3$, $R^{3a}$, $R^{3b}$, $R^{3c1}$, $R^{3c2}$, $R^{3d}$, or $R^{3e}$ is

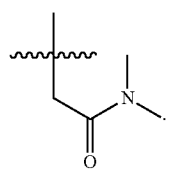

In some embodiments, $R^3$, $R^{3a}$, $R^{3b}$, $R^{3c1}$, $R^{3c2}$, $R^{3d}$, or $R^{3e}$ is

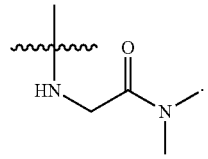

In some embodiments, $R^3$, $R^{3a}$, $R^{3b}$, $R^{3c1}$, $R^{3c2}$, $R^{3d}$, or $R^{3e}$ is

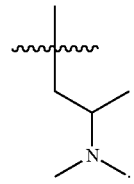

In some embodiments, $R^3$, $R^{3a}$, $R^{3b}$, $R^{3c1}$, $R^{3c2}$, $R^{3d}$, or $R^{3e}$ is

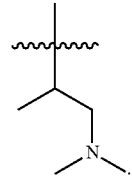

In some embodiments, $R^3$, $R^{3a}$, $R^{3b}$, $R^{3c1}$, $R^{3c2}$, $R^{3d}$, or $R^{3e}$ is

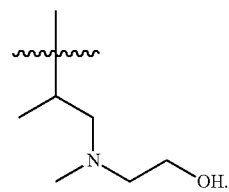 [SMILES: *C(C)CN(C)CCO]

In some embodiments, $R^3$, $R^{3a}$, $R^{3b}$, $R^{3c1}$, $R^{3c2}$, $R^{3d}$, or $R^{3e}$ is

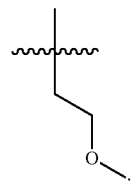

In some embodiments, $R^3$, $R^{3a}$, $R^{3b}$, $R^{3c1}$, $R^{3c2}$, $R^{3d}$, or $R^{3e}$ is

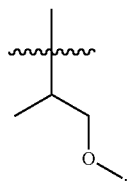

In some embodiments, $R^3$, $R^{3a}$, $R^{3b}$, $R^{3c1}$, $R^{3c2}$, $R^{3d}$, or $R^{3e}$ is

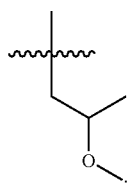

In some embodiments, $R^3$, $R^{3a}$, $R^{3b}$, $R^{3c1}$, $R^{3c2}$, $R^{3d}$, or $R^{3e}$ is

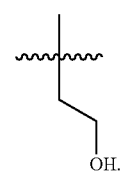

In some embodiments, $R^3$, $R^{3a}$, $R^{3b}$, $R^{3c1}$, $R^{3c2}$, $R^{3d}$, or $R^{3e}$ is

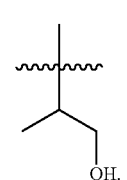

In some embodiments, $R^3$, $R^{3a}$, $R^{3b}$, $R^{3c1}$, $R^{3c2}$, $R^{3d}$, or $R^{3e}$ is

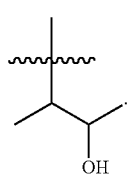

In some embodiments, $R^3$, $R^{3a}$, $R^{3b}$, $R^{3c1}$, $R^{3c2}$, $R^{3d}$, or $R^{3e}$ is

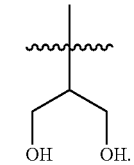 [SMILES: *C(CO)CO]

In some embodiments, $R^3$, $R^{3a}$, $R^{3b}$, $R^{3c1}$, $R^{3c2}$, $R^{3d}$, or $R^{3e}$ is

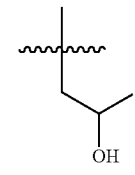

In some embodiments, $R^3$, $R^{3a}$, $R^{3b}$, $R^{3c1}$, $R^{3+2}$, $R^{3d}$, or $R^{3e}$ is

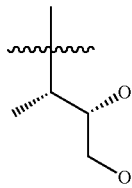

In some embodiments $R^3$, $R^{3a}$, $R^{3b}$, $R^{3c1}$, $R^{3c2}$, $R^{3d}$, or $R^{3e}$ is

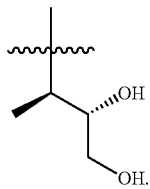 [SMILES: *[C@H](C)[C@H](O)CO]

In some embodiments, $R^3$, $R^{3a}$, $R^{3b}$, $R^{3c1}$, $R^{3c2}$, $R^{3d}$, or $R^{3e}$ is

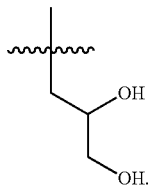 [SMILES: *CC(O)CO]

In some embodiments, $R^3$, $R^{3a}$, $R^{3b}$, $R^{3c1}$, $R^{3c2}$, $R^{3d}$, or $R^{3e}$ is

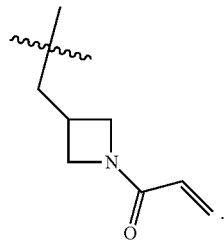 [SMILES: *CC1CN(C(=O)C=C)C1]

In some embodiments, $R^3$, $R^{3a}$, $R^{3b}$, $R^{3c1}$, $R^{3c2}$, $R^{3d}$, or $R^{3e}$ is

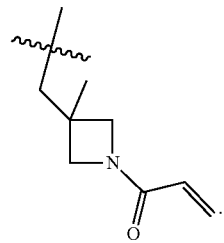 [SMILES: *CC1(C)CN(C(=O)C=C)C1]

In some embodiments, $R^3$, $R^{3a}$, $R^{3b}$, $R^{3c1}$, $R^{3c2}$, $R^{3d}$, or $R^{3e}$ is

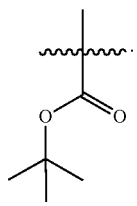 [SMILES: *C(=O)OC(C)(C)C]

In some embodiments, $R^3$, $R^{3a}$, $R^{3b}$, $R^{3c1}$, $R^{3c2}$, $R^{3d}$, or $R^{3e}$ is

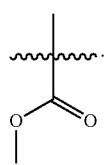

In some embodiments, $R^3$, $R^{3a}$, $R^{3b}$, $R^{3c1}$, $R^{3c2}$, $R^{3d}$, or $R^{3e}$ is

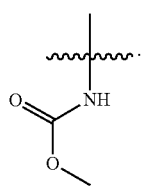 [SMILES: *NC(=O)OC]

In some embodiments, $R^3$, $R^{3a}$, $R^{3b}$, $R^{3c1}$, $R^{3c2}$, $R^{3d}$, or $R^{3e}$ is

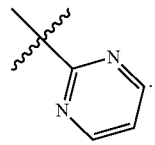 [SMILES: *c1ncccn1]

In some embodiments, $R^3$, $R^{3a}$, $R^{3b}$, $R^{3c1}$, $R^{3c2}$, $R^{3d}$, or $R^{3e}$ is

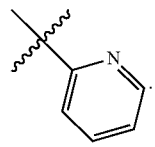 [SMILES: *c1ccccn1]

In some embodiments, $R^3$, $R^{3a}$, $R^{3b}$, $R^{3c1}$, $R^{3c2}$, $R^{3d}$, or $R^{3e}$ is

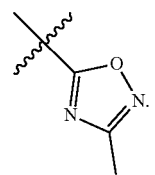

In some embodiments, $R^3$, $R^{3a}$, $R^{3b}$, $R^{3c1}$, $R^{3c2}$, $R^{3d}$, or $R^{3e}$ is

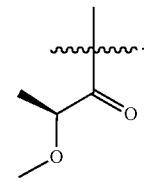 [SMILES: *C(=O)[C@H](C)OC]

In some embodiments, $R^3$, $R^{3a}$, $R^{3b}$, $R^{3c1}$, $R^{3c2}$, $R^{3d}$, or $R^{3e}$ is

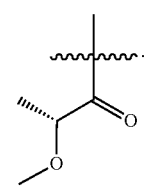 [SMILES: *C(=O)[C@@H](C)OC]

In some embodiments, $R^3$, $R^{3a}$, $R^{3b}$, $R^{3c1}$, $R^{3c2}$, $R^{3d}$, or $R^{3e}$ is

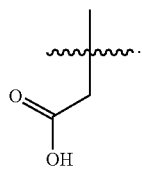 [SMILES: *CC(=O)O]

In some embodiments, $R^3$, $R^{3a}$, $R^{3b}$, $R^{3c1}$, $R^{3c2}$, $R^{3d}$, or $R^{3e}$ is

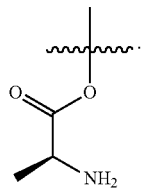 [SMILES: *OC(=O)[C@H](C)N]

In some embodiments, $R^3$, $R^{3a}$, $R^{3b}$, $R^{3c1}$, $R^{3c2}$, $R^{3d}$, or $R^{3e}$ is

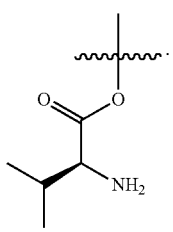 [SMILES: *OC(=O)[C@@H](N)C(C)C]

In some embodiments, $R^3$, $R^{3a}$, $R^{3b}$, $R^{3c1}$, $R^{3c2}$, $R^{3d}$, or $R^{3e}$ is

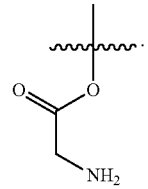

In some embodiments, $R^3$, $R^{3a}$, $R^{3b}$, $R^{3c1}$, $R^{3c2}$, $R^{3d}$, or $R^{3e}$ is

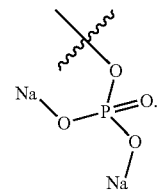

In some embodiments, $R^3$, $R^{3a}$, $R^{3b}$, $R^{3c1}$, $R^{3c2}$, $R^{3d}$, or $R^{3e}$ is

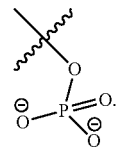

In one embodiment, the compound of formula (I), (IA), (IB)-(IB-3), (IC-a)-(II-a), (IC-b)-(II-b), (III-a)-(III-h), (IV) or (IV-a) has one of the following structures shown in Table A below.

TABLE A

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 1 | 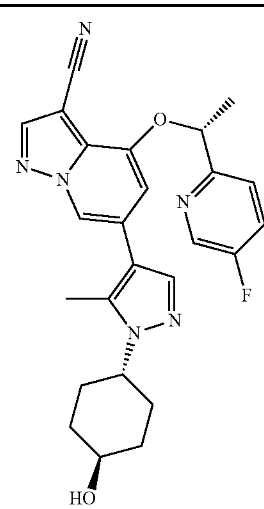 | 4-[(1R)-1-(5-fluoro-2-pyridyl)ethoxy]-6-[1-(4-hydroxycyclohexyl)-5-methyl-pyrazol-4-yl]pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 2 | 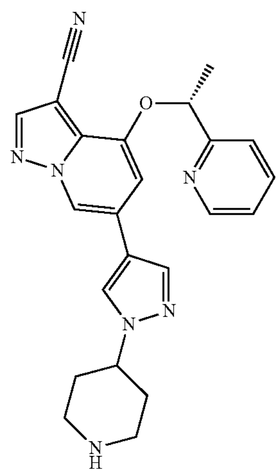 [SMILES: C[C@@H](Oc1cc(-c2cnn(C3CCNCC3)c2)cn2ncc(C#N)c12)c1ccccn1] | (R)-6-(1-(piperidin-4-yl)-1H-pyrazol-4-yl)-4-(1-(pyridin-2-yl)ethoxy)pyrazolo[1,5-a]pyridine-3-carbonitrile |
| 3 | 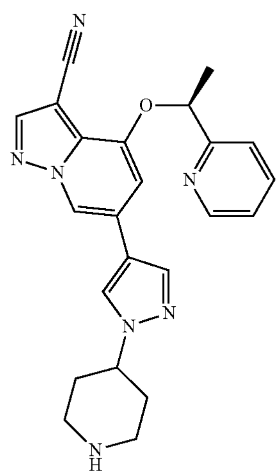 [SMILES: C[C@H](Oc1cc(-c2cnn(C3CCNCC3)c2)cn2ncc(C#N)c12)c1ccccn1] | (S)-6-(1-(piperidin-4-yl)-1H-pyrazol-4-yl)-4-(1-(pyridin-2-yl)ethoxy)pyrazolo[1,5-a]pyridine-3-carbonitrile |
| 4 | 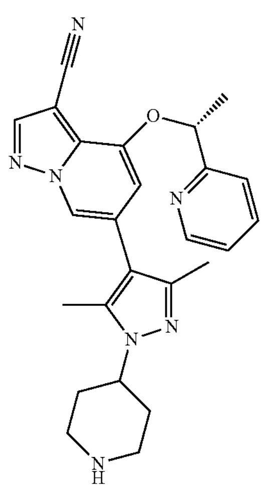 [SMILES: Cc1nn(C2CCNCC2)c(C)c1-c1cc(O[C@H](C)c2ccccn2)c2c(C#N)cnn2c1] | (R)-6-(3,5-dimethyl-1-(piperidin-4-yl)-1H-pyrazol-4-yl)-4-(1-(pyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 5 | 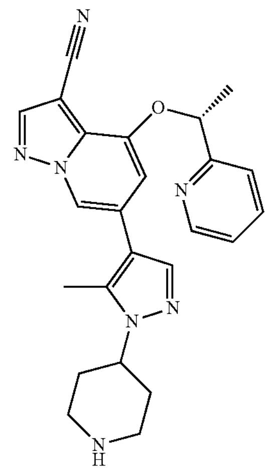 [SMILES: Cc1c(-c2cc(O[C@H](C)c3ccccn3)c3c(C#N)cnn3c2)cnn1C1CCNCC1] | (R)-6-(5-methyl-1-(piperidin-4-yl)-1H-pyrazol-4-yl)-4-(1-(pyridin-2-yl)ethoxy)pyrazolo[1,5-a]pyridine-3-carbonitrile |
| 6 | 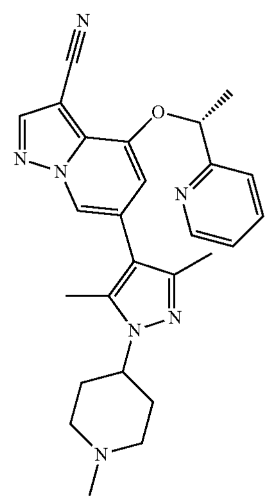 [SMILES: Cc1nn(C2CCN(C)CC2)c(C)c1-c1cc(O[C@H](C)c2ccccn2)c2c(C#N)cnn2c1] | (R)-6-(3,5-dimethyl-1-(1-methylpiperidin-4-yl)-1H-pyrazol-4-yl)-4-(1-(pyridin-2-yl)ethoxy)pyrazolo[1,5-a]pyridine-3-carbonitrile |
| 7 | 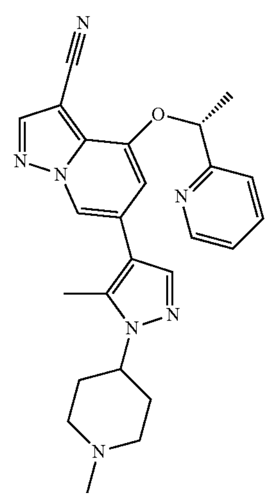 [SMILES: Cc1c(-c2cc(O[C@H](C)c3ccccn3)c3c(C#N)cnn3c2)cnn1C1CCN(C)CC1] | (R)-6-(5-methyl-1-(1-methylpiperidin-4-yl)-1H-pyrazol-4-yl)-4-(1-(pyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 8 | 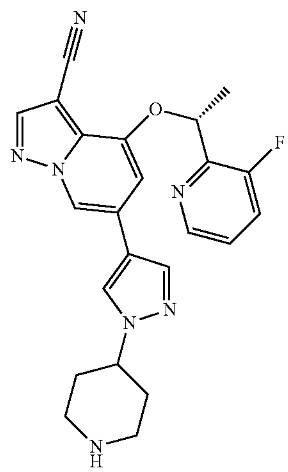 [SMILES: C[C@@H](Oc1cc(-c2cnn(C3CCNCC3)c2)cn2ncc(C#N)c12)c1ncccc1F] | (R)-4-(1-(3-fluoropyridin-2-yl)ethoxy)-6-(1-(piperidin-4-yl)-1H-pyrazol-4-yl)pyrazolo[1,5-a]pyridine-3-carbonitrile |
| 9 | 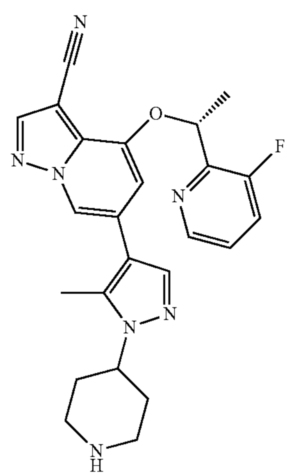 | (R)-4-(1-(3-fluoropyridin-2-yl)ethoxy)-6-(5-methyl-1-(piperidin-4-yl)-1H-pyrazol-4-yl)pyrazolo[1,5-a]pyridine-3-carbonitrile |
| 10 | 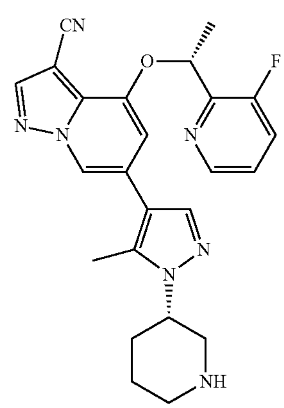 [SMILES: Cc1c(-c2cc(O[C@H](C)c3ncccc3F)c3c(C#N)cnn3c2)cnn1[C@H]1CCCNC1] | 4-((R)-1-(3-fluoropyridin-2-yl)ethoxy)-6-(5-methyl-1-((S)-piperidin-3-yl)-1H-pyrazol-4-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 11 | 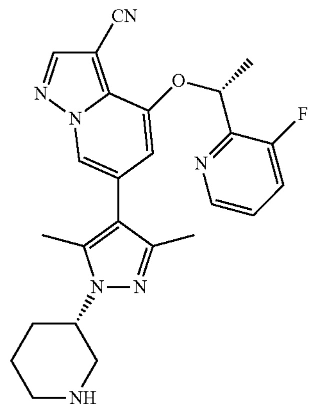 [SMILES: Cc1nn([C@H]2CCCNC2)c(C)c1-c1cc(O[C@H](C)c2ncccc2F)c2c(C#N)cnn2c1] | 6-(3,5-dimethyl-1-((S)-piperidin-3-yl)-1H-pyrazol-4-yl)-4-((R)-1-(3-fluoropyridin-2-yl)ethoxy)pyrazolo[1,5-a]pyridine-3-carbonitrile |
| 12 | 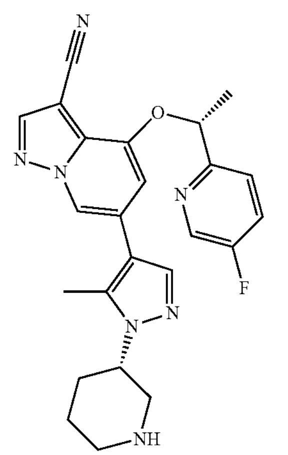 [SMILES: Cc1c(-c2cc(O[C@H](C)c3ccc(F)cn3)c3c(C#N)cnn3c2)cnn1[C@H]1CCCNC1] | 4-((R)-1-(5-fluoropyridin-2-yl)ethoxy)-6-(5-methyl-1-((S)-piperidin-3-yl)-1H-pyrazol-4-yl)pyrazolo[1,5-a]pyridine-3-carbonitrile |
| 13 | 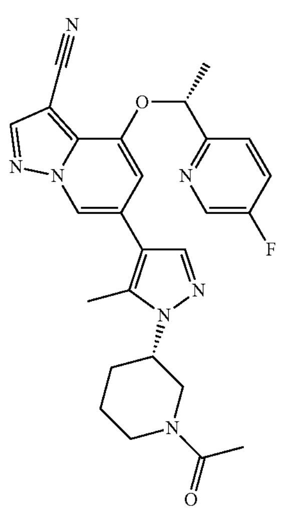 [SMILES: CC(=O)N1CCC[C@H](n2ncc(-c3cc(O[C@H](C)c4ccc(F)cn4)c4c(C#N)cnn4c3)c2C)C1] | 6-(1-((S)-1-acetylpiperidin-3-yl)-5-methyl-1H-pyrazol-4-yl)-4-((R)-1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 14 | 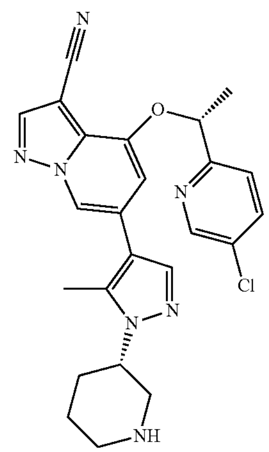 [SMILES: Cc1c(-c2cc(O[C@H](C)c3ccc(Cl)cn3)c3c(C#N)cnn3c2)cnn1[C@H]1CCCNC1] | 4-((R)-1-(5-chloropyridin-2-yl)ethoxy)-6-(5-methyl-1-((S)-piperidin-3-yl)-1H-pyrazol-4-yl)pyrazolo[1,5-a]pyridine-3-carbonitrile |
| 15 | 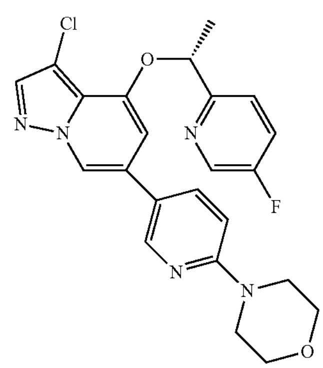 [SMILES: C[C@@H](Oc1cc(-c2ccc(N3CCOCC3)nc2)cn2ncc(Cl)c12)c1ccc(F)cn1] | (R)-4-(1-(5-fluoropyridin-2-yl)ethoxy)-6-(6-morpholinopyridin-3-yl)pyrazolo[1,5-a]pyridine-3-carbonitrile |
| 16 | 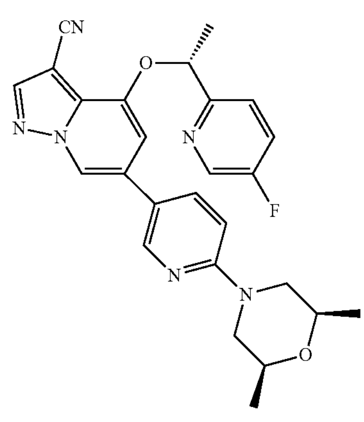 [SMILES: C[C@@H]1CN(c2ccc(-c3cc(O[C@H](C)c4ccc(F)cn4)c4c(C#N)cnn4c3)cn2)C[C@H](C)O1] | 6-(6-((2S,6R)-2,6-dimethylmorpholino)pyridin-3-yl)-4-((R)-1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 17 | 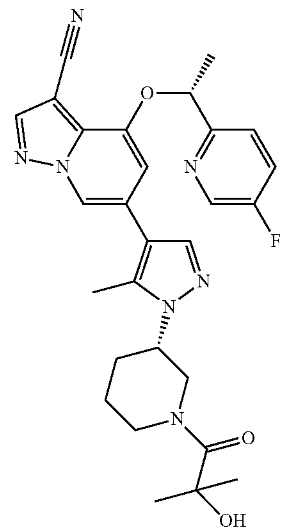 [SMILES: Cc1c(-c2cc(O[C@H](C)c3ccc(F)cn3)c3c(C#N)cnn3c2)cnn1[C@H]1CCCN(C(=O)C(C)(C)O)C1] | 4-((R)-1-(5-fluoropyridin-2-yl)ethoxy)-6-(1-((S)-1-(2-hydroxy-2-methylpropanoyl)piperidin-3-yl)-5-methyl-1H-pyrazol-4-yl)pyrazolo[1,5-a]pyridine-3-carbonitrile |
| 18 | 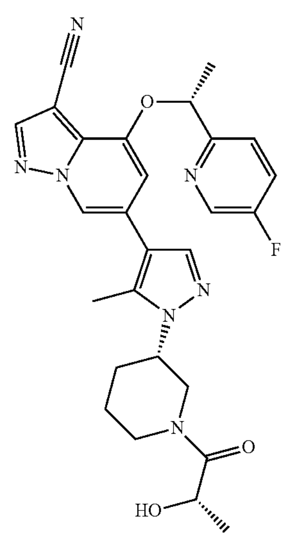 [SMILES: Cc1c(-c2cc(O[C@H](C)c3ccc(F)cn3)c3c(C#N)cnn3c2)cnn1[C@H]1CCCN(C(=O)[C@H](C)O)C1] | 4-((R)-1-(5-fluoropyridin-2-yl)ethoxy)-6-(1-((S)-1-((S)-2-hydroxypropanoyl)piperidin-3-yl)-5-methyl-1H-pyrazol-4-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 19 | 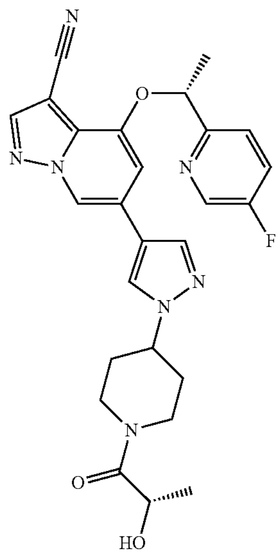 [SMILES: C[C@H](O)C(=O)N1CCC(n2cc(-c3cc(O[C@H](C)c4ccc(F)cn4)c4c(C#N)cnn4c3)cn2)CC1] | 4-((R)-1-(5-fluoropyridin-2-yl)ethoxy)-6-(1-(1-((S)-2-hydroxypropanoyl)piperidin-4-yl)-1H-pyrazol-4-yl)pyrazolo[1,5-a]pyridine-3-carbonitrile |
| 20 | 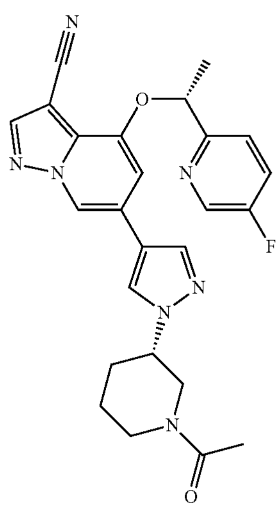 | (R)-6-(1,5-dimethyl-1H-pyrazol-4-yl)-4-(1-(5-fluoropyridin-2-yl)ethoxy)pyrazolo[1,5-a]pyridine-3-carbonitrile |
| 21 | 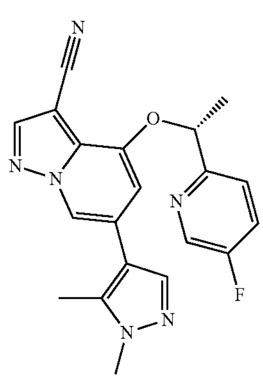 [SMILES: Cc1c(-c2cc(O[C@H](C)c3ccc(F)cn3)c3c(C#N)cnn3c2)cnn1C] | 6(R)-6-(1,5-dimethyl-1H-pyrazol-4-yl)-4-(1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 22 | 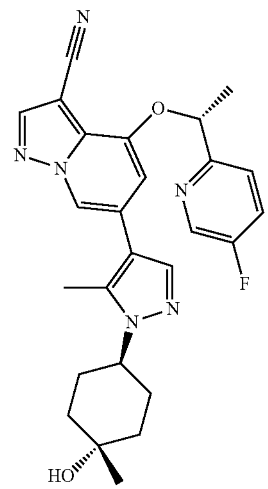 [SMILES: Cc1c(-c2cc(O[C@H](C)c3ccc(F)cn3)c3c(C#N)cnn3c2)cnn1[C@H]1CC[C@](C)(O)CC1] | 4-((R)-1-(5-fluoropyridin-2-yl)ethoxy)-6-(1-((1r,4R)-4-hydroxy-4-methylcyclohexyl)-5-methyl-1H-pyrazol-4-yl)pyrazolo[1,5-a]pyridine-3-carbonitrile |
| 23 | 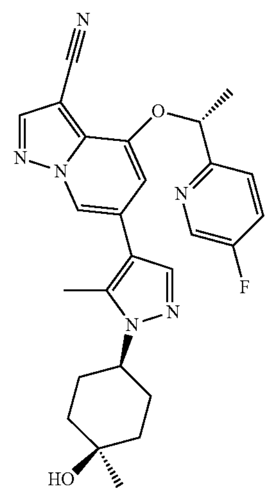 [SMILES: Cc1c(-c2cc(O[C@H](C)c3ccc(F)cn3)c3c(C#N)cnn3c2)cnn1[C@H]1CC[C@@](C)(O)CC1] | 4-((R)-1-(5-fluoropyridin-2-yl)ethoxy)-6-(1-((1s,4S)-4-hydroxy-4-methylcyclohexyl)-5-methyl-1H-pyrazol-4-yl)pyrazolo[1,5-a]pyridine-3-carbonitrile |
| 24 | 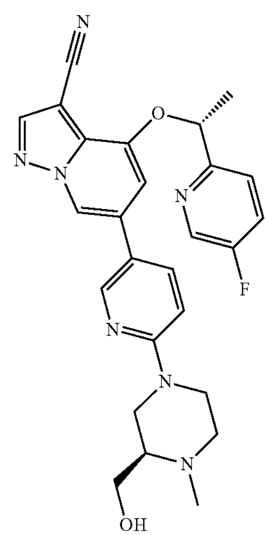 [SMILES: C[C@@H](Oc1cc(-c2ccc(N3CCN(C)[C@@H](CO)C3)nc2)cn2ncc(C#N)c12)c1ccc(F)cn1] | 4-((R)-1-(5-fluoropyridin-2-yl)ethoxy)-6-(6-((R)-3-(hydroxymethyl)-4-methylpiperazin-1-yl)pyridin-3-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 25 | 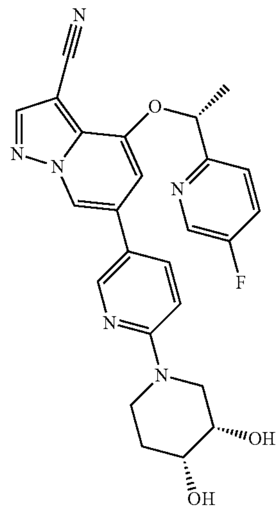 [SMILES: C[C@@H](Oc1cc(-c2ccc(N3CC[C@@H](O)[C@@H](O)C3)nc2)cn2ncc(C#N)c12)c1ccc(F)cn1] | 6-(6-((3S,4R)-3,4-dihydroxypiperidin-1-yl)pyridin-3-yl)-4-((R)-1-(5-fluoropyridin-2-yl)ethoxy)pyrazolo[1,5-a]pyridine-3-carbonitrile |
| 26 | 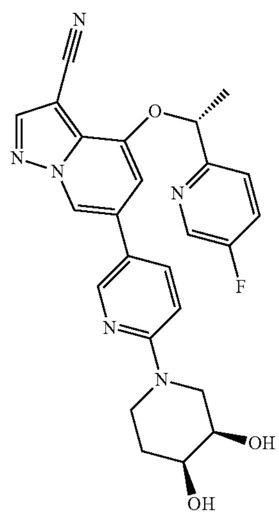 [SMILES: C[C@@H](Oc1cc(-c2ccc(N3CC[C@H](O)[C@H](O)C3)nc2)cn2ncc(C#N)c12)c1ccc(F)cn1] | 6-(6-((3R,4S)-3,4-dihydroxypiperidin-1-yl)pyridin-3-yl)-4-((R)-1-(5-fluoropyridin-2-yl)ethoxy)pyrazolo[1,5-a]pyridine-3-carbonitrile |
| 27 | 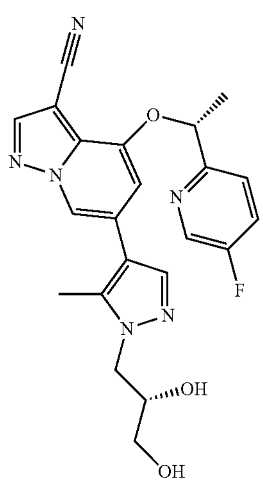 [SMILES: Cc1c(-c2cc(O[C@H](C)c3ccc(F)cn3)c3c(C#N)cnn3c2)cnn1C[C@H](O)CO] | 6-(1-((S)-2,3-dihydroxypropyl)-5-methyl-1H-pyrazol-4-yl)-4-((R)-1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 28 | 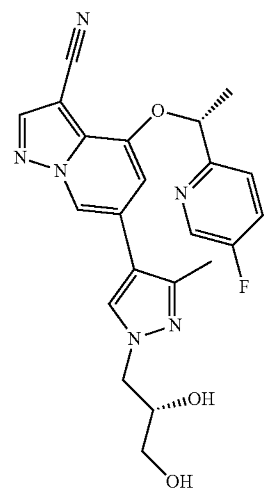 [SMILES: Cc1nn(C[C@H](O)CO)cc1-c1cc(O[C@H](C)c2ccc(F)cn2)c2c(C#N)cnn2c1] | 6-(1-((S)-2,3-dihydroxypropyl)-3-methyl-1H-pyrazol-4-yl)-4-((R)-1-(5-fluoropyridin-2-yl)ethoxy)pyrazolo[1,5-a]pyridine-3-carbonitrile |
| 29 | 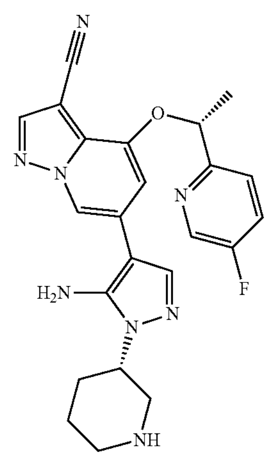 [SMILES: C[C@@H](Oc1cc(-c2cnn([C@H]3CCCNC3)c2N)cn2ncc(C#N)c12)c1ccc(F)cn1] | 6-(5-amino-1-((S)-piperidin-3-yl)-1H-pyrazol-4-yl)-4-((R)-1-(5-fluoropyridin-2-yl)ethoxy)pyrazolo[1,5-a]pyridine-3-carbonitrile |
| 30 | 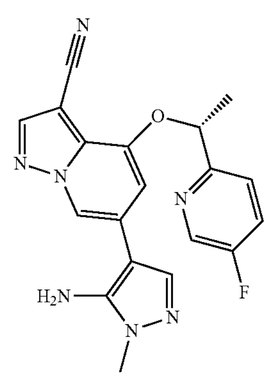 | (R)-6-(5-amino-1-methyl-1H-pyrazol-4-yl)-4-(1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 31 | 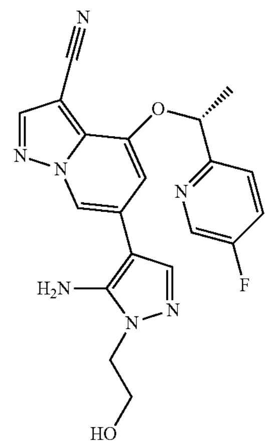 [SMILES: C[C@@H](Oc1cc(-c2cnn(CCO)c2N)cn2ncc(C#N)c12)c1ccc(F)cn1] | (R)-6-(5-amino-1-(2-hydroxyethyl)-1H-pyrazol-4-yl)-4-(1-(5-fluoropyridin-2-yl)ethoxy)pyrazolo[1,5-a]pyridine-3-carbonitrile |
| 32 | 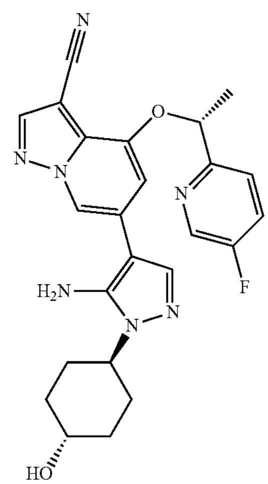 [SMILES: C[C@@H](Oc1cc(-c2cnn([C@H]3CC[C@H](O)CC3)c2N)cn2ncc(C#N)c12)c1ccc(F)cn1] | 6-(5-amino-1-((1r,4R)-4-hydroxycyclohexyl)-1H-pyrazol-4-yl)-4-((R)-1-(5-fluoropyridin-2-yl)ethoxy)pyrazolo[1,5-a]pyridine-3-carbonitrile |
| 33 | 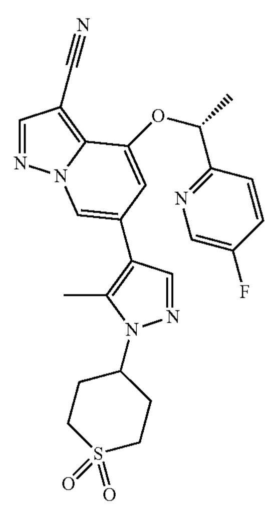 [SMILES: Cc1c(-c2cc(O[C@H](C)c3ccc(F)cn3)c3c(C#N)cnn3c2)cnn1C1CCS(=O)(=O)CC1] | (R)-6-(1-(1,1-dioxidotetrahydro-2H-thiopyran-4-yl)-5-methyl-1H-pyrazol-4-yl)-4-(1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 34 | 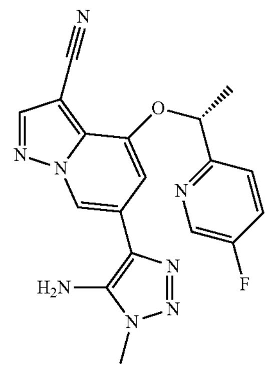 [SMILES: C[C@@H](Oc1cc(-c2nnn(C)c2N)cn2ncc(C#N)c12)c1ccc(F)cn1] | (R)-6-(5-amino-1-methyl-1H-1,2,3-triazol-4-yl)-4-(1-(5-fluoropyridin-2-yl)ethoxy)pyrazolo[1,5-a]pyridine-3-carbonitrile |
| 35 | 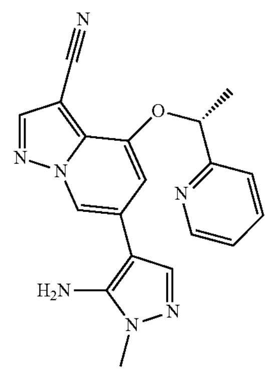 [SMILES: C[C@@H](Oc1cc(-c2cnn(C)c2N)cn2ncc(C#N)c12)c1ccccn1] | (R)-6-(5-amino-1-methyl-1H-pyrazol-4-yl)-4-(1-(pyridin-2-yl)ethoxy)pyrazolo[1,5-a]pyridine-3-carbonitrile |
| 36 | 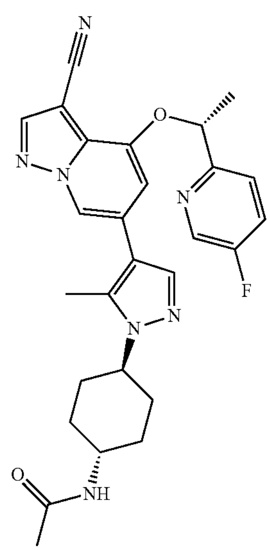 [SMILES: CC(=O)N[C@H]1CC[C@H](n2ncc(-c3cc(O[C@H](C)c4ccc(F)cn4)c4c(C#N)cnn4c3)c2C)CC1] | N-((1R,4r)-4-(4-(3-cyano-4-((R)-1-(5-fluoropyridin-2-yl)ethoxy)pyrazolo[1,5-a]pyridin-6-yl)-5-methyl-1H-pyrazol-1-yl)cyclohexyl)acetamide |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 37 | 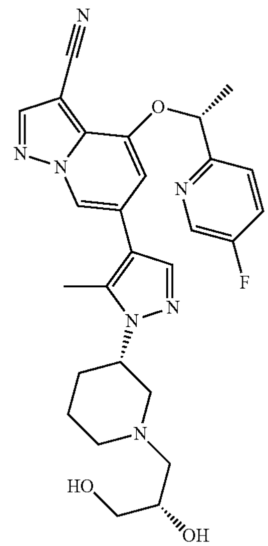 [SMILES: Cc1c(-c2cc(O[C@H](C)c3ccc(F)cn3)c3c(C#N)cnn3c2)cnn1[C@H]1CCCN(C[C@H](O)CO)C1] | 6-(1-((S)-1-((S)-2,3-dihydroxypropyl)piperidin-3-yl)-5-methyl-1H-pyrazol-4-yl)-4-((R)-1-(5-fluoropyridin-2-yl)ethoxy)pyrazolo[1,5-a]pyridine-3-carbonitrile |
| 38 | 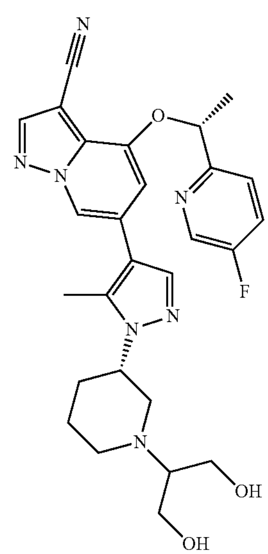 [SMILES: Cc1c(-c2cc(O[C@H](C)c3ccc(F)cn3)c3c(C#N)cnn3c2)cnn1[C@H]1CCCN(C(CO)CO)C1] | 6-(1-((S)-1-(1,3-dihydroxypropan-2-yl)piperidin-3-yl)-5-methyl-1H-pyrazol-4-yl)-4-((R)-1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 39 | 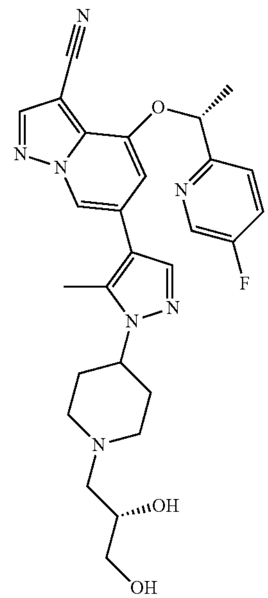 [SMILES: Cc1c(-c2cc(O[C@H](C)c3ccc(F)cn3)c3c(C#N)cnn3c2)cnn1C1CCN(C[C@H](O)CO)CC1] | 6-(1-(1-((S)-2,3-dihydroxypropyl)piperidin-4-yl)-5-methyl-1H-pyrazol-4-yl)-4-((R)-1-(5-fluoropyridin-2-yl)ethoxy)pyrazolo[1,5-a]pyridine-3-carbonitrile |
| 40 | 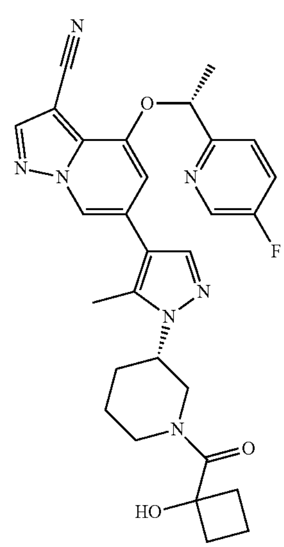 [SMILES: Cc1c(-c2cc(O[C@H](C)c3ccc(F)cn3)c3c(C#N)cnn3c2)cnn1[C@H]1CCCN(C(=O)C2(O)CCC2)C1] | 4-((R)-1-(5-fluoropyridin-2-yl)ethoxy)-6-(1-((S)-1-(1-hydroxycyclobutane-1-carbonyl)piperidin-3-yl)-5-methyl-1H-pyrazol-4-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 41 | 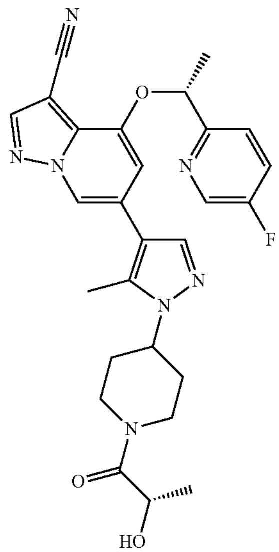 [SMILES: Cc1c(-c2cc(O[C@H](C)c3ccc(F)cn3)c3c(C#N)cnn3c2)cnn1C1CCN(C(=O)[C@H](C)O)CC1] | 4-((R)-1-(5-fluoropyridin-2-yl)ethoxy)-6-(1-(1-((S)-2-hydroxypropanoyl)piperidin-4-yl)-5-methyl-1H-pyrazol-4-yl)pyrazolo[1,5-a]pyridine-3-carbonitrile |
| 42 | 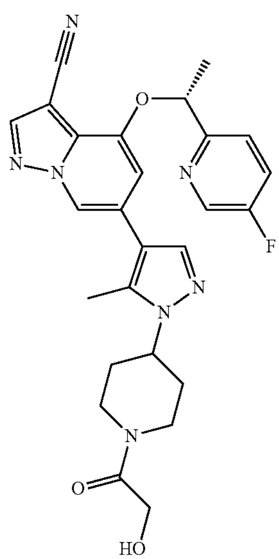 [SMILES: Cc1c(-c2cc(O[C@H](C)c3ccc(F)cn3)c3c(C#N)cnn3c2)cnn1C1CCN(C(=O)CO)CC1] | (R)-4-(1-(5-fluoropyridin-2-yl)ethoxy)-6-(1-(1-(2-hydroxyacetyl)piperidin-4-yl)-5-methyl-1H-pyrazol-4-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 43 | 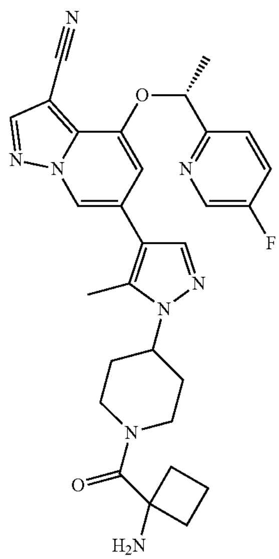 [SMILES: Cc1c(-c2cc(O[C@H](C)c3ccc(F)cn3)c3c(C#N)cnn3c2)cnn1C1CCN(C(=O)C2(N)CCC2)CC1] | (R)-6-(1-(1-(1-aminocyclobutane-1-carbonyl)piperidin-4-yl)-5-methyl-1H-pyrazol-4-yl)-4-(1-(5-fluoropyridin-2-yl)ethoxy)pyrazolo[1,5-a]pyridine-3-carbonitrile |
| 44 | 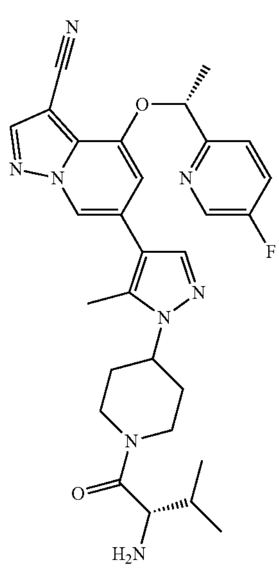 [SMILES: Cc1c(-c2cc(O[C@H](C)c3ccc(F)cn3)c3c(C#N)cnn3c2)cnn1C1CCN(C(=O)[C@@H](N)C(C)C)CC1] | 6-(1-(1-(L-valyl)piperidin-4-yl)-5-methyl-1H-pyrazol-4-yl)-4-((R)-1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 45 | 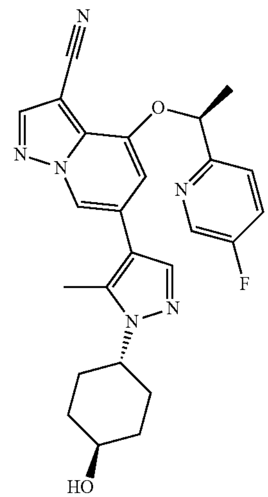 [SMILES: Cc1c(-c2cc(O[C@@H](C)c3ccc(F)cn3)c3c(C#N)cnn3c2)cnn1[C@H]1CC[C@H](O)CC1] | 4-((S)-1-(5-fluoropyridin-2-yl)ethoxy)-6-(1-((1r,4S)-4-hydroxycyclohexyl)-5-methyl-1H-pyrazol-4-yl)pyrazolo[1,5-a]pyridine-3-carbonitrile |
| 46 | 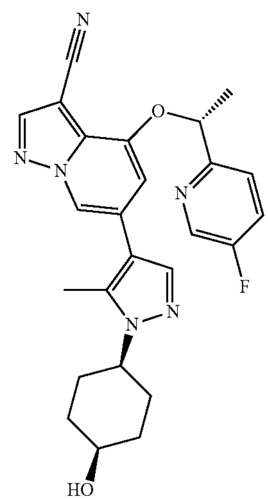 [SMILES: Cc1c(-c2cc(O[C@H](C)c3ccc(F)cn3)c3c(C#N)cnn3c2)cnn1[C@H]1CC[C@@H](O)CC1] | 4-((R)-1-(5-fluoropyridin-2-yl)ethoxy)-6-(1-((1s,4S)-4-hydroxycyclohexyl)-5-methyl-1H-pyrazol-4-yl)pyrazolo[1,5-a]pyridine-3-carbonitrile |
| 47 | 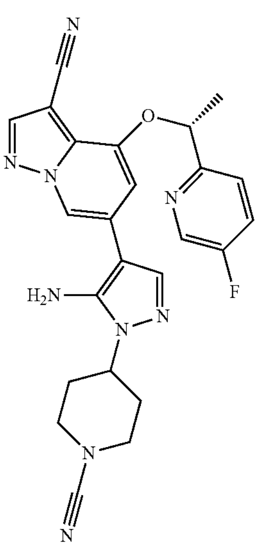 [SMILES: C[C@@H](Oc1cc(-c2cnn(C3CCN(C#N)CC3)c2N)cn2ncc(C#N)c12)c1ccc(F)cn1] | (R)-6-(5-amino-1-(1-cyanopiperidin-4-yl)-1H-pyrazol-4-yl)-4-(1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 48 | 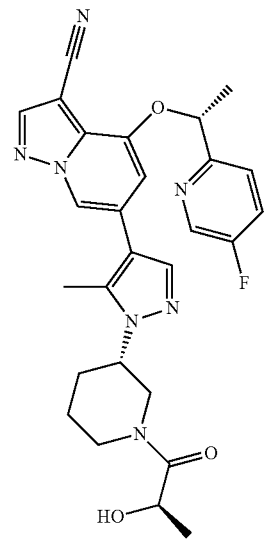 [SMILES: Cc1c(-c2cc(O[C@H](C)c3ccc(F)cn3)c3c(C#N)cnn3c2)cnn1[C@H]1CCCN(C(=O)[C@@H](C)O)C1] | 4-((R)-1-(5-fluoropyridin-2-yl)ethoxy)-6-(1-((S)-1-((R)-2-hydroxypropanoyl)piperidin-3-yl)-5-methyl-1H-pyrazol-4-yl)pyrazolo[1,5-a]pyridine-3-carbonitrile |
| 49 | 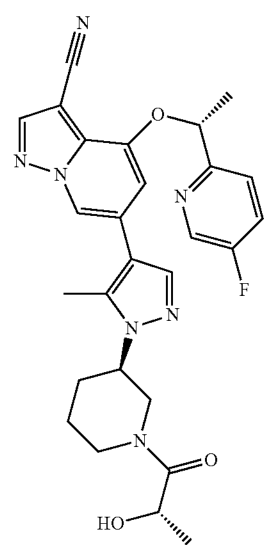 [SMILES: Cc1c(-c2cc(O[C@H](C)c3ccc(F)cn3)c3c(C#N)cnn3c2)cnn1[C@@H]1CCCN(C(=O)[C@H](C)O)C1] | 4-((R)-1-(5-fluoropyridin-2-yl)ethoxy)-6-(1-((R)-1-((S)-2-hydroxypropanoyl)piperidin-3-yl)-5-methyl-1H-pyrazol-4-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 50 | 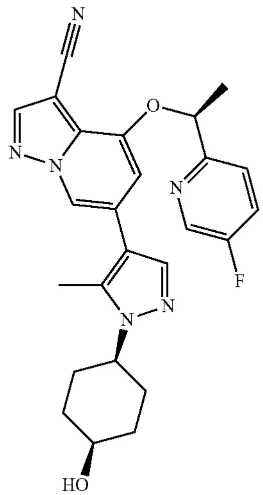 [SMILES: Cc1c(-c2cc(O[C@@H](C)c3ccc(F)cn3)c3c(C#N)cnn3c2)cnn1[C@H]1CC[C@@H](O)CC1] | 4-((S)-1-(5-fluoropyridin-2-yl)ethoxy)-6-(1-((1s,4R)-4-hydroxycyclohexyl)-5-methyl-1H-pyrazol-4-yl)pyrazolo[1,5-a]pyridine-3-carbonitrile |
| 51 | 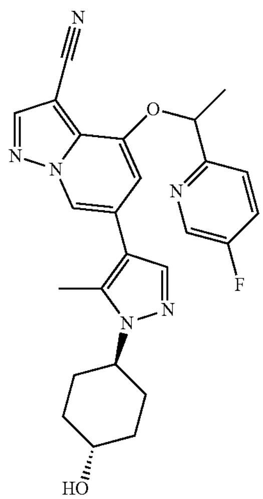 [SMILES: Cc1c(-c2cc(OC(C)c3ccc(F)cn3)c3c(C#N)cnn3c2)cnn1[C@H]1CC[C@H](O)CC1] | 4-(1-(5-fluoropyridin-2-yl)ethoxy)-6-(1-((1r,4r)-4-hydroxycyclohexyl)-5-methyl-1H-pyrazol-4-yl)pyrazolo[1,5-a]pyridine-3-carbonitrile |
| 52 | 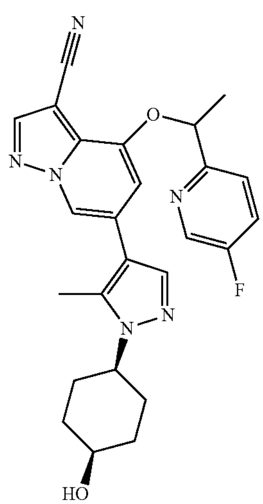 [SMILES: Cc1c(-c2cc(OC(C)c3ccc(F)cn3)c3c(C#N)cnn3c2)cnn1[C@H]1CC[C@@H](O)CC1] | 4-(1-(5-fluoropyridin-2-yl)ethoxy)-6-(1-((1s,4s)-4-hydroxycyclohexyl)-5-methyl-1H-pyrazol-4-yl)pyrazolo[1,5-a]pyridine-3-carbonitrile |

TABLE A-continued
List of Compounds of (I), (IA), (IB)-(IB-3), (IC-a)-(II-a), (IC-b)-(II-b), (III-a)-(III-h), (IV) or (IV-a)
| Compound number | Structure | Chemical Name |
|---|---|---|
| 53 | 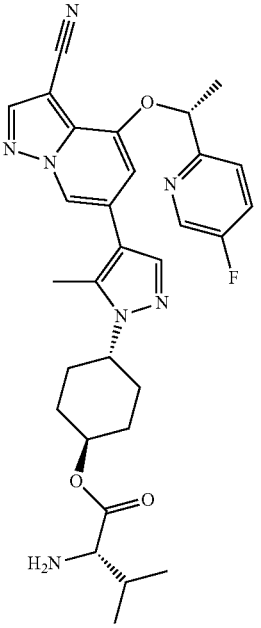 [SMILES: Cc1c(-c2cc(O[C@H](C)c3ccc(F)cn3)c3c(C#N)cnn3c2)cnn1[C@H]1CC[C@H](OC(=O)[C@@H](N)C(C)C)CC1] | (1R,4S)-4-(4-(3-cyano-4-((R)-1-(5-fluoropyridin-2-yl)ethoxy)pyrazolo[1,5-a]pyridin-6-yl)-5-methyl-1H-pyrazol-1-yl)cyclohexyl L-valinate |
| 54 | 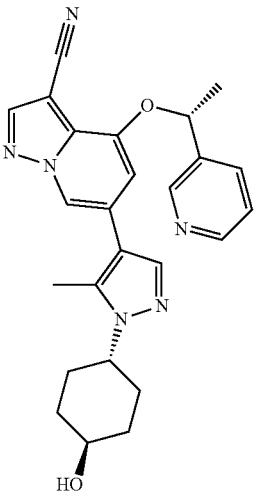 [SMILES: Cc1c(-c2cc(O[C@H](C)c3cccnc3)c3c(C#N)cnn3c2)cnn1[C@H]1CC[C@H](O)CC1] | 6-(1-((1r,4R)-4-hydroxycyclohexyl)-5-methyl-1H-pyrazol-4-yl)-4-((R)-1-(pyridin-3-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 55 | 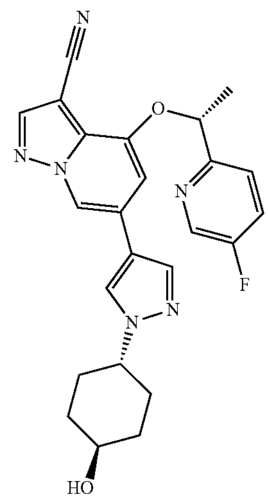 [SMILES: C[C@@H](Oc1cc(-c2cnn([C@H]3CC[C@H](O)CC3)c2)cn2ncc(C#N)c12)c1ccc(F)cn1] | 4-((R)-1-(5-fluoropyridin-2-yl)ethoxy)-6-(1-((1r,4R)-4-hydroxycyclohexyl)-1H-pyrazol-4-yl)pyrazolo[1,5-a]pyridine-3-carbonitrile |
| 56 | 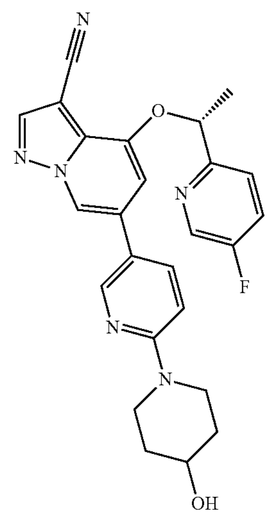 [SMILES: C[C@@H](Oc1cc(-c2ccc(N3CCC(O)CC3)nc2)cn2ncc(C#N)c12)c1ccc(F)cn1] | (R)-4-(1-(5-fluoropyridin-2-yl)ethoxy)-6-(6-(4-hydroxypiperidin-1-yl)pyridin-3-yl)pyrazolo[1,5-a]pyridine-3-carbonitrile |
| 57 | 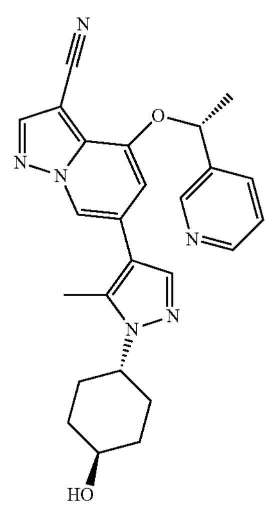 [SMILES: Cc1c(-c2cc(O[C@H](C)c3cccnc3)c3c(C#N)cnn3c2)cnn1[C@H]1CC[C@H](O)CC1] | 6-(1-((1r,4R)-4-hydroxycyclohexyl)-5-methyl-1H-pyrazol-4-yl)-4-((R)-1-(pyridin-3-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 58 | 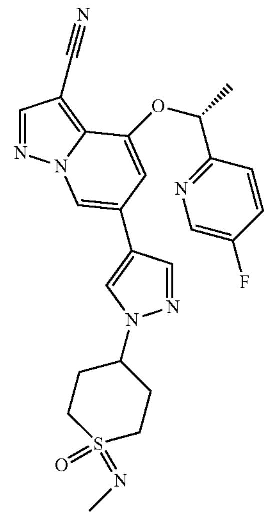 [SMILES: CN=S1(=O)CCC(n2cc(-c3cc(O[C@H](C)c4ccc(F)cn4)c4c(C#N)cnn4c3)cn2)CC1] | (R)-4-(1-(5-fluoropyridin-2-yl)ethoxy)-6-(1-(1-(methylimino)-1-oxidohexahydro-1l6-thiopyran-4-yl)-1H-pyrazol-4-yl)pyrazolo[1,5-a]pyridine-3-carbonitrile |
| 59 | 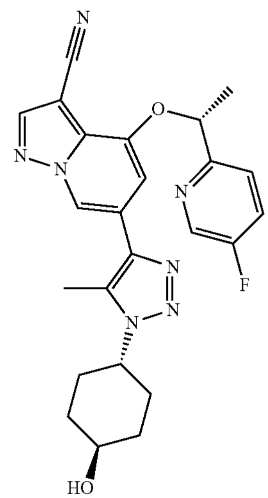 | 4-((R)-1-(5-fluoropyridin-2-yl)ethoxy)-6-(1-((1r,4R)-4-hydroxycyclohexyl)-5-methyl-1H-1,2,3-triazol-4-yl)pyrazolo[1,5-a]pyridine-3-carbonitrile |
| 60 | 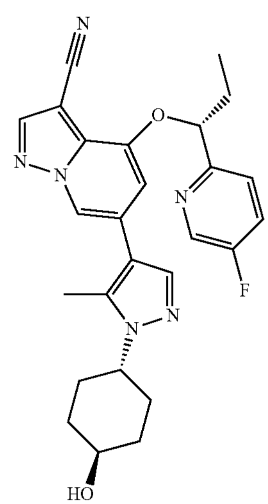 [SMILES: CC[C@@H](Oc1cc(-c2cnn([C@H]3CC[C@H](O)CC3)c2C)cn2ncc(C#N)c12)c1ccc(F)cn1] | 4-((R)-1-(5-fluoropyridin-2-yl)propoxy)-6-(1-((1r,4R)-4-hydroxycyclohexyl)-5-methyl-1H-pyrazol-4-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
| --- | --- | --- |
| 61 | 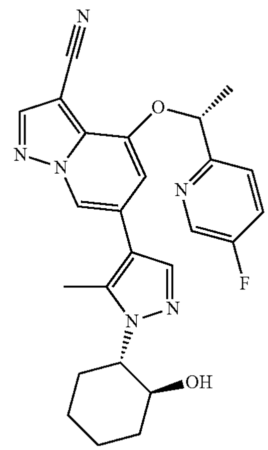 [SMILES: Cc1c(-c2cc(O[C@H](C)c3ccc(F)cn3)c3c(C#N)cnn3c2)cnn1[C@H]1CCCC[C@@H]1O] | 4-((R)-1-(5-fluoropyridin-2-yl)ethoxy)-6-(1-((1S,2S)-2-hydroxycyclohexyl)-5-methyl-1H-pyrazol-4-yl)pyrazolo[1,5-a]pyridine-3-carbonitrile |
| 62 | 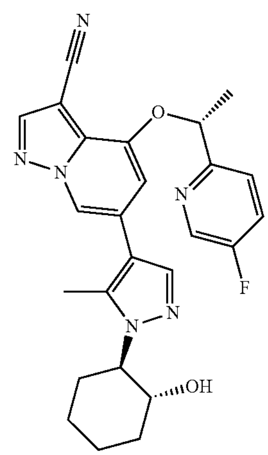 [SMILES: Cc1c(-c2cc(O[C@H](C)c3ccc(F)cn3)c3c(C#N)cnn3c2)cnn1[C@@H]1CCCC[C@H]1O] | 4-((R)-1-(5-fluoropyridin-2-yl)ethoxy)-6-(1-((1R,2R)-2-hydroxycyclohexyl)-5-methyl-1H-pyrazol-4-yl)pyrazolo[1,5-a]pyridine-3-carbonitrile |
| 63 | 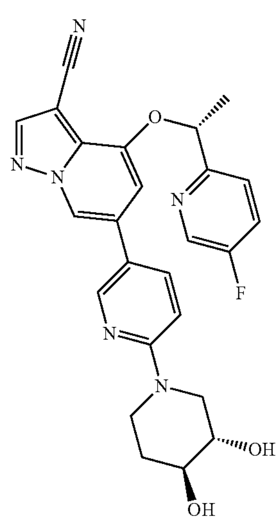 [SMILES: C[C@@H](Oc1cc(-c2ccc(N3CC[C@H](O)[C@@H](O)C3)nc2)cn2ncc(C#N)c12)c1ccc(F)cn1] | 6-(6-((3S,4S)-3,4-dihydroxypiperidin-1-yl)pyridin-3-yl)-4-((R)-1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 64 | 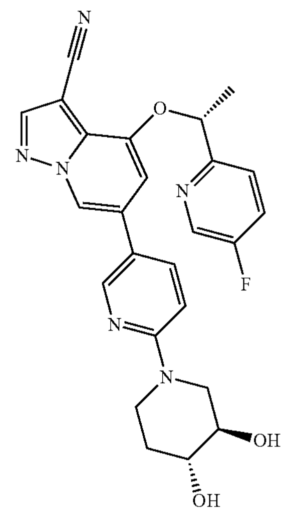 [SMILES: C[C@@H](Oc1cc(-c2ccc(N3CC[C@@H](O)[C@H](O)C3)nc2)cn2ncc(C#N)c12)c1ccc(F)cn1] | 6-(6-((3R,4R)-3,4-dihydroxypiperidin-1-yl)pyridin-3-yl)-4-((R)-1-(5-fluoropyridin-2-yl)ethoxy)pyrazolo[1,5-a]pyridine-3-carbonitrile |
| 65 | 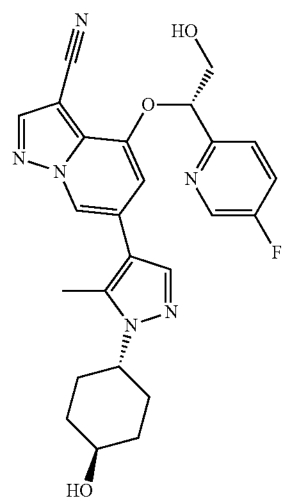 [SMILES: Cc1c(-c2cc(O[C@H](CO)c3ccc(F)cn3)c3c(C#N)cnn3c2)cnn1[C@H]1CC[C@H](O)CC1] | 4-((S)-1-(5-fluoropyridin-2-yl)-2-hydroxyethoxy)-6-(1-((1r,4S)-4-hydroxycyclohexyl)-5-methyl-1H-pyrazol-4-yl)pyrazolo[1,5-a]pyridine-3-carbonitrile |
| 66 | 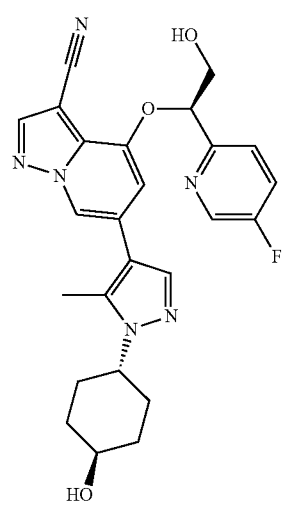 [SMILES: Cc1c(-c2cc(O[C@@H](CO)c3ccc(F)cn3)c3c(C#N)cnn3c2)cnn1[C@H]1CC[C@H](O)CC1] | 4-((R)-1-(5-fluoropyridin-2-yl)-2-hydroxyethoxy)-6-(1-((1r,4R)-4-hydroxycyclohexyl)-5-methyl-1H-pyrazol-4-yl)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 67 | 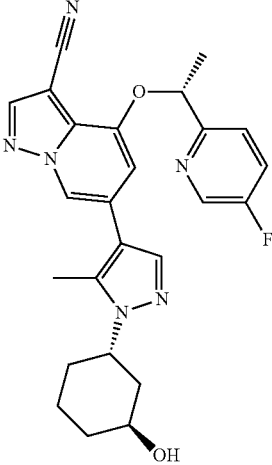 [SMILES: Cc1c(-c2cc(O[C@H](C)c3ccc(F)cn3)c3c(C#N)cnn3c2)cnn1[C@H]1CCC[C@H](O)C1] | 4-((R)-1-(5-fluoropyridin-2-yl)ethoxy)-6-(1-((1S,3S)-3-hydroxycyclohexyl)-5-methyl-1H-pyrazol-4-yl)pyrazolo[1,5-a]pyridine-3-carbonitrile |
| 68 | 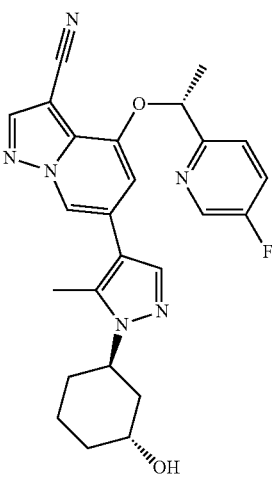 [SMILES: Cc1c(-c2cc(O[C@H](C)c3ccc(F)cn3)c3c(C#N)cnn3c2)cnn1[C@@H]1CCC[C@@H](O)C1] | 4-((R)-1-(5-fluoropyridin-2-yl)ethoxy)-6-(1-((1R,3R)-3-hydroxycyclohexyl)-5-methyl-1H-pyrazol-4-yl)pyrazolo[1,5-a]pyridine-3-carbonitrile |
| 69 | 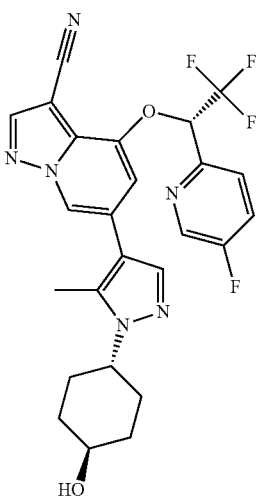 [SMILES: Cc1c(-c2cc(O[C@@H](c3ccc(F)cn3)C(F)(F)F)c3c(C#N)cnn3c2)cnn1[C@H]1CC[C@H](O)CC1] | 6-(1-((1r,4S)-4-hydroxycyclohexyl)-5-methyl-1H-pyrazol-4-yl)-4-((S)-2,2,2-trifluoro-1-(5-fluoropyridin-2-yl)ethoxy)pyrazolo[1,5-a]pyridine-3-carbonitrile |

TABLE A-continued

List of Compounds of (I), (IA), (IB)-(IB-3), (IC-a)-(II-a), (IC-b)-(II-b), (III-a)-(III-h), (IV) or (IV-a)

| Compound number | Structure | Chemical Name |
|---|---|---|
| 70 | 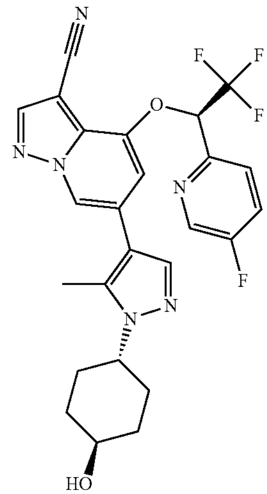 [SMILES: Cc1c(-c2cc(O[C@H](c3ccc(F)cn3)C(F)(F)F)c3c(C#N)cnn3c2)cnn1[C@H]1CC[C@H](O)CC1] | 6-(1-((1r,4R)-4-hydroxycyclohexyl)-5-methyl-1H-pyrazol-4-yl)-4-((R)-2,2,2-trifluoro-1-(5-fluoropyridin-2-yl)ethoxy)pyrazolo[1,5-a]pyridine-3-carbonitrile |
| 71 | 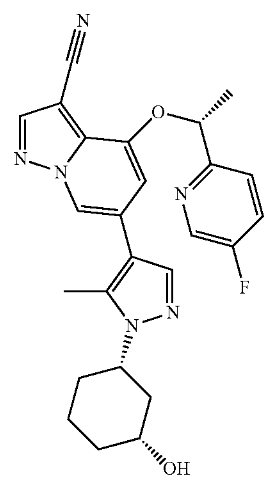 [SMILES: Cc1c(-c2cc(O[C@H](C)c3ccc(F)cn3)c3c(C#N)cnn3c2)cnn1[C@H]1CCC[C@@H](O)C1] | 4-((R)-1-(5-fluoropyridin-2-yl)ethoxy)-6-(1-((1S,3R)-3-hydroxycyclohexyl)-5-methyl-1H-pyrazol-4-yl)pyrazolo[1,5-a]pyridine-3-carbonitrile |
| 72 | 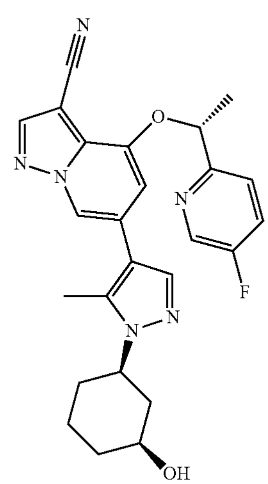 [SMILES: Cc1c(-c2cc(O[C@H](C)c3ccc(F)cn3)c3c(C#N)cnn3c2)cnn1[C@@H]1CCC[C@H](O)C1] | 4-((R)-1-(5-fluoropyridin-2-yl)ethoxy)-6-(1-((1R,3S)-3-hydroxycyclohexyl)-5-methyl-1H-pyrazol-4-yl)pyrazolo[1,5-a]pyridine-3-carbonitrile |

As can be appreciated, the ionizable lipids described herein enable the development of new therapies for disease without the need for exotic chemistry or specialized reagents or manufacturing techniques.

III. Pharmaceutical Compositions

Other embodiments are directed to pharmaceutical compositions. In an embodiment, the pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such additional therapeutic agents are described below.

Suitable routes of administration include, but are not limited to, oral, intravenous, rectal, aerosol, parenteral, ophthalmic, pulmonary, transmucosal, transdermal, vaginal, optical, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the compound is delivered in a targeted drug delivery system, for example, in a liposome coated with and organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In treatment methods according to embodiments of the disclosure, an effective amount of at least one compound of Formula (I), (IA), (IB)-(IB-3), (IC-a)-(II-a), (IC-b)-(II-b), (III-a)-(III-h), (IV) or (IV-a) is administered to a subject suffering from or diagnosed as having such a disease, disorder, or medical condition. Effective amounts or doses may be ascertained by methods such as modeling, dose escalation studies or clinical trials, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

The compounds according to the disclosure are effective over a wide dosage range. For example, in the treatment of adult humans, dosages from about 0.001 to 0.1 mg, 0.01 to 0.1 mg, 0.5 to 5 mg, 0.5 to 10 mg, 0.01-10 mg, 0.1 to 10 mg, 10 to 5000 mg, 100 to 5000 mg, 1000 mg to 4000 mg per day, or 1000 to 3000 mg per day are examples of dosages that are used in some embodiments. The exact dosage will depend upon the route of administration, the form in which the compound is administered, the subject to be treated, the body weight of the subject to be treated, and the preference and experience of the attending physician.

In some embodiments, compounds of the disclosure are administered in a single dose. In an embodiment, the single dose is administered orally. In another embodiment, the single dose is administered topically. However, other routes are used as appropriate. In some embodiments, compounds of the disclosure are administered in multiple doses. In some embodiments, dosing is about once, twice, three times, four times, five times, six times, or more than six times per day. In other embodiments, dosing is about once a month, once every two weeks, once a week, or once every other day. In another embodiment compounds of the disclosure and another agent (e.g., anti-cancer agent) are administered together about once per day to about 6 times per day. In another embodiment the administration of compounds of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of compounds of the disclosure may continue as long as necessary. In some embodiments, compounds of the disclosure are administered for more than 1, 2, 3, 4, 5, 6, 7, 14, or 28 days. In some embodiments, compounds of the disclosure are administered for less than 28, 14, 7, 6, 5, 4, 3, 2, or 1 day. In some embodiments, compounds of the disclosure are administered chronically on an ongoing basis, e.g., for the treatment of chronic effects.

In some embodiments, the compounds of the disclosure are administered in individual dosage forms. It is known in the art that due to intersubject variability in compound pharmacokinetics, individualization of dosing regimen is necessary for optimal therapy.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the disclosed compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising one or more compounds of Formula (I), (IA), (IB)-(IB-3), (IC-a)-(II-a), (IC-b)-(II-b), (III-a)-(III-h), (IV) or (IV-a), and a pharmaceutically acceptable carrier. Also provided herein are pharmaceutical compositions comprising one or more compounds selected from compounds of Formula (I), (IA), (IB)-(IB-3), (IC-a)-(II-a), (IC-b)-(II-b), (III-a)-(III-h), (IV) or (IV-a) and pharmaceutically acceptable diluent(s), excipient(s), and carrier(s). In certain embodiments, the compounds described are administered as pharmaceutical compositions in which one or more compounds selected from compounds of Formula (I), (IA), (IB)-(IB-3), (IC-a)-(II-a), (IC-b)-(II-b), (III-a)-(III-h), (IV) or (IV-a) are mixed with other active ingredients, as in combination therapy. Encompassed herein are all combinations of actives set forth in the combination therapies section below and throughout this disclosure. In specific embodiments, the pharmaceutical compositions include one or more compounds of Formula (I), (IA), (IB)-(IB-3), (IC-a)-(II-a), (IC-b)-(II-b), (III-a)-(III-h), (IV) or (IV-a).

A pharmaceutical composition, as used herein, refers to a mixture of one or more compounds selected from compounds of Formula (I), (IA), (IB)-(IB-3), (IC-a)-(II-a), (IC-b)-(II-b), (III-a)-(III-h), (IV) or (IV-a) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, therapeutically effective amounts of one or more compounds selected from compounds of Formula (I), (IA), (IB)-(IB-3), (IC-a)-(II-a), (IC-b)-(II-b), (III-a)-(III-h), (IV) or (IV-a) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds selected from compounds of Formula (I), (IA), (IB)-(IB-3), (IC-a)-(II-a), (IC-b)-(II-b), (III-a)-(III-h), (IV) or (IV-a) are formulated in aqueous solutions. In specific embodiments, the aqueous solution is selected from, by way of example only, a physiologically compatible buffer, such as Hank's solution, Ringer's solution, or physiological saline buffer. In other embodiments, one or more compounds selected from compounds of Formula (I), (IA), (IB)-(IB-3), (IC-a)-(II-a), (IC-b)-(II-b), (III-a)-(III-h), (IV) or (IV-a) are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross linked croscarmellose sodium, polyvinylpyrrolidone, agar, or alginic acid or a salt thereof such as sodium alginate.

In one embodiment, the oral dosage forms, such as a pill, capsule or tablet, comprises one or more suitable layers or coatings. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push fit capsules made of gelatin, as well as soft, sealed capsules made of gelatin and a plasticizer, such as glycerol or sorbitol. In specific embodiments, push fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds described herein are formulated for parental injection, including formulations suitable for bolus injection or continuous infusion. In specific embodiments, formulations for injection are presented in unit dosage form (e.g., in ampoules) or in multi dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water soluble form. In additional embodiments, suspensions of one or more compounds selected from compounds of Formula (I), (IA), (IB)-(IB-3), (IC-a)-(II-a), (IC-b)-(II-b), (III-a)-(III-h), (IV) or (IV-a) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions include at least one pharmaceutically acceptable carrier, diluent or excipient, and one or more compounds selected from compounds of Formula (I), (IA), (IB)-(IB-3), (IC-a)-(II-a), (IC-b)-(II-b), (III-a)-(III-h), (IV) or (IV-a) as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compound(s) with one or more inert, pharmaceutically acceptable excipients or carriers to form a solid, semi-solid or liquid composition. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, ointments, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical compositions comprising one or more compounds selected from compounds of Formula (I), (IA), (IB)-(IB-3), (IC-a)-(II-a), (IC-b)-(II-b), (III-a)-(III-h), (IV) or (IV-a) illustratively takes the form of a liquid where the agents are present in solution, in suspension or both. Typically when the composition is administered as a suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of one or more compounds selected from compounds of Formula (I), (IA), (IB)-(IB-3), (IC-a)-(II-a), (IC-b)-(II-b), (III-a)-(III-h), (IV) or (IV-a). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained release system, such as semipermeable matrices of solid hydrophobic polymers containing the therapeutic agent. Various sustained release materials are useful herein. In some embodiments, sustained release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

In some embodiments, the concentration of one or more compounds selected from compounds of Formula (I), (IA), (IB)-(IB-3), (IC-a)-(II-a), (IC-b)-(II-b), (III-a)-(III-h), (IV) or (IV-a) provided in the pharmaceutical compositions is greater than 90%, 80%, 75%, 70%, 65%, 60%, 55%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25%, 7%, 6.75%, 6.50%, 6.25% 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v. In another embodiment, the amount of a compound selected from compounds of Formula (I), (IA), (IB)-(IB-3), (IC-a)-(II-a), (IC-b)-(II-b), (III-a)-(III-h), (IV) or (IV-a) in the pharmaceutical compositions is an amount between about any two of the values recited in the preceding sentence, for example, between about 2-70 w/w %, 3.5-80 w/w %, 1-30 w/w %, etc.

In some embodiments, the concentration of one or more compounds selected from compounds of Formula (I), (IA), (IB)-(IB-3), (IC-a)-(II-a), (IC-b)-(II-b), (III-a)-(III-h), (IV) or (IV-a) provided in the pharmaceutical compositions of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the amount the one or more compounds selected from compounds of Formula (I), (IA), (IB)-(IB-3), (IC-a)-(II-a), (IC-b)-(II-b), (III-a)-(III-h), (IV) or (IV-a) provided in the pharmaceutical compositions of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the one or more compounds selected from compounds of Formula (I), (IA), (IB)-(IB-3), (IC-a)-(II-a), (IC-b)-(II-b), (III-a)-(III-h), (IV) or (IV-a) provided in the pharmaceutical compositions of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Packaging materials for use in packaging pharmaceutical compositions described herein include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container (s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

As mentioned above, the compounds and compositions of the disclosure will find utility in a broad range of diseases and conditions mediated by protein kinases, including diseases and conditions mediated by kinase. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colon-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In some embodiments, a pharmaceutical composition has a compound described above and a pharmaceutically acceptable carrier including, for example, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In some embodiments, the compound of the pharmaceutical composition for use in treating a disease associated with mutations in fibroblast growth factor receptor 2 (FGFR2) or fibroblast growth factor receptor 3 (FGFR3) is provided.

In some embodiments, the compounds of the present disclosure may have enhanced solubility, ADME profile (e.g., permeability, metabolic stability), pharmacokinetics, selectivity against hERG, selectivity against FGFR1, and/or selectivity against anti-targets as compared to other FGFR inhibitors. In some embodiments, a method of treating a disease associated with mutations in FGFR2 or FGFR3, comprising: administering the compound or the pharmaceutical composition to a subject in need thereof. In some embodiments, the subject is an animal. In some embodiments, the subject is a human. In some embodiments, the disease associated with mutations in FGFR2 is a cancer or craniosynostoic syndrome. In some certain embodiments, the cancer is intrahepatic cholangiocarcinoma, hepatocellular carcinoma, breast cancer, prostate cancer, lung squamous cell carcinoma, thyroid cancer, gastric cancer, ovarian cancer, endometrial cancer, non-small cell lung cancer, urothelial cancers, colorectal cancer, colon cancer, metastatic cholangiocarcinoma, cholangiocarcinoma, osteosarcoma, gastroesophageal junction adenocarcinoma, biliary tract cancer, anaplastic thyroid carcinoma, ganglioglioma, pancreatic intraductal tubulopapillary neoplasm, gallbladder carcinoma, renal cell carcinoma, myxoid lipocarcinoma, triple negative breast cancer, or rectal cancer. In some certain embodiments, the craniosynostoic syndrome is craniosynostosis, bent bone dysplasia, crouzon syndrome, apert syndrome, pfeiffer syndrome, antley-bixler, beare-stevenson syndrome, jackson-weiss syndrome, or seathre-chotzen-like syndromes. In some embodiments, the disease associated with mutations in FGFR3 is systemic sclerosis, fibrosis, pulmonary fibrosis, achondroplasia, thanatophoric dysplasia, severe achondroplasia with developmental delay and acanthosis nigricans (SADDAN syndrome), muenke syndrome, FGFR3 associated cancer, hypochondroplasia, FGFR3 related craniosynostosis, LADD syndrome, or Alzheimer disease.

IV. Methods of Preparation and Examples

Preparation methods for the above compounds and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Syntheses for the compounds of Formula (I) are described below.
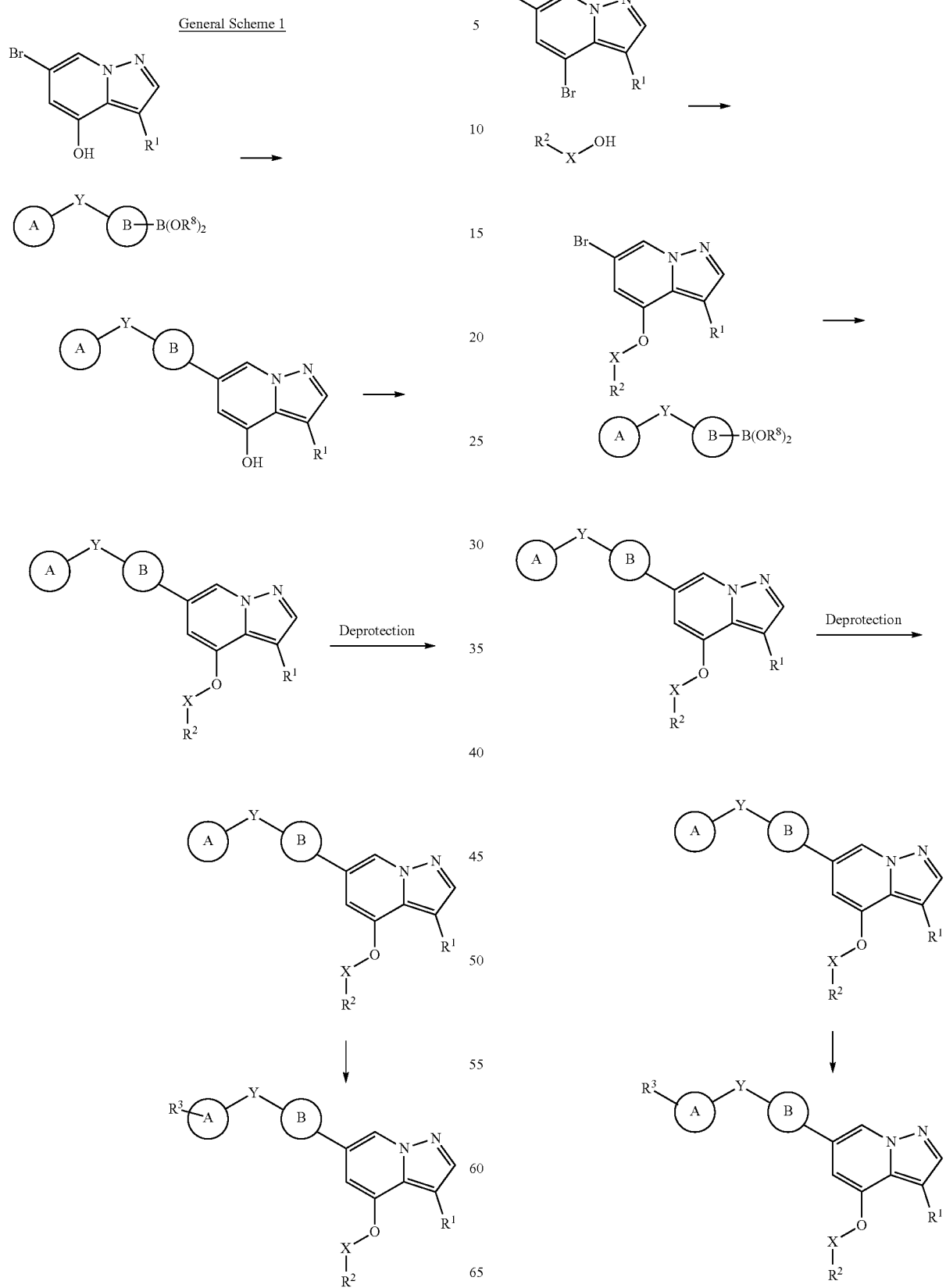

Intermediate 1

6-bromo-4-[(1R)-1-(5-fluoro-2-pyridyl)ethoxy]pyrazolo[1,5-a]pyridine-3-carbonitrile

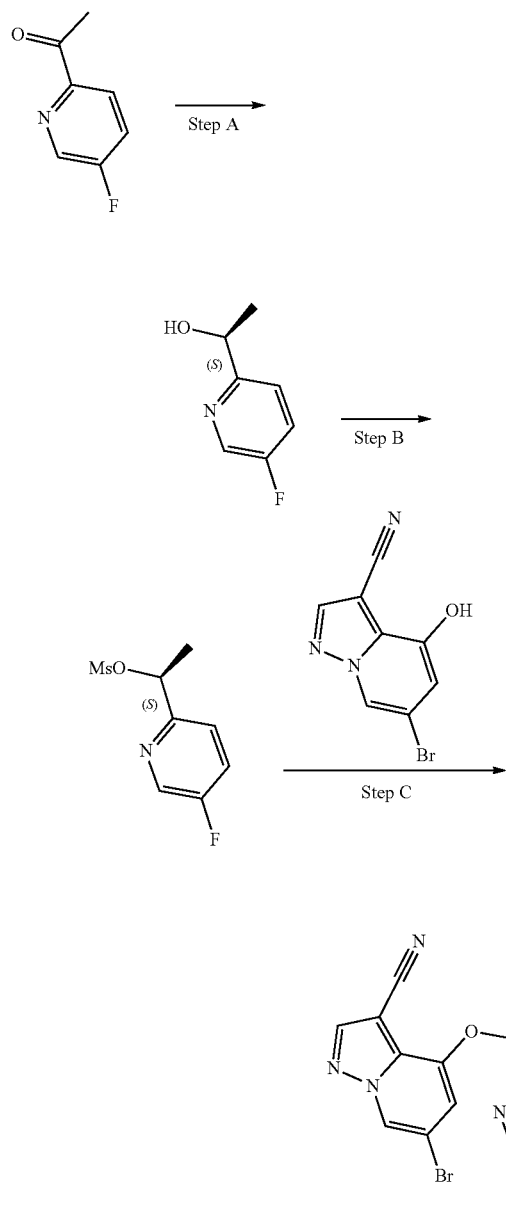

Step A. (1S)-1-(5-fluoro-2-pyridyl)ethanol. To a 500 mL three-necked round-bottom flask equipped with a magnetic stir bar was added (3aR)-1-methyl-3,3-diphenyl-3a,4,5,6-tetrahydropyrrolo[1,2-c][1,3,2]oxazaborole (1 M, 35.94 mL) followed by the addition of THF (100 mL). The flask was then evacuated and backfilled with nitrogen three times. The mixture was cooled to 0° C. $BH_3\text{-}Me_2S$ (10 M, 3.59 mL) was added dropwise and the reaction mixture was stirred for 1 h. The mixture was cooled to −20° C., 1-(5-fluoro-2-pyridyl)ethanone (5 g, 35.94 mmol) dissolved in THF (20 mL) was added dropwise over 0.5 h. The mixture was stirred at −20° C. under an atmosphere of nitrogen for 1 h. The mixture was quenched by slow addition of 1 M HCl (100 mL), the pH of mixture was adjusted to pH=8 by using saturated aqueous sodium bicarbonate. The resulting mixture was extracted with dichloromethane (100 mL×3). The combined organic layers were dried over anhydrous sodium sulfate, filtered, concentrated under reduced pressure and purified by silica gel column chromatography (5-20% ethyl acetate in petroleum ether) to give the desired product (1S)-1-(5-fluoro-2-pyridyl)ethanol (4 g, 74% yield) as a colorless oil.

Step B. [(1S)-1-(5-fluoro-2-pyridyl)ethyl]methanesulfonate. To a 100 mL round bottom flask equipped with a magnetic stir bar was added (1S)-1-(5-fluoro-2-pyridyl)ethanol (800 mg, 5.54 mmol) followed by the addition of DCM (10 mL). TEA (1.9 mL, 13.54 mmol) was added dropwise. The solution was cooled to 0° C. Methylsulfonyl methanesulfonate (1.43 g, 8.21 mmol) in DCM (10 mL) was added dropwise. The mixture was allowed to warm to 25° C. and stir for 1 h. Water (20 mL) was added to the reaction and the mixture was transferred to a separatory funnel and the aqueous layer was extracted with dichloromethane (30 mL×3). The combined organic layer was dried over anhydrous sodium sulfate, filtered, concentrated under reduced pressure affording the residue as a brown oil, [(1S)-1-(5-fluoro-2-pyridyl)ethyl]methanesulfonate (1.2 g, crude product) and used into the next step without further purification.

Step C. 6-bromo-4-[(1R)-1-(5-fluoro-2-pyridyl)ethoxy]pyrazolo[1,5-a]pyridine-3-carbonitrile. To a 40 mL vial equipped with a magnetic stir bar was added 6-bromo-4-hydroxy-pyrazolo[1,5-a]pyridine3-carbonitrile (450 mg, 1.89 mmol) and [(1S)-1-(5-fluoro-2-pyridyl)ethyl]methanesulfonate (600 mg, 2.74 mmol) followed by the addition of DMF (8 mL). $K_2CO_3$ (765 mg, 5.54 mmol) was added into the mixture at 25° C. The mixture was stirred at 90° C. for 1 h. The mixture was quenched by slow addition of $H_2O$ (15 mL). The resulting mixture was extracted with ethyl acetate (15 mL×3). The combined organic layers were washed with brine (15 mL×3), dried over anhydrous sodium sulfate, filtered, concentrated under reduced pressure and purified by silica gel column chromatography (8-12% ethyl acetate in petroleum ether) to give 6-bromo-4-[(1R)-1-(5-fluoro-2-pyridyl)ethoxy]pyrazolo[1,5-a]pyridine-3-carbonitrile (1.25 g, 91% yield) as a colorless oil. LCMS (MM-ES+APCI, Pos): m/z 360.8 (M+H).

Intermediate 2

4-[(1R)-1-(5-fluoro-2-pyridyl)ethoxy]-6-(4,4,5,5-tetramethyl-1,3,2-dioxaborolan-2-yl) pyrazolo[1,5-a]pyridine-3-carbonitrile

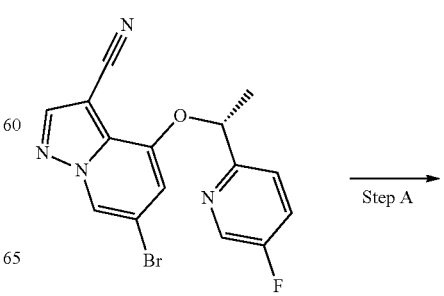

-continued

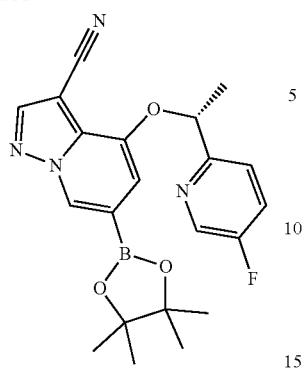

Step A. (R)-4-(1-(5-fluoropyridin-2-yl)ethoxy)-6-(4,4,5,5-tetramethyl-1,3,2-dioxaborolan-2-yl) pyrazolo[1,5-a]pyridine-3-carbonitrile. To a 40 mL vial equipped with a magnetic stir bar was added 6-bromo-4-[(1R)-1-(5-fluoro-2-pyridyl)ethoxy]pyrazolo[1,5-a]pyridine-3-carbonitrile (1 g, 2.74 mmol), 4,4,5,5-tetramethyl-2-(4,4,5,5-tetramethyl-1,3,2-dioxaborolan-2-yl)-1,3,2-dioxaborolane (1.04 g, 4.11 mmol) followed by the addition of dioxane (20 mL). [2-(2-Aminoethyl)phenyl]-chloro-palladium; dicyclohexyl-[2-(2,4,6-triisopropylphenyl)phenyl]phosphane (101 mg, 0.13 mmol), XPhos (131 mg, 0.27 mmol) and KOAc (538 mg, 5.48 mmol) were added into the mixture at 25° C. The vial was then purged with nitrogen for 2 min. The mixture was stirred at 100° C. under an atmosphere of nitrogen for 1 h. Water (30 mL) was added to the reaction and the mixture was transferred to a separatory funnel and the aqueous layer was extracted with ethyl acetate (20 mL×3). The combined organic layer was washed with brine (65 mL), dried over anhydrous sodium sulfate, filtered, concentrated under reduced pressure and purified by silica gel column chromatography (25-30% petroleum ether/ethyl acetate) to give 4-[(1R)-1-(5-fluoro-2-pyridyl)ethoxy]-6-(4,4,5,5-tetramethyl-1,3,2-dioxaborolan-2-yl) pyrazolo[1,5-a]pyridine-3-carbonitrile (900 mg, 76% yield) as a yellow oil. LCMS (MM-ES+APCI, Pos): m/z 326.8 (M+H).

Intermediate 3 t-Butyl 4-[4-(4-bromo-3-cyano-pyrazolo[1,5-a]pyridin-6-yl)-5-methyl-pyrazol-1-yl]piperidine-1-carboxylate

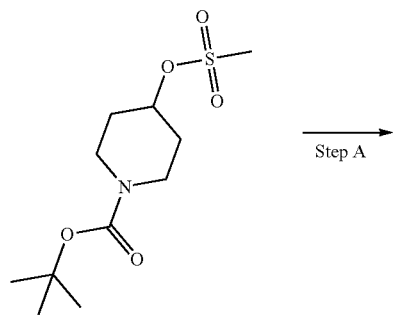

-continued

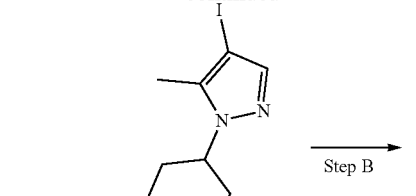

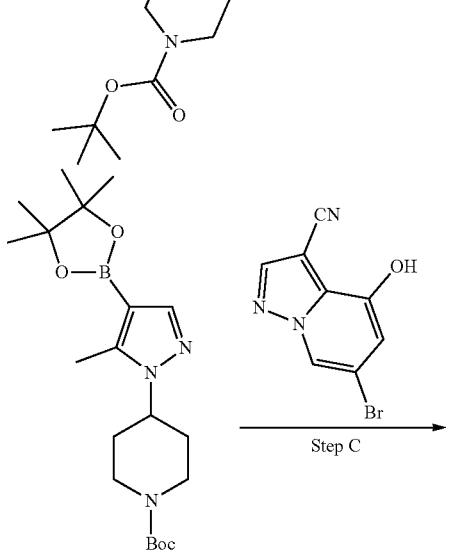

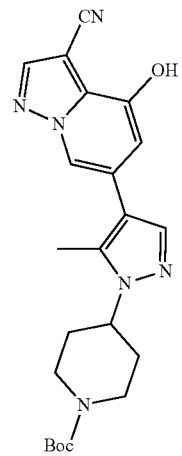

Step A. t-Butyl 4-(4-iodo-5-methyl-pyrazol-1-yl) piperidine-1-carboxylate. To a round-bottom flask equipped with a magnetic stir bar and a reflux condenser was added 4-iodo-5-methyl-1H-pyrazole (10 g, 48 mmol), tert-butyl 4-methylsulfonyloxypiperidine-1-carboxylate (20 g, 72 mmol) and cesium carbonate (31 g, 96 mmol) followed by the addition of N, N-dimethylformamide (300 mL). The mixture was stirred at 90° C. for 4.5 hr. Water (600 mL) was added to the reaction and the mixture was transferred to a separatory funnel. The aqueous layer mixture was extracted with ethyl acetate (200 mL×3). The combined organic layers were washed with brine (800 mL), dried over anhydrous sodium sulfate, filtered, concentrated under reduced pressure and purified by silica gel column chromatography (0-60% EtOAc/petroleum ether) to give tert-butyl 4-(4-iodo-5-methyl-pyrazol-1-yl) piperidine-1-carboxylate (4.4 g, 23% yield) as a white solid.

Step B. t-Butyl 4-[5-methyl-4-(4,4,5,5-tetramethyl-1,3,2-dioxaborolan-2-yl) pyrazol-1-yl]piperidine-1-carboxylate.

To a 250 mL round-bottom flask equipped with a magnetic stir bar was added tert-butyl 4-(4-iodo-5-methyl-pyrazol-1-yl) piperidine-1-carboxylate (4.4 g, 11.3 mmol) followed by the addition of THF (120 mL). Isopropylmagnesium chloride (2 M, 23 mL, 45 mmol) was added to the mixture and stirred for 1 h at 25° C. 2-methoxy-4,4,5,5-tetramethyl-1,3,2-dioxaborolane (8.9 g, 56 mmol) was added to the mixture and stirred at 25° C. for 3 h. Water (300 mL) was added to the reaction and the mixture was transferred to a separatory funnel. The aqueous mixture was extracted with ethyl acetate (3×100 mL). The combined organic layers were washed with brine (400 mL×3), dried over anhydrous sodium sulfate, filtered, concentrated under reduced pressure and purified by silica gel column chromatography (0-10% EtOAc/petroleum ether) to give tert-butyl 4-[5-methyl-4-(4,4,5,5-tetramethyl-1,3,2-dioxaborolan-2-yl) pyrazol-1-yl]piperidine-1-carboxylate (1.9 g, 40% yield) as a white solid. LCMS (MM-ES+APCI, Pos): m/z 392.4 (M+H).

Step C. t-Butyl 4-[4-(3-cyano-4-hydroxy-pyrazolo[1,5-a] pyridin-6-yl)-5-methyl-pyrazol-1-yl]piperidine-1-carboxylate. Synthesized according to Intermediate 2, Step A, substituting tert-butyl 4-[5-methyl-4-(4,4,5,5-tetramethyl-1,3,2-dioxaborolan-2-yl) pyrazol-1-yl]piperidine-1-carboxylate for tert-butyl(3S)-3-[4-(4,4,5,5-tetramethyl-1,3,2-dioxaborolan-2-yl) pyrazol-1-yl]piperidine-1-carboxylate to give tert-butyl 4-[4-(3-cyano-4-hydroxy-pyrazolo[1,5-a]pyridin-6-yl)-5-methyl-pyrazol-1-yl]piperidine-1-carboxylate (10 g, 80% yield) as a white solid. LCMS (MM-ES+APCI, Pos): m/z 367.0 (M-tBu+H).

Intermediate 4 tert-butyl(3S)-3-[5-methyl-4-(4,4,5,5-tetramethyl-1,3,2-dioxaborolan-2-yl) pyrazol-1-yl]piperidine-1-carboxylate

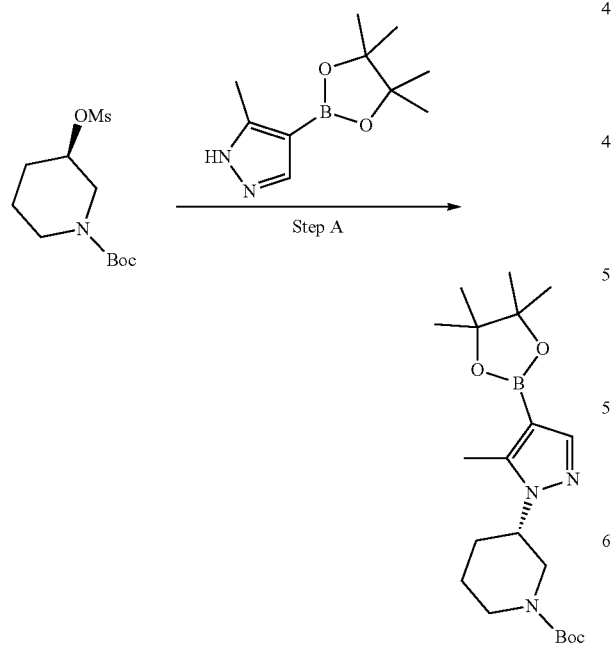

Step A. tert-butyl(3S)-3-[5-methyl-4-(4,4,5,5-tetramethyl-1,3,2-dioxaborolan-2-yl) pyrazol-1-yl]piperidine-1-carboxylate. To a 250 mL three-necked round-bottom equipped with a magnetic stir bar and a reflux condenser was added tert-butyl(3R)-3-methylsulfonyloxypiperidine-1-carboxylate (8.0 g, 28.84 mmol) followed by the addition of DMF (20 mL). 5-Methyl-4-(4,4,5,5-tetramethyl-1,3,2-dioxaborolan-2-yl)-1H-pyrazole (2.0 g, 9.61 mmol) and Cs₂CO₃ (18.8 g, 57.67 mmol) were added into the mixture dropwise at 25° C. The mixture was heated to 90° C. and stirred for 1 h. Water (20 mL) was added to the reaction and the mixture was transferred to a separatory funnel. The aqueous mixture was extracted with ethyl acetate (4×10 mL). The combined organic layers were washed with brine (20 mL), dried over anhydrous sodium sulfate, filtered, concentrated under reduced pressure and purified by silica gel column chromatography (0-50% petroleum ether/ethyl acetate) to give tert-butyl(3S)-3-[5-methyl-4-(4,4,5,5-tetramethyl-1,3,2-dioxaborolan-2-yl) pyrazol-1-yl]piperidine-1-carboxylate (200.0 mg, 5% yield) as an orange oil.

Intermediate 5 tert-butyl-dimethyl-[4-[5-methyl-4-(4,4,5,5-tetramethyl-1,3,2-dioxaborolan-2-yl) pyrazol-1-yl]cyclohexoxy]silane

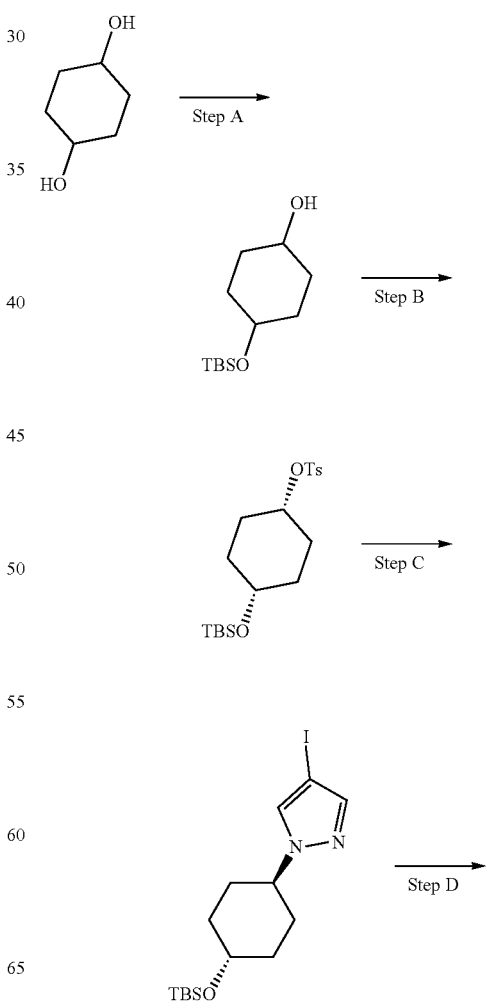

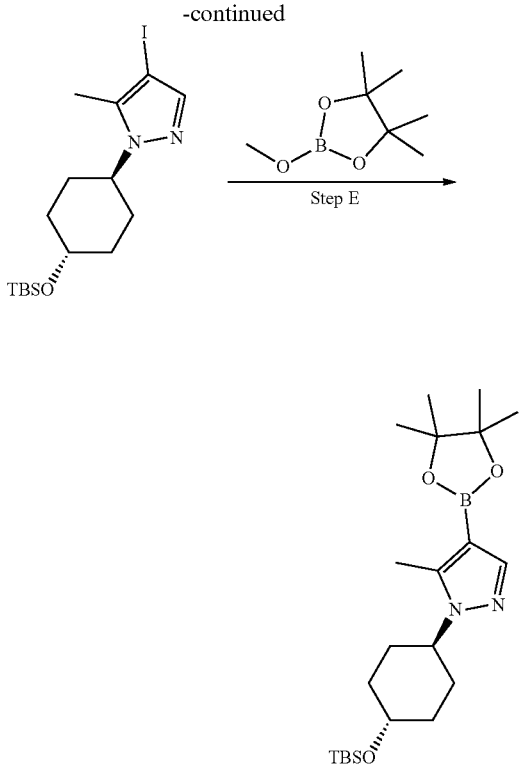

Step A. 4-[tert-butyl(dimethyl) silyl]qoxycyclohexanol. To a 1000 mL round-bottom flask equipped with a magnetic stir bar was added cyclohexane-1,4-diol (25 g, 215.22 mmol) and imidazole (29.30 g, 430.45 mmol) followed by the addition of THF (300 mL). The solution was cooled to 0° C. Tert-butyl-chloro-dimethyl-silane (21.2 mL, 172.18 mmol) dissolved in THF (100 mL) was added dropwise. The mixture was allowed to warm to 25° C. and stir for 2 h. Water (50 mL) was added to the reaction and the mixture was transferred to a separatory funnel. The aqueous mixture was extracted with petroleum ether (3×50 mL). The combined organic layers were washed with brine (20 mL×3), dried over anhydrous sodium sulfate, filtered, concentrated under reduced pressure and purified by silica gel column chromatography (5-20% ethyl acetate/petroleum ether) to give 4-[tert-butyl(dimethyl) silyl]qoxycyclohexanol (25 g, 34% yield) as a colorless oil.

Step B. [4-[tert-butyl(dimethyl) silyl]oxycyclohexyl]4-methylbenzenesulfonate. Five parallel reactions. To a 250 mL three-necked round-bottom equipped with a magnetic stir bar was added 4-[tertbutyl(dimethyl) silyl]oxycyclohexanol (20 g, 86.80 mmol) followed by the addition of pyridine (80 mL). The solution was cooled to 0° C. 4-Methylbenzenesulfonyl chloride (33.10 g, 173.60 mmol) was added into mixture. The mixture was allowed to warm to 25° C. and stir for 16 h. The mixture was poured into H₂O (6000 mL) and stirred for 60 min. The solids were filtered, washed with water, and dried under vacuum to give a light yellow solid. The light yellow solid was suspended in hexanes (80 mL) and heated to reflux. The solution was allowed to fully cool to 25° C. The resultant solids were filtered to afford a white solid. Repeat the re-crystallization steps seven times to get [4-[tert-butyl(dimethyl) silyl]oxycyclohexyl]4-methylbenzenesulfonate (29.4 g, 17% yield) as a white solid.

Step C. tert-butyl-[4-(4-iodopyrazol-1-yl)cyclohexoxy]-dimethyl-silane. To a 250 mL round-bottom flask equipped with a magnetic stir bar was added 4-iodo-1H-pyrazole (1.98 g, 10.22 mmol) and [4-[tert-butyl(dimethyl) silyl]oxycyclohexyl]4-methylbenzenesulfonate (5 g, 12.49 mmol) followed by the addition of DMF (60 mL). Cs₂CO₃ (7.41 g, 22.73 mmol) was added into the mixture at 25° C. The mixture was heated to 90° C. and stirred for 16 h. The mixture was quenched by slow addition of H₂O (250 mL). The resulting mixture was transferred to a separatory funnel, and the aqueous layer mixture was extracted with ethyl acetate (150 mL×3). The combined organic layers were washed with brine (100 mL×3), dried over anhydrous sodium sulfate, filtered, concentrated under reduced pressure affording the residue and purified by silica gel column chromatography (10-20% ethyl acetate/petroleum ether) to give tert-butyl-[4-(4-iodopyrazol-1-yl)cyclohexoxy]-dimethyl-silane (5.75 g, 43% yield) as a colorless oil. LCMS (MM-ES+APCI, Pos): m/z 407.2 (M+H).

Step D. tert-butyl-[4-(4-iodo-5-methyl-pyrazol-1-yl)cyclohexoxy]-dimethyl-silane. To a 250 mL three-necked round-bottom flask equipped with a magnetic stir bar was added tert-butyl-[4-(4-iodopyrazol-1-yl)cyclohexoxy]-dimethyl-silane (5.75 g, 12.18 mmol) followed by the addition of THF (100 mL). The solution was cooled to -75° C. The flask was then evacuated and backfilled with nitrogen for three times. LDA (2 M, 9.50 mL, 19 mmol) was added dropwise. The mixture was stirred at -75° C. for 1 h. Iodomethane (1.14 mL, 18.27 mmol) was added dropwise. The mixture was stirred at -75° C. for 1 h. The mixture was quenched by slow addition of H₂O (50 mL). The resulting mixture was transferred to a separatory funnel, and the aqueous layer mixture was extracted with ethyl acetate (100 mL×3). The combined organic layers were washed with brine (50 mL), dried over anhydrous sodium sulfate, filtered, concentrated under reduced pressure and purified by silica gel column chromatography (5-10% ethyl acetate/petroleum ether) to give tert-butyl-[4-(4-iodo-5-methyl-pyrazol-1-yl) cyclohexoxy]-dimethyl-silane (3.75 g, 73% yield) as a colorless oil. LCMS (MM-ES+APCI, Pos): m/z 421.0 (M+H).

Step E. tert-butyl-dimethyl-[4-[5-methyl-4-(4,4,5,5-tetramethyl-1,3,2-dioxaborolan-2-yl) pyrazol-1-yl]cyclohexoxy]silane. To a 250 mL three-necked round-bottom flask equipped with a magnetic stir bar was added tert-butyl-[4-(4-iodo-5-methyl-pyrazol-1-yl)cyclohexoxy]-dimethyl-silane (5 g, 11.89 mmol) followed by the addition of THF (100 mL). The flask was then evacuated and backfilled with nitrogen for three times. i-PrMgCl (2 M, 25 mL, 48.63 mmol) was added dropwise. The mixture was stirred at 25° C. under an atmosphere of nitrogen for 1 h. 2-Methoxy-4,4,5,5-tetramethyl-1,3,2-dioxaborolane (9.40 g, 59.47 mmol) was added dropwise at 25° C. The mixture was stirred at 25° C. under an atmosphere of nitrogen for 1 h. The mixture was quenched by slow addition of NH₄Cl (33 mL) and H₂O (33 mL). The resulting mixture was transferred to a separatory funnel, and the aqueous layer mixture was extracted with ethyl acetate (33 mL×3). The combined organic layers were washed with brine (33 mL), dried over anhydrous sodium sulfate, filtered, concentrated under reduced pressure and purified by silica gel column chromatography (3-5% ethyl acetate/petroleum ether to give tert-butyl-dimethyl-[4-[5-methyl-4-(4,4,5,5-tetramethyl-1,3,2-dioxaborolan-2-yl) pyrazol-1-yl]cyclohexoxy]silane (6.2 g, 36% yield) as a white solid. LCMS (MM-ES+APCI, Pos): m/z 421.0 (M+H).

Example 1

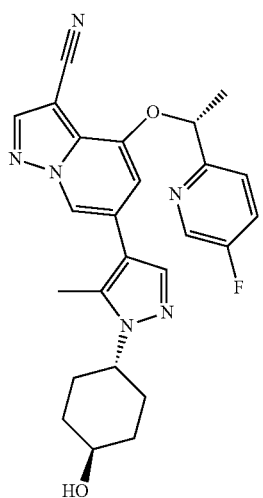 [SMILES: Cc1c(-c2cc(O[C@H](C)c3ccc(F)cn3)c3c(C#N)cnn3c2)cnn1[C@H]1CC[C@H](O)CC1]

4-[(1R)-1-(5-fluoro-2-pyridyl)ethoxy]-6-[1-(4-hydroxycyclohexyl)-5-methyl-pyrazol-4-yl]pyrazolo[1,5-a]pyridine-3-carbonitrile (1)

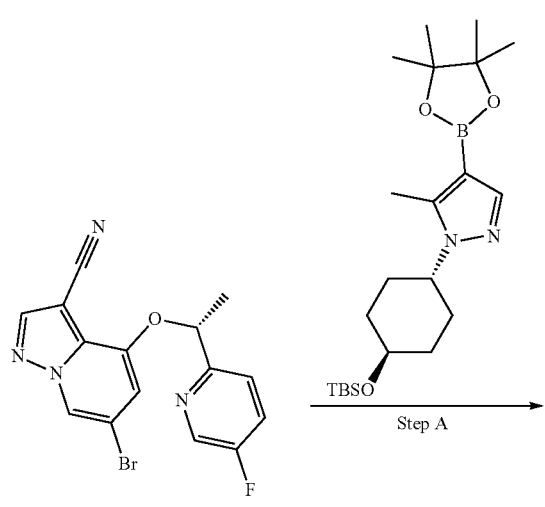

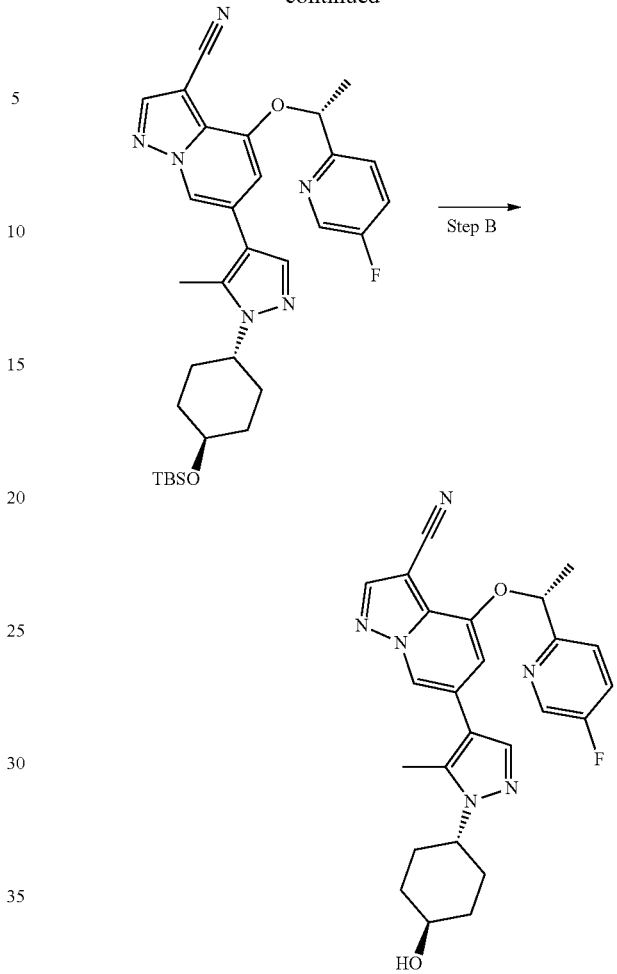

Step A. 6-[1-[4-[tert-butyl(dimethyl) silyl]oxycyclohexyl]-5-methyl-pyrazol-4-yl]-4-[(1R)-1-(5-fluoro-2-pyridyl)ethoxy]pyrazolo[1,5-a]pyridine-3-carbonitrile. To a 40 mL vial equipped with a magnetic stir bar was added Intermediate 1 (250 mg, 0.68 mmol) followed by the addition of dioxane (5 mL). $K_2CO_3$ (190 mg, 1.37 mmol), CATACXIUM® A PD G3 (50 mg, 0.07 mmol), tert-butyl-dimethyl-[4-[5-methyl-4-(4,4,5,5-tetramethyl-1,3,2-dioxaborolan-2-yl) pyrazol-1-yl]cyclohexoxy]silane, Intermediate 5 (453 mg, 1.01 mmol), $H_2O$ (1 mL) was added into the mixture at 25° C. The vial was purged with nitrogen for three min. The mixture was heated to 90° C. under an atmosphere of nitrogen for 1 h. Water (5 mL) was added to the reaction and the mixture was transferred to a separatory funnel. The aqueous layer was extracted with ethyl acetate (10 mL×3). The combined organic layers were washed with brine (5 mL), dried over anhydrous sodium sulfate, filtered, concentrated under reduced pressure and purified by silica gel column chromatography (25-45% ethyl acetate/petroleum ether) to give 6-[1-[4-[tert-butyl(dimethyl) silyl]oxycyclohexyl]-5-methyl-pyrazol-4-yl]-4-[(1R)-1-(5-fluoro-2-pyridyl)ethoxy]pyrazolo[1,5-a]pyridine-3-carbonitrile (352 mg, 87% yield) as a yellow oil. LCMS (MM-ES+APCI, Pos): m/z 575.1 (M+H).

Step B. 4-[(1R)-1-(5-fluoro-2-pyridyl)ethoxy]-6-[1-(4-hydroxycyclohexyl)-5-methyl-pyrazol-4-yl]pyrazolo[1,5-a]pyridine-3-carbonitrile. To a 100 mL round-bottom flask equipped with a magnetic stir bar was added 6-[1-[4-

[tertbutyl(dimethyl) silyl]oxycyclohexyl]-5-methyl-pyrazol-4-yl]-4-[(1R)-1-(5-fluoro-2-pyridyl)ethoxy]pyrazolo[1,5-a]pyridine-3-carbonitrile (342 mg, 0.58 mmol) followed by the addition of DCM (3 mL). HCl/dioxane (4 M, 3 mL) was added into the mixture at 25° C. The mixture was stirred at 25° C. for 0.2 h. The mixture was concentrated under reduced and purified by preparative HPLC: (22%-52% acetonitrile/0.08% aqueous ammonia hydroxide+10 mM NH$_4$HCO$_3$). After lyophilization, 4-[(1R)-1-(5-fluoro-2-pyridyl)ethoxy]-6-[1-(4-hydroxycyclohexyl)-5-methyl-pyrazol-4-yl]pyrazolo[1,5-a]pyridine-3-carbonitrile (161.3 mg, 60% yield) was obtained as white solid. LCMS (MM-ES+APCI, Pos): m/z 460.9 (M+H).

Example 2

6-[5-methyl-1-(4-piperidyl) pyrazol-4-yl]-4-[(1R)-1-(2-pyridyl)ethoxy]pyrazolo[1,5-a]pyridine-3-carbonitrile (5)

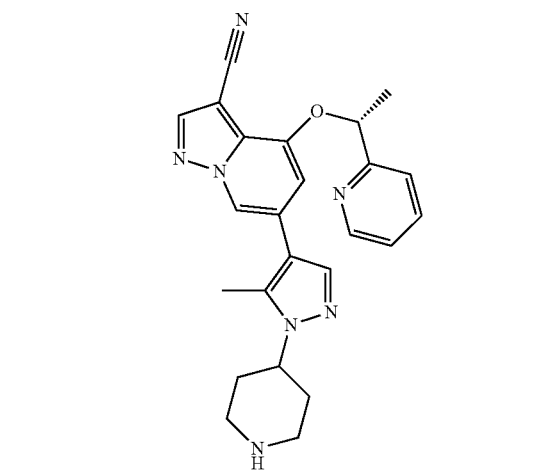 [SMILES: Cc1c(-c2cc(O[C@H](C)c3ccccn3)c3c(C#N)cnn3c2)cnn1C1CCNCC1]

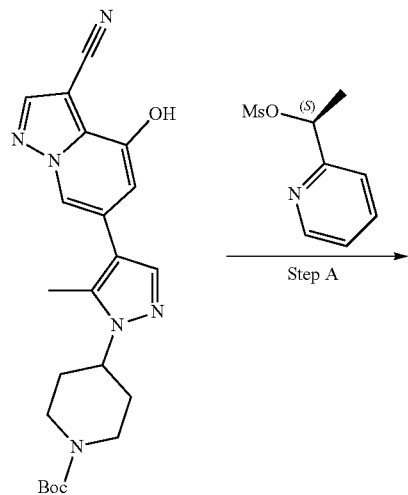

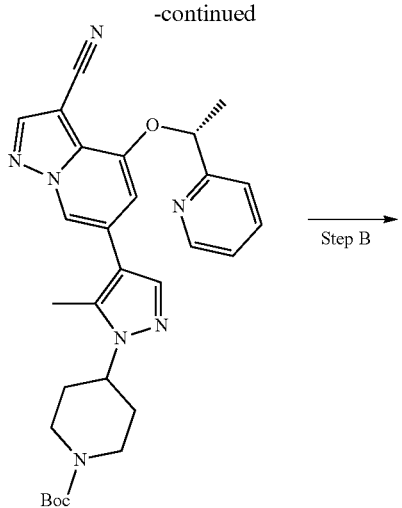

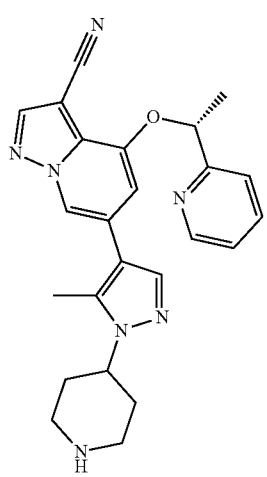

Step A. tert-butyl 4-[4-[3-cyano-4-[(1R)-1-(2-pyridyl)ethoxy]pyrazolo[1,5-a]pyridin-6-yl]-5-methyl-pyrazol-1-yl]piperidine-1-carboxylate. To a 40 mL vial equipped was added [(1S)-1-(2-pyridyl)ethyl]methanesulfonate (143 mg, 0.71 mmol), tert-butyl 4-[4-(3-cyano-4-hydroxy-pyrazolo[1,5-a]pyridin-6-yl)-5-methyl-pyrazol-1-yl]piperidine-1-carboxylate, Intermediate 3 (200 mg, 0.473.40 mmol), Cs$_2$CO$_3$ (308 mg, 0.95 mmol) and DMF (5 mL), the reaction mixture was stirred at 90° C. for 12 hr. The mixture was transferred to a separatory funnel, and the aqueous layer mixture was extracted with DCM (50 mL×3). The combined organic layers were dried over anhydrous sodium sulfate, filtered, and concentrated under reduced pressure and purified by silica gel column chromatography (30-50% petroleum ether/ethyl acetate) to give tert-butyl 4-[4-[3-cyano-4-[(1R)-1-(2-pyridyl)ethoxy]pyrazolo[1,5-a]pyridin-6-yl]-5-methyl-pyrazol-1-yl]piperidine-1-carboxylate (208 mg, 83% yield) as a yellow oil.

Step B. 6-[5-methyl-1-(4-piperidyl) pyrazol-4-yl]-4-[(1R)-1-(2-pyridyl)ethoxy]pyrazolo[1,5-a]pyridine-3-carbonitrile. To a 50 mL round-bottom flask equipped with a magnetic stir bar was added HCl/dioxane (1 mL) followed by the addition of DCM (4 mL). Tert-butyl 4-[4-[3-cyano-4-[(1R)-1-(2-pyridyl)ethoxy]pyrazolo[1,5-a]pyridin-6-yl]-5-methyl-pyrazol-1-yl]piperidine-1-carboxylate (200 mg, 0.38 mmol) was added into the mixture at 25° C. The mixture was stirred at 25° C. for 1 hr. The reaction mixture was concentrated and purified by prep-HPLC [5-35%

Acetonitrile/water (FA)]. After lyophilization, 6-[5-methyl-1-(4-piperidyl) pyrazol-4-yl]-4-[(1R)-1-(2-pyridyl)ethoxy]pyrazolo[1,5-a]pyridine-3-carbonitrile (65.1 mg, 40% yield) was obtained as a white solid. LCMS (MM-ES+APCI, Pos): m/z 428.2 (M+H).

Example 3

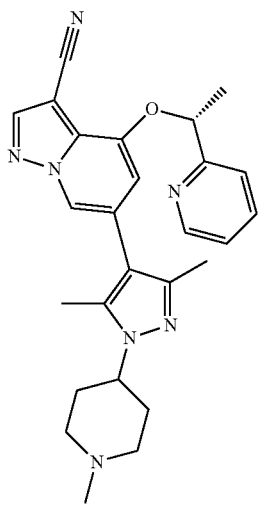 [SMILES: Cc1nn(C2CCN(C)CC2)c(C)c1-c1cc(O[C@H](C)c2ccccn2)c2c(C#N)cnn2c1]

6-[3,5-dimethyl-1-(1-methyl-4-piperidyl) pyrazol-4-yl]-4-[(1R)-1-(2-pyridyl)ethoxy]pyrazolo[1,5-a]pyridine-3-carbonitrile (6)

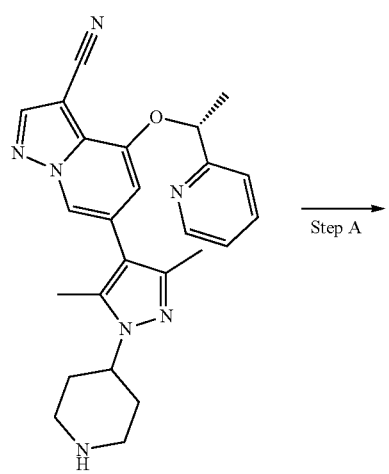

Step A

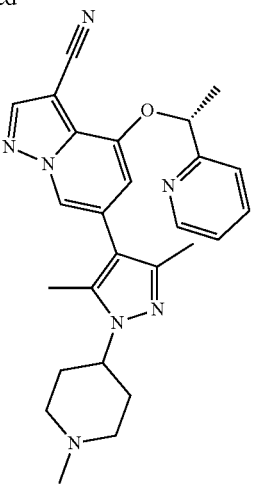

Step A. 6-[3,5-dimethyl-1-(1-methyl-4-piperidyl) pyrazol-4-yl]-4-[(1R)-1-(2-pyridyl)ethoxy]pyrazolo[1,5-a]pyridine-3-carbonitrile. To a 50 mL round-bottom flask equipped with a magnetic stir bar were 6-[3,5-dimethyl-1-(4-piperidyl) pyrazol-4-yl]-4-[(1R)-1-(2-pyridyl)ethoxy] pyrazolo[1,5-a]pyridine-3-carbonitrile (120 mg, 0.27 mmol) followed by the addition of MeOH (3 mL). (HCHO)n (44 mg, 1.36 mmol), acetic acid (0.016 mL, 0.27 mmol) and NaBH$_3$CN (34 mg, 0.54 mmol) was added into the mixture at 25° C. The mixture was stirred at 50° C. for 2 h. The mixture was concentrated and purified by preparative HPLC (8-38% acetonitrile/water (FA)), the purified solution was lyophilized to give 6-[3,5-dimethyl-1-(1-methyl-4-piperidyl) pyrazol-4-yl]-4-[(1R)-1-(2-pyridyl)ethoxy]pyrazolo[1,5-a]pyridine-3-carbonitrile (46.49 mg, 38% yield) as a white solid. LCMS (MM-ES+APCI, Pos): m/z 456.4 (M+H).

Example 4

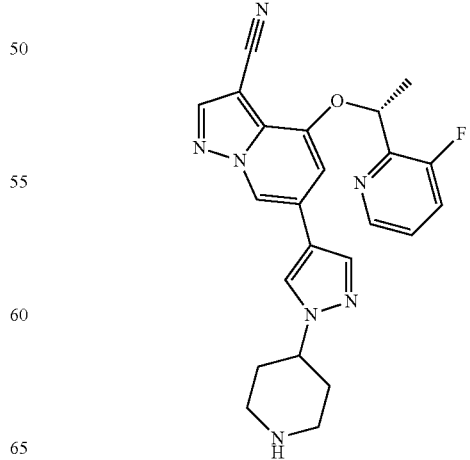

(R)-4-(1-(3-fluoropyridin-2-yl)ethoxy)-6-(1-(piperidin-4-yl)-1H-pyrazol-4-yl) pyrazolo[1,5-a]pyridine-3-carbonitrile (8)

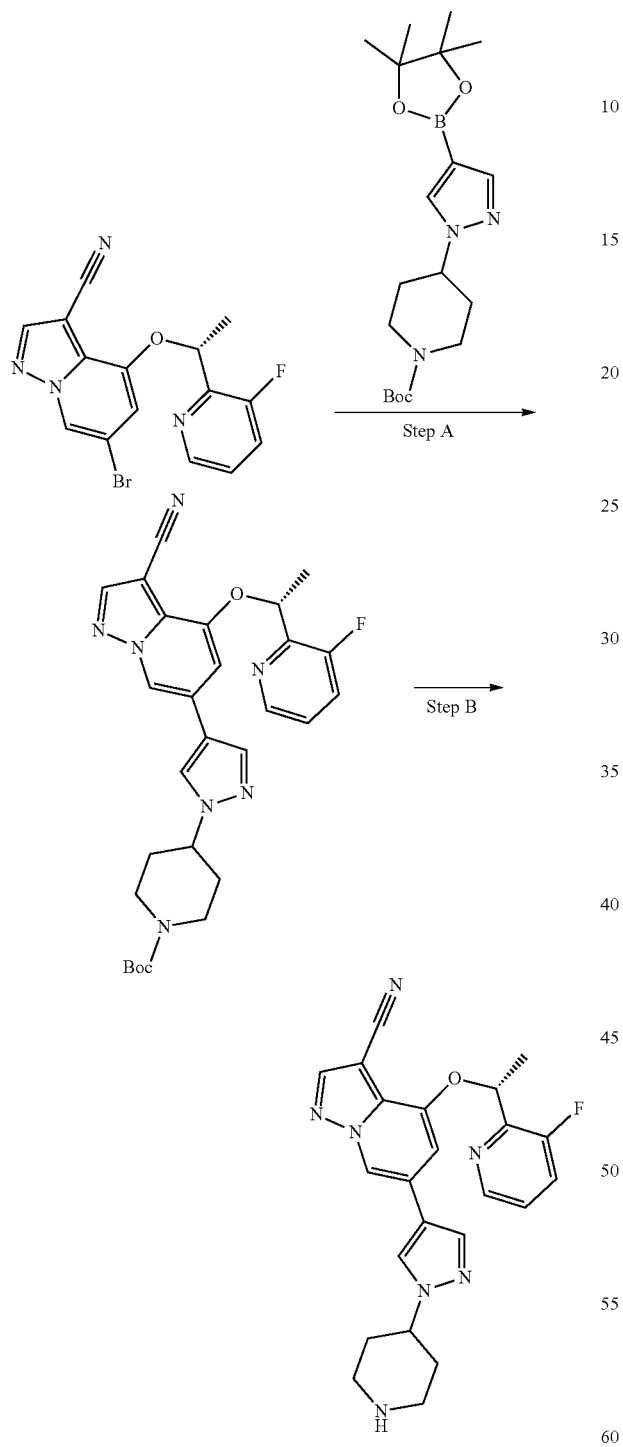

Step A. tert-butyl 4-(4-(3-cyano-4-hydroxypyrazolo[1,5-a]pyridin-6-yl)-1H-pyrazol-1-yl) piperidine-1-carboxylate. To a solution of Intermediate 1 (5.0 g, 21.0 mmol) in 4:1 dioxane:water (70 mL) was added tert-butyl 4-(4-(4,4,5,5-tetramethyl-1,3,2-dioxaborolan-2-yl)-1H-pyrazol-1-yl) piperidine-2-carboxylate (14.3 g, 37.8 mmol) and Na2CO3 (4.45 g, 42.0 mmol). The reaction was capped, purged with Argon for 5 minutes. PdCl2(dppf) (1.54 g, 2.10 mmol) was added and the reaction immediately sealed and purged for an additional 5 minutes. The reaction stirred at 90° C. for 18 h. The mixture was allowed to cool to rt, quenched slowly with water (100 mL), diluted with EA (100 mL), combined extracts washed with brine (3×75 mL), organic layer filtered through 1PS paper, evap in vac and purified by silica gel chromatography (0-100% EA/hex) to give tert-butyl 4-(4-(3-cyano-4-hydroxypyrazolo[1,5-a]pyridin-6-yl)-1H-pyrazol-1-yl) piperidine-1-carboxylate (1.16 g, 13% yield). LCMS (MM-ES+APCI, Pos): m/z 353.2 (M+H–tBu).

Step B. tert-butyl(R)-4-(4-(3-cyano-4-(1-(3-fluoropyridin-2-yl)ethoxy) pyrazo[1,5a]pyridin-6-yl)-1H-pyrazol-1-yl) piperidine-1-carboxylate. Triphenylphosphine (193 mg, 0.73 mmol) was added to a solution of tert-butyl 4-(4-(3-cyano-4-hydroxypyrazolo[1,5-a]pyridin-6-yl)-1H-pyrazol-1-yl) piperidine-1-carboxylate (100 mg, 0.24 mmol) and (1S)-1-(3-fluoropyridin-2-yl) ethan-1-ol (51.8 mg, 0.237 mmol) in DCM (3 mL). After stirring at 0° C. for 15 min, di-tert-butyl diazene-1,2-dicarboxylate (DBAD) (113 mg, 0.49 mmol) was added dropwise. The mixture was allowed to stir at rt for 18 h. The mixture was diluted with EA (10 mL) and water (10 mL), aqueous was extracted with EA (3×10 mL), combined extracts were filtered through 1PS paper, evaporated in vac and purified by silica gel chromatography (0-100% EA/hex) to give tert-butyl(R)-4-(4-(3-cyano-4-(1-(3-fluoropyridin-2-yl)ethoxy) pyrazo[1,5a]pyridin-6-yl)-1H-pyrazol-1-yl) piperidine-1-carboxylate (76 mg, 59% yield). LCMS (MM-ES+APCI, Pos): m/z 532.25 (M+H).

Step C. (R)-4-(1-(3-fluoropyridin-2-yl)ethoxy)-6-(1-(piperidin-4-yl)-1H-pyrazol-4-yl) pyrazolo[1,5-a]pyridine-3-carbonitrile. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl] piperidine-1-carboxylate for tert-butyl(R)-4-(4-(3-cyano-4-(1-(3-fluoropyridin-2-yl)ethoxy) pyrazo[1,5a]pyridin-6-yl)-1H-pyrazol-1-yl) piperidine-1-carboxylate to give (R)-4-(1-(3-fluoropyridin-2-yl)ethoxy)-6-(1-(piperidin-4-yl)-1H-pyrazol-4-yl) pyrazolo[1,5-a]pyridine-3-carbonitrile (34 mg, 42% yield). LCMS (MM-ES+APCI, Pos): m/z 432.2 (M+H).

Example 5

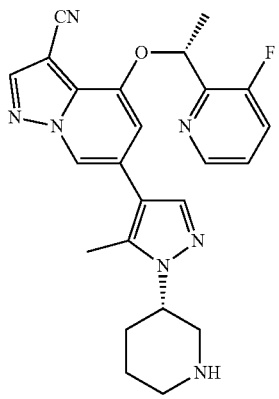 [SMILES: Cc1c(-c2cc(O[C@H](C)c3ncccc3F)c3c(C#N)cnn3c2)cnn1[C@H]1CCCNC1]

4-((R)-1-(3-fluoropyridin-2-yl)ethoxy)-6-(5-methyl-1-((S)-piperidin-3-yl)-1H-pyrazol-4-yl) pyrazolo[1,5-a]pyridine-3-carbonitrile (10)

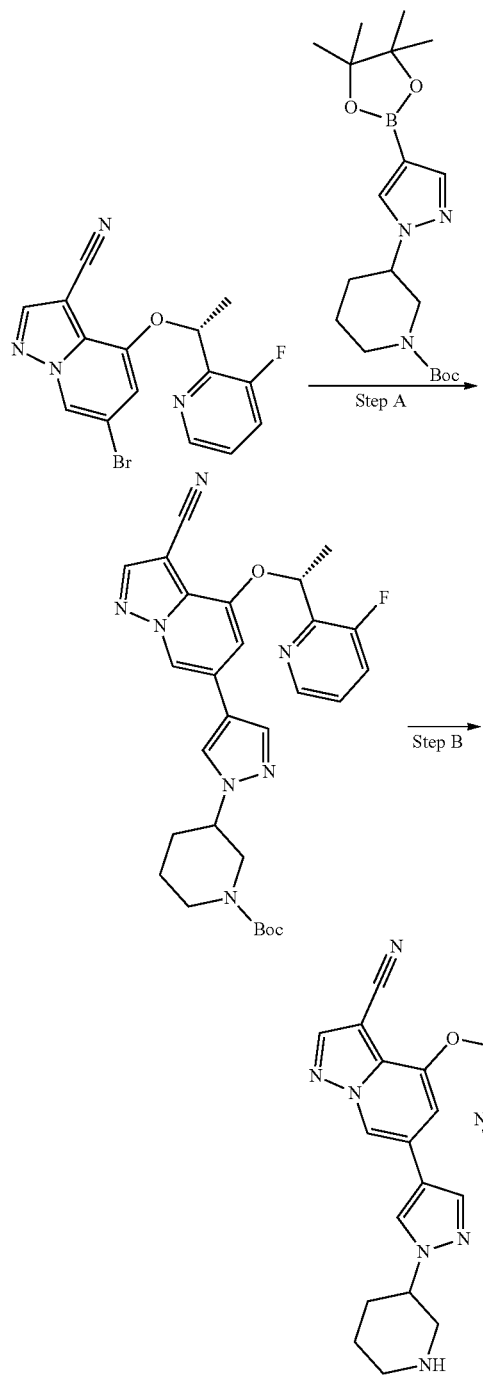

Step A. tert-butyl(S)-3-(4-(3-cyano-4-((R)-1-(3-fluoropyridin-2-yl)ethoxy)pyrazolo[1,5-a]pyridin-6-yl)-5-methyl-1H-pyrazol-1-yl) piperidine-1-carboxylate. Synthesized according to Example 4, Step A substituting tert-butyl 4-(4-(4,4,5,5-tetramethyl-1,3,2-dioxaborolan-2-yl)-1H-pyrazol-1-yl) piperidine-2-carboxylate for tert-butyl(S)-3-(5-methyl-4-(4,4,5,5-tetramethyl-1,3,2-dioxaborolan-2-yl)-1H-pyrazol-1-yl) piperidine-1-carboxylate to give tert-butyl(S)-3-(4-(3-cyano-4-((R)-1-(3-fluoropyridin-2-yl)ethoxy) pyrazolo[1,5-a]pyridin-6-yl)-5-methyl-1H-pyrazol-1-yl) piperidine-1-carboxylate (88 mg, 93% yield). LCMS (MM-ES+APCI, Pos): m/z 546.3 (M+H).

Step B. t-Butyl(3S)-3-[4-[3-cyano-4-[(3-fluoro-6-methyl-2-pyridyl) sulfanyl]pyrazolo[1,5-a]pyridin-6-yl]pyrazol-1-yl]piperidine-1-carboxylate. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl]piperidine-1-carboxylate for tert-butyl (S)-3-(4-(3-cyano-4-((R)-1-(3-fluoropyridin-2-yl)ethoxy) pyrazolo[1,5-a]pyridin-6-yl)-5-methyl-1H-pyrazol-1-yl) piperidine-1-carboxylate to give 4-((R)-1-(3-fluoropyridin-2-yl)ethoxy)-6-(5-methyl-1-((S)-piperidin-3-yl)-1H-pyrazol-4-yl) pyrazolo[1,5-a]pyridine-3-carbonitrile (36 mg, 81% yield). LCMS (MM-ES+APCI, Pos): m/z 446.2 (M+H).

Example 6

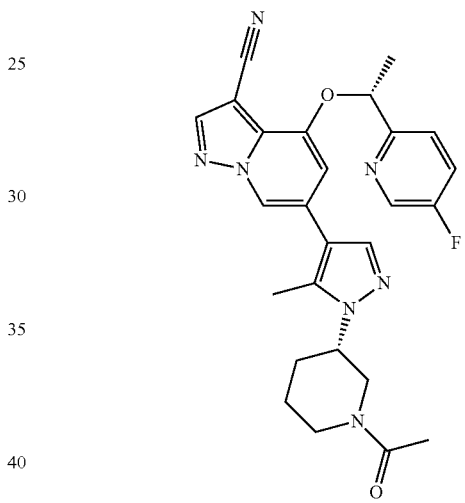

6-(1-((S)-1-acetylpiperidin-3-yl)-5-methyl-1H-pyrazol-4-yl)-4-((R)-1-(5-fluoropyridin-2-yl)ethoxy) pyrazolo[1,5-a]pyridine-3-carbonitrile (13)

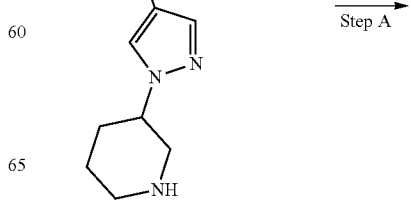

191
-continued

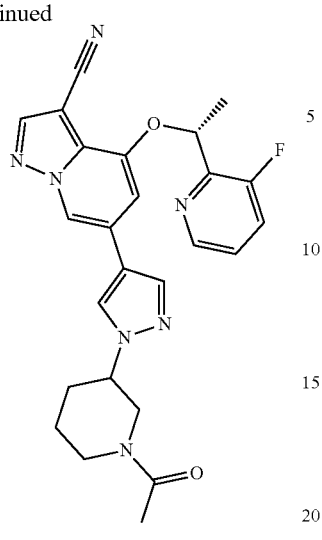

192
4-((R)-1-(5-fluoropyridin-2-yl)ethoxy)-6-(6-((R)-3-(hydroxymethyl)-4-methylpiperazin-1-yl)pyridin-3-yl) pyrazolo[1,5-a]pyridine-3-carbonitrile (24)

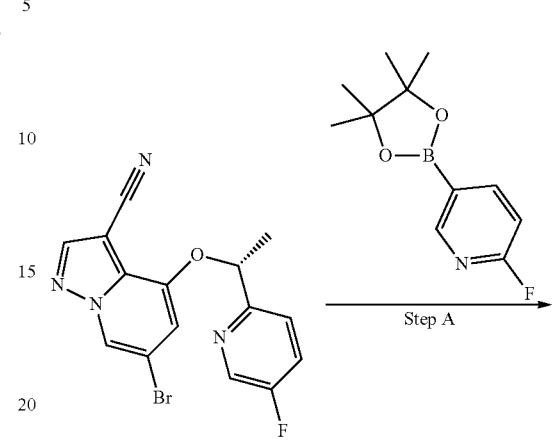

Step A. 6-(1-((S)-1-acetylpiperidin-3-yl)-5-methyl-1H-pyrazol-4-yl)-4-((R)-1-(5-fluoropyridin-2-yl)ethoxy)pyrazolo[1,5-a]pyridine-3-carbonitrile. To a solution of 4-((R)-1-(5-fluoropyridin-2-yl)ethoxy)-6-(5-methyl-1-((S)-piperidin-3-yl)-1H-pyrazol-4-yl) pyrazolo[1,5-a]pyridine-3-carbonitrile (28 mg, 0.06 mmol) in DCM (0.5 mL) at 0° C. was added acetyl chloride (0.005 mL, 0.069 mmol) and DIEA (0.044 mL, 0.25 mmol). The reaction was warmed to rt and stirred for 18 hours. The reaction was partitioned between 30% IPA/CHCL3 (10 mL) and water (15 mL). The aqueous layer was washed with 30% IPA/CHCL3 (2×5 mL). The combined organic layers were filtered through 1PS paper and purified by silica gel chromatography (0%-25% (20% MeOH/DCM with 2% NH4OH in DCM to give 6-(1-((S)-1-acetylpiperidin-3-yl)-5-methyl-1H-pyrazol-4-yl)-4-((R)-1-(5-fluoropyridin-2-yl)ethoxy)pyrazolo[1,5-a]pyridine-3-carbonitrile (25 mg, 82% yield). LCMS (MM-ES+APCI, Pos): m/z 488.25 (M+H).

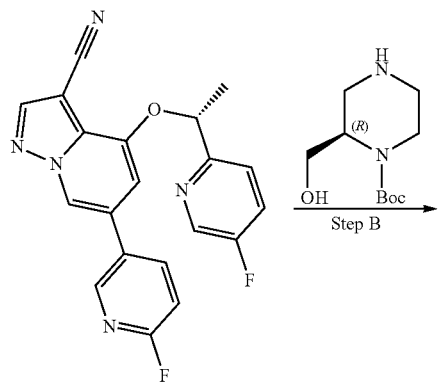

Example 7

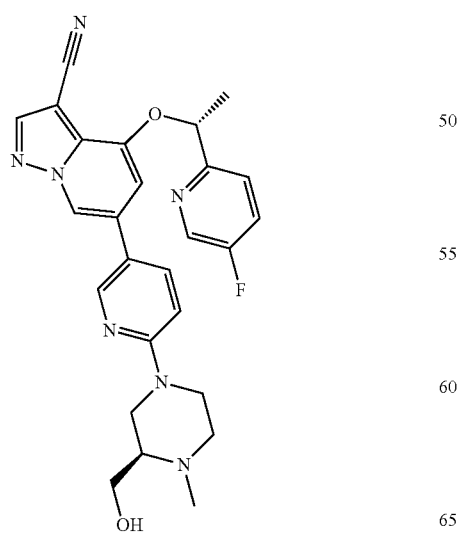

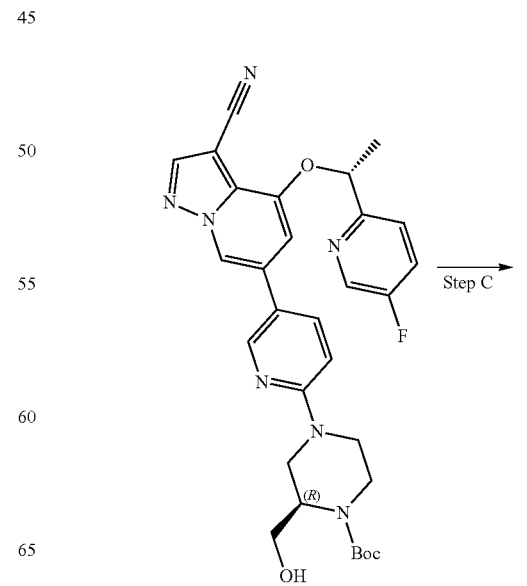

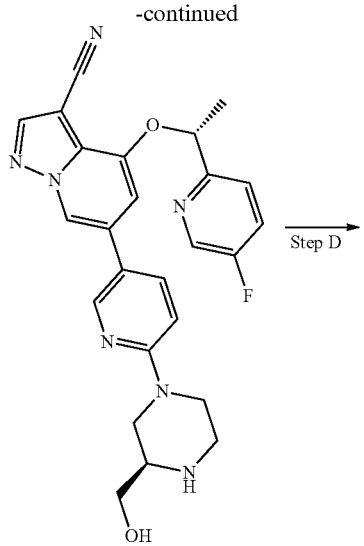

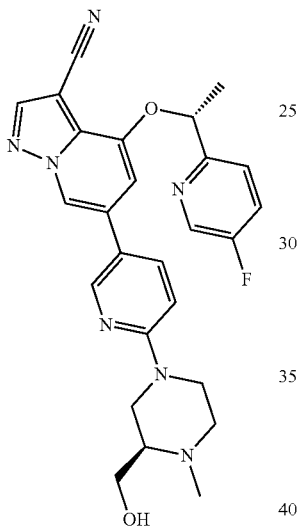

Step A. 6-(6-fluoro-3-pyridyl)-4-[(1R)-1-(5-fluoro-2-pyridyl)ethoxy]pyrazolo[1,5-a]pyridine-3-carbonitrile. Synthesized according to Example 4, Step A substituting tert-butyl 4-(4-(4,4,5,5-tetramethyl-1,3,2-dioxaborolan-2-yl)-1H-pyrazol-1-yl) piperidine-2-carboxylate for 2-fluoro-5-(4,4,5,5-tetramethyl 1,3,2-dioxaborolan-2-yl)pyridine to give 6-(6-fluoro-3-pyridyl)-4-[(1R)-1-(5-fluoro-2-pyridyl)ethoxy]pyrazolo[1,5-a]pyridine-3-carbonitrile (470 mg, 90% yield). LCMS (MM-ES+APCI, Pos): m/z 377.9 (M+H).

Step B. tert-butyl(2R)-4-[5-[3-cyano-4-[(1R)-1-(5-fluoro-2-pyridyl)ethoxy]pyrazolo[1,5-a]pyridin-6-yl]-2-pyridyl]-2-(hydroxymethyl) piperazine-1-carboxylate. To a 40 mL vial equipped with a magnetic stir bar was added 6-(6-fluoro-3-pyridyl)-4-[(1R)-1-(5-fluoro-2-pyridyl)ethoxy]pyrazolo[1,5-a]pyridine-3-carbonitrile (240 mg, 0.63 mmol) and tert-butyl (2R)-2-(hydroxymethyl) piperazine-1-carboxylate (0.14 g, 0.66 mmol) followed by the addition of DMSO (5 mL). DIEA (0.23 mL, 1.30 mmol) was added into the mixture at 25° C. The mixture was stirred at 100° C. for 39 h. Water (10 mL) was added to the reaction and the mixture was transferred to a separatory funnel. The aqueous layer was extracted with ethyl acetate (20 mL×3). The combined organic layers were washed with brine (20 mL×3), dried over anhydrous sodium sulfate, filtered, concentrated under reduced pressure and purified by silica gel column chromatography (60-80% ethyl acetate in petroleum ether) to give the desired product tert-butyl(2R)-4-[5-[3-cyano-4-[(1R)-1-(5-fluoro-2-pyridyl)ethoxy]pyrazolo[1,5-a]pyridin-6-yl]-2-pyridyl]-2-(hydroxymethyl) piperazine-1-carboxylate (250 mg, 69% yield) as a brown solid. LCMS (MM-ES+APCI, Pos): m/z 381.8 (M+H).

Step C. 4-[(1R)-1-(5-fluoro-2-pyridyl)ethoxy]-6-[6-[(3R)-3-(hydroxymethyl) piperazin-1-yl]-3-pyridyl]pyrazolo[1,5-a]pyridine-3-carbonitrile. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl]piperidine-1-carboxylate for tert-butyl (2R)-4-[5-[3-cyano-4-[(1R)-1-(5-fluoro-2-pyridyl)ethoxy]pyrazolo[1,5-a]pyridin-6-yl]-2-pyridyl]-2-(hydroxymethyl) piperazine-1-carboxylate to give 4-[(1R)-1-(5-fluoro-2-pyridyl)ethoxy]-6-[6-[(3R)-3-(hydroxymethyl) piperazin-1-yl]-3-pyridyl]pyrazolo[1,5-a]pyridine-3-carbonitrile (55 mg, 26% yield). LCMS (MM-ES+APCI, Pos): m/z 488.3 (M+H).

Step D. T-Butyl(3S)-3-[4-[3-cyano-4-[1-(2-trimethylsilylethoxymethyl) indazol-7-yl]sulfanyl-pyrazolo[1,5-a]pyridin-6-yl]pyrazol-1-yl]piperidine-1-carboxylate. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl]piperidine-1-carboxylate for 4-[(1R)-1-(5-fluoro-2-pyridyl)ethoxy]-6-[6-[(3R)-3-(hydroxymethyl) piperazin-1-yl]-3-pyridyl]pyrazolo[1,5-a]pyridine-3-carbonitrile to give tert-butyl(3S)-3-[4-[3-cyano-4-[1-(2-trimethylsilylethoxymethyl) indazol-7-yl]sulfanyl-pyrazolo[1,5-a]pyridin-6-yl]pyrazol-1-yl]piperidine-1-carboxylate (0.13 g, 36% yield). LCMS (MM-ES+APCI, Pos): m/z 671.5 (M+H).

Example 8

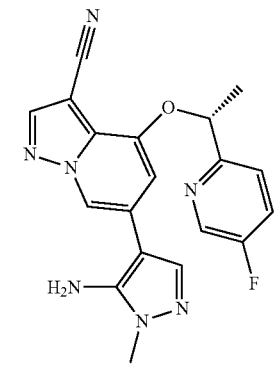 [SMILES: C[C@@H](Oc1cc(-c2cnn(C)c2N)cn2ncc(C#N)c12)c1ccc(F)cn1]

(R)-6-(5-amino-1-methyl-1H-pyrazol-4-yl)-4-(1-(5-fluoropyridin-2-yl)ethoxy)pyrazolo[1,5-a]pyridine-3-carbonitrile (30)

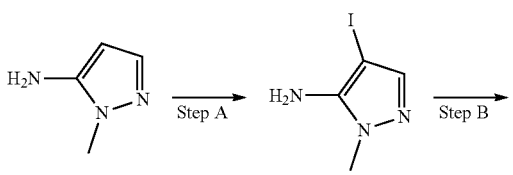

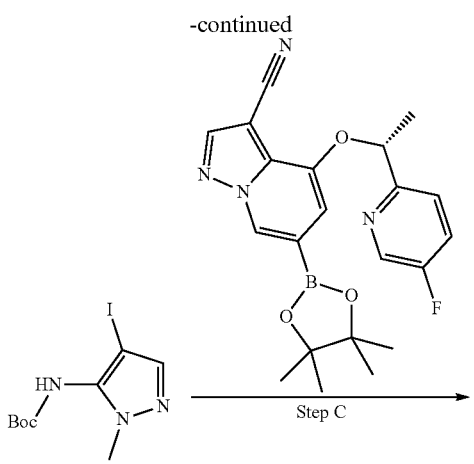

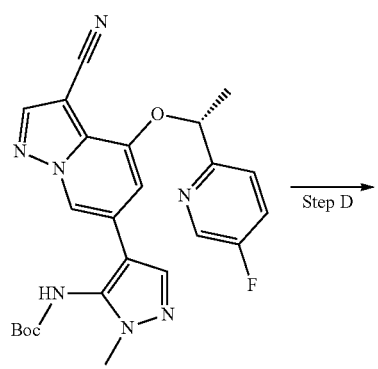

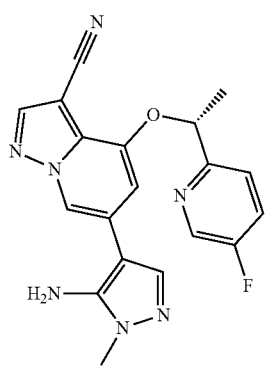

Step A. 4-iodo-2-methyl-pyrazol-3-amine. To a 40 mL vial equipped with a magnetic stir bar was added 2-methylpyrazol-3-amine (500 mg, 5.15 mmol) followed by the addition of DCM (6 mL). NIS (1.39 g, 6.18 mmol) was added into the mixture at 25° C. The mixture was stirred at 25° C. for 0.5 h. Water (5 mL) was added to the reaction and the mixture was transferred to a separatory funnel. The aqueous layer was extracted with ethyl acetate (50 mL×3). The combined organic layers were washed with brine (50 mL), dried over anhydrous sodium sulfate, filtered, concentrated under reduced pressure and purified by silica gel column chromatography (10-30% petroleum ether/ethyl acetate) to give 4-iodo-2-methyl-pyrazol-3-amine (860 mg, 73% yield) as a red solid. LCMS (MM-ES+APCI, Pos): m/z 224.0 (M+H).

Step B. N-(4-iodo-2-methyl-pyrazol-3-yl) carbamate. To a 100 mL round-bottom flask equipped with a magnetic stir bar was added 4-iodo-2-methyl-pyrazol-3-amine (860 mg, 3.76 mmol), TEA (1.05 mL, 7.52 mmol) and DMAP (45.93 mg, 0.38 mmol) followed by the addition of DCM (9 mL). Boc₂O (1.23 g, 5.64 mmol) in DCM (1 mL) was added dropwise. The mixture was stirred for 16 h at 25° C. Water (10 mL) was added to the reaction and the mixture was transferred to a separatory funnel. The aqueous layer was extracted with ethyl acetate (50 mL×3). The combined organic layers were washed with brine (50 mL), dried over anhydrous sodium sulfate, filtered, concentrated under reduced pressure and purified by silica gel column chromatography (10-20% ethyl acetate in petroleum ether) to give tert-butyl N-(4-iodo-2-methyl-pyrazol-3-yl) carbamate (430 mg, 29% yield) as a yellow solid. LCMS (MM-ES+APCI, Pos): m/z 324.0 (M+H).

Step C. tert-butyl N-[4-[3-cyano-4-[(1R)-1-(5-fluoro-2-pyridyl)ethoxy]pyrazolo[1,5-a]pyridin-6-yl]-2-methyl-pyrazol-3-yl]carbamate. To a 40 mL vial equipped with a magnetic stir bar was added tert-butyl N-(4-iodo-2-methyl-pyrazol-3-yl) carbamate (55 mg, 0.14 mmol), 4-[(1R)-1-(5-fluoro-2-pyridyl)ethoxy]-6-(4,4,5,5-tetramethyl-1,3,2-dioxaborolan-2-yl) pyrazolo[1,5-a]pyridine-3-carbonitrile, Intermediate (78.70 mg, 0.19 mmol), K₂CO₃ (38.06 mg, 0.27 mmol) and XantPhos Pd G3 (13.06 mg, 0.014 mmol) followed by the addition of dioxane (4 mL) and H₂O (1 mL). The vial was then evacuated and purged with nitrogen for one minute. The mixture was stirred at 90° C. under an atmosphere of nitrogen for 16 h. The suspension was filtered through a pad of Celite. The Celite pad was eluted with ethyl acetate (10 mL). The organic phase was concentrated under reduced pressure and purified by preparative TLC (1:1 petroleum ether/ethyl acetate) to give tert-butyl N-[4-[3-cyano-4-[(1R)-1-(5-fluoro-2-pyridyl)ethoxy]pyrazolo[1,5-a]pyridin-6-yl]-2-methyl-pyrazol-3-yl]carbamate (18 mg, 13% yield) as yellow oil. LCMS (MM-ES+APCI, Pos): m/z 478.3 (M+H).

Step D. 6-(5-amino-1-methyl-pyrazol-4-yl)-4-[(1R)-1-(5-fluoro-2-pyridyl)ethoxy]pyrazolo[1,5-a]pyridine-3-carbonitrile. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl] piperidine-1-carboxylate for tert-butyl N-[4-[3-cyano-4-[(1R)-1-(5-fluoro-2-pyridyl)ethoxy]pyrazolo[1,5-a]pyridin-6-yl]-2-methyl-pyrazol-3-yl]carbamate to give 6-(5-amino-1-methyl-pyrazol-4-yl)-4-[(1R)-1-(5-fluoro-2-pyridyl) ethoxy]pyrazolo[1,5-a]pyridine-3-carbonitrile (2.83 mg, 42% yield). LCMS (MM-ES+APCI, Pos): m/z 378.1 (M+H).

Example 9

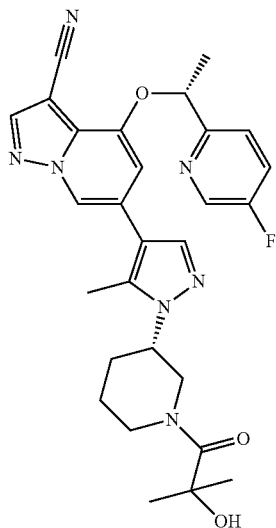 [SMILES: Cc1c(-c2cc(O[C@H](C)c3ccc(F)cn3)c3c(C#N)cnn3c2)cnn1[C@H]1CCCN(C(=O)C(C)(C)O)C1]

4-((R)-1-(5-fluoropyridin-2-yl)ethoxy)-6-(1-((S)-1-(2-hydroxy-2-methylpropanoyl) piperidin-3-yl)-5-methyl-1H-pyrazol-4-yl) pyrazolo[1,5-a]pyridine-3-carbonitrile (17)

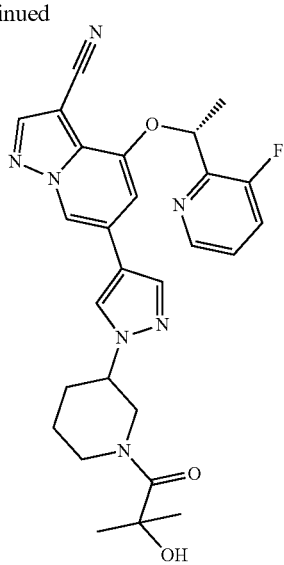

Step A. 6-[5-Methyl-1-[(3S)-3-piperidyl]pyrazol-4-yl]-4-(3-pyridylsulfanyl) pyrazolo[1,5-a]pyridine-3-carbonitrile. To a solution of 4-((R)-1-(5-fluoropyridin-2-yl)ethoxy)-6-(5-methyl-1-((S)-piperidin-3-yl)-1H-pyrazol-4-yl) pyrazolo[1,5-a]pyridine-3-carbonitrile (17 mg, 0.04 mmol) in DMF (1 mL) was added alpha-hydroxybutyric acid (4.77 mg, 0.046 mmol), HATU (14.5 mg, 0.038 mmol) and DIEA (0.03 mL, 0.19 mmol). The mixture was stirred at 50° C. for 18 h. The mixture was diluted with 20% MeOH/DCM (10 mL) and water (10 mL), aqueous extracted with 20% MeOH/DCM (3×15 mL), organic layer filtered through 1PS paper, evaporated in vac and purified by silica gel chromatography (0-20% MeOH/DCM with 2% NH4OH) to give 4-((R)-1-(5-fluoropyridin-2-yl)ethoxy)-6-(1-((S)-1-(2-hydroxy-2-methylpropanoyl) piperidin-3-yl)-5-methyl-1H-pyrazol-4-yl) pyrazolo[1,5-a]pyridine-3-carbonitrile (8 mg, 38% yield). LCMS (MM-ES+APCI, Pos): m/z 532.3 (M+H).

Example 10

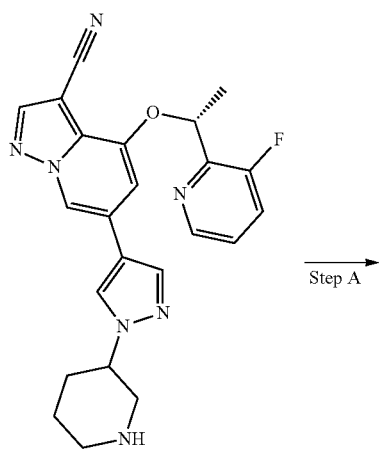

Step A

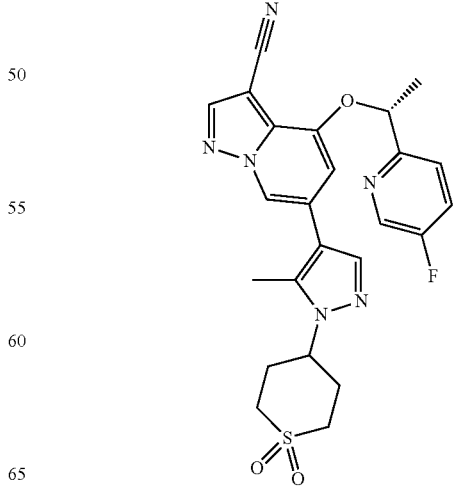

(R)-6-(1-(1,1-dioxidotetrahydro-2H-thiopyran-4-yl)-5-methyl-1H-pyrazol-4-yl)-4-(1-(5-fluoropyridin-2-yl)ethoxy)pyrazolo[1,5-a]pyridine-3-carbonitrile (33)

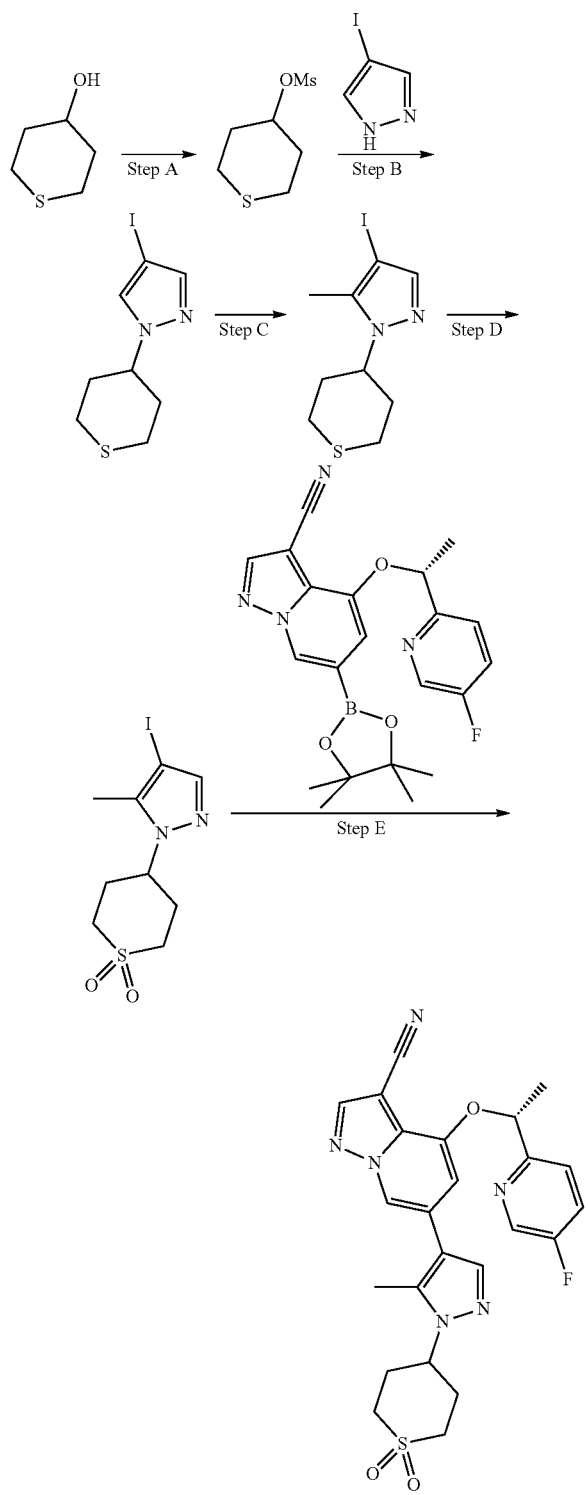

Step A. Tetrahydrothiopyran-4-yl methanesulfonate. To a 50 mL round-bottom flask with a magnetic stir bar was added tetrahydrothiopyran-4-ol (1 g, 8.46 mmol) and TEA (2.36 mL, 16.92 mmol) followed by the addition of DCM (5 mL). Methylsulfonyl methanesulfonate (2.95 g, 16.92 mmol) was dissolved into DCM (5 mL) and added dropwise to the mixture at 0° C. The mixture was allowed to warm to 25° C. and stir for 1 hr. Water (15 mL) was added to the reaction and the mixture was transferred to a separatory funnel. The aqueous layer was extracted with ethyl acetate (15 mL×3). The combined organic layers were washed with brine (15 mL), dried over anhydrous sodium sulfate, filtered, concentrated under reduced pressure and used into the next step without further purification. Compound tetrahydrothiopyran-4-yl methanesulfonate (1.5 g, crude) was obtained as a yellow oil.

Step B. 4-iodo-1-tetrahydrothiopyran-4-yl-pyrazole. To a 50 mL round-bottom flask equipped with a magnetic stir bar was added 4-iodo-1H-pyrazole (1.48 g, 7.64 mmol) and tetrahydrothiopyran-4-yl methanesulfonate (1.5 g, 7.64 mmol) followed by the addition of DMF (20 mL). $Cs_2CO_3$ (4.98 g, 15.28 mmol) was added into the mixture at 25° C. The mixture was stirred at 90° C. for 3 h. Water (50 mL) was added to the reaction and the mixture was transferred to a separatory funnel. The aqueous layer was extracted with ethyl acetate (30 mL×3). The combined organic layers were washed with brine (30 mL), dried over anhydrous sodium sulfate, filtered, concentrated under reduced pressure and purified by slurry in ethyl acetate (5 mL) at 25° C. for 10 min. After filtration and drying under vacuum, 4-iodo-1-tetrahydrothiopyran-4-yl-pyrazole (1.05 g, 46% yield) was obtained as a white solid. LCMS (MM-ES+APCI, Pos): m/z 294.9 (M+H).

Step C. 4-iodo-5-methyl-1-tetrahydrothiopyran-4-yl-pyrazole. To a 100 mL three-necked round-bottom equipped with a magnetic stir bar was added 4-iodo-1-tetrahydrothiopyran-4-yl-pyrazole (800 mg, 2.71 mmol) followed by the addition of THF (10 mL). LDA (2 M, 2.71 mL, 5.42 mmol) was added dropwise into the mixture at −78° C. under $N_2$ atmosphere. The mixture was stirred at −78° C. for 1 h. MeI (0.33 mL, 5.42 mmol) was added dropwise at −78° C. The mixture was stirred at −78° C. for 1 h. Water (20 mL) was added to the reaction and the mixture was transferred to a separatory funnel. The aqueous layer was extracted with ethyl acetate (10 mL×3). The combined organic layers were washed with brine (10 mL), dried over anhydrous sodium sulfate, filtered, concentrated under reduced pressure and residue recrystallization from ethyl acetate (3 mL) at 25° C. for 5 min. After filtration and drying under vacuum, the desired product was obtained 4-iodo-5-methyl-1-tetrahydrothiopyran-4-yl-pyrazole (700 mg, 83% yield) as a white solid. LCMS (MM-ES+APCI, Pos): m/z 308.1 (M+H).

Step D. 4-(4-iodo-5-methyl-pyrazol-1-yl) thiane 1,1-dioxide. To a 100 mL round-bottom flask equipped with a magnetic stir bar was added 4-iodo-5-methyl-1-tetrahydrothiopyran-4-yl-pyrazole (700 mg, 2.26 mmol) followed by the addition of THF (10 mL) and $H_2O$ (2 mL). Potassium oxidooxy hydrogen sulfate (1.90 g, 11.29 mmol) was added into the mixture at 0° C. The mixture was stirred at 25° C. for 2 hr. The mixture was quenched by slow addition of saturated sodium sulfite solution (10 mL) and transferred to a separatory funnel. The aqueous layer was extracted with dichloromethane (10 mL×3). The combined organic layers were washed with brine (15 mL), dried over anhydrous sodium sulfate, filtered, concentrated under reduced pressure and purified by slurry in ethyl acetate (5 mL) at 25° C. for 10 min. After filtration and drying under vacuum, 4-(4-iodo-5-methyl-pyrazol-1-yl) thiane 1,1-dioxide (730 mg, 91% yield) was obtained as a white solid. LCMS (MM-ES+APCI, Pos): m/z 341.1 (M+H).

Step E. 6-[1-(1,1-dioxothian-4-yl)-5-methyl-pyrazol-4-yl]-4-[(1R)-1-(5-fluoro-2-pyridyl)ethoxy]pyrazolo[1,5-a]pyridine-3-carbonitrile. To a 40 mL vial equipped with a magnetic stir bar was added 4-[(1R)-1-(5-fluoro-2-pyridyl)ethoxy]-6-(4,4,5,5-tetramethyl-1,3,2-dioxaborolan-2-yl)pyrazolo[1,5-a]pyridine-3-carbonitrile (110.53 mg, 0.2 mmol) and 4-(4-iodo-5-methyl-pyrazol-1-yl) thiane 1,1-dioxide (71 mg, 0.2 mmol) followed by the addition of dioxane (3 mL) and H₂O (0.3 mL). K₂CO₃ (56.88 mg, 0.411 mmol) and CATACXIUM® A PD G3 (14.99 mg, 0.021 mmol) was added into the mixture at 25° C. The vial was backfilled with nitrogen for three min. The mixture was heated to 90° C. and stirred for 0.5 h. Water (3 mL) was added to the reaction and the mixture was transferred to a separatory funnel. The aqueous layer was extracted with ethyl acetate (3 mL×3). The combined organic layers were washed with brine (5 mL), dried over anhydrous sodium sulfate, filtered, concentrated under reduced pressure and purified by preparative HPLC (32%-62% acetonitrile/0.04% aqueous ammonia hydroxide+10 mM NH₄HCO₃). After lyophilization, 6-[1-(1,1-dioxothian-4-yl)-5-methyl-pyrazol-4-yl]-4-[(1R)-1-(5-fluoro-2-pyridyl)ethoxy]pyrazolo[1,5-a]pyridine-3-carbonitrile (50 mg, 49% yield) was obtained as a white solid. LCMS (MM-ES+APCI, Pos): m/z 495.1 (M+H).

Example 11

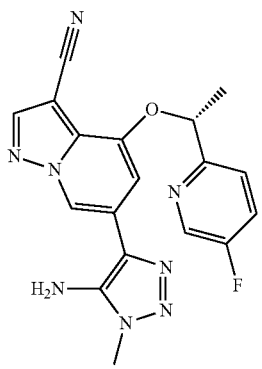 [SMILES: C[C@@H](Oc1cc(-c2nnn(C)c2N)cn2ncc(C#N)c12)c1ccc(F)cn1]

(R)-6-(5-amino-1-methyl-1H-1,2,3-triazol-4-yl)-4-(1-(5-fluoropyridin-2-yl)ethoxy)pyrazolo[1,5-a]pyridine-3-carbonitrile (34)

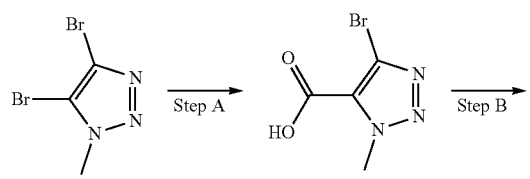

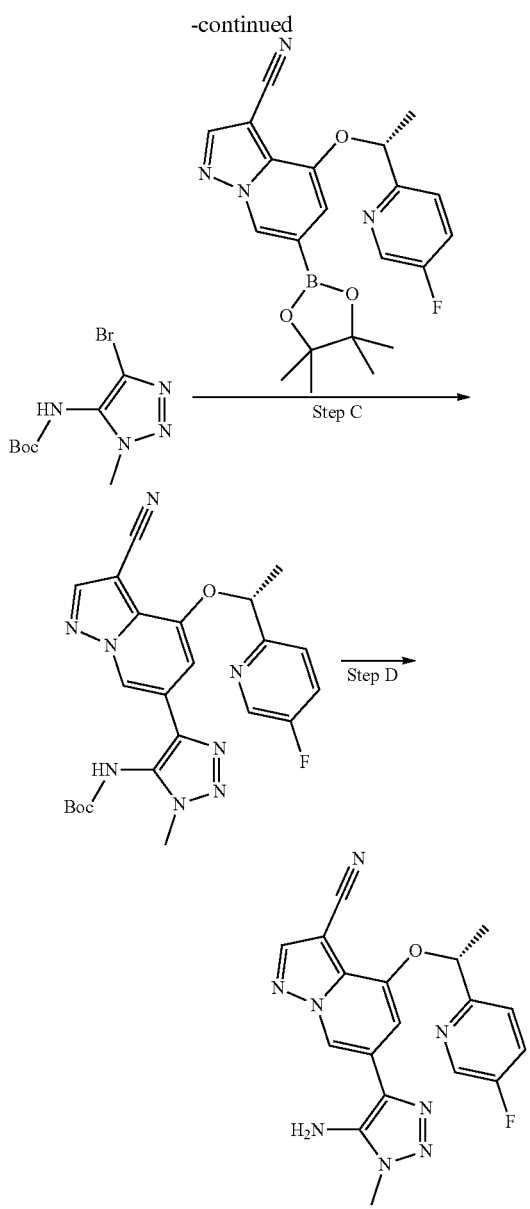

Step A. 5-bromo-3-methyl-triazole-4-carboxylic acid. To a 100 mL three-necked round-bottom flask equipped with a magnetic stir bar was added 4,5-dibromo-1-methyl-triazole (2 g, 8.30 mmol) followed by the addition of THF (25 mL). The solution was cooled to −78° C. The flask was then evacuated and backfilled with nitrogen three times. n-BuLi (2.5 M, 3.65 mL, 9.13 mmol) was added dropwise. The mixture was stirred at −78° C. and for 1 h. CO₂ (dry ice) was added in one portion. The mixture was allowed to warm to 25° C. and stir for 15 h. Water (40 mL) was added to the reaction and pH adjusted to 3 by using hydrochloric acid (1 M). The resulting mixture was transferred to a separatory funnel, and the aqueous layer mixture was extracted with ethyl acetate (30 mL×3). The combined organic layers were washed with brine (30 mL), dried over anhydrous sodium sulfate, filtered, and concentrated under reduced pressure affording the 5-bromo-3-methyl-triazole-4-carboxylic acid (650 mg, 38% yield) as a yellow solid. More product was obtained from the water phase from lyophilization affording 5-bromo-3-methyl-triazole-4-carboxylic acid (1 g, 4.85 mmol, 58.47% yield) as a yellow solid. The crude product was used into the next step without further purification.

Step B. tert-butyl N-(5-bromo-3-methyl-triazol-4-yl) carbamate. To a 40 mL Schlenk tube with a magnetic stir bar was added 5-bromo-3-methyl-triazole-4-carboxylic acid (600 mg, 2.91 mmol), t-BuOH (1.39 mL, 14.56 mmol) and TEA (0.81 mL, 5.83 mmol) followed by the addition of toluene (12 mL). DPPA (0.75 mL, 3.50 mmol) was added into the mixture at 25° C. The mixture was heated to 80° C. and stirred for 3 h. The mixture was concentrated under reduced pressure and purified by silica gel chromatography (0-25% Ethyl acetate/Petroleum ether) to give tert-butyl N-(5-bromo-3-methyl-triazol-4-yl) carbamate (560 mg, 69% yield) as a white solid. LCMS (MM-ES+APCI, Pos): m/z 279.0 (M+H).

Step C. tert-butyl N-[5-[3-cyano-4-[(1R)-1-(5-fluoro-2-pyridyl)ethoxy]pyrazolo[1,5-a]pyridin-6-yl]-3-methyl-triazol-4-yl]carbamate. Synthesized according to Example 10, Step E substituting 4-(4-iodo-5-methyl-pyrazol-1-yl) thiane 1,1-dioxide for tert-butyl N-(5-bromo-3-methyl-triazol-4-yl) carbamate to give tert-butyl N-[5-[3-cyano-4-[(1R)-1-(5-fluoro-2-pyridyl)ethoxy]pyrazolo[1,5-a]pyridin-6-yl]-3-methyl-triazol-4-yl]carbamate (98 mg, 55% yield) as a yellow oil. LCMS (MM-ES+APCI, Pos): m/z 479.2 (M+H).

Step D. 6-(5-amino-1-methyl-triazol-4-yl)-4-[(1R)-1-(5-fluoro-2-pyridyl)ethoxy]pyrazolo[1,5-a]pyridine-3-carbonitrile. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl] piperidine-1-carboxylate for tert-butyl N-[5-[3-cyano-4-[(1R)-1-(5-fluoro-2-pyridyl)ethoxy]pyrazolo[1,5-a]pyridin-6-yl]-3-methyl-triazol-4-yl]carbamate to give 6-(5-amino-1-methyl-triazol-4-yl)-4-[(1R)-1-(5-fluoro-2-pyridyl)ethoxy]pyrazolo[1,5-a]pyridine-3-carbonitrile (24.5 mg, 46% yield) as a white solid. LCMS (MM-ES+APCI, Pos): m/z 379.1 (M+H).

Example 12

6-(1-((S)-1-((S)-2,3-dihydroxypropyl) piperidin-3-yl)-5-methyl-1H-pyrazol-4-yl)-4-((R)-1-(5-fluoropyridin-2-yl)ethoxy)pyrazolo[1,5-a]pyridine-3-carbonitrile (37)

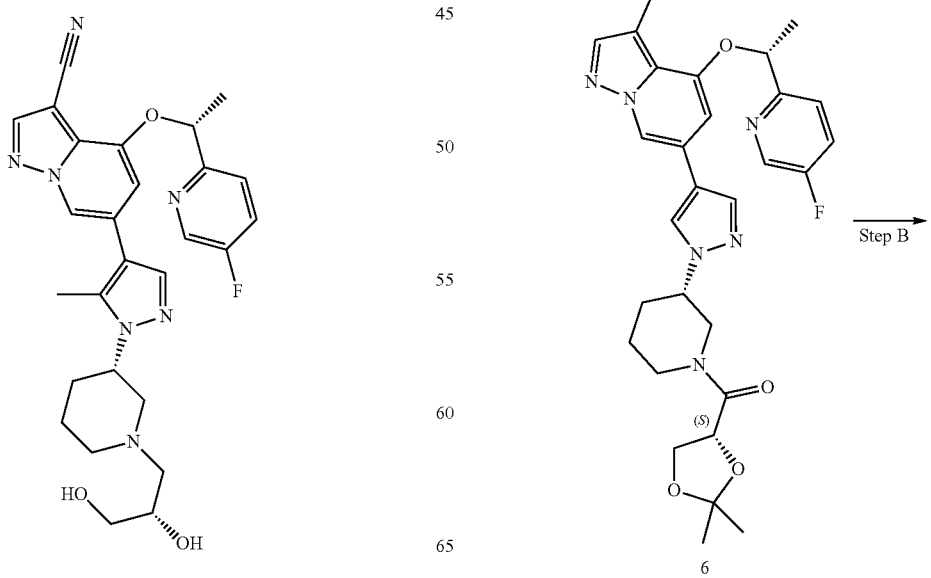

205

-continued

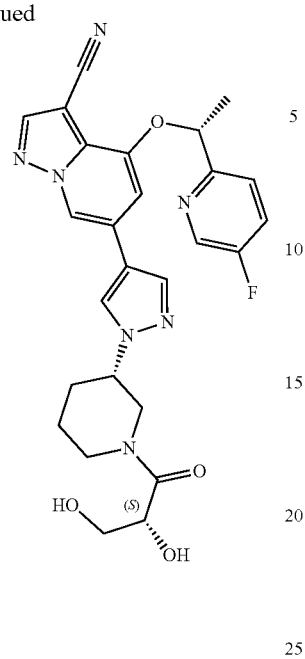

Example 13

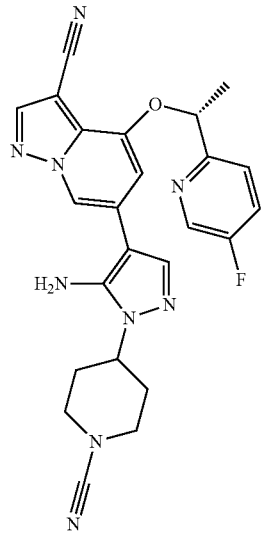 [SMILES: C[C@@H](Oc1cc(-c2cnn(C3CCN(C#N)CC3)c2N)cn2ncc(C#N)c12)c1ccc(F)cn1]

(R)-6-(5-amino-1-(1-cyanopiperidin-4-yl)-1H-pyrazol-4-yl)-4-(1-(5-fluoropyridin-2-yl)ethoxy)pyrazolo[1,5-a]pyridine-3-carbonitrile (47)

Step A. 6-[1-[(3S)-1-[[(4S)-2,2-dimethyl-1,3-dioxolan-4-yl]methyl]-3-piperidyl]-5-methyl-pyrazol-4-yl]-4-[(1R)-1-(5-fluoro-2-pyridyl)ethoxy]pyrazolo[1,5-a]pyridine-3-carbonitrile. To a 40 mL vial equipped with a magnetic stir bar were added 4-[(1R)-1-(5-fluoro-2-pyridyl)ethoxy]-6-[5-methyl-1-[(3S)-3-piperidyl]pyrazol-4-yl]pyrazolo[1,5-a]pyridine-3-carbonitrile (161 mg, 0.36 mmol) and (4R)-4-(chloromethyl)-2,2-dimethyl-1,3-dioxolane (161.19 mg, 1.07 mmol) followed by the addition of DMSO (4 mL). NaI (27.05 mg, 0.18 mmol) and K₂CO₃ (98.45 mg, 0.71 mmol) were added into the mixture in one portion at 25° C. The mixture was heated to 100° C. and stirred for 22 h. Water (20 mL) was added to the reaction and the mixture was transferred to a separatory funnel. The aqueous layer was extracted with ethyl acetate (10 mL×4). The combined organic layers were washed with brine (20 mL), dried over anhydrous sodium sulfate, filtered, concentrated under reduced pressure and purified by preparative TLC (0-10% petroleum ether/ethyl acetate) to give 6-[1-[(3S)-1-[[(4S)-2,2-dimethyl-1,3-dioxolan-4-yl]methyl]-3-piperidyl]-5-methyl-pyrazol-4-yl]-4-[(1R)-1-(5-fluoro-2-pyridyl)ethoxy]pyrazolo[1,5-a]pyridine-3-carbonitrile (65 mg, 29% yield) as a yellow gum. LCMS (MM-ES+APCI, Pos): m/z 560.3 (M+H).

Step B. 6-(1-((S)-1-((S)-2,3-dihydroxypropyl) piperidin-3-yl)-5-methyl-1H-pyrazol-4-yl)-4—((R)-1-(5-fluoropyridin-2-yl)ethoxy)pyrazolo[1,5-a]pyridine-3-carbonitrile. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl]piperidine-1-carboxylate for 6-[1-[(3S)-1-[[(4S)-2,2-dimethyl-1,3-dioxolan-4-yl]methyl]-3-piperidyl]-5-methyl-pyrazol-4-yl]-4-[(1R)-1-(5-fluoro-2-pyridyl)ethoxy]pyrazolo[1,5-a]pyridine-3-carbonitrile to give 6-(1-((S)-1-((S)-2,3-dihydroxypropyl) piperidin-3-yl)-5-methyl-1H-pyrazol-4-yl)-4-((R)-1-(5-fluoropyridin-2-yl)ethoxy)pyrazolo[1,5-a]pyridine-3-carbonitrile (16 mg, 30% yield). LCMS (MM-ES+APCI, Pos): m/z 520.3 (M+H).

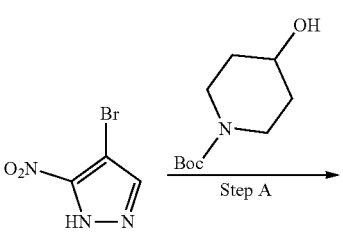

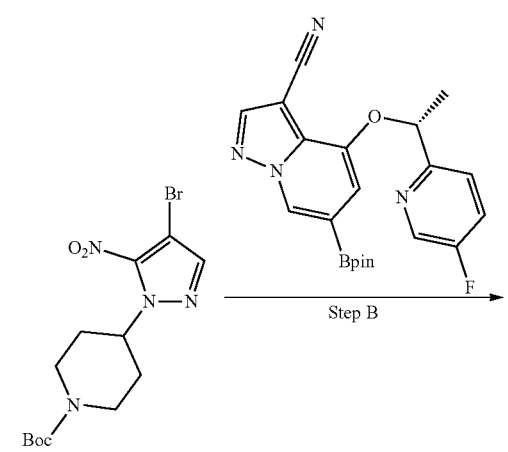

207
-continued

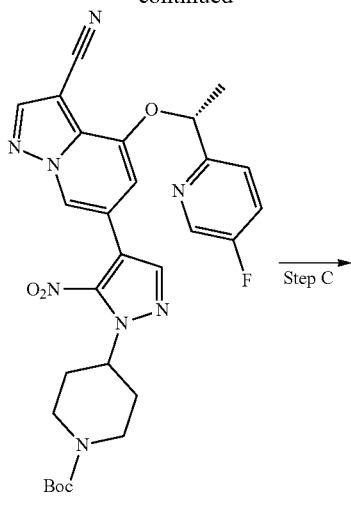

Step C →

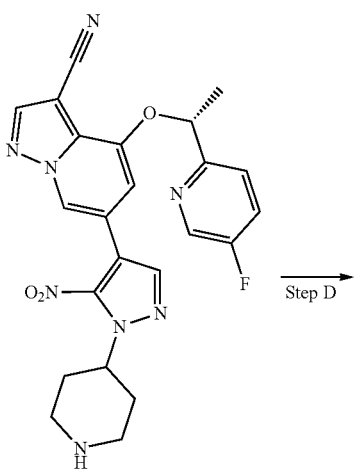

Step D →

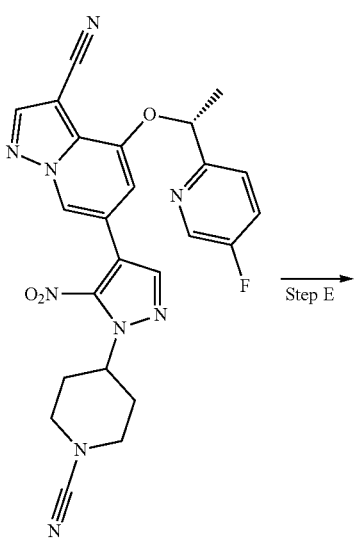

Step E →

208
-continued

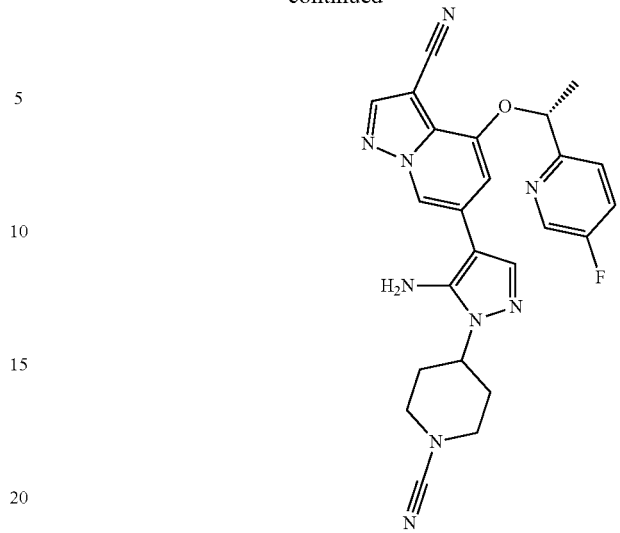

Step A. Compound tert-butyl 4-(4-bromo-5-nitro-pyrazol-1-yl) piperidine-1-carboxylate. To a 100 mL three-necked round-bottom flask equipped with a magnetic stir bar was added 4-bromo-5-nitro-1H-pyrazole (1 g, 5.21 mmol), tert-butyl 4-hydroxypiperidine-1-carboxylate (1.57 g, 7.81 mmol) and PPh₃ (2.73 g, 10.42 mmol) followed by the addition of THF (20 mL). The flask was then evacuated and backfilled with nitrogen three times. The solution was cooled to 0° C. DIAD (2 mL 10.42 mmol) was added dropwise. The mixture was allowed to warm to 25° C. and stir for 16 h. The mixture was concentrated under reduced pressure and purified by flash silica gel chromatography (0~3% Ethyl acetate/Petroleum ether). Compound tert-butyl 4-(4-bromo-5-nitro-pyrazol-1-yl) piperidine-1-carboxylate (1.5 g, 76% yield) was obtained as a yellow oil. LCMS (MM-ES+APCI, Pos): m/z 318.9 (M+H).

Step B. tert-butyl 4-[4-[3-cyano-4-[(1R)-1-(5-fluoro-2-pyridyl)ethoxy]pyrazolo[1,5-a]pyridin-6-yl]-5-nitro-pyrazol-1-yl]piperidine-1-carboxylate. Synthesized according to Example 10, Step E substituting 4-(4-iodo-5-methyl-pyrazol-1-yl) thiane 1,1-dioxide for tert-butyl 4-(4-bromo-5-nitro-pyrazol-1-yl) piperidine-1-carboxylate to give tert-butyl 4-[4-[3-cyano-4-[(1R)-1-(5-fluoro-2-pyridyl)ethoxy] pyrazolo[1,5-a]pyridin-6-yl]-5-nitro-pyrazol-1-yl] piperidine-1-carboxylate (169 mg, 47% yield) as a green oil. LCMS (MM-ES+APCI, Pos): m/z 577.3 (M+H).

Step C. 4-[(1R)-1-(5-fluoro-2-pyridyl)ethoxy]-6-[5-nitro-1-(4-piperidyl) pyrazol-4-yl]pyrazolo[1,5-a]pyridine-3-carbonitrile. Synthesized according to Example 2, Step B substituting tert-butyl 4-[4-[3-cyano-4-[(1R)-1-(2-pyridyl)ethoxy]pyrazolo[1,5-a]pyridin-6-yl]-5-methyl-pyrazol-1-yl] piperidine-1-carboxylate for tert-butyl 4-[4-[3-cyano-4-[(1R)-1-(5-fluoro-2-pyridyl)ethoxy]pyrazolo[1,5-a]pyridin-6-yl]-5-nitro-pyrazol-1-yl]piperidine-1-carboxylate to give 4-[(1R)-1-(5-fluoro-2-pyridyl)ethoxy]-6-[5-nitro-1-(4-piperidyl) pyrazol-4-yl]pyrazolo[1,5-a]pyridine-3-carbonitrile (110 mg, quantitative yield).

Step D. 6-[1-(1-cyano-4-piperidyl)-5-nitro-pyrazol-4-yl]-4-[(1R)-1-(5-fluoro-2-pyridyl)ethoxy]pyrazolo[1,5-a]pyridine-3-carbonitrile. To a 40 mL vial equipped with a magnetic stir bar was added 4-[(1R)-1-(5-fluoro-2-pyridyl) ethoxy]-6-[5-nitro-1-(4-piperidyl) pyrazol-4-yl]pyrazolo[1,5-a]pyridine-3-carbonitrile (100 mg, 0.2 mmol) and K₂CO₃ (162 mg, 1.17 mmol) followed by the addition of ACN (4 mL). The solution was cooled to 0° C. Carbononitridic bromide (0.03 mL, 0.4 mmol) was added. The mixture was allowed to warm to 25° C. and stir for 2 h. The pH of mixture was adjusted to 9 by using saturated sodium bicarbonate. The resulting mixture was extracted with DCM (4 mL×3), combined organic layers washed with brine (4 mL), dried over anhydrous sodium sulfate, filtered, concentrated under reduced pressure and purified by flash silica gel chromatography (0~33% Ethylacetate/Petroleum ether). Compound 6-[1-(1-cyano-4-piperidyl)-5-nitro-pyrazol-4-yl]-4-[(1R)-1-(5-fluoro-2-pyridyl)ethoxy]pyrazolo[1,5-a]pyridine-3-carbonitrile (105 mg, 95% yield) was obtained as a green oil. LCMS (MM-ES+APCI, Pos): m/z 502.2 (M+H).

Step E. 6-[5-amino-1-(1-cyano-4-piperidyl) pyrazol-4-yl]-4-[(1R)-1-(5-fluoro-2-pyridyl)ethoxy]pyrazolo[1,5-a]pyridine-3-carbonitrile. To a 40 mL vial equipped with a magnetic stir bar was added 6-[1-(1-cyano-4-piperidyl)-5-nitro-pyrazol-4-yl]-4-[(1R)-1-(5-fluoro-2-pyridyl)ethoxy]pyrazolo[1,5-a]pyridine-3-carbonitrile (90 mg, 0.17 mmol), NH₄Cl (75.03 mg, 1.40 mmol) followed by the addition of Water (1 mL) and THF (5 mL). Then Fe (78.34 mg, 1.40 mmol) was added into the mixture. The mixture was heated to 60° C. and stirred for 50 min. The suspension was filtered and the filter cake was washed with EtOAc (5 mL). The filtrate was diluted with H₂O (5 mL), transferred to a 40 mL vial, the aqueous layer mixture was extracted with ethyl acetate (5 mL×3), combined organic layers washed with brine (10 mL), dried over anhydrous sodium sulfate, filtered, concentrated under reduced pressure and purified by preparative HPLC (30%-60% acetonitrile/0.1% ammonium hydrogen carbonate). After lyophilization, 6-[5-amino-1-(1-cyano-4-piperidyl) pyrazol-4-yl]-4-[(1R)-1-(5-fluoro-2-pyridyl)ethoxy]pyrazolo[1,5-a]pyridine-3-(34.6 mg, 42% yield) was obtained as an off-white solid. LCMS (MM-ES+APCI, Pos): m/z 472.2 (M+H).

Example 14

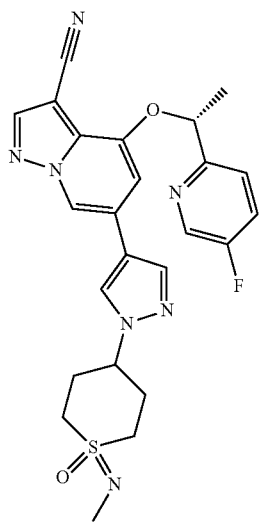 [SMILES: CN=S1(=O)CCC(n2cc(-c3cc(O[C@H](C)c4ccc(F)cn4)c4c(C#N)cnn4c3)cn2)CC1]

4-[(1R)-1-(5-fluoro-2-pyridyl)ethoxy]-6-[1-(1-methylimino-1-oxo-thian-4-yl) pyrazol-4-yl]pyrazolo[1,5-a]pyridine-3-carbonitrile

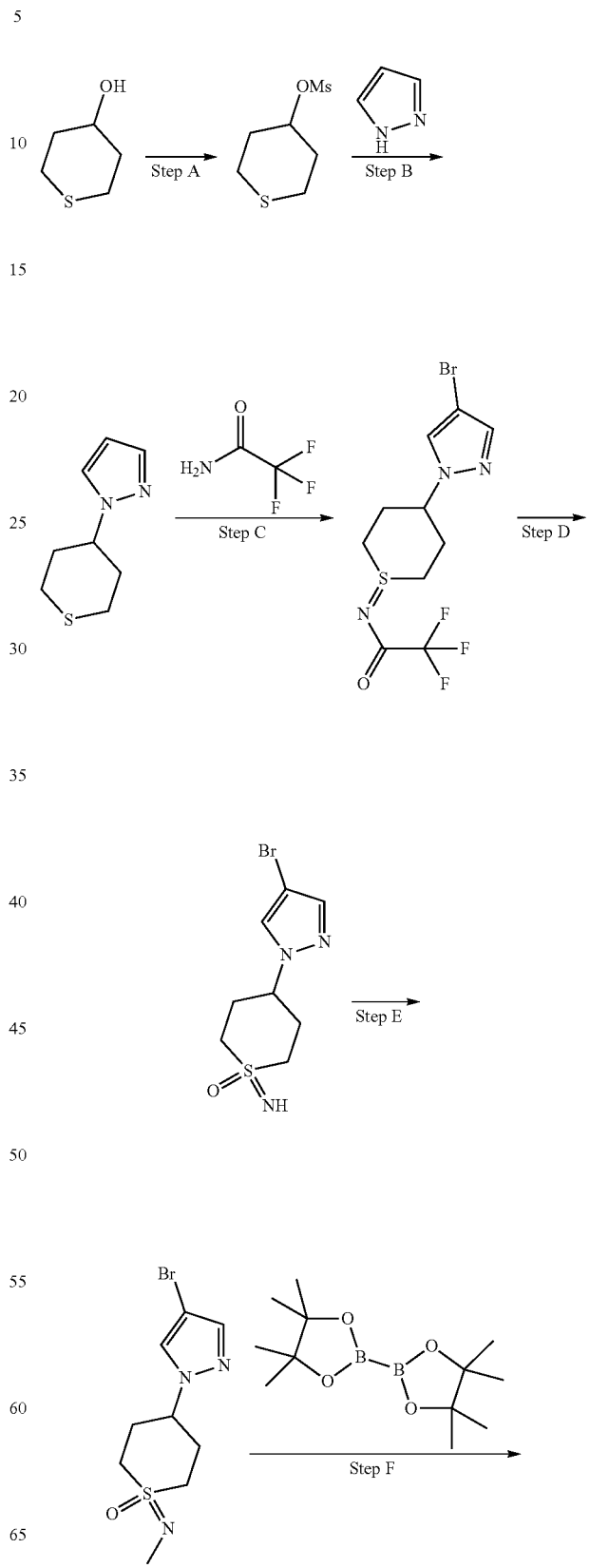

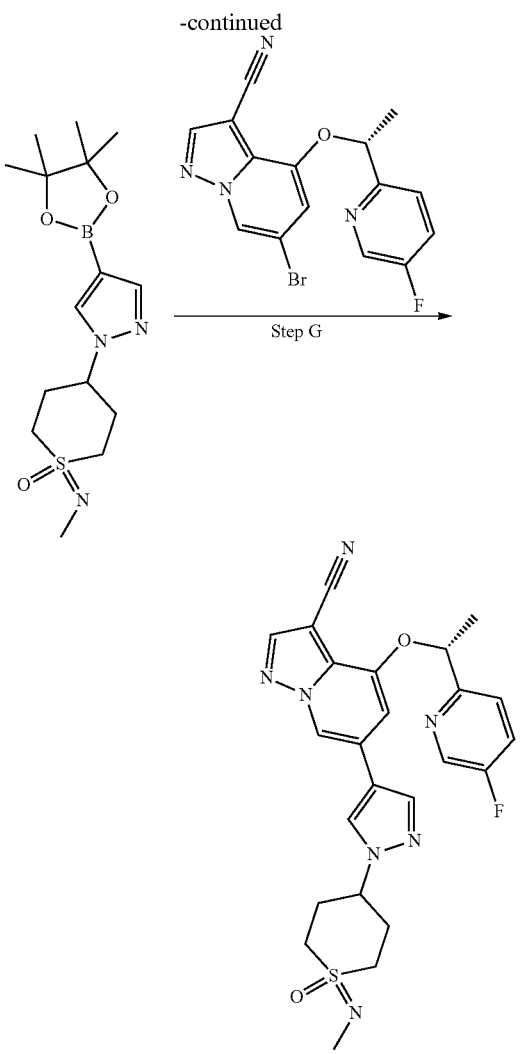

Step A. Tetrahydrothiopyran-4-yl methanesulfonate. To a solution of tetrahydrothiopyran-4-ol (2 g, 16.92 mmol) in DCM (20 mL) was added TEA (7.07 mL 50.8 mmol). Methylsulfonyl methanesulfonate (5.90 g, 33.84 mmol) was slowly added to the mixture. The mixture was stirred at 25° C. for 16 h. The mixture was added to DCM (20 mL). The resulting mixture was transferred to a separatory funnel, organic layers were washed with $H_2O$ (15 mL×3), dried over anhydrous sodium sulfate, filtered, and concentrated under reduced pressure affording tetrahydrothiopyran-4-yl methanesulfonate (3.35 g, crude) as brown oil, and used into the next step without further purification.

Step B. 1-tetrahydrothiopyran-4-ylpyrazole. To a solution of tetrahydrothiopyran-4-yl methanesulfonate (3.35 g, 17.1 mmol) in DMF (30 mL) was added $Cs_2CO_3$ (11.1 g, 34.13 mmol) and 1H-pyrazole (1.16 g, 17.07 mmol). The mixture was stirred at 80° C. for 2 hr. The mixture was added to $H_2O$ (100 mL). The resulting mixture was transferred to a separatory funnel, and the aqueous layer mixture was extracted with ethyl acetate (30 mL×3), combined organic layers washed with $H_2O$ (30 mL×3), brine (40 mL), dried over anhydrous sodium sulfate, filtered, concentrated under reduced pressure and purified by flash silica gel chromatography (10~15% Ethylacetate/Petroleum ether) to give 1-tetrahydrothiopyran-4-ylpyrazole (1.1 g, 37% yield) as a yellow solid. LCMS (MM-ES+APCI, Pos): m/z 169.1 (M+H).

Step C. N-[4-(4-bromopyrazol-1-yl) thian-1-ylidene]-2,2,2-trifluoro-acetamide. To a 100 mL round-bottom flask equipped with a magnetic stir bar was added 1-tetrahydrothiopyran-4-ylpyrazole (1.10 g, 6.40 mmol) and 2,2,2-trifluoroacetamide (724 mg, 6.40 mmol) followed by the addition of MTBE (6 mL). The solution was cooled to 0° C. t-BuOK (1.10 g, 9.60 mmol) was added in portions, the reaction was stirred at 0° C. for 1 h. Next, a solution of 1,3-dibromo-5,5-dimethyl-imidazolidine-2,4-dione (4.60 g, 16.0 mmol) in THF (6 mL) was added dropwise. The mixture was stirred at 0° C. for 1 h. The reaction mixture was quenched by slow addition of saturated aqueous sodium bisulfite (15 mL). The resulting mixture was transferred to a separatory funnel, and the aqueous layer mixture was extracted with ethyl acetate (10 mL×3), combined organic layers were washed with brine (15 mL), dried over anhydrous sodium sulfate, filtered, concentrated under reduced pressure and purified by flash silica gel chromatography (30~34% Ethylacetate/Petroleum ether). N-[4-(4-bromopyrazol-1-yl) thian-1-ylidene]-2,2,2-trifluoro-acetamide (1.4 g, 61% yield) was obtained as a light yellow solid.

Step D. 4-(4-bromopyrazol-1-yl)-1-imino-thiane 1-oxide. To a 100 mL round-bottom flask equipped with a magnetic stir bar was added benzyl N-[4-(4-bromopyrazol-1-yl) thian-1-ylidene]-2,2,2-trifluoro-acetamide (1.4 g, 3.91 mmol) followed by the addition of MeOH (8 mL), $H_2O$ (1 mL), $K_2CO_3$ (1.08 g, 7.82 mmol) and ACN (8 mL). $H_2O_2$ (2 mL, 21.79 mmol) was added dropwise into the mixture at 25° C. The mixture was stirred at 25° C. for 2 h. The reaction mixture was quenched by slow addition of saturated aqueous sodium bisulfite (10 mL) and stirred for 0.5 h. The reaction mixture was concentrated, diluted with ethyl acetate (10 mL), transferred to a separatory funnel, aqueous layer mixture was extracted with ethyl acetate (10 mL×3), combined organic layers washed with brine (10 mL), dried over anhydrous sodium sulfate, filtered, and concentrated under reduced pressure affording the crude product. 4-(4-bromopyrazol-1-yl)-1-imino-thiane 1-oxide (600 mg, 55% yield) was obtained as a white solid, and used into the next step without further purification Step E. 4-(4-bromopyrazol-1-yl)-1-methylimino-thiane 1-oxide. To a 40 mL vial equipped with a magnetic stir bar was added 4-(4-bromopyrazol-1-yl)-1-imino-thiane 1-oxide (600 mg, 2.16 mmol), TFA (1.6 mL, 21.57 mmol), (HCHO), (694 mg, 21.57 mmol) and triethylsilane (3.45 mL, 21.57 mmol, 3.45 mL) followed by the addition of ACN (15 mL). The mixture was stirred at 25° C. for 16 h. The pH of mixture was adjusted to 8 by using saturated aqueous sodium bicarbonate. The mixture was concentrated under reduced pressure, residue was added to $H_2O$ (20 mL) transferred to a separatory funnel, the aqueous layer mixture extracted with EA (15 mL×3), combined organic layers washed with brine (20 mL), dried over anhydrous sodium sulfate, filtered, and concentrated under reduced pressure affording the crude product. The crude product was purified by recrystallization from PE (20 mL) at 25° C. for 0.5 h. After filtration and drying under vacuum, the desired product was obtained as a white solid. 4-(4-bromopyrazol-1-yl)-1-methylimino-thiane 1-oxide (320 mg, crude) was obtained as a white solid, and used into the next step without further purification.

Step F. 1-methylimino-4-[4-(4,4,5,5-tetramethyl-1,3,2-dioxaborolan-2-yl) pyrazol-1-yl]thiane 1-oxide. Synthesized according to Intermediate 2, Step A substituting 6-bromo-4-[(1R)-1-(5-fluoro-2-pyridyl)ethoxy]pyrazolo[1,5-a]pyridine-3-carbonitrile for 4-(4-bromopyrazol-1-yl)-1-methylimino-thiane 1-oxide to give a solution of 1-methylimino- 4-[4-(4,4,5,5-tetramethyl-1,3,2-dioxaborolan-2-yl) pyrazol-1-yl]thiane 1-oxide (313.0 mg, crude) in dioxane (6 mL) as a brown liquid, and used into the next step without further purification.

Step G. 4-[(1R)-1-(5-fluoro-2-pyridyl)ethoxy]-6-[1-(1-methylimino-1-oxo-thian-4-yl) pyrazol-4-yl]pyrazolo[1,5-a]pyridine-3-carbonitrile. Synthesized according to Example 4, Step A substituting tert-butyl 4-(4-(4,4,5,5-tetramethyl-1,3,2-dioxaborolan-2-yl)-1H-pyrazol-1-yl) piperidine-2-carboxylate for 1-methylimino-4-[4-(4,4,5,5-tetramethyl-1,3,2-dioxaborolan-2-yl) pyrazol-1-yl]thiane 1-oxide to give 4-[(1R)-1-(5-fluoro-2-pyridyl)ethoxy]-6-[1-(1-methylimino-1-oxo-thian-4-yl) pyrazol-4-yl]pyrazolo[1,5-a]pyridine-3-carbonitrile (106.3 mg, 34% yield) as an off-white solid. LCMS (MM-ES+APCI, Pos): m/z 494.2 (M+H).

Example 15

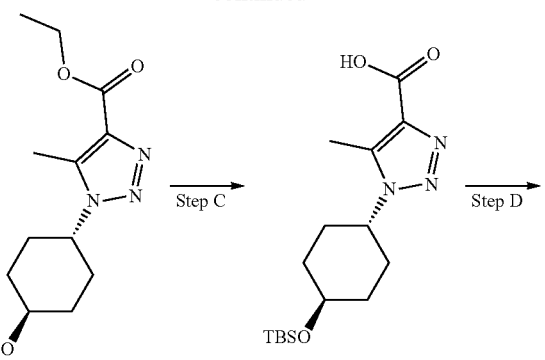

4-[(1R)-1-(5-fluoro-2-pyridyl)ethoxy]-6-[1-(4-hydroxycyclohexyl)-5-methyl-triazol-4-yl]pyrazolo[1,5-a]pyridine-3-carbonitrile

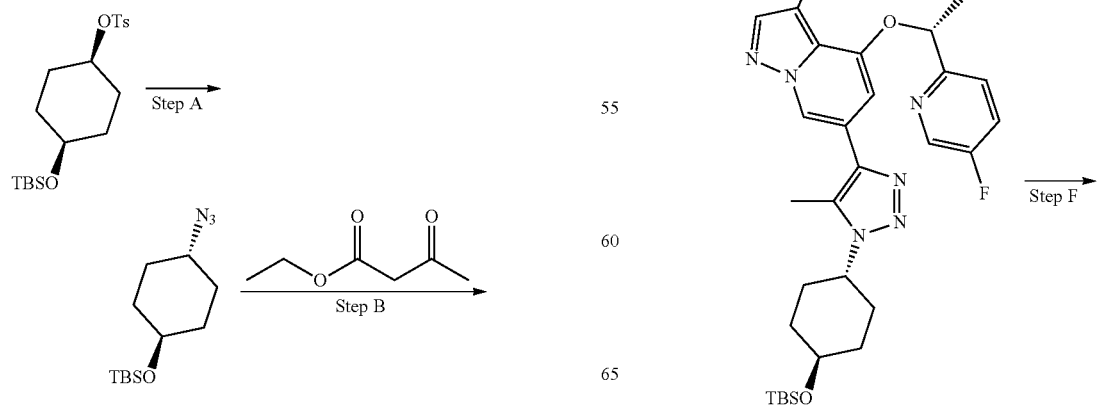

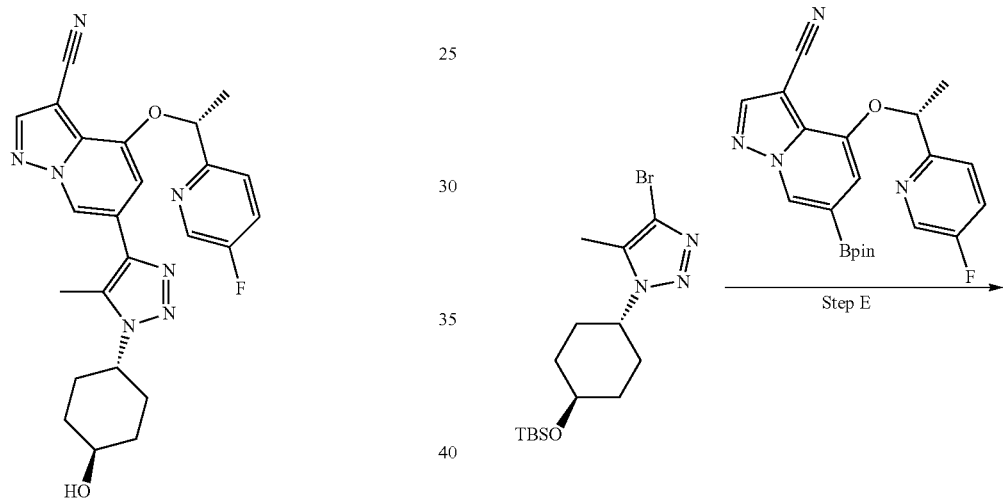

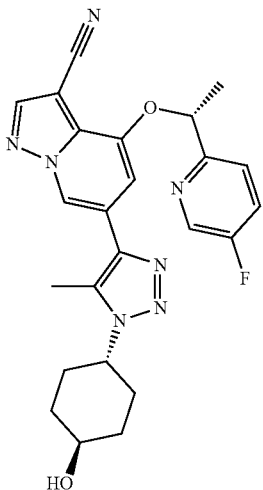 [SMILES: Cc1c(-c2cc(O[C@H](C)c3ccc(F)cn3)c3c(C#N)cnn3c2)nnn1[C@H]1CC[C@H](O)CC1]

Step A. (4-azidocyclohexoxy)-tert-butyl-dimethyl-silane. To a 100 mL three-necked round-bottom equipped with a magnetic stir bar was added [4-[tert-butyl(dimethyl) silyl]oxycyclohexyl]4-methylbenzenesulfonate (1.5 g, 3.90 mmol) followed by the addition of DMSO (15 mL). NaN3 (740 mg, 11.38 mmol) was added into the mixture at 25° C. The mixture was heated to 65° C. and stirred for 16 h. After cooling to 25° C., the solution was diluted with H$_2$O (500 mL). The pH of mixture was adjusted to 9 by using saturated aqueous sodium bicarbonate. The resulting mixture was transferred to a separatory funnel, aqueous layer mixture extracted with ethyl acetate (250 mL×3), combined organic layers washed with H$_2$O (100 mL×3), brine (100 mL), dried over anhydrous sodium sulfate, filtered and concentrated to give (4-azidocyclohexoxy)-tert-butyl-dimethyl-silane (990 mg, crude) as yellow oil.

Step B. Ethyl 1-[4-[tert-butyl(dimethyl) silyl]oxycyclohexyl]-5-methyl-triazole-4-carboxylate. A mixture of (4-azidocyclohexoxy)-tert-butyl-dimethyl-silane (650 mg, 2.54 mmol), ethyl 3-oxobutanoate (0.48 mL, 3.82 mmol) and K$_2$CO$_3$ (1.06 g, 7.63 mmol) in DMSO (6 mL) was degassed and purged with N$_2$ for 3 times, and then the mixture was stirred at 80° C. for 1.5 h under N$_2$ atmosphere. The mixture was quenched by slow addition of H$_2$O (30 mL). The resulting mixture was transferred to a separatory funnel, the aqueous layer mixture extracted with ethyl acetate (10 mL×3), combined organic layers washed with brine (20 mL), dried over anhydrous sodium sulfate, filtered, concentrated under reduced pressure and purified by flash silica gel chromatography (10~25% Ethylacetate/Petroleum ether) to give ethyl 1-[4-[tert-butyl(dimethyl) silyl]oxycyclohexyl]-5-methyl-triazole-4-carboxylate (480 mg, 50% yield) as a white solid. LCMS (MM-ES+APCI, Pos): m/z 368.2 (M+H).

Step C. 1-[4-[tert-butyl(dimethyl) silyl]oxycyclohexyl]-5-methyl-triazole-4-carboxylic acid. To a 40 mL vial equipped with a magnetic stir bar was added ethyl 1-[4-[tert-butyl(dimethyl) silyl]oxycyclohexyl]-5-methyl-triazole-4-carboxylate (350 mg, 0.9 mmol) and KOH (155 mg, 2.77 mmol) followed by the addition of H$_2$O (3 mL). The mixture was stirred at 50° C. for 16 h. The mixture was quenched by slow addition of H$_2$O (100 mL). The resulting mixture was transferred to a separatory funnel, aqueous layer mixture extracted with ethyl acetate (30 mL×3), combined organic layers washed with brine (100 mL), dried over anhydrous sodium sulfate, filtered, and concentrated under reduced pressure affording 1-[4-[tert-butyl(dimethyl) silyl]oxycyclohexyl]-5-methyl-triazole-4-carboxylic acid (306 mg, 98% yield) as a yellow solid, which was used into the next step without further purification. LCMS (MM-ES+APCI, Pos): m/z 340.1 (M+H).

Step D. [4-(4-bromo-5-methyl-triazol-1-yl)cyclohexoxy]-tert-butyl-dimethyl-silane. To a 20 mL Schlenk tube equipped with a magnetic stir bar was added 1-[4-[tert-butyl (dimethyl) silyl]oxycyclohexyl]-5-methyl-triazole-4-carboxylic acid (200 mg, 0.59 mmol) followed by the addition of KOH (60.2 mg, 1.07 mmol) and H$_2$O (2 mL). Br$_2$ (0.07 mL, 1.18 mmol) was added into the mixture. The mixture was stirred at 40° C. for 4 h. The mixture was quenched by slow addition of H$_2$O (100 mL), resulting mixture was transferred to a separatory funnel, aqueous layer mixture extracted with ethyl acetate (20 mL×3), combined organic layers washed with brine (100 mL), dried over anhydrous sodium sulfate, filtered, and concentrated under reduced pressure affording [4-(4-bromo-5-methyl-triazol-1-yl)cyclohexoxy]-tert-butyl-dimethyl-silane (122 mg, 53% yield) as yellow oil, which was used into the next step without further purification. LCMS (MM-ES+APCI, Pos): m/z 374.1 (M+H).

Step E. 6-[1-[4-[tert-butyl(dimethyl) silyl]oxycyclohexyl]-5-methyl-triazol-4-yl]-4-[(1R)-1-(5-fluoro-2-pyridyl)ethoxy]pyrazolo[1,5-a]pyridine-3-carbonitrile. Synthesized according to Example 10, Step E substituting 4-(4-iodo-5-methyl-pyrazol-1-yl) thiane 1,1-dioxide for [4-(4-bromo-5-methyl-triazol-1-yl)cyclohexoxy]-tert-butyl-dimethyl-silane to give 6-[1-[4-[tert-butyl (dimethyl) silyl]oxycyclohexyl]-5-methyl-triazol-4-yl]-4-[(1R)-1-(5-fluoro-2-pyridyl)ethoxy]pyrazolo[1,5-a]pyridine-3-carbonitrile (113 mg, 51% yield) as yellow oil. LCMS (MM-ES+APCI, Pos): m/z 576.3 (M+H).

Step F. 4-[(1R)-1-(5-fluoro-2-pyridyl)ethoxy]-6-[1-(4-hydroxycyclohexyl)-5-methyl-triazol-4-yl]pyrazolo[1,5-a]pyridine-3-carbonitrile. To a 40 mL vial equipped with a magnetic stir bar was added 6-[1-[4-[tert-butyl(dimethyl) silyl]oxycyclohexyl]-5-methyl-triazol-4-yl]-4-[(1R)-1-(5-fluoro-2-pyridyl)ethoxy]pyrazolo[1,5-a]pyridine-3-carbonitrile (113 mg, 0.13 mmol) followed by the addition of DCM (2 mL). HCl/dioxane (2 M, 1.5 mL) was added into the mixture. The mixture was stirred at 25° C. for 1 h. The mixture was concentrated under reduced pressure and purified by preparative HPLC (18%-48% acetonitrile/aqueous ammonia hydroxide+10 mM NH$_4$HCO$_3$). After lyophilization, 4-[(1R)-1-(5-fluoro-2-pyridyl)ethoxy]-6-[1-(4-hydroxycyclohexyl)-5-methyl-triazol-4-yl]pyrazolo[1,5-a]pyridine-3-carbonitrile (31.5 mg, 50% yield) was obtained as a white solid. LCMS (MM-ES+APCI, Pos): m/z 462.2 (M+H).

Example 16

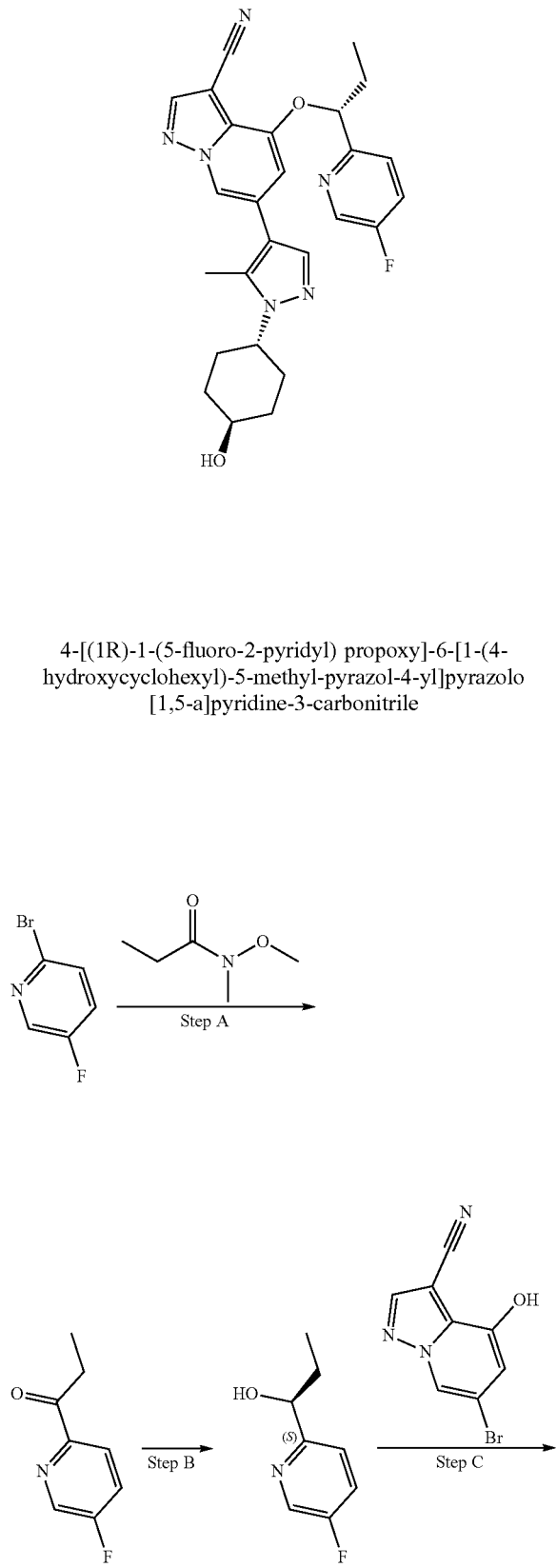

4-[(1R)-1-(5-fluoro-2-pyridyl) propoxy]-6-[1-(4-hydroxycyclohexyl)-5-methyl-pyrazol-4-yl]pyrazolo[1,5-a]pyridine-3-carbonitrile

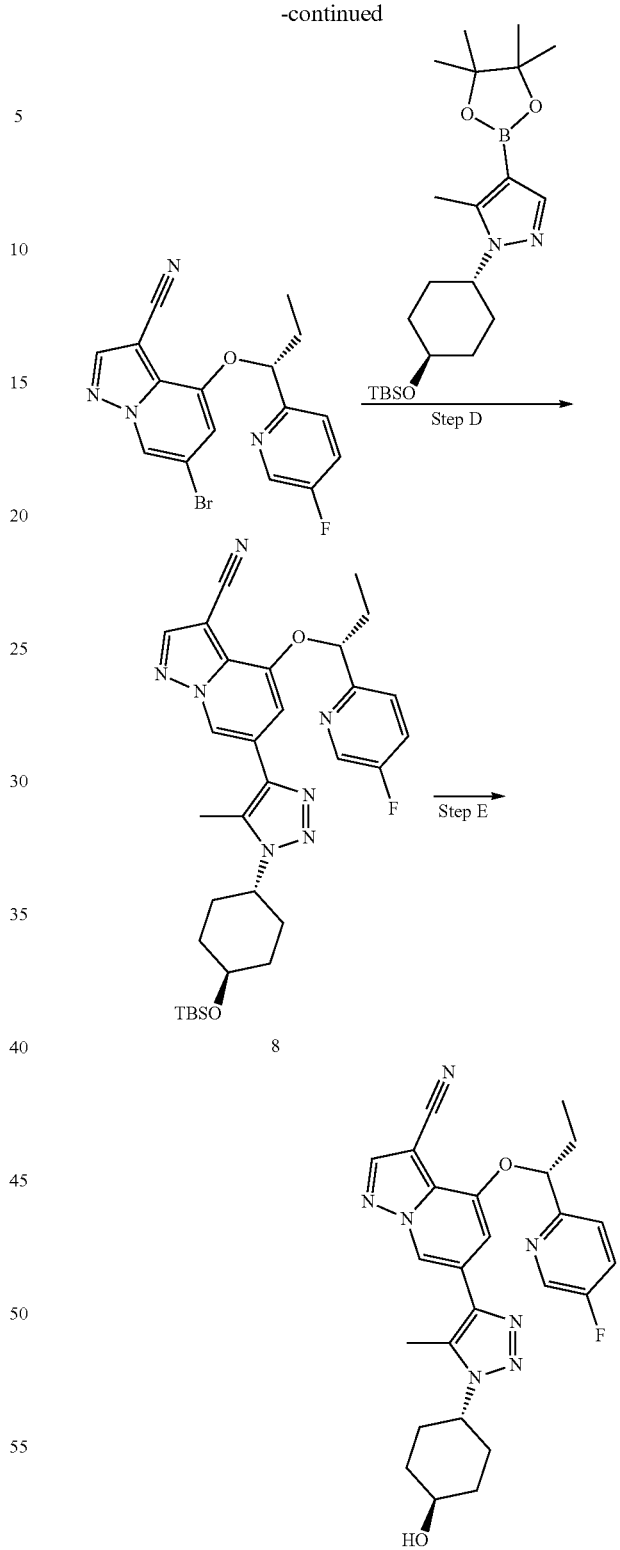

Step A. 1-(5-fluoro-2-pyridyl) propan-1-one. To a 250 mL three-necked round-bottom flask equipped with a magnetic stir bar was added 2-bromo-5-fluoro-pyridine (5 g, 28.41 mmol) followed by the addition of toluene (50 mL), and the mixture was evacuated and backfilled with nitrogen three times. The solution was cooled to −78° C., n-BuLi (2.5 M, 13.64 mL) was added dropwise at −78° C. and stirred for 0.5 h. N-methoxy-N-methyl-propanamide (4.00 g, 34.15 mmol) was added into the mixture dropwise at −78° C. The mixture was stirred at −78° C. for 1 h. The mixture was quenched by slow addition of saturated aqueous ammonium chloride (50 mL). The resulting mixture was extracted with ethyl acetate (50 mL×3), combined organic layers were dried over anhydrous sodium sulfate, filtered, concentrated under reduced pressure and purified by silica gel column chromatography (0-3% ethyl acetate in petroleum ether) to give 1-(5-fluoro-2-pyridyl) propan-1-one (2.9 g, 65% yield) as brown oil. LCMS (MM-ES+APCI, Pos): m/z 154.1 (M+H).

Step B. (1S)-1-(5-fluoro-2-pyridyl) propan-1-ol. To a 100 mL three-necked round-bottom flask equipped with a magnetic stir bar was added (3aR)-1-methyl-3,3-diphenyl-3a,4,5,6-tetrahydropyrrolo[1,2-c][1,3,2]oxazaborole (1 M, 9.6 mL) followed by the addition of THF (20 mL). The flask was then evacuated and backfilled with nitrogen three times. The mixture was cooled to 0° C. $BH_3$-$Me_2S$ (10 M, 0.96 mL) was added dropwise and the reaction mixture was stirred for 1 h. The mixture was cooled to −30° C., 1-(5-fluoro-2-pyridyl) propan-1-one (1 g, 6.39 mmol) dissolved in THF (4 mL) was added dropwise over 0.5 h. The mixture was stirred at −30° C. under an atmosphere of nitrogen for 1 h. The mixture was quenched by slow addition of 1 M HCl (30 mL). The pH of mixture was adjusted to pH8 by using saturated aqueous sodium bicarbonate. The resulting mixture was extracted with dichloromethane (50 mL×3), combined organic layers dried over anhydrous sodium sulfate, filtered, concentrated under reduced pressure and purified by silica gel column chromatography (20-50% ethyl acetate in petroleum ether) to give (1S)-1-(5-fluoro-2-pyridyl) propan-1-ol (360 mg, 35% yield) as colorless oil.

Step C. 6-bromo-4-[(1R)-1-(5-fluoro-2-pyridyl) propoxy]pyrazolo[1,5-a]pyridine-3-carbonitrile. To a 40 mL vial equipped with a magnetic stir bar was added 6-bromo-4-hydroxy-pyrazolo[1,5-a]pyridine-3-carbonitrile (150 mg, 0.63 mmol) followed by the addition of DCM (3 mL). $PPh_3$ (330.00 mg, 1.26 mmol) and (1S)-1-(5-fluoro-2-pyridyl) propan-1-ol (160 mg, 1.03 mmol) were added into the mixture at 25° C. The vial was then evacuated and backfilled with nitrogen for one minute. The mixture was cooled to 0° C., DBAD (300.00 mg, 1.30 mmol) in DCM (3 mL) was added dropwise. Finally, the mixture was allowed to warm to 25° C. and stir under an atmosphere of nitrogen for 1 h. The mixture was quenched by slow addition of $H_2O$ (10 mL). The resulting mixture was transferred to a separatory funnel, and the aqueous layer mixture was extracted with dichloromethane (10 mL×3). The combined organic layers were dried over anhydrous sodium sulfate, filtered, concentrated under reduced pressure and purified by silica gel column chromatography (10-30% ethyl acetate in petroleum ether) to give 6-bromo-4-[(1R)-1-(5-fluoro-2-pyridyl) propoxy]pyrazolo[1,5-a]pyridine-3-carbonitrile (220 mg, 91% yield) as colorless oil. LCMS (MM-ES+APCI, Pos): m/z 374.9 (M+H).

Step D. 6-[1-[4-[tert-butyl(dimethyl) silyl]oxycyclohexyl]-5-methyl-pyrazol-4-yl]-4-[(1R)-1-(5-fluoro-2-pyridyl) propoxy]pyrazolo[1,5-a]pyridine-3-carbonitrile. Synthesized according to Example 4, Step A substituting tert-butyl 4-(4-(4,4,5,5-tetramethyl-1,3,2-dioxaborolan-2-yl)-1H-pyrazol-1-yl) piperidine-2-carboxylate for tert-butyl-dimethyl-[4-[5-methyl-4-(4,4,5,5-tetramethyl-1,3,2-dioxaborolan-2-yl) pyrazol-1-yl]cyclohexoxy]silane and tert-butyl 4-(4-(4,4,5,5-tetramethyl-1,3,2-dioxaborolan-2-yl)-1H-pyrazol-1-yl) piperidine-2-carboxylate for 6-bromo-4-[(1R)-1-(5-fluoro-2-pyridyl) propoxy]pyrazolo[1,5-a]pyridine-3-carbonitrile to give 6-[1-[4-[tert-butyl(dimethyl) silyl]oxycyclohexyl]-5-methyl-pyrazol-4-yl]-4-[(1R)-1-(5-fluoro-2-pyridyl) propoxy]pyrazolo[1,5-a]pyridine-3-carbonitrile (100 mg, 64% yield) as yellow oil. LCMS (MM-ES+APCI, Pos): m/z 589.3 (M+H).

Step E. 4-[(1R)-1-(5-fluoro-2-pyridyl) propoxy]-6-[1-(4-hydroxycyclohexyl)-5-methyl-pyrazol-4-yl]pyrazolo[1,5-a]pyridine-3-carbonitrile. To a 100 mL round-bottom flask equipped with a magnetic stir bar was added 6-[1-[4-[tert-butyl(dimethyl) silyl]oxycyclohexyl]-5-methyl-pyrazol-4-yl]-4-[(1R)-1-(5-fluoro-2-pyridyl) propoxy]pyrazolo[1,5-a]pyridine-3-carbonitrile (100 mg, 0.17 mmol) followed by the addition of DCM (1 mL). HCl/dioxane (2 M, 10 mL) was added into the mixture at 25° C. The mixture was stirred at 25° C. for 0.5 h. The mixture was concentrated under reduced pressure and purified by preparative HPLC (32%-62% acetonitrile/0.04% aqueous ammonia hydroxide+10 mM $NH_4HCO_3$). The residual aqueous solution was lyophilized to give 4-[(1R)-1-(5-fluoro-2-pyridyl) propoxy]-6-[1-(4-hydroxycyclohexyl)-5-methyl-pyrazol-4-yl]pyrazolo[1,5-a]pyridine-3-carbonitrile (57.2 mg, 72% yield) as a white solid. LCMS (MM-ES+APCI, Pos): m/z 475.2 (M+H).

Example 17

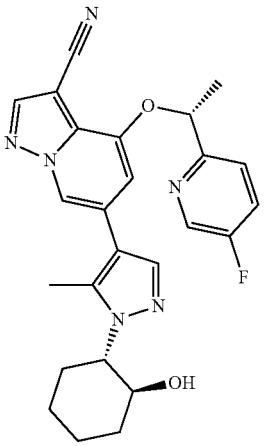 [SMILES: Cc1c(-c2cc(O[C@H](C)c3ccc(F)cn3)c3c(C#N)cnn3c2)cnn1[C@H]1CCCC[C@@H]1O]

4-[(1R)-1-(5-fluoro-2-pyridyl)ethoxy]-6-[1-[(1S,2S)-2-hydroxycyclohexyl]-5-methyl-pyrazol-4-yl]pyrazolo[1,5-a]pyridine-3-carbonitrile

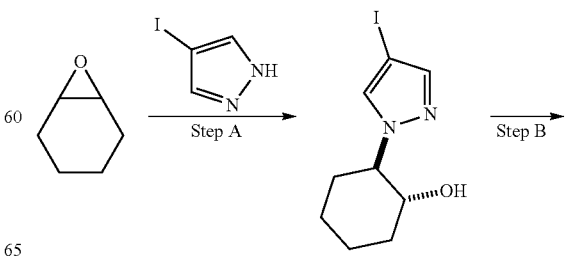

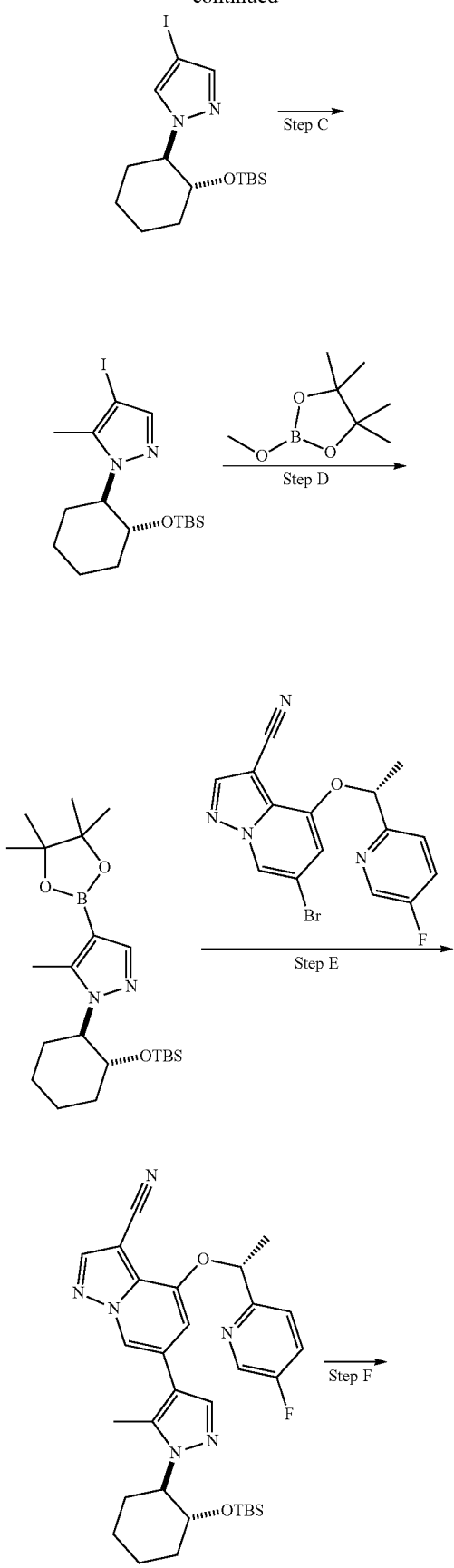

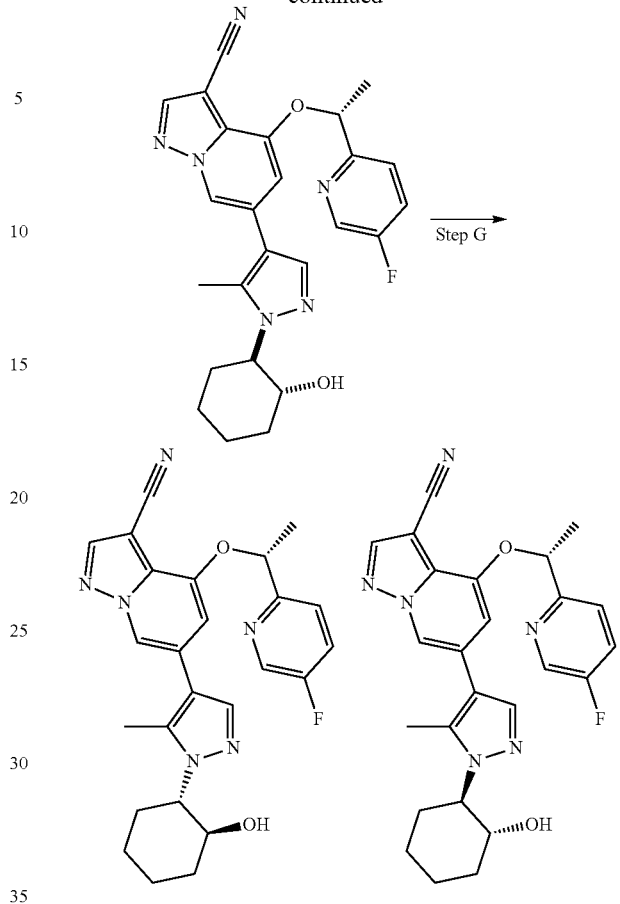

Step A. 2-(4-iodopyrazol-1-yl)cyclohexanol. To a 250 mL three-necked round-bottom flask equipped with a magnetic stir bar and a reflux condenser was added 4-iodo-1H-pyrazole (2.00 g, 10.3 mmol) followed by the addition of DMF (25 mL). 7-oxabicyclo[4.1.0]heptane (1.25 mL 12.4 mmol) and $Cs_2CO_3$ (5.04 g, 15.5 mmol) were added into the mixture dropwise at 25° C. The mixture was heated to 80° C. and stirred for 16 h. The mixture was quenched by slow addition of $H_2O$ (100 mL). The resulting mixture was transferred to a separatory funnel, aqueous layer mixture extracted with ethyl acetate (100 mL×3), combined organic layers washed with brine (20 mL), dried over anhydrous sodium sulfate, filtered, and concentrated under reduced pressure affording 2-(4-iodopyrazol-1-yl)cyclohexanol (3 g, crude) as yellow oil. LCMS (MM-ES+APCI, Pos): m/z 292.9 (M+H).

Step B. tert-butyl-[2-(4-iodopyrazol-1-yl)cyclohexoxy]-dimethyl-silane. To a 100 mL round-bottom flask equipped with a magnetic stir bar was added 2-(4-iodopyrazol-1-yl) cyclohexanol (2.80 g, 9.59 mmol) followed by the addition of DMF (20 mL) and imidazole (2.61 g, 38.3 mmol). TBSCl (3.54 mL, 28.8 mmol) was added into the mixture at 25° C. The mixture was stirred at 25° C. for 5 min. The mixture was quenched by slow addition of $H_2O$ (100 mL). The resulting mixture was transferred to a separatory funnel, and the aqueous layer mixture was extracted with ethyl acetate (100 mL×3). The combined organic layers were washed with brine (20 mL), dried over anhydrous sodium sulfate, filtered, concentrated under reduced pressure and purified by flash silica gel chromatography (0~5% Ethylacetate/Petroleum ether) to give tert-butyl-[2-(4-iodopyrazol-1-yl)cyclohexoxy]-dimethyl-silane (3.4 g, 86% yield, 98.5% purity) as a white solid. LCMS (MM-ES+APCI, Pos): m/z 407.2 (M+H).

Step C. tert-butyl-[2-(4-iodo-5-methyl-pyrazol-1-yl)cyclohexoxy]-dimethyl-silane. To a 100 mL three-necked round-bottom flask equipped with a magnetic stir bar was added tert-butyl-[2-(4-iodopyrazol-1-yl)cyclohexoxy]-dimethyl-silane (1.2 g, 2.91 mmol) followed by the addition of THF (5 mL). The solution was cooled to −78° C. LDA (2 M, 3.64 mL) was added dropwise. The mixture was stirred at −78° C. for 1 h. MeI (0.54 mL, 8.73 mmol) was added dropwise. The mixture was stirred at −78° C. for 1 h. The mixture was quenched by slow addition of H₂O (30 mL), transferred to a separatory funnel, aqueous layer mixture extracted with ethyl acetate (20 mL×3). The combined organic layers were washed with brine (10 mL), dried over anhydrous sodium sulfate, filtered, concentrated under reduced pressure and purified by flash silica gel chromatography (0~8% Ethylacetate/Petroleum ether) to give tert-butyl-[2-(4-iodo-5-methyl-pyrazol-1-yl)cyclohexoxy]-dimethyl-silane (500 mg, 38% yield) as a yellow oil. LCMS (MM-ES+APCI, Pos): m/z 421.1 (M+H).

Step D. tert-butyl-dimethyl-[2-[5-methyl-4-(4,4,5,5-tetramethyl-1,3,2-dioxaborolan-2-yl) pyrazol-1-yl]cyclohexoxy]silane. To a 100 mL three-necked round-bottom flask equipped with a magnetic stir bar was added tert-butyl-[2-(4-iodo-5-methyl-pyrazol-1-yl)cyclohexoxy]-dimethyl-silane (420 mg, 0.93 mmol) followed by the addition of THF (5 mL). The flask was then evacuated and backfilled with nitrogen three times. i-PrMgCl (1.3 M, 3.59 mL) was added into the mixture at 25° C. The mixture was stirred at 25° C. for 1 h. 2-methoxy-4,4,5,5-tetramethyl-1,3,2-dioxaborolane (737 mg, 4.67 mmol) was added into the mixture dropwise at 25° C. The mixture was stirred at 25° C. under an atmosphere of nitrogen for 1 h. The mixture was quenched by slow addition of H₂O (20 mL). The resulting mixture was transferred to a separatory funnel, and the aqueous layer mixture was extracted with ethyl acetate (20 mL×3). The combined organic layers were washed with brine (10 mL), dried over anhydrous sodium sulfate, filtered, concentrated under reduced pressure to afford tert-butyl-dimethyl-[2-[5-methyl-4-(4,4,5,5-tetramethyl-1,3,2-dioxaborolan-2-yl) pyrazol-1-yl]cyclohexoxy]silane (530 mg, crude) as yellow oil. LCMS (MM-ES+APCI, Pos): m/z 421.4 (M+H).

Step E. 6-[1-[2-[tert-butyl(dimethyl) silyl]oxycyclohexyl]-5-methyl-pyrazol-4-yl]-4-[(1R)-1-(5-fluoro-2-pyridyl)ethoxy]pyrazolo[1,5-a]pyridine-3-carbonitrile. Synthesized according to Example 4, Step A substituting tert-butyl 4-(4-(4,4,5,5-tetramethyl-1,3,2-dioxaborolan-2-yl)-1H-pyrazol-1-yl) piperidine-2-carboxylate for tert-butyl-dimethyl-[2-[5-methyl-4-(4,4,5,5-tetramethyl-1,3,2-dioxaborolan-2-yl) pyrazol-1-yl]cyclohexoxy]silane to give 6-[1-[2-[tert-butyl(dimethyl) silyl]oxycyclohexyl]-5-methyl-pyrazol-4-yl]-4-[(1R)-1-(5-fluoro-2-pyridyl)ethoxy] pyrazolo[1,5-a]pyridine-3-carbonitrile (140 mg, 41% yield) as a yellow solid. LCMS (MM-ES+APCI, Pos): m/z 575.4 (M+H).

Step F. 4-[(1R)-1-(5-fluoro-2-pyridyl)ethoxy]-6-[1-(2-hydroxycyclohexyl)-5-methyl-pyrazol-4-yl]pyrazolo[1,5-a]pyridine-3-carbonitrile. Synthesized according to Example 16, Step E substituting 6-[1-[4-[tert-butyl(dimethyl) silyl]oxycyclohexyl]-5-methyl-pyrazol-4-yl]-4-[(1R)-1-(5-fluoro-2-pyridyl) propoxy]pyrazolo[1,5-a]pyridine-3-carbonitrile for 6-[1-[2-[tert-butyl(dimethyl) silyl]oxycyclohexyl]-5-methyl-pyrazol-4-yl]-4-[(1R)-1-(5-fluoro-2-pyridyl)ethoxy]pyrazolo[1,5-a]pyridine-3-carbonitrile to give 4-[(1R)-1-(5-fluoro-2-pyridyl)ethoxy]-6-[1-(2-hydroxycyclohexyl)-5-methyl-pyrazol-4-yl] pyrazolo[1,5-a]pyridine-3-carbonitrile (80 mg, 79% yield, HCl) as a yellow solid. LCMS (MM-ES+APCI, Pos): m/z 461.2 (M+H).

Step G. 4-[(1R)-1-(5-fluoro-2-pyridyl)ethoxy]-6-[1-[(1S,2S)-2-hydroxycyclohexyl]-5-methyl-pyrazol-4-yl]pyrazolo[1,5-a]pyridine-3-carbonitrile. 4-[(1R)-1-(5-fluoro-2-pyridyl)ethoxy]-6-[1-(2-hydroxycyclohexyl)-5-methyl-pyrazol-4-yl]pyrazolo[1,5-a]pyridine-3-carbonitrile. The racemate 4-[(1R)-1-(5-fluoro-2-pyridyl)ethoxy]-6-[1-(2-hydroxycyclohexyl)-5-methyl-pyrazol-4-yl]pyrazolo[1,5-a]pyridine-3-carbonitrile (80 mg, 0.17 mmol) was separated by SFC (46% [CO₂-EtOH (0.1% NH₃H₂O)]). After lyophilization, 4-[(1R)-1-(5-fluoro-2-pyridyl)ethoxy]-6-[1-[(1S,2S)-2-hydroxycyclohexyl]-5-methyl-pyrazol-4-yl]pyrazolo[1,5-a]pyridine-3-carbonitrile (25 mg, 30% yield) was obtained as a white solid. LCMS (MM-ES+APCI, Pos): m/z 461.2 (M+H).

Example 18

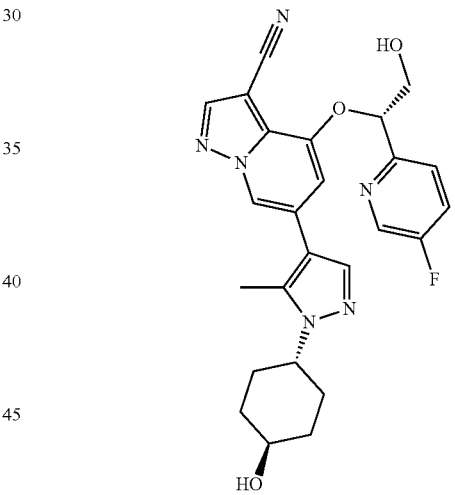

4-[(1S)-1-(5-fluoro-2-pyridyl)-2-hydroxy-ethoxy]-6-[1-(4-hydroxycyclohexyl)-5-methylpyrazol-4-yl]
pyrazolo[1,5-a]pyridine-3-carbonitrile

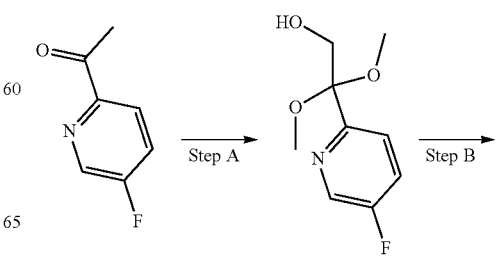

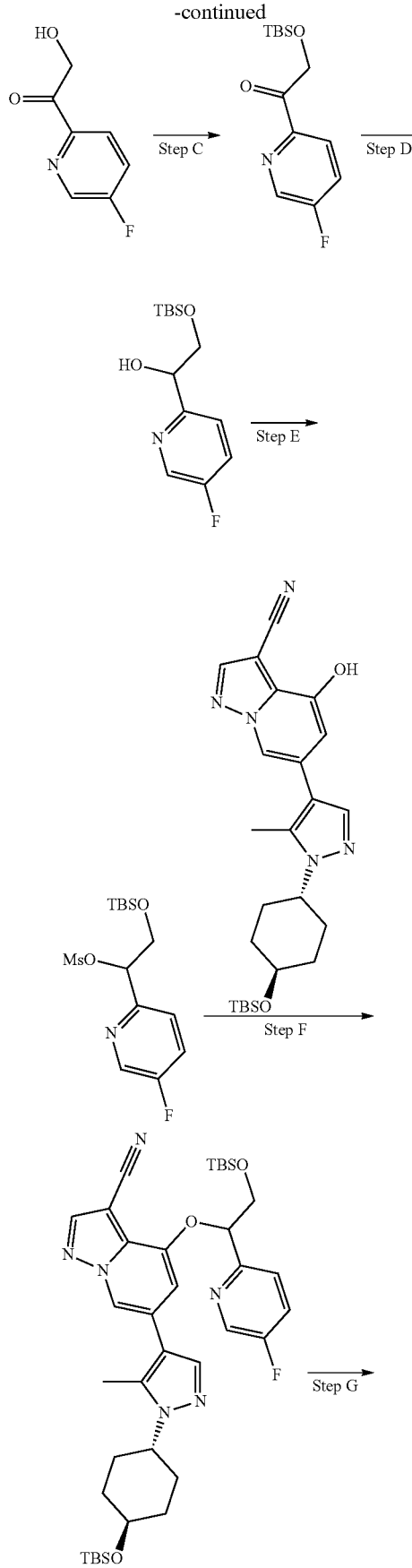
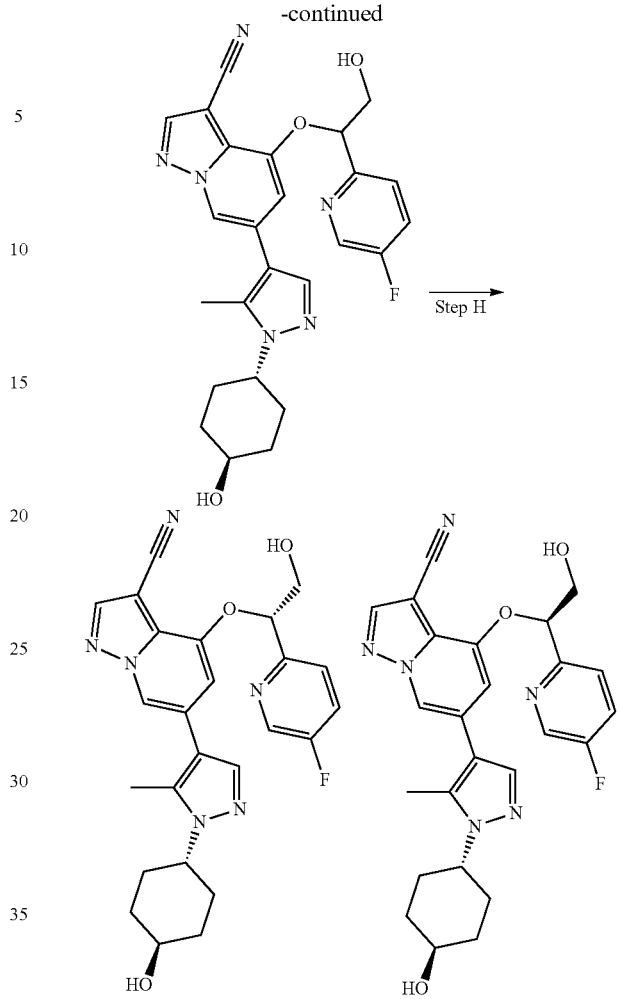

Step A. 2-(5-fluoro-2-pyridyl)-2,2-dimethoxy-ethanol. To a 40 mL vial equipped with a magnetic stir bar was added 1-(5-fluoro-2-pyridyl)ethanone (2 g, 14.38 mmol) followed by the addition of MeOH (30 mL). PhI(OAc)$_2$ (9.26 g, 28.75 mmol) and KOH (1.65 g, 29.41 mmol) was added into the mixture at 25-30° C. The vial was purged with nitrogen for 2 min. The mixture was stirred at 25° C. under atmosphere of nitrogen for 16 h. The mixture was concentrated under reduced pressure, H$_2$O (50 mL) was added into the mixture, the resulting mixture extracted with dichloromethane (50 mL×3), combined organic layers washed with Na2CO$_3$ (10 mL), dried over anhydrous sodium sulfate, filtered, concentrated under reduced pressure and was purified by silica gel column chromatography (30-40% ethyl acetate in petroleum ether) to give 2-(5-fluoro-2-pyridyl)-2,2-dimethoxy-ethanol (650 mg, 22% yield) as a brown solid.

Step B. 1-(fluoro-2-pyridyl)-2-hydroxy-ethanone. To a 50 mL round-bottom equipped with a magnetic stir bar and a reflux condenser was added 2-(5-fluoro-2-pyridyl)-2,2-dimethoxy-ethanol (320 mg, 1.59 mmol) followed by the addition of THF (9 mL) and H$_2$O (3 mL). TsOH (544.00 mg, 3.16 mmol) was added into the mixture at 25° C. The mixture was stirred at 70° C. for 1 h. The mixture was quenched by slow addition of H$_2$O (10 mL), pH adjusted to pH8 with saturated aqueous sodium bicarbonate. The resulting mixture was extracted with ethyl acetate (10 mL×3), combined organic layers dried over anhydrous sodium sulfate, filtered, concentrated under reduced pressure 1-(5-fluoro-2-pyridyl)-2-hydroxy-ethanone (250 mg, crude) as a brown solid, used into the next step without further purification.

Step C. 2-[tert-butyl(dimethyl) silyl]oxy-1-(5-fluoro-2-pyridyl)ethanone. To a 50 mL round-bottom flask equipped with a magnetic stir bar was added 1-(5-fluoro-2-pyridyl)-2-hydroxyethanone (250 mg, 1.61 mmol) and imidazole (625.00 mg, 9.18 mmol) followed by the addition of THF (10 mL). The solution was cooled to 0° C. Tert-butyl-chloro-dimethyl-silane (0.6 mL, 4.81 mmol) was added. The mixture was allowed to warm to 25° C. and stir for 2 h. The mixture was quenched by slow addition of $H_2O$ (20 mL), transferred to a separatory funnel, the aqueous layer mixture extracted with ethyl acetate (20 mL×3). The combined organic layers were dried over anhydrous sodium sulfate, filtered, concentrated under reduced pressure and purified by silica gel column chromatography (0-10% ethyl acetate in petroleum ether) to give 2-[tert-butyl(dimethyl) silyl]oxy-1-(5-fluoro-2-pyridyl)ethanone (590 mg, 71% yield) as a white solid. LCMS (MM-ES+APCI, Pos): m/z 270.1 (M+H).

Step D. 2-[tert-butyl(dimethyl) silyl]oxy-1-(5-fluoro-2-pyridyl)ethanol. To a 100 mL round-bottom flask equipped with a magnetic stir bar was added 2-[tert-butyl(dimethyl) silyl]oxy-1-(5-fluoro-2-pyridyl)ethanone (290 mg, 1.06 mmol) followed by the addition of EtOH (3 mL). The flask was then evacuated and purged with nitrogen three times. The solution was cooled to 0° C. $NaBH_4$ (50 mg, 1.32 mmol) was added into the mixture. The mixture was allowed to warm to 25° C. and stir for 1 h. The mixture was quenched by slow addition of saturated aqueous ammonium chloride (5 mL), transferred to a separatory funnel, and the aqueous layer mixture extracted with ethyl acetate (10 mL×3). The combined organic layers were washed with brine (10 mL), dried over anhydrous sodium sulfate, filtered, and concentrated under reduced pressure affording 2-[tert-butyl(dimethyl) silyl]oxy-1-(5-fluoro-2-pyridyl)ethanol (290 mg, 98% yield) as a colorless gum. LCMS (MM-ES+APCI, Pos): m/z 272.1 (M+H).

Step E. [2-[tert-butyl(dimethyl) silyl]oxy-1-(5-fluoro-2-pyridyl)ethyl]methanesulfonate. To a 10 mL round-bottom flask equipped with a magnetic stir bar was added 2-[tert-butyl(dimethyl) silyl]oxy-1-(5-fluoro-2-pyridyl)ethanol (150 mg, 0.54 mmol) and TEA (0.22 mL, 1.61 mmol) followed by the addition of DCM (1.5 mL). The solution was cooled to 0° C. Methylsulfonyl methanesulfonate (140 mg, 0.8 mmol) in DCM (1.5 mL) was added dropwise. The mixture was allowed to warm to 25° C. and stir for 1 h. The mixture was quenched by slow addition of $H_2O$ (5 mL). The resulting mixture was extracted with DCM (5 mL×3), combined organic layers washed with brine (5 mL), dried over anhydrous sodium sulfate, filtered, and concentrated under reduced pressure affording [2-[tert-butyl(dimethyl) silyl]oxy-1-(5-fluoro-2-pyridyl)ethyl]methanesulfonate (185 mg, crude) as a yellow gum.

Step F. 6-[1-[4-[tert-butyl(dimethyl) silyl]oxycyclohexyl]-5-methyl-pyrazol-4-yl]-4-[2-[tert-butyl(dimethyl) silyl]oxy-1-(5-fluoro-2-pyridyl)ethoxy]pyrazolo[1,5-a]pyridine-3-carbonitrile. Synthesized according to Intermediate 1, Step A substituting 6-bromo-4-hydroxy-pyrazolo[1,5-a]pyridine3-carbonitrile for 6-[1-[4-[tertbutyl(dimethyl) silyl]oxycyclohexyl]-5-methyl-pyrazol-4-yl]-4-hydroxy-pyrazolo[1,5-a]pyridine-3-carbonitrile and [(1S)-1-(5-fluoro-2-pyridyl)ethyl]methanesulfonate for [2-[tert-butyl(dimethyl) silyl]oxy-1-(5-fluoro-2-pyridyl)ethyl]methanesulfonate to give 6-[1-[4-[tert-butyl(dimethyl) silyl]oxycyclohexyl]-5-methyl-pyrazol-4-yl]-4-[2-[tert-butyl(dimethyl) silyl]oxy-1-(5-fluoro-2-pyridyl)ethoxy]pyrazolo[1,5-a]pyridine-3-carbonitrile (195 mg, 67% yield) was obtained as a yellow gum. LCMS (MM-ES+APCI, Pos): m/z 461.2 (M+H).

Step G. 4-[1-(5-fluoro-2-pyridyl)-2-hydroxy-ethoxy]-6-[1-(4-hydroxycyclohexyl)-5-methyl-pyrazol-4-yl]pyrazolo[1,5-a]pyridine-3-carbonitrile. Synthesized according to Example 16, Step E substituting 6-[1-[4-[tert-butyl(dimethyl) silyl]oxycyclohexyl]-5-methyl-pyrazol-4-yl]-4-[(1R)-1-(5-fluoro-2-pyridyl) propoxy]pyrazolo[1,5-a]pyridine-3-carbonitrile for 6-[1-[4-[tertbutyl(dimethyl) silyl]oxycyclohexyl]-5-methyl-pyrazol-4-yl]-4-[2-[tert-butyl(dimethyl) silyl]oxy-1-(5-fluoro-2-pyridyl)ethoxy]pyrazolo[1,5-a]pyridine-3-carbonitrile to give 4-[1-(5-fluoro-2-pyridyl)-2-hydroxy-ethoxy]-6-[1-(4-hydroxycyclohexyl)-5-methyl-pyrazol-4-yl]pyrazolo[1,5-a]pyridine-3-carbonitrile (40 mg, 34% yield) as a white solid.

Step H. 4-[(1S)-1-(5-fluoro-2-pyridyl)-2-hydroxy-ethoxy]-6-[1-(4-hydroxycyclohexyl)-5-methylpyrazol-4-yl]pyrazolo[1,5-a]pyridine-3-carbonitrile. The racemate 4-[1-(5-fluoro-2-pyridyl)-2-hydroxy-ethoxy]-6-[1-(4-hydroxycyclohexyl)-5-methyl-pyrazol-4-yl]pyrazolo[1,5-a]pyridine-3-carbonitrile (40 mg, 0.09 mmol) was separated by SFC (20% [$CO_2$-MeOH (0.1% $NH_3H_2O$)]). After lyophilization, 4-[(1R)-1-(5-fluoro-2-pyridyl)ethoxy]-6-[1-[(1S,2S)-2-hydroxycyclohexyl]-5-methyl-pyrazol-4-yl]pyrazolo[1,5-a]pyridine-3-carbonitrile (25 mg, 30% yield) was obtained as a white solid. LCMS (MM-ES+APCI, Pos): m/z 477.2 (M+H).

Example 19

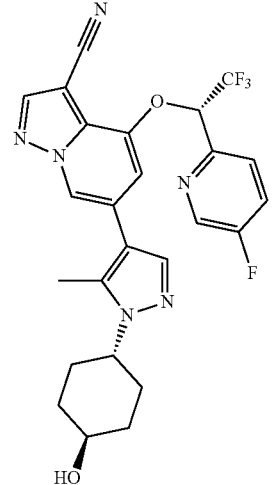 [SMILES: Cc1c(-c2cc(O[C@@H](c3ccc(F)cn3)C(F)(F)F)c3c(C#N)cnn3c2)cnn1[C@H]1CC[C@H](O)CC1]

6-[1-(4-hydroxycyclohexyl)-5-methyl-pyrazol-4-yl]-4-[(1S)-2,2,2-trifluoro-1-(5-fluoro-2-pyridyl)ethoxy]pyrazolo[1,5-a]pyridine-3-carbonitrile

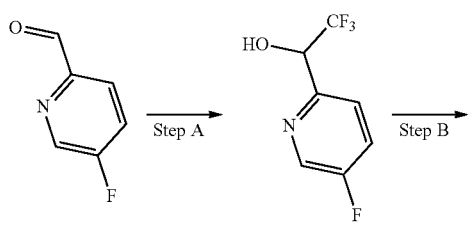

-continued

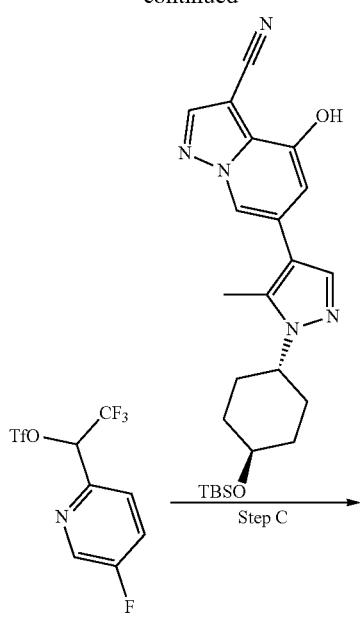

Step C

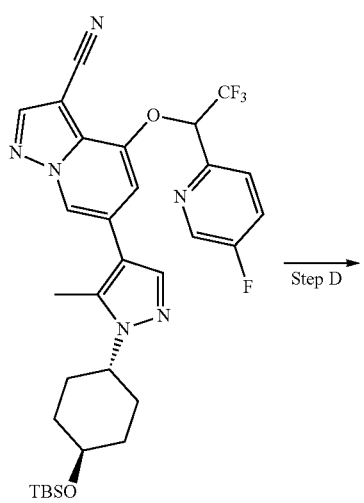

Step D

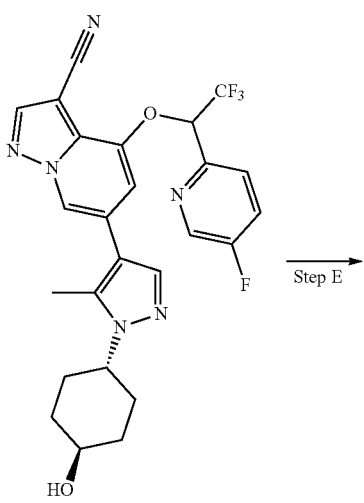

Step E

-continued

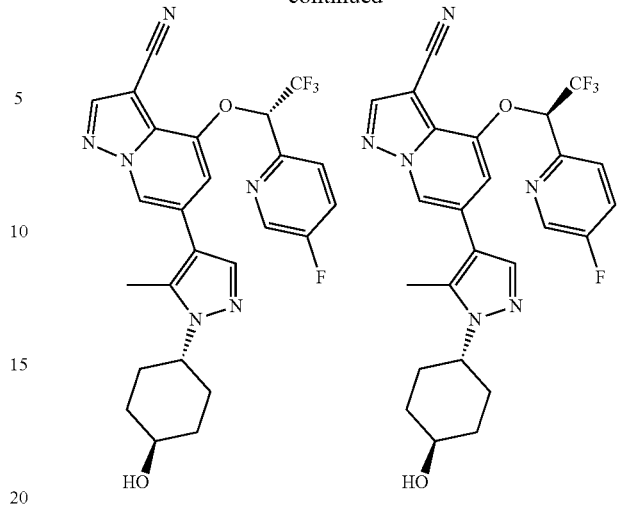

Step A. 2,2,2-trifluoro-1-(5-fluoro-2-pyridyl)ethanol. To a 50 mL Schlenk tube equipped with a magnetic stir bar was added 5-fluoropyridine-2-carbaldehyde (300 mg, 2.40 mmol) followed by the addition of THF (5 mL). The solution was cooled to 0° C. Trimethyl(trifluoromethyl) silane (511.49 mg, 3.60 mmol) was added dropwise to the mixture at 0° C. After stirring at 0° C. for 30 min, TBAF (1 M, 6.00 mL) was added dropwise to the mixture at 0° C. The mixture was allowed to warm to 25° C. and stir for 1 h. The mixture was quenched by slow addition of $H_2O$ (10 mL). The resulting mixture was transferred to a 40 mL vial, aqueous layer mixture extracted with ethyl acetate (5 mL×3), combined organic layers washed with brine (5 mL), dried over anhydrous sodium sulfate, filtered, concentrated under reduced pressure and purified by silica gel column chromatography (0-30% ethyl acetate/petroleum ether) to afford 2,2,2-trifluoro-1-(5-fluoro-2-pyridyl)ethanol (330 mg, 65% yield) as a yellow oil. LCMS (MM-ES+APCI, Pos): m/z 196.0 (M+H).

Step B. [2,2,2-trifluoro-1-(5-fluoro-2-pyridyl)ethyl]trifluoromethanesulfonate. To a 40 mL vail equipped with a magnetic stir bar was added 2,2,2-trifluoro-1-(5-fluoro-2-pyridyl)ethanol (300 mg, 1.41 mmol) followed by the addition of THF (5 mL). The vial was purged with nitrogen for 2 min. The solution was cooled to 0° C., NaH (112.91 mg, 2.82 mmol, 60% purity) was added into the mixture at 0° C. The mixture was stirred at 25° C. for 30 min. Trifluoromethanesulfonyl chloride (0.3 mL, 2.82 mmol) was added into the mixture at 25° C. The mixture was stirred at 25° C. for 30 min. The mixture was quenched by slow addition of $H_2O$ (10 mL), transferred to a 40 mL vial, the aqueous layer mixture extracted with ethyl acetate (5 mL×3). The combined organic layers were washed with brine (5 mL), dried over anhydrous sodium sulfate, filtered, concentrated under reduced pressure and purified by silica gel column chromatography (0-5% ethyl acetate/petroleum ether) to give [2,2,2-trifluoro-1-(5-fluoro-2-pyridyl)ethyl]trifluoromethanesulfonate (330 mg, 70% yield) as a yellow oil. LCMS (MM-ES+APCI, Pos): m/z 328.0 (M+H).

Step C. 6-[1-[4-[tert-butyl(dimethyl) silyl]oxycyclohexyl]-5-methyl-pyrazol-4-yl]-4-[2,2,2-trifluoro-1-(5-fluoro-2-pyridyl)ethoxy]pyrazolo[1,5-a]pyridine-3-carbonitrile. To a 40 mL vial equipped with a magnetic stir bar was added 6-[1-[4-[tert-butyl(dimethyl) silyl]oxycyclohexyl]-5-methyl-pyrazol-4-yl]-4-hydroxy-pyrazolo[1,5-a]pyridine-3-carbonitrile (300 mg, 0.63 mmol) and [2,2,2-trifluoro-1-(5- fluoro-2-pyridyl)ethyl]trifluoromethanesulfonate (253.30 mg, 0.75 mmol) followed by the addition of MeCN (5 mL). K$_2$CO$_3$ (173.69 mg, 1.26 mmol, 2 eq) was added into the mixture at 25° C. The mixture was stirred at 80° C. for 1 hr. The mixture quenched by slow addition of H$_2$O (10 mL), transferred to a 40 mL vial, the aqueous layer mixture was extracted with ethyl acetate (5 mL×3). The combined organic layers were washed with brine (5 mL), dried over anhydrous sodium sulfate, filtered, concentrated under reduced pressure and purified by silica gel column chromatography (0-5% ethyl acetate/petroleum ether) to give 6-[1-[4-[tert-butyl(dimethyl) silyl]oxycyclohexyl]-5-methyl-pyrazol-4-yl]-4-[2,2,2-trifluoro-1-(5-fluoro-2-pyridyl)ethoxy]pyrazolo[1,5-a]pyridine-3-carbonitrile (270 mg, 66% yield) as a black brown solid. LCMS (MM-ES+APCI, Pos): m/z 629.3 (M+H).

Step D. 6-[1-(4-hydroxycyclohexyl)-5-methyl-pyrazol-4-yl]-4-([2,2,2-trifluoro-1-(5-fluoro-2-pyridyl)ethoxy]pyrazolo[1,5-a]pyridine-3-carbonitrile. Synthesized according to Example 16, Step E substituting 6-[1-[4-[tert-butyl(dimethyl) silyl]oxycyclohexyl]-5-methyl-pyrazol-4-yl]-4-[(1R)-1-(5-fluoro-2-pyridyl) propoxy]pyrazolo[1,5-a]pyridine-3-carbonitrile for 6-[1-[4-[tertbutyl(dimethyl) silyl]oxycyclohexyl]-5-methyl-pyrazol-4-yl]-4-[2,2,2-trifluoro-1-(5-fluoro-2-pyridyl)ethoxy]pyrazolo[1,5-a]pyridine-3-carbonitrile to give 6-[1-(4-hydroxycyclohexyl)-5-methyl-pyrazol-4-yl]-4-[2,2,2-trifluoro-1-(5-fluoro-2-pyridyl)ethoxy]pyrazolo[1,5-a]pyridine-3-carbonitrile (180 mg, 81% yield) as a brown solid. LCMS (MM-ES+APCI, Pos): m/z 515.0 (M+H).

Step E. 6-[1-(4-hydroxycyclohexyl)-5-methyl-pyrazol-4-yl]-4-[(1S)-2,2,2-trifluoro-1-(5-fluoro-2-pyridyl)ethoxy]pyrazolo[1,5-a]pyridine-3-carbonitrile. The racemate 6-[1-(4-hydroxycyclohexyl)-5-methyl-pyrazol-4-yl]-4-[2,2,2-trifluoro-1-(5-fluoro-2-pyridyl)ethoxy]pyrazolo[1,5-a]pyridine-3-carbonitrile (180 mg, 0.38 mmol) was separated by SFC (45% [CO$_2$-EtOH (0.1% NH$_3$H$_2$O)]). After lyophilization, 6-[1-(4-hydroxycyclohexyl)-5-methyl-pyrazol-4-yl]-4-[(1S)-2,2,2-trifluoro-1-(5-fluoro-2-pyridyl)ethoxy]pyrazolo[1,5-a]pyridine-3-carbonitrile (78.2 mg, 45% yield) was obtained as a white solid. LCMS (MM-ES+APCI, Pos): m/z 515.2 (M+H).

| Compound number | Structure | Chemical Name | Reference Procedure | MS APCI (m/z) | Enz FGFR2 (nM) |
|---|---|---|---|---|---|
| 1 | 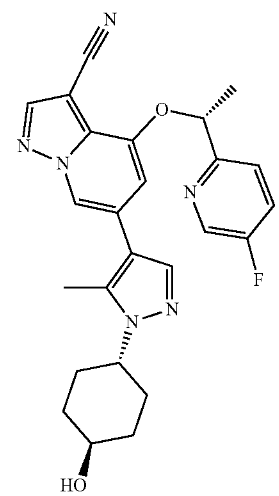 [SMILES: Cc1c(-c2cc(O[C@H](C)c3ccc(F)cn3)c3c(C#N)cnn3c2)cnn1[C@H]1CC[C@H](O)CC1] | 4-((R)-1-(5-fluoropyridin-2-yl)ethoxy)-6-(1-((1r,4R)-4-hydroxycyclohexyl)-5-methyl-1H-pyrazol-4-yl)-pyrazolo[1,5-a]pyridine-3-carbonitrile | Example 1 | 460.9 | 0.3 |
| 2 | 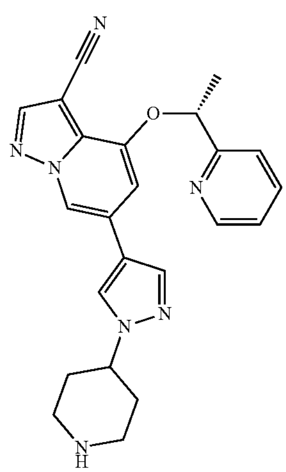 [SMILES: C[C@@H](Oc1cc(-c2cnn(C3CCNCC3)c2)cn2ncc(C#N)c12)c1ccccn1] | (R)-6-(1-(piperidin-4-yl)-1H-pyrazol-4-yl)-4-(1-(pyridin-2-yl)ethoxy)pyrazolo[1,5-a]pyridine-3-carbonitrile | Example 4 | 414.3 | 0.16 |

-continued

| Compound number | Structure | Chemical Name | Reference Procedure | MS APCI (m/z) | Enz FGFR2 (nM) |
|---|---|---|---|---|---|
| 3 | 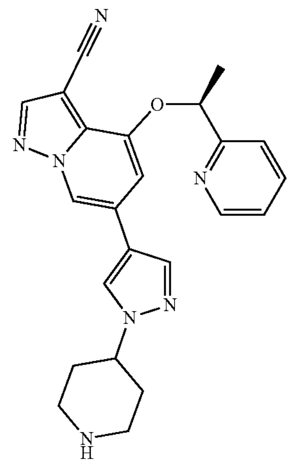 [SMILES: C[C@H](Oc1cc(-c2cnn(C3CCNCC3)c2)cn2ncc(C#N)c12)c1ccccn1] | (S)-6-(1-(piperidin-4-yl)-1H-pyrazol-4-yl)-4-(1-(pyridin-2-yl)ethoxy)pyrazolo[1,5-a]pyridine-3-carbonitrile | Example 4 | 414.3 | 21 |
| 4 | 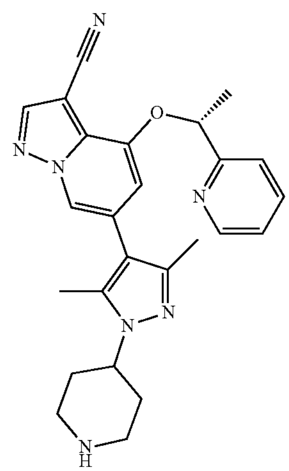 [SMILES: Cc1nn(C2CCNCC2)c(C)c1-c1cc(O[C@H](C)c2ccccn2)c2c(C#N)cnn2c1] | (R)-6-(3,5-dimethyl-1-(piperidin-4-yl)-1H-pyrazol-4-yl)-4-(1-(pyridin-2-yl)ethoxy)pyrazolo[1,5-a]pyridine-3-carbonitrile | Example 1 | 442.4 | 1 |
| 5 | 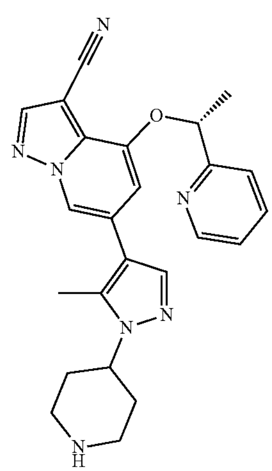 [SMILES: Cc1c(-c2cc(O[C@H](C)c3ccccn3)c3c(C#N)cnn3c2)cnn1C1CCNCC1] | (R)-6-(5-methyl-1-(piperidin-4-yl)-1H-pyrazol-4-yl)-4-(1-(pyridin-2-yl)ethoxy)pyrazolo[1,5-a]pyridine-3-carbonitrile | Example 2 | 428.2 | 0.25 |

| Compound number | Structure | Chemical Name | Reference Procedure | MS APCI (m/z) | Enz FGFR2 (nM) |
|---|---|---|---|---|---|
| 6 | 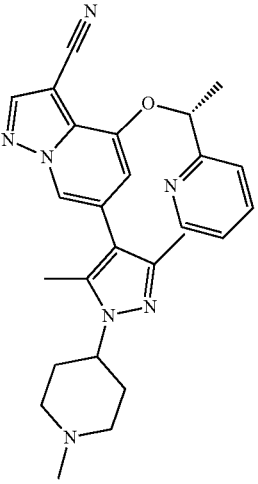 [SMILES: Cc1nn(C2CCN(C)CC2)c(C)c1-c1cc(O[C@H](C)c2ccccn2)c2c(C#N)cnn2c1] | (R)-6-(3,5-dimethyl-1-(1-methylpiperidin-4-yl)-1H-pyrazol-4-yl)-4-(1-(pyridin-2-yl)ethoxy)pyrazolo[1,5-a]pyridine-3-carbonitrile | Example 3 | 456.4 | 1 |
| 7 | 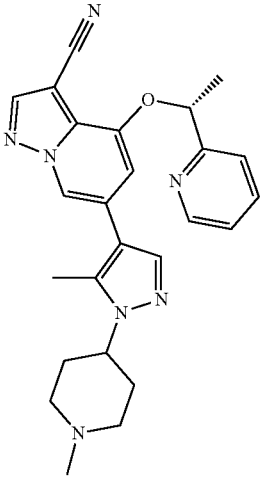 [SMILES: Cc1c(-c2cc(O[C@H](C)c3ccccn3)c3c(C#N)cnn3c2)cnn1C1CCN(C)CC1] | (R)-6-(5-methyl-1-(1-methylpiperidin-4-yl)-1H-pyrazol-4-yl)-4-(1-(pyridin-2-yl)ethoxy)pyrazolo[1,5-a]pyridine-3-carbonitrile | Example 3 | 442.2 | 0.3 |
| 8 | 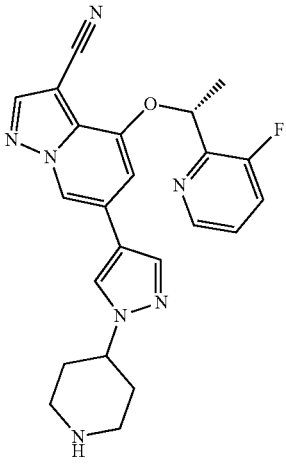 [SMILES: C[C@@H](Oc1cc(-c2cnn(C3CCNCC3)c2)cn2ncc(C#N)c12)c1ncccc1F] | (R)-4-(1-(3-fluoropyridin-2-yl)ethoxy)-6-(1-(piperidin-4-yl)-1H-pyrazol-4-yl)pyrazolo[1,5-a]pyridine-3-carbonitrile | Example 4 | 432.2 | 0.2 |

-continued

| Compound number | Structure | Chemical Name | Reference Procedure | MS APCI (m/z) | Enz FGFR2 (nM) |
|---|---|---|---|---|---|
| 9 | 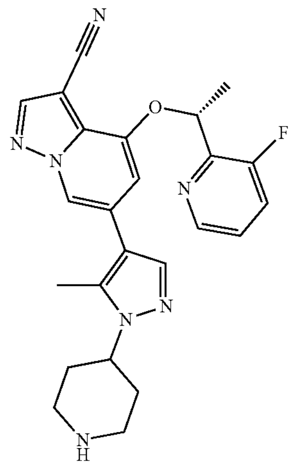 [SMILES: Cc1c(-c2cc(O[C@H](C)c3ncccc3F)c3c(C#N)cnn3c2)cnn1C1CCNCC1] | (R)-4-(1-(3-fluoropyridin-2-yl)ethoxy)-6-(5-methyl-1-(piperidin-4-yl)-1H-pyrazol-4-yl)pyrazolo[1,5-a]pyridine-3-carbonitrile | Example 1 | 446.2 | 0.3 |
| 10 | 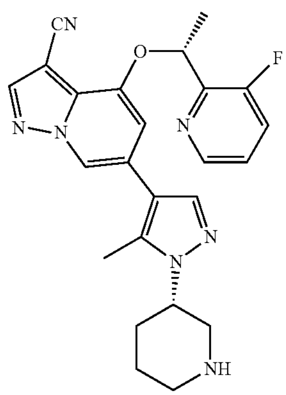 [SMILES: Cc1c(-c2cc(O[C@H](C)c3ncccc3F)c3c(C#N)cnn3c2)cnn1[C@H]1CCCNC1] | 4-((R)-1-(3-fluoropyridin-2-yl)ethoxy)-6-(5-methyl-1-((S)-piperidin-3-yl)-1H-pyrazol-4-yl)pyrazolo[1,5-a]pyridine-3-carbonitrile | Example 5 | 446.2 | 0.3 |
| 11 | 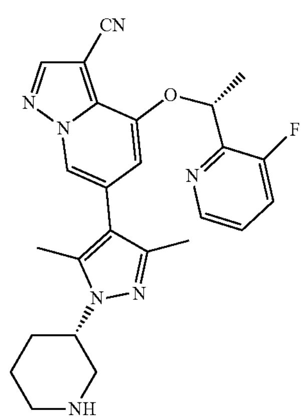 [SMILES: Cc1nn([C@H]2CCCNC2)c(C)c1-c1cc(O[C@H](C)c2ncccc2F)c2c(C#N)cnn2c1] | 6-(3,5-dimethyl-1-((S)-piperidin-3-yl)-1H-pyrazol-4-yl)-4-((R)-1-(3-fluoropyridin-2-yl)ethoxy)pyrazolo[1,5-a]pyridine-3-carbonitrile | Example 1 | 460.2 | 0.5 |

-continued

| Compound number | Structure | Chemical Name | Reference Procedure | MS APCI (m/z) | Enz FGFR2 (nM) |
|---|---|---|---|---|---|
| 12 | 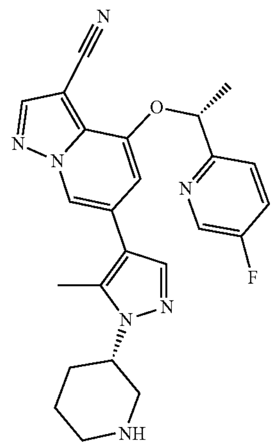 [SMILES: Cc1c(-c2cc(O[C@H](C)c3ccc(F)cn3)c3c(C#N)cnn3c2)cnn1[C@H]1CCCNC1] | 4-((R)-1-(5-fluoropyridin-2-yl)ethoxy)-6-(5-methyl-1-((S)-piperidin-3-yl)-1H-pyrazol-4-yl)pyrazolo[1,5-a]pyridine-3-carbonitrile | Example 4 | 446.2 | 0.5 |
| 13 | 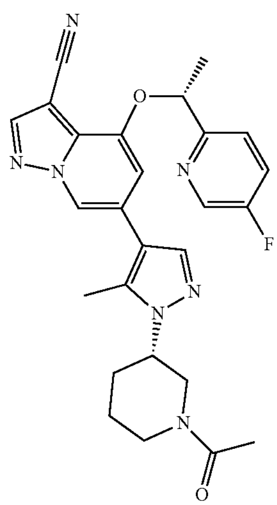 [SMILES: CC(=O)N1CCC[C@H](n2ncc(-c3cc(O[C@H](C)c4ccc(F)cn4)c4c(C#N)cnn4c3)c2C)C1] | 6-(1-((S)-1-acetylpiperidin-3-yl)-5-methyl-1H-pyrazol-4-yl)-4-((R)-1-(5-fluoropyridin-2-yl)ethoxy)pyrazolo[1,5-a]pyridine-3-carbonitrile | Example 6 | 488.25 | 0.6 |
| 14 | 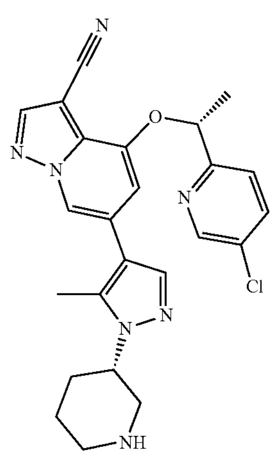 [SMILES: Cc1c(-c2cc(O[C@H](C)c3ccc(Cl)cn3)c3c(C#N)cnn3c2)cnn1[C@H]1CCCNC1] | 4-((R)-1-(5-chloropyridin-2-yl)ethoxy)-6-(5-methyl-1-((S)-piperidin-3-yl)-1H-pyrazol-4-yl)pyrazolo[1,5-a]pyridine-3-carbonitrile | Example 4 | 462.2 | 12.5 |

-continued

| Compound number | Structure | Chemical Name | Reference Procedure | MS APCI (m/z) | Enz FGFR2 (nM) |
|---|---|---|---|---|---|
| 15 | 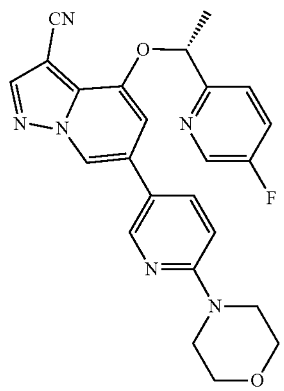 | (R)-4-(1-(5-fluoropyridin-2-yl)ethoxy)-6-(6-morpholinopyridin-3-yl)pyrazolo[1,5-a]pyridine-3-carbonitrile | Example 1 | 534.2 | 0.4 |
| 16 | 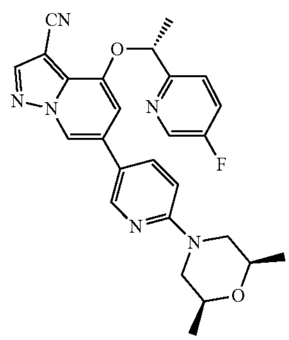 | 6-(6-((2S,6R)-2,6-dimethylmorpholino)pyridin-3-yl)-4-((R)-1-(5-fluoropyridin-2-yl)ethoxy)pyrazolo[1,5-a]pyridine-3-carbonitrile | Example 1 | 473.2 | 0.5 |
| 17 | 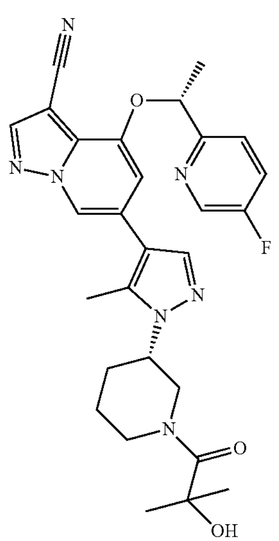 [SMILES: Cc1c(-c2cc(O[C@H](C)c3ccc(F)cn3)c3c(C#N)cnn3c2)cnn1[C@H]1CCCN(C(=O)C(C)(C)O)C1] | 4-((R)-1-(5-fluoropyridin-2-yl)ethoxy)-6-(1-((S)-1-(2-hydroxy-2-methylpropanoyl)piperidin-3-yl)-5-methyl-1H-pyrazol-4-yl)-pyrazolo[1,5-a]pyridine-3-carbonitrile | Example 9 | 532.3 | 0.6 |

| Compound number | Structure | Chemical Name | Reference Procedure | MS APCI (m/z) | Enz FGFR2 (nM) |
|---|---|---|---|---|---|
| 18 | 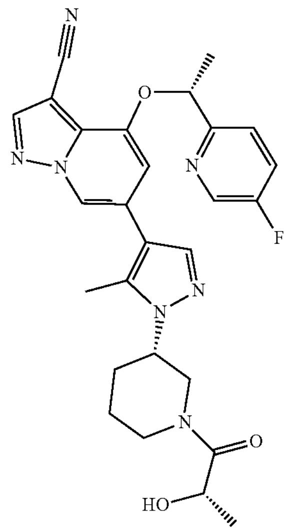 [SMILES: Cc1c(C2C=Cn3ncc(C#N)c3C(O[C@H](C)c3ccc(F)cn3)=C2)cnn1[C@H]1CCCN(C(=O)[C@H](C)O)C1] | 4-((R)-1-(5-fluoropyridin-2-yl)ethoxy)-6-(1-((S)-1-((S)-2-hydroxypropanoyl)-piperidin-3-yl)-5-methyl-1H-pyrazol-4-yl)pyrazolo[1,5-a]pyridine-3-carbonitrile | Example 9 | 517.9 | 0.6 |
| 19 | 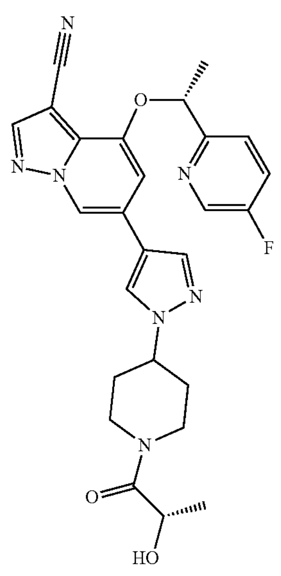 [SMILES: C[C@H](O)C(=O)N1CCC(n2cc(-c3cc(O[C@H](C)c4ccc(F)cn4)c4c(C#N)cnn4c3)cn2)CC1] | 4-((R)-1-(5-fluoropyridin-2-yl)ethoxy)-6-(1-(1-((S)-2-hydroxypropanoyl)-piperidin-4-yl)-1H-pyrazol-4-yl)pyrazolo[1,5-a]pyridine-3-carbonitrile | Example 9 | 504.3 | 0.15 |

| Compound number | Structure | Chemical Name | Reference Procedure | MS APCI (m/z) | Enz FGFR2 (nM) |
|---|---|---|---|---|---|
| 20 | 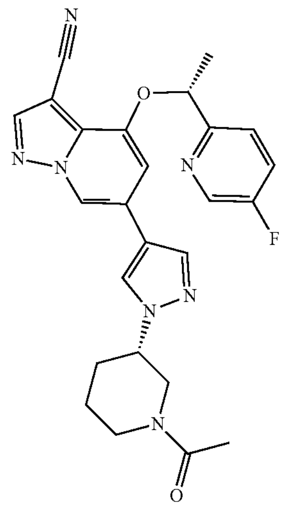 [SMILES: CC(=O)N1CCC[C@H](n2cc(C3C=Cn4ncc(C#N)c4C(O[C@H](C)c4ccc(F)cn4)=C3)cn2)C1] | (R)-6-(1,5-dimethyl-1H-pyrazol-4-yl)-4-(1-(5-fluoropyridin-2-yl)ethoxy)pyrazolo[1,5-a]pyridine-3-carbonitrile | Example 6 | 474.2 | 0.14 |
| 21 | 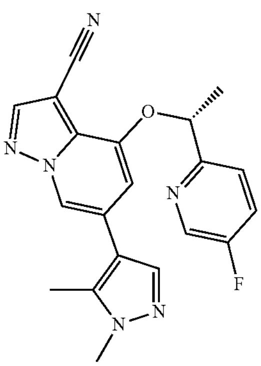 [SMILES: Cc1c(-c2cc(O[C@H](C)c3ccc(F)cn3)c3c(C#N)cnn3c2)cnn1C] | 6(R)-6-(1,5-dimethyl-1H-pyrazol-4-yl)-4-(1-(5-fluoropyridin-2-yl)ethoxy)pyrazolo[1,5-a]pyridine-3-carbonitrile | Example 1 | 377.2 | 1.7 |
| 22 | 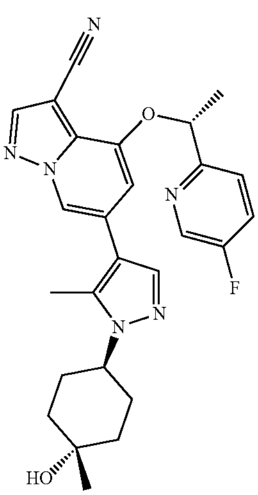 [SMILES: Cc1c(-c2cc(O[C@H](C)c3ccc(F)cn3)c3c(C#N)cnn3c2)cnn1[C@H]1CC[C@](C)(O)CC1] | 4-((R)-1-(5-fluoropyridin-2-yl)ethoxy)-6-(1-((1r,4R)-4-hydroxy-4-methylcyclohexyl)-5-methyl-1H-pyrazol-4-yl)pyrazolo[1,5-a]pyridine-3-carbonitrile | Example 1 | 475.2 | 0.3 |

| Compound number | Structure | Chemical Name | Reference Procedure | MS APCI (m/z) | Enz FGFR2 (nM) |
|---|---|---|---|---|---|
| 23 | 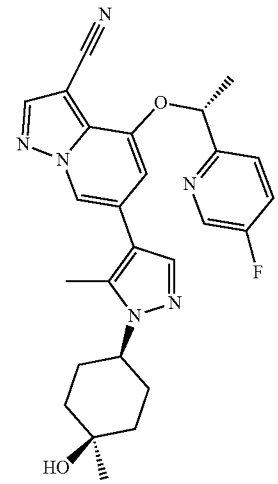 [SMILES: Cc1c(-c2cc(O[C@H](C)c3ccc(F)cn3)c3c(C#N)cnn3c2)cnn1[C@H]1CC[C@@](C)(O)CC1] | 4-((R)-1-(5-fluoropyridin-2-yl)ethoxy)-6-(1-((1s,4S)-4-hydroxy-4-methylcyclohexyl)-5-methyl-1H-pyrazol-4-yl)pyrazolo[1,5-a]pyridine-3-carbonitrile | Example 1 | 474.9 | 0.4 |
| 24 | 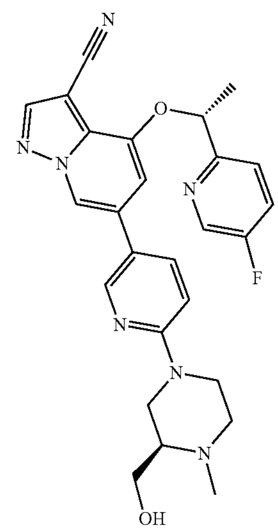 [SMILES: C[C@@H](Oc1cc(-c2ccc(N3CCN(C)[C@@H](CO)C3)nc2)cn2ncc(C#N)c12)c1ccc(F)cn1] | 4-((R)-1-(5-fluoropyridin-2-yl)ethoxy)-6-(6-((R)-3-(hydroxymethyl)-4-methylpiperazin-1-yl)pyridin-3-yl)pyrazolo[1,5-a]pyridine-3-carbonitrile | Example 7 | 488.3 | 0.3 |
| 25 | 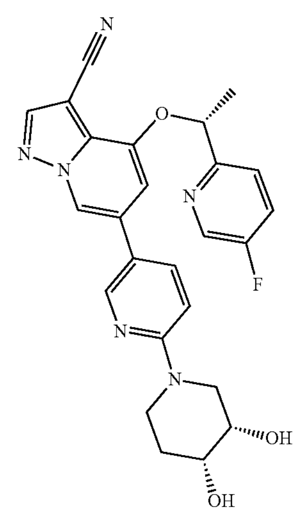 [SMILES: C[C@@H](Oc1cc(-c2ccc(N3CC[C@@H](O)[C@@H](O)C3)nc2)cn2ncc(C#N)c12)c1ccc(F)cn1] | 6-(6-((3S,4R)-3,4-dihydroxypiperidin-1-yl)pyridin-3-yl)-4-((R)-1-(5-fluoropyridin-2-yl)ethoxy)pyrazolo[1,5-a]pyridine-3-carbonitrile | Example 7 | 475.2 | 0.3 |

| Compound number | Structure | Chemical Name | Reference Procedure | MS APCI (m/z) | Enz FGFR2 (nM) |
|---|---|---|---|---|---|
| 26 | 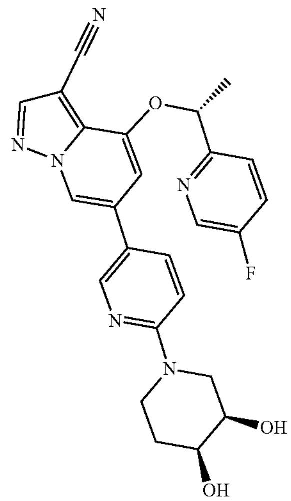 [SMILES: C[C@@H](Oc1cc(-c2ccc(N3CC[C@H](O)[C@H](O)C3)nc2)cn2ncc(C#N)c12)c1ccc(F)cn1] | 6-(6-((3R,4S)-3,4-dihydroxypiperidin-1-yl)pyridin-3-yl)-4-((R)-1-(5-fluoropyridin-2-yl)ethoxy)pyrazolo[1,5-a]pyridine-3-carbonitrile | Example 7 | 475.2 | 0.5 |
| 27 | 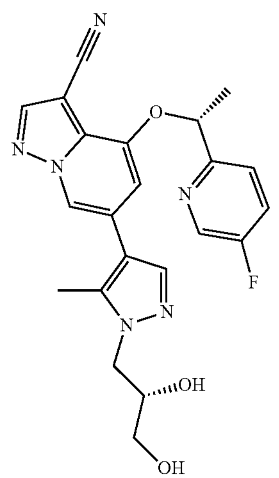 [SMILES: Cc1c(-c2cc(O[C@H](C)c3ccc(F)cn3)c3c(C#N)cnn3c2)cnn1C[C@H](O)CO] | 6-(1-((S)-2,3-dihydroxypropyl)-5-methyl-1H-pyrazol-4-yl)-4-((R)-1-(5-fluoropyridin-2-yl)ethoxy)pyrazolo[1,5-a]pyridine-3-carbonitrile | Example 1 | 437.1 | 3 |
| 28 | 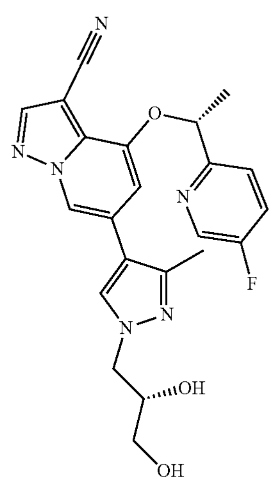 [SMILES: Cc1nn(C[C@H](O)CO)cc1-c1cc(O[C@H](C)c2ccc(F)cn2)c2c(C#N)cnn2c1] | 6-(1-((S)-2,3-dihydroxypropyl)-3-methyl-1H-pyrazol-4-yl)-4-((R)-1-(5-fluoropyridin-2-yl)ethoxy)pyrazolo[1,5-a]pyridine-3-carbonitrile | Example 1 | 437.1 | 3 |

-continued

| Compound number | Structure | Chemical Name | Reference Procedure | MS APCI (m/z) | Enz FGFR2 (nM) |
|---|---|---|---|---|---|
| 29 | 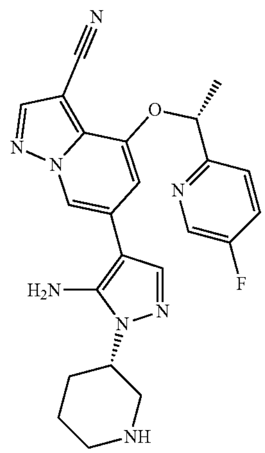 [SMILES: C[C@@H](Oc1cc(-c2cnn([C@H]3CCCNC3)c2N)cn2ncc(C#N)c12)c1ccc(F)cn1] | 6-(5-amino-1-((S)-piperidin-3-yl)-1H-pyrazol-4-yl)-4-((R)-1-(5-fluoropyridin-2-yl)ethoxy)pyrazolo[1,5-a]pyridine-3-carbonitrile | Example 1 | 447.3 | 0.3 |
| 30 | 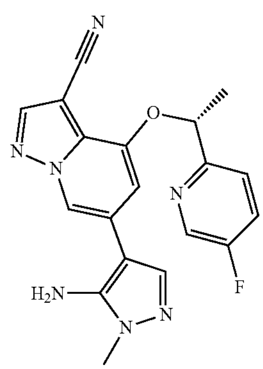 [SMILES: C[C@@H](Oc1cc(-c2cnn(C)c2N)cn2ncc(C#N)c12)c1ccc(F)cn1] | (R)-6-(5-amino-1-methyl-1H-pyrazol-4-yl)-4-(1-(5-fluoropyridin-2-yl)ethoxy)pyrazolo[1,5-a]pyridine-3-carbonitrile | Example 8 | 378.1 | 1 |
| 31 | 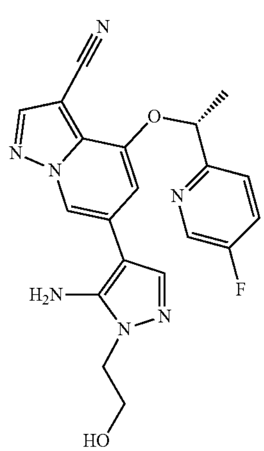 [SMILES: C[C@@H](Oc1cc(-c2cnn(CCO)c2N)cn2ncc(C#N)c12)c1ccc(F)cn1] | (R)-6-(5-amino-1-(2-hydroxyethyl)-1H-pyrazol-4-yl)-4-(1-(5-fluoropyridin-2-yl)ethoxy)pyrazolo[1,5-a]pyridine-3-carbonitrile | Example 1 | 408.1 | 1 |

| Compound number | Structure | Chemical Name | Reference Procedure | MS APCI (m/z) | Enz FGFR2 (nM) |
|---|---|---|---|---|---|
| 32 | 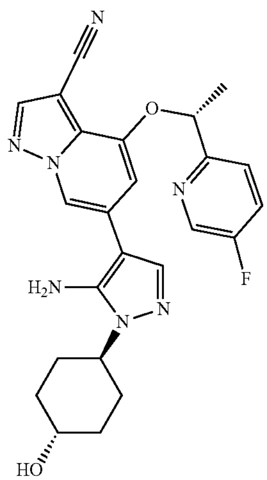 [SMILES: C[C@@H](Oc1cc(-c2cnn([C@H]3CC[C@H](O)CC3)c2N)cn2ncc(C#N)c12)c1ccc(F)cn1] | 6-(5-amino-1-((1r,4R)-4-hydroxycyclohexyl)-1H-pyrazol-4-yl)-4-((R)-1-(5-fluoropyridin-2-yl)-ethoxy)pyrazolo[1,5-a]pyridine-3-carbonitrile | Example 1 | 462.2 | 0.4 |
| 33 | 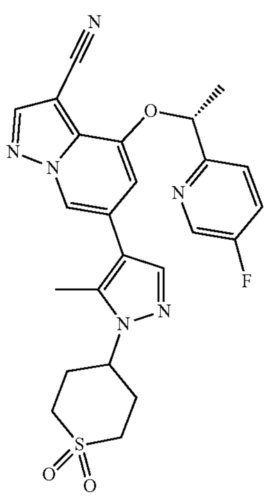 [SMILES: Cc1c(-c2cc(O[C@H](C)c3ccc(F)cn3)c3c(C#N)cnn3c2)cnn1C1CCS(=O)(=O)CC1] | (R)-6-(1-(1,1-dioxido-tetrahydro-2H-thiopyran-4-yl)-5-methyl-1H-pyrazol-4-yl)-4-(1-(5-fluoropyridin-2-yl)ethoxy)pyrazolo[1,5-a]pyridine-3-carbonitrile | Example 10 | 495.1 | 1 |
| 34 | 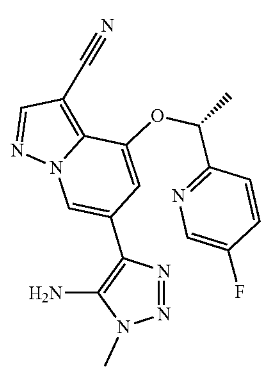 [SMILES: C[C@@H](Oc1cc(-c2nnn(C)c2N)cn2ncc(C#N)c12)c1ccc(F)cn1] | (R)-6-(5-amino-1-methyl-1H-1,2,3-triazol-4-yl)-4-(1-(5-fluoropyridin-2-yl)-ethoxy)pyrazolo[1,5-a]pyridine-3-carbonitrile | Example 11 | 379.1 | 2.6 |

-continued

| Compound number | Structure | Chemical Name | Reference Procedure | MS APCI (m/z) | Enz FGFR2 (nM) |
|---|---|---|---|---|---|
| 35 | 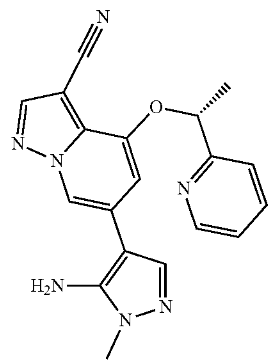 [SMILES: C[C@@H](Oc1cc(-c2cnn(C)c2N)cn2ncc(C#N)c12)c1ccccn1] | (R)-6-(5-amino-1-methyl-1H-pyrazol-4-yl)-4-(1-(pyridin-2-yl)ethoxy)pyrazolo[1,5-a]pyridine-3-carbonitrile | Example 1 | 360.1 | 1 |
| 36 | 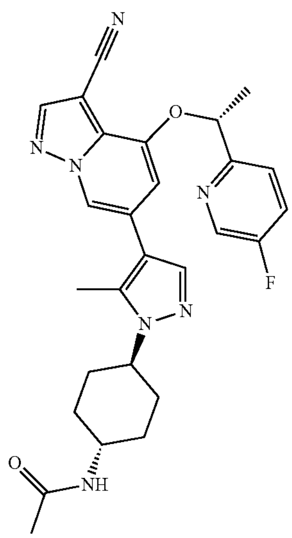 [SMILES: CC(=O)N[C@H]1CC[C@H](n2ncc(-c3cc(O[C@H](C)c4ccc(F)cn4)c4c(C#N)cnn4c3)c2C)CC1] | N-((1R,4r)-4-(4-(3-cyano-4-((R)-1-(5-fluoropyridin-2-yl)ethoxy)pyrazolo[1,5-a]pyridin-6-yl)-5-methyl-1H-pyrazol-1-yl)cyclohexyl)acetamide | Example 1 | 502.2 | 0.4 |
| 37 | 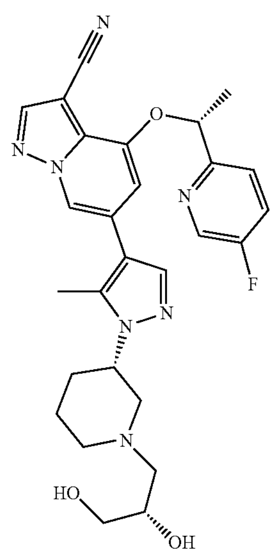 [SMILES: Cc1c(-c2cc(O[C@H](C)c3ccc(F)cn3)c3c(C#N)cnn3c2)cnn1[C@H]1CCCN(C[C@H](O)CO)C1] | 6-(1-((S)-1-((S)-2,3-dihydroxypropyl)piperidin-3-yl)-5-methyl-1H-pyrazol-4-yl)-4-((R)-1-(5-fluoropyridin-2-yl)ethoxy)pyrazolo[1,5-a]pyridine-3-carbonitrile | Example 12 | 520.3 | 0.5 |

| Compound number | Structure | Chemical Name | Reference Procedure | MS APCI (m/z) | Enz FGFR2 (nM) |
|---|---|---|---|---|---|
| 38 | 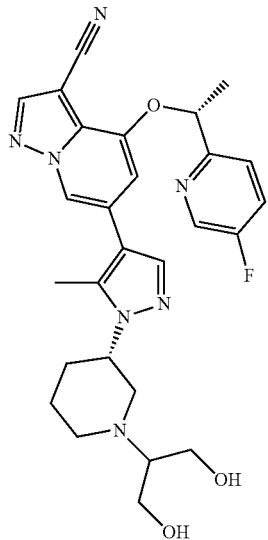 [SMILES: Cc1c(-c2cc(O[C@H](C)c3ccc(F)cn3)c3c(C#N)cnn3c2)cnn1[C@H]1CCCN(C(CO)CO)C1] | 6-(1-((S)-1-(1,3-dihydroxypropan-2-yl)piperidin-3-yl)-5-methyl-1H-pyrazol-4-yl)-4-((R)-1-(5-fluoropyridin-2-yl)ethoxy)pyrazolo[1,5-a]pyridine-3-carbonitrile | Example 12 | 520.3 | 0.4 |
| 39 | 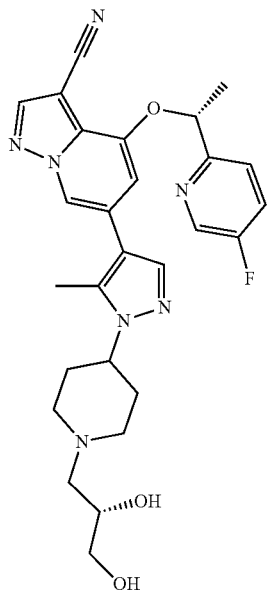 [SMILES: Cc1c(-c2cc(O[C@H](C)c3ccc(F)cn3)c3c(C#N)cnn3c2)cnn1C1CCN(C[C@H](O)CO)CC1] | 6-(1-(1-((S)-2,3-dihydroxypropyl)piperidin-4-yl)-5-methyl-1H-pyrazol-4-yl)-4-((R)-1-(5-fluoropyridin-2-yl)ethoxy)pyrazolo[1,5-a]pyridine-3-carbonitrile | Example 12 | 520.2 | 0.5 |

| Compound number | Structure | Chemical Name | Reference Procedure | MS APCI (m/z) | Enz FGFR2 (nM) |
|---|---|---|---|---|---|
| 40 | 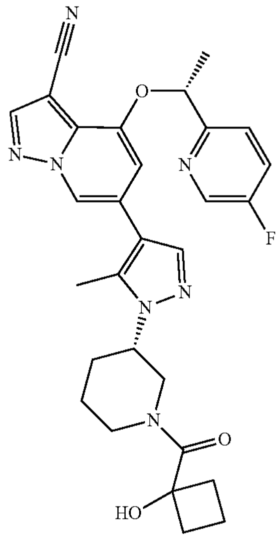 [SMILES: Cc1c(-c2cc(O[C@H](C)c3ccc(F)cn3)c3c(C#N)cnn3c2)cnn1[C@H]1CCCN(C(=O)C2(O)CCC2)C1] | 4-((R)-1-(5-fluoropyridin-2-yl)ethoxy)-6-(1-((S)-1-(1-hydroxycyclobutane-1-carbonyl)piperidin-3-yl)-5-methyl-1H-pyrazol-4-yl)pyrazolo[1,5-a]pyridine-3-carbonitrile | Example 9 | 544.3 | 1 |
| 41 | 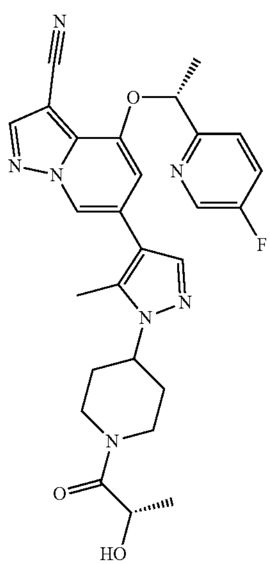 [SMILES: Cc1c(-c2cc(O[C@H](C)c3ccc(F)cn3)c3c(C#N)cnn3c2)cnn1C1CCN(C(=O)[C@H](C)O)CC1] | 4-((R)-1-(5-fluoropyridin-2-yl)ethoxy)-6-(1-(1-((S)-2-hydroxypropanoyl)-piperidin-4-yl)-5-methyl-1H-pyrazol-4-yl)pyrazolo[1,5-a]pyridine-3-carbonitrile | Example 9 | 518.3 | 0.5 |

| Compound number | Structure | Chemical Name | Reference Procedure | MS APCI (m/z) | Enz FGFR2 (nM) |
|---|---|---|---|---|---|
| 42 | 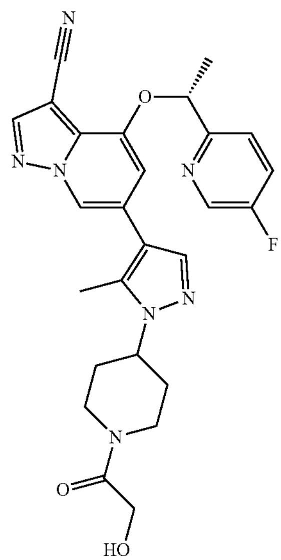 [SMILES: Cc1c(-c2cc(O[C@H](C)c3ccc(F)cn3)c3c(C#N)cnn3c2)cnn1C1CCN(C(=O)CO)CC1] | (R)-4-(1-(5-fluoropyridin-2-yl)ethoxy)-6-(1-(1-(2-hydroxyacetyl)piperidin-4-yl)-5-methyl-1H-pyrazol-4-yl)pyrazolo[1,5-a]pyridine-3-carbonitrile | Example 9 | 504.25 | 0.6 |
| 43 | 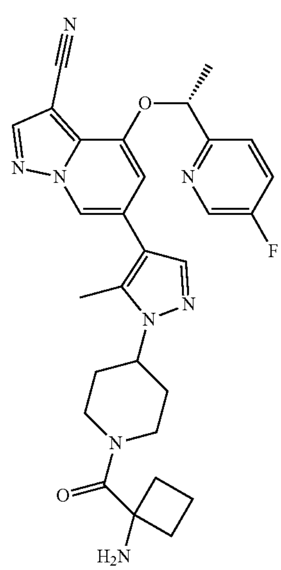 [SMILES: Cc1c(-c2cc(O[C@H](C)c3ccc(F)cn3)c3c(C#N)cnn3c2)cnn1C1CCN(C(=O)C2(N)CCC2)CC1] | (R)-6-(1-(1-(1-aminocyclobutane-1-carbonyl)-piperidin-4-yl)-5-methyl-1H-pyrazol-4-yl)-4-(1-(5-fluoropyridin-2-yl)ethoxy)pyrazolo[1,5-a]pyridine-3-carbonitrile | Example 9 | 543.3 | 1 |

| Compound number | Structure | Chemical Name | Reference Procedure | MS APCI (m/z) | Enz FGFR2 (nM) |
|---|---|---|---|---|---|
| 44 | 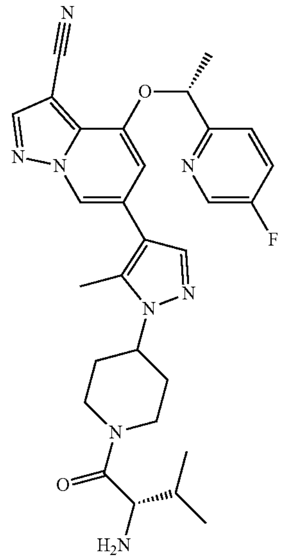 [SMILES: Cc1c(-c2cc(O[C@H](C)c3ccc(F)cn3)c3c(C#N)cnn3c2)cnn1C1CCN(C(=O)[C@@H](N)C(C)C)CC1] | 6-(1-(1-(L-valyl)piper-idin-4-yl)-5-methyl-1H-pyrazol-4-yl)-4-((R)-1-(5-fluoropyridin-2-yl)eth-oxy)pyrazolo[1,5-a]pyr-idine-3-carbonitrile | Example 9 | 544.64 | 0.5 |
| 45 | 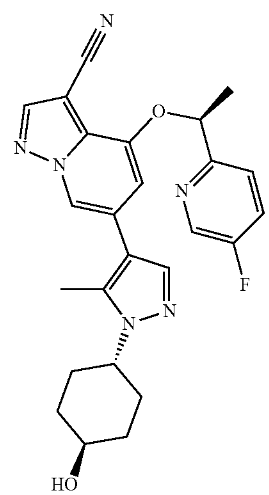 [SMILES: Cc1c(-c2cc(O[C@@H](C)c3ccc(F)cn3)c3c(C#N)cnn3c2)cnn1[C@H]1CC[C@H](O)CC1] | 4-((S)-1-(5-fluoropyridin-2-yl)ethoxy)-6-(1-((1r,4S)-4-hydroxycyclohexyl)-5-methyl-1H-pyrazol-4-yl)-pyrazolo[1,5-a]pyridine-3-carbonitrile | Example 1 | 460.51 | 6.5 |
| 46 | 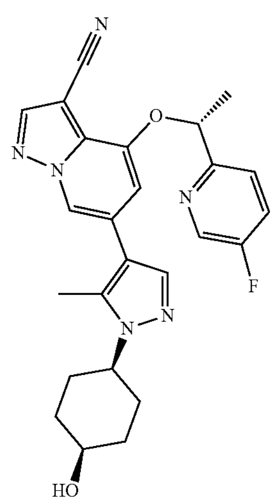 [SMILES: Cc1c(-c2cc(O[C@H](C)c3ccc(F)cn3)c3c(C#N)cnn3c2)cnn1[C@H]1CC[C@@H](O)CC1] | 4-((R)-1-(5-fluoropyridin-2-yl)ethoxy)-6-(1-((1s,4S)-4-hydroxycyclohexyl)-5-methyl-1H-pyrazol-4-yl)-pyrazolo[1,5-a]pyridine-3-carbonitrile | Example 1 | 460.51 | 0.3 |

| Compound number | Structure | Chemical Name | Reference Procedure | MS APCI (m/z) | Enz FGFR2 (nM) |
|---|---|---|---|---|---|
| 47 | 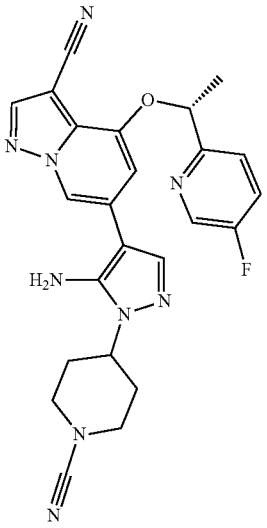 [SMILES: C[C@@H](Oc1cc(-c2cnn(C3CCN(C#N)CC3)c2N)cn2ncc(C#N)c12)c1ccc(F)cn1] | (R)-6-(5-amino-1-(1-cyanopiperidin-4-yl)-1H-pyrazol-4-yl)-4-(1-(5-fluoropyridin-2-yl)ethoxy)pyrazolo[1,5-a]pyridine-3-carbonitrile | Example 13 | 471.5 | 0.3 |
| 48 | 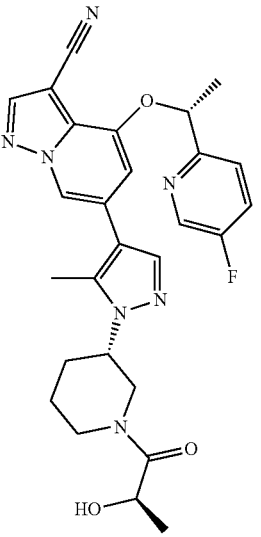 [SMILES: Cc1c(-c2cc(O[C@H](C)c3ccc(F)cn3)c3c(C#N)cnn3c2)cnn1[C@H]1CCCN(C(=O)[C@@H](C)O)C1] | 4-((R)-1-(5-fluoropyridin-2-yl)ethoxy)-6-(1-((S)-1-((R)-2-hydroxypropanoyl)-piperidin-3-yl)-5-methyl-1H-pyrazol-4-yl)pyrazolo[1,5-a]pyridine-3-carbonitrile | Example 9 | 517.57 | 0.4 |

-continued

| Compound number | Structure | Chemical Name | Reference Procedure | MS APCI (m/z) | Enz FGFR2 (nM) |
|---|---|---|---|---|---|
| 49 | 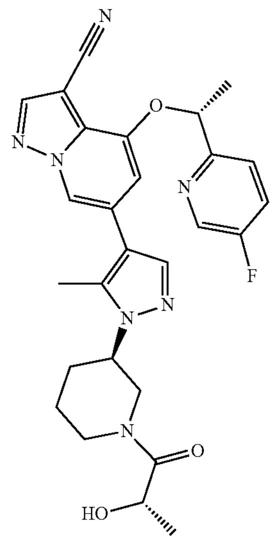 [SMILES: Cc1c(-c2cc(O[C@H](C)c3ccc(F)cn3)c3c(C#N)cnn3c2)cnn1[C@@H]1CCCN(C(=O)[C@H](C)O)C1] | 4-((R)-1-(5-fluoropyridin-2-yl)ethoxy)-6-(1-((R)-1-((S)-2-hydroxypropanoyl)-piperidin-3-yl)-5-methyl-1H-pyrazol-4-yl)pyrazolo[1,5-a]pyridine-3-carbonitrile | Example 9 | 517.57 | 2.6 |
| 50 | 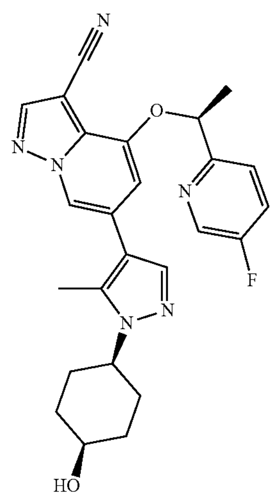 [SMILES: Cc1c(-c2cc(O[C@@H](C)c3ccc(F)cn3)c3c(C#N)cnn3c2)cnn1[C@H]1CC[C@@H](O)CC1] | 4-((S)-1-(5-fluoropyridin-2-yl)ethoxy)-6-(1-((1s,4R)-4-hydroxycyclohexyl)-5-methyl-1H-pyrazol-4-yl)-pyrazolo[1,5-a]pyridine-3-carbonitrile | Example 1 | 460.51 | 5.5 |
| 51 | 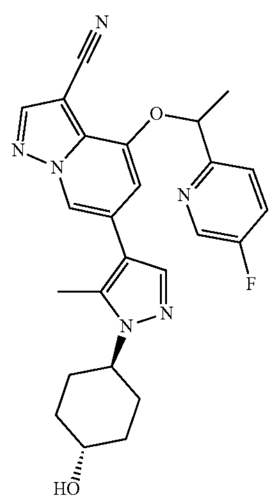 [SMILES: Cc1c(-c2cc(OC(C)c3ccc(F)cn3)c3c(C#N)cnn3c2)cnn1[C@H]1CC[C@H](O)CC1] | 4-(1-(5-fluoropyridin-2-yl)ethoxy)-6-(1-((1r,4r)-4-hydroxycyclohexyl)-5-methyl-1H-pyrazol-4-yl)-pyrazolo[1,5-a]pyridine-3-carbonitrile | Example 1 | 460.51 | 1 |

-continued

| Compound number | Structure | Chemical Name | Reference Procedure | MS APCI (m/z) | Enz FGFR2 (nM) |
|---|---|---|---|---|---|
| 52 | 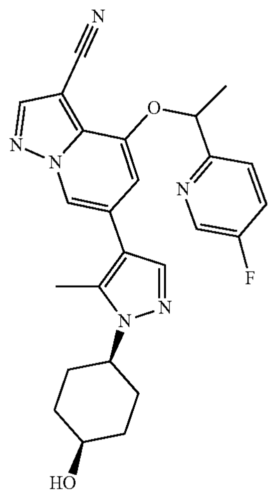 [SMILES: Cc1c(-c2cc(OC(C)c3ccc(F)cn3)c3c(C#N)cnn3c2)cnn1[C@H]1CC[C@@H](O)CC1] | 4-(1-(5-fluoropyridin-2-yl)ethoxy)-6-(1-((1s,4s)-4-hydroxycyclohexyl)-5-methyl-1H-pyrazol-4-yl)-pyrazolo[1,5-a]pyridine-3-carbonitrile | Example 1 | 460.51 | 0.7 |
| 53 | 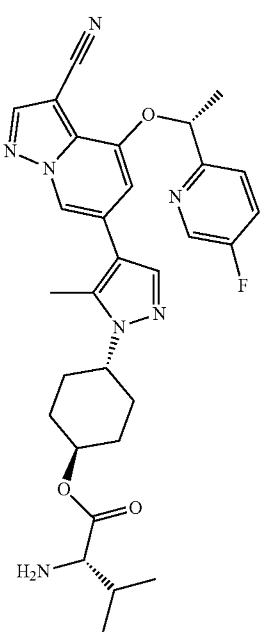 [SMILES: Cc1c(-c2cc(O[C@H](C)c3ccc(F)cn3)c3c(C#N)cnn3c2)cnn1[C@H]1CC[C@H](OC(=O)[C@@H](N)C(C)C)CC1] | (1R,4S)-4-(4-(3-cyano-4-((R)-1-(5-fluoropyridin-2-yl)ethoxy)pyrazolo[1,5-a]pyridin-6-yl)-5-methyl-1H-pyrazol-1-yl)cyclohexyl L-valinate | Example 9 | 559.65 | 0.3 |

| Compound number | Structure | Chemical Name | Reference Procedure | MS APCI (m/z) | Enz FGFR2 (nM) |
|---|---|---|---|---|---|
| 54 | 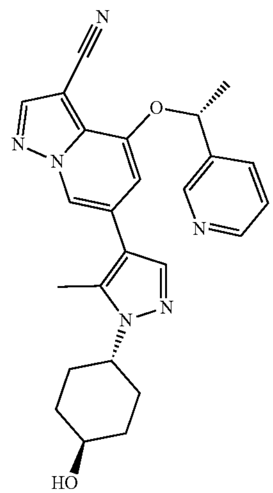 [SMILES: Cc1c(-c2cc(O[C@H](C)c3cccnc3)c3c(C#N)cnn3c2)cnn1[C@H]1CC[C@H](O)CC1] | 6-(1-((1r,4R)-4-hydroxy-cyclohexyl)-5-methyl-1H-pyrazol-4-yl)-4-((R)-1-(pyridin-3-yl)ethoxy)pyrazolo[1,5-a]pyridine-3-carbonitrile | Example 1 | 442.52 | 0.4 |
| 55 | 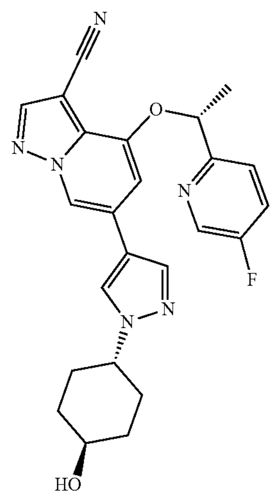 [SMILES: C[C@@H](Oc1cc(-c2cnn([C@H]3CC[C@H](O)CC3)c2)cn2ncc(C#N)c12)c1ccc(F)cn1] | 4-((R)-1-(5-fluoropyridin-2-yl)ethoxy)-6-(1-((1r,4R)-4-hydroxycyclohexyl)-1H-pyrazol-4-yl)pyrazolo[1,5-a]pyridine-3-carbonitrile | Example 1 | 446.49 | 0.2 |
| 56 | 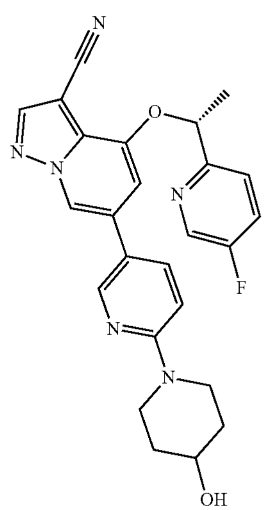 [SMILES: C[C@@H](Oc1cc(-c2ccc(N3CCC(O)CC3)nc2)cn2ncc(C#N)c12)c1ccc(F)cn1] | (R)-4-(1-(5-fluoropyridin-2-yl)ethoxy)-6-(6-(4-hydroxypiperidin-1-yl)-pyridin-3-yl)pyrazolo[1,5-a]pyridine-3-carbonitrile | Example 1 | 458.5 | 0.2 |

| Compound number | Structure | Chemical Name | Reference Procedure | MS APCI (m/z) | Enz FGFR2 (nM) |
|---|---|---|---|---|---|
| 57 | 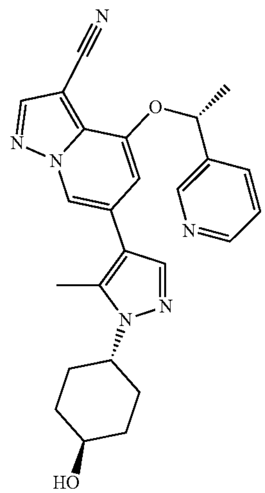 [SMILES: Cc1c(-c2cc(O[C@H](C)c3cccnc3)c3c(C#N)cnn3c2)cnn1[C@H]1CC[C@H](O)CC1] | 6-(1-((1r,4R)-4-hydroxy-cyclohexyl)-5-methyl-1H-pyrazol-4-yl)-4-((R)-1-(pyridin-3-yl)ethoxy)pyrazolo[1,5-a]pyridine-3-carbonitrile | Example 1 | 442.52 | 0.4 |
| 58 | 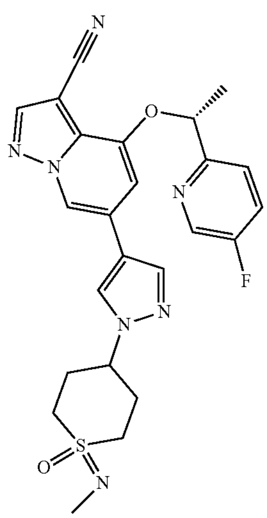 [SMILES: CN=S1(=O)CCC(n2cc(-c3cc(O[C@H](C)c4ccc(F)cn4)c4c(C#N)cnn4c3)cn2)CC1] | (R)-4-(1-(5-fluoropyridin-2-yl)ethoxy)-6-(1-(1-(methylimino)-1-oxido-hexahydro-1l6-thiopyran-4-yl)-1H-pyrazol-4-yl)-pyrazolo[1,5-a]pyridine-3-carbonitrile | Example 14 | 493.56 | 0.15 |
| 59 | 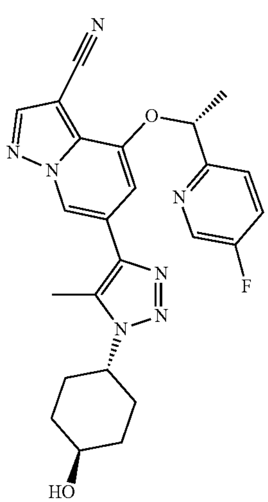 [SMILES: Cc1c(-c2cc(O[C@H](C)c3ccc(F)cn3)c3c(C#N)cnn3c2)nnn1[C@H]1CC[C@H](O)CC1] | 4-((R)-1-(5-fluoropyridin-2-yl)ethoxy)-6-(1-((1r,4R)-4-hydroxycyclohexyl)-5-methyl-1H-1,2,3-triazol-4-yl)pyrazolo[1,5-a]pyridine-3-carbonitrile | Example 15 | 461.5 | 0.5 |

-continued

| Compound number | Structure | Chemical Name | Reference Procedure | MS APCI (m/z) | Enz FGFR2 (nM) |
|---|---|---|---|---|---|
| 60 | 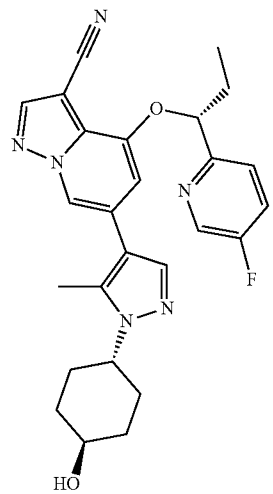 [SMILES: CC[C@@H](Oc1cc(-c2cnn([C@H]3CC[C@H](O)CC3)c2C)cn2ncc(C#N)c12)c1ccc(F)cn1] | 4-((R)-1-(5-fluoropyridin-2-yl)propoxy)-6-(1-((1r,4R)-4-hydroxycyclohexyl)-5-methyl-1H-pyrazol-4-yl)pyrazolo[1,5-a]pyridine-3-carbonitrile | Example 16 | 474.54 | 0.4 |
| 61 | 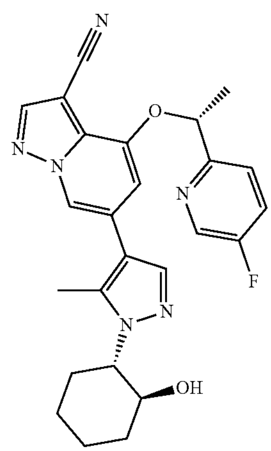 [SMILES: Cc1c(-c2cc(O[C@H](C)c3ccc(F)cn3)c3c(C#N)cnn3c2)cnn1[C@H]1CCCC[C@@H]1O] | 4-((R)-1-(5-fluoropyridin-2-yl)ethoxy)-6-(1-((1S,2S)-2-hydroxycyclohexyl)-5-methyl-1H-pyrazol-4-yl)pyrazolo[1,5-a]pyridine-3-carbonitrile | Example 17 | 460.51 | 0.3 |
| 62 | 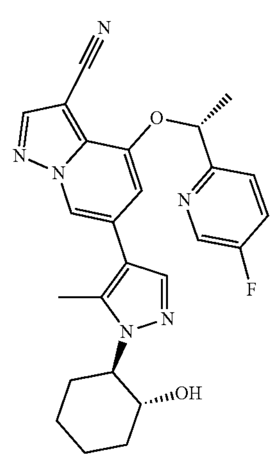 [SMILES: Cc1c(-c2cc(O[C@H](C)c3ccc(F)cn3)c3c(C#N)cnn3c2)cnn1[C@@H]1CCCC[C@H]1O] | 4-((R)-1-(5-fluoropyridin-2-yl)ethoxy)-6-(1-((1R,2R)-2-hydroxycyclohexyl)-5-methyl-1H-pyrazol-4-yl)pyrazolo[1,5-a]pyridine-3-carbonitrile | Example 17 | 460.51 | 8 |

-continued

| Compound number | Structure | Chemical Name | Reference Procedure | MS APCI (m/z) | Enz FGFR2 (nM) |
|---|---|---|---|---|---|
| 63 | 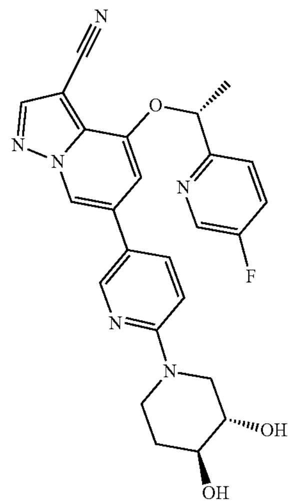 [SMILES: C[C@@H](Oc1cc(-c2ccc(N3CC[C@H](O)[C@@H](O)C3)nc2)cn2ncc(C#N)c12)c1ccc(F)cn1] | 6-(6-((3S,4S)-3,4-dihydroxypiperidin-1-yl)pyridin-3-yl)-4-((R)-1-(5-fluoropyridin-2-yl)ethoxy)pyrazolo[1,5-a]pyridine-3-carbonitrile | Example 7 | 474.5 | 0.3 |
| 64 | 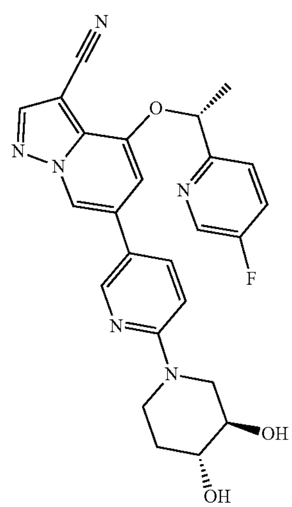 [SMILES: C[C@@H](Oc1cc(-c2ccc(N3CC[C@@H](O)[C@H](O)C3)nc2)cn2ncc(C#N)c12)c1ccc(F)cn1] | 6-(6-((3R,4R)-3,4-dihydroxypiperidin-1-yl)pyridin-3-yl)-4-((R)-1-(5-fluoropyridin-2-yl)ethoxy)pyrazolo[1,5-a]pyridine-3-carbonitrile | Example 7 | 474.5 | |
| 65 | 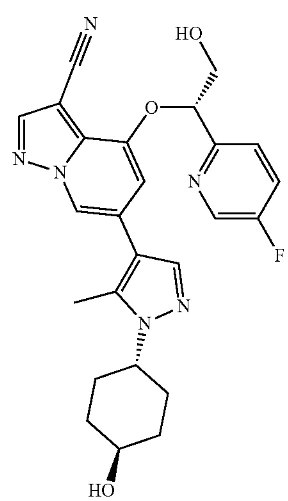 [SMILES: Cc1c(-c2cc(O[C@H](CO)c3ccc(F)cn3)c3c(C#N)cnn3c2)cnn1[C@H]1CC[C@H](O)CC1] | 4-((S)-1-(5-fluoropyridin-2-yl)-2-hydroxyethoxy)-6-(1-((1r,4S)-4-hydroxycyclohexyl)-5-methyl-1H-pyrazol-4-yl)pyrazolo[1,5-a]pyridine-3-carbonitrile | Example 18 | 476.51 | 3 |

| Compound number | Structure | Chemical Name | Reference Procedure | MS APCI (m/z) | Enz FGFR2 (nM) |
|---|---|---|---|---|---|
| 66 | 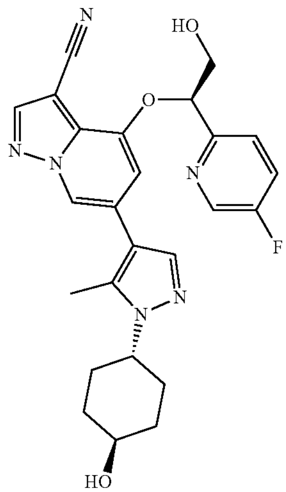 [SMILES: Cc1c(-c2cc(O[C@@H](CO)c3ccc(F)cn3)c3c(C#N)cnn3c2)cnn1[C@H]1CC[C@H](O)CC1] | 4-((R)-1-(5-fluoropyridin-2-yl)-2-hydroxyethoxy)-6-(1-((1r,4R)-4-hydroxycyclohexyl)-5-methyl-1H-pyrazol-4-yl)pyrazolo[1,5-a]pyridine-3-carbonitrile | Example 18 | 476.51 | 110 |
| 67 | 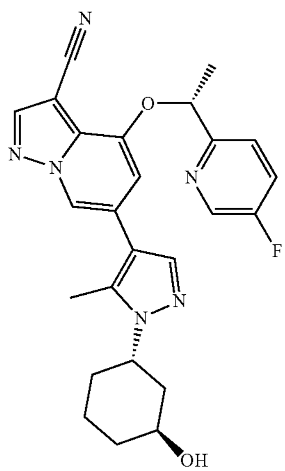 [SMILES: Cc1c(-c2cc(O[C@H](C)c3ccc(F)cn3)c3c(C#N)cnn3c2)cnn1[C@H]1CCC[C@H](O)C1] | 4-((R)-1-(5-fluoropyridin-2-yl)ethoxy)-6-(1-((1S,3S)-3-hydroxycyclohexyl)-5-methyl-1H-pyrazol-4-yl)pyrazolo[1,5-a]pyridine-3-carbonitrile | Example 1 | 460.51 | 0.4 |
| 68 | 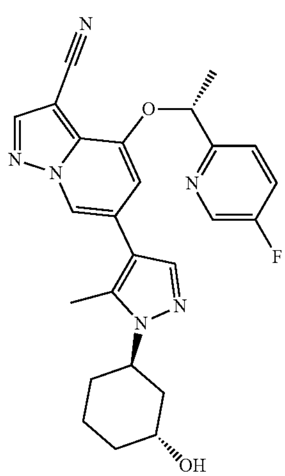 [SMILES: Cc1c(-c2cc(O[C@H](C)c3ccc(F)cn3)c3c(C#N)cnn3c2)cnn1[C@@H]1CCC[C@@H](O)C1] | 4-((R)-1-(5-fluoropyridin-2-yl)ethoxy)-6-(1-((1R,3R)-3-hydroxycyclohexyl)-5-methyl-1H-pyrazol-4-yl)pyrazolo[1,5-a]pyridine-3-carbonitrile | Example 1 | 460.51 | 1 |

| Compound number | Structure | Chemical Name | Reference Procedure | MS APCI (m/z) | Enz FGFR2 (nM) |
|---|---|---|---|---|---|
| 69 | 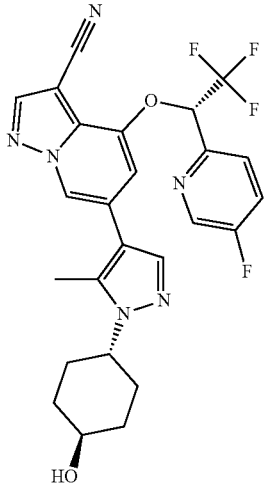 [SMILES: Cc1c(-c2cc(O[C@@H](c3ccc(F)cn3)C(F)(F)F)c3c(C#N)cnn3c2)cnn1[C@H]1CC[C@H](O)CC1] | 6-(1-((1r,4S)-4-hydroxy-cyclohexyl)-5-methyl-1H-pyrazol-4-yl)-4-((S)-2,2,2-trifluoro-1-(5-fluoropyr-idin-2-yl)ethoxy)pyrazolo[1,5-a]pyridine-3-carbo-nitrile | Example 19 | 514.48 | 0.4 |
| 70 | 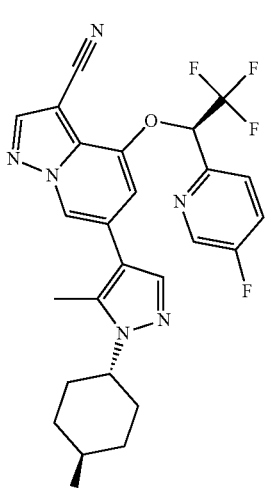 | 6-(1-((1r,4R)-4-hydroxy-cyclohexyl)-5-methyl-1H-pyrazol-4-yl)-4-((R)-2,2,2-trifluoro-1-(5-fluoropyr-idin-2-yl)ethoxy)pyrazolo[1,5-a]pyridine-3-carbo-nitrile | Example 19 | 514.48 | 110 |
| 71 | 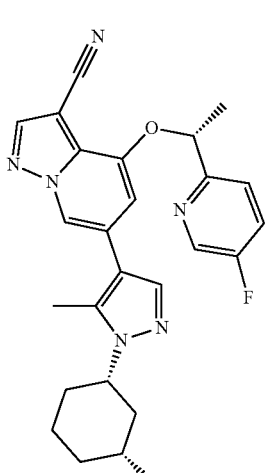 | 4-((R)-1-(5-fluoropyri-din-2-yl)ethoxy)-6-(1-((1S,3R)-3-hydroxycyclo-hexyl)-5-methyl-1H-pyr-azol-4-yl)pyrazolo[1,5-a]pyridine-3-carbonitrile | Example 1 | 460.51 | 1 |

| Compound number | Structure | Chemical Name | Reference Procedure | MS APCI (m/z) | Enz FGFR2 (nM) |
|---|---|---|---|---|---|
| 72 | 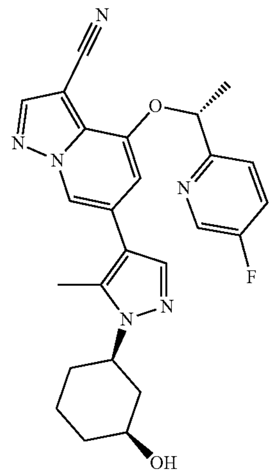 | 4-((R)-1-(5-fluoropyridin-2-yl)ethoxy)-6-(1-((1R,3S)-3-hydroxycyclohexyl)-5-methyl-1H-pyrazol-4-yl)pyrazolo[1,5-a]pyridine-3-carbonitrile | Example 1 | 460.51 | 0.4 |

V. Methods OF Use

FGFR Wild Type and Mutant Enzyme Assays

Activity against FGFR wild type and mutant enzymes were determined in biochemical assays using purified intracellular domains of the respective isoforms using HTRF KinEASE-TK assay technology from CisBio, now PerkinElmer. (Catalogue number 62TK0PEC). Briefly test compounds were tested in 11 point 1:3 serial dilutions, typical final concentration range from 10,000 nM to 0.17 nM. Test compounds were dissolved in DMSO and added to assay plates using acoustic transfer. Enzyme was pre-incubated with test compound for 30 minutes and the assay was initiated by addition of ATP and TK-peptide substrate. After 60 minutes at room temperature the reaction was quenched with detection reagent and incubated for an additional 60 minutes at room temperature. The plates were read using a multimode reader and the emission ratio of 665 nm to 615 nm was determined. This ratio was converted to percent of control (POC). [1-(high control-sample signal)/(high control-low control)]*100. Wells without compound were used to determine high control values and wells without enzyme were used to determine low control values. The POC values were fit using a four-parameter logistic model and the value where the fit curve was equal to 50 POC was reported as the IC50 using the Signals Vitro Vivo software package (PerkinElmer). Final assay conditions were: 50 mM HEPES pH7.5, 10 mM $MgCl_2$, 1 mM EDTA, 0.01% Brij-35, 2 mM $MnCl2$, 1 mM DTT, and 0.5 uM TK-peptide. The enzyme source, catalogue number, final enzyme concentration, and final ATP concentration can be found in the tables 1-2 below.

TABLE 1

A summary of FGFR1-FGFR4 enzyme assay

| Enzyme | FGFR1 | FGFR2 | FGFR3 | FGFR4 |
|---|---|---|---|---|
| Enzyme source | Invitrogen | Carna Bioscience | Carna Bioscience | Carna Bioscience |
| Catalog Number | PV4105 | 08-134 | 08-135 | 08-136 |
| Enzyme conc. | 0.02 nM | 0.03 nM | 0.03 nM | 0.13 nM |
| ATP conc. | 40 uM | 2 uM | 5 uM | 80 uM |

TABLE 2

A summary of FGFR1-FGFR4 enzyme assay

| Enzyme | FGFR1 V561M | FGFR2 N549H | FGFR2 V564F | FGFR2 V564I | FGFR3 V555M |
|---|---|---|---|---|---|
| Enzyme source | Carna Bioscience | Carna Bioscience | SignalChem Biotech | Carna Bioscience | Carna Bioscience |
| Catalog Number | 08-536 | 08-532 | F05-12FG | 08-546 | 08-543 |
| Enzyme conc. | 0.13 nM | 0.02 nM | 0.02 nM | 0.02 nM | 0.01 nM |
| ATP conc. | 1.4 uM | 0.9 uM | 1.5 uM | 0.4 uM | 1.5 uM |

Detection of phosphorylated FGFR1 (pFGFR1) and FGFR2 (pFGFR2).

Phosphorylated FGFR1 (pFGFR1) Cell Assay

KG-1 cells were grown in IMDM supplemented with 20% fetal bovine serum. KG-1 cells were plated into a 384-well at $10 \times 10^5$ cells/25 µL/well. Cells were treated with compound using three-fold serial dilutions at final concentrations ranging from 10 UM to 0.5 nM. Compound was incubated on cells for 1 hour at 37° C., 5% $CO_2$.

Following the 1-hour incubation with compound, cell lysates were prepared and phospho FGFR1 was measured using the HTRF Phospho-FGFR1 (TYR653/654) Detection Kits (CisBio, cat #64FGFR1Y6PEG). 8 µL of cell lysis buffer (4×) supplied with 1× Phospho and Total protein blocking reagent (CisBio, cat #64FGFR1Y6PEG, CisBio, cat #64KB1AAC) was then added to the well. Cells were incubated with lysis buffer for 40 minutes at 4° C. under shaking conditions. Plates were centrifuged at 1500 rpm for 3 min then 16 µL of cell lysate was transferred from the cell-culture plate to a small volume detection plate with the added premixed antibody solutions (4 µL) (CisBio, cat

64FGFR1Y6PEG). Plates were centrifuged at 1000 rpm for 1 min then incubated at 25° C. for 120 min, then overnight at 4° C. Plates were read on the En Vision multimode plate reader via HTRF dual wavelength detection. One hundred percent of control (POC) was determined using DMSO treated samples, and 0 POC was determined using a control compound. A 4-parameter logistic curve was fit to the POC values as a function of compound concentration and the $IC_{50}$ value is the point where the curve crosses 50 POC.

Phosphorylated FGFR2-WT (pFGFR2-WT) Cell Assay

KATOIII cells were grown in the appropriate growth medium, IMDM supplemented with 20% fetal bovine serum. Cells were seeded into a 384-well at $1\times10^5$ cells/25 µL/well. Cells were treated with compound using three-fold serial dilutions at final concentrations ranging from 10 µM to 0.5 nM. Compound was incubated on cells for 1 hour at 37° C., 5% $CO_2$.

Following the 1-hour incubation with compounds, cell lysates were prepared and phospho FGFR2 was measured using the HTRF Phospho-FGFR2 (TYR653/654) Detection Kits (CisBio, cat #64FGFR2Y6PEG). 8 µL of cell lysis buffer (4x) supplied with 1x Phospho and Total protein blocking reagent (CisBio, cat #64FGFR2Y6PEG, CisBio, cat #64KB1AAC) was then added to the wells. Cells were incubated with lysis buffer for 40 minutes at 4° C. under shaking conditions. Plates were centrifuged at 1500 rpm for 3 min and then 16 µL of cell lysate was transferred from the cell-culture plate to a small volume detection plate with the added premixed antibody solutions (4 µL) (CisBio, cat #64FGFR2Y6PEG). Plates were centrifuged at 1000 rpm for 1 min then incubated at 25° C. for 120 min, then overnight at 4° C. Plates were read on the En Vision multimode plate reader via HTRF dual wavelength detection. One hundred percent of control (POC) was determined using DMSO treated samples, and 0 POC was determined using the top concentration of a control compound. A 4-parameter logistic curve was fit to the POC values as a function of compound concentration to determine the IC50 value.

Phosphorylated FGFR2-Mutant (pFGFR2-Mutant) Cell Assay

HEK-293 cells were engineered to express FGFR2-V564F/I/L or FGFR2-N549K mutations with constructs obtained from GenScript. Cells were grown in appropriate growth medium DMEM supplemented with 10% fetal bovine serum and 150 µg/mL hygromycin. Cells were plated in 96-well poly-D-lysine coated flat bottom plate at $7\times10^5$ cells/well and allowed to attached overnight at 37° C., 5% $CO_2$. Cells were treated with compounds using three-fold serial dilutions at final concentrations ranging from 1 µM to 0.05 nM. Compound was incubated on cells for 1 hour at 37° C., 5% $CO_2$. Cells were stimulated with 100 ng/ml aFGF/bFGF (gibco, cat #13241-013, gibco cat #13256-029) for 10 min at 37° C., 5% $CO_2$. Medium was removed, and cells were lysed with lysis buffer containing phosphatase and protease inhibitors (Sigma, cat #P8340-5ML, Sigma, cat #P5726-5ML). Phospho FGFR2 was measured by ELISA (R&D Systems, cat #DYC684). Optical density was measured for each well using the BioTek Cytation 5 at wavelength of 450 nm. One hundred percent of control (POC) was determined using DMSO treated samples, and 0 POC was determined using a control compound. A 4-parameter logistic curve was fit to the POC values as a function of compound concentration and the $IC_{50}$ value is the point where the curve crosses 50 POC.

TABLE 3

FGFR cellular assay results

| Compound Number | FGFR2 Enz (nM) | FGFR2 WT cell (nM) | FGFR2 N549H Enzyme (nM) | FGFR2 V564F Enzyme (nM) | FGFR2 V564I Enzyme (nM) |
|---|---|---|---|---|---|
| 1 | 0.3 | 3.4 | 0.4 | 1 | 1.4 |
| 2 | 0.16 | 2.5 | 0.05 | 0.14 | 0.24 |
| 3 | 21 | 128 | | | |
| 4 | 1 | 26 | 2 | 3 | 4 |
| 5 | 0.25 | 5 | 0.7 | 1 | 1.4 |
| 6 | 1 | 15 | 2.4 | 4 | 4.3 |
| 7 | 0.3 | 6 | 0.5 | 1 | 1 |
| 8 | 0.2 | 2 | 0.05 | 0.08 | 0.1 |
| 9 | 0.3 | 7 | 0.5 | 1 | 1 |
| 10 | 0.3 | 5 | 0.55 | 0.8 | 1 |
| 11 | 1.4 | 23 | 4.6 | 4.4 | 5.8 |
| 12 | 0.45 | 4.7 | 0.7 | 1.3 | 1.8 |
| 13 | 0.5 | 3.8 | 0.6 | 1.6 | 2 |
| 14 | 12.5 | 267 | 14 | 15 | 38 |
| 15 | 0.4 | 6 | 0.4 | 1 | 1 |
| 16 | 0.5 | 8 | 0.3 | 0.8 | 1 |
| 17 | 0.6 | 3.4 | 0.5 | 1 | 1.7 |
| 18 | 0.5 | 4 | 0.5 | 1 | 2 |
| 19 | 0.15 | 1.25 | 0.1 | 0.3 | 0.4 |
| 20 | 0.14 | 1.7 | 0.1 | 0.3 | 0.5 |
| 21 | 1.7 | 24 | 3 | 6 | 11 |
| 22 | 0.3 | 2.7 | 0.4 | 1 | 1.4 |
| 23 | 0.4 | 4 | 0.6 | 1 | 2 |
| 24 | 0.3 | 3 | 0.3 | 1 | 1 |
| 25 | 0.3 | 3 | 0.25 | 0.7 | 1 |
| 26 | 0.5 | 4 | 0.3 | 1 | 1 |
| 27 | 3 | 23 | 5 | 11 | 17 |
| 28 | 3 | 17 | 5 | 10 | 12 |
| 29 | 0.3 | 4 | 0.6 | 1.4 | 1.5 |
| 30 | 1 | 9 | 2 | 3.7 | 6 |
| 31 | 1 | 7 | 2 | 5 | 5.6 |
| 32 | 0.4 | 2.5 | 0.3 | 1 | 1 |
| 33 | 1 | 6 | 0.7 | 2 | 3 |
| 34 | 2.6 | 17 | 3 | 10 | 12 |
| 35 | 1 | 5 | 1 | 2 | 2.7 |
| 36 | 0.4 | 4 | 0.5 | 1.5 | 2 |
| 37 | 0.5 | 5.6 | 0.3 | 1 | 1.6 |
| 38 | 0.4 | 6 | 0.3 | 1 | 1.3 |
| 39 | 0.5 | 5.5 | 0.4 | 1 | 1 |
| 40 | 1 | 6.7 | 0.6 | 2 | 3 |
| 41 | 0.5 | 4 | 0.7 | 2 | 2 |
| 42 | 0.6 | 4 | 0.65 | 1.7 | 2 |
| 43 | 1 | 9 | 1 | 3 | 3 |
| 44 | 0.5 | 8 | 0.4 | 1 | 1.5 |
| 45 | 6.5 | 60 | 7 | 13 | 23 |
| 46 | 0.3 | 3 | 0.3 | 1 | 1 |
| 47 | 0.3 | 4 | 0.4 | 1 | 1 |
| 48 | 0.4 | 3 | 0.4 | 1 | 1 |
| 49 | 2.6 | 15 | 3 | 8 | 10 |
| 50 | 5.5 | 57 | 6 | 11 | 20 |
| 51 | 1 | 6.5 | 1 | 2 | 4 |
| 52 | 0.7 | 6 | 1 | 2.4 | 3 |
| 53 | 0.3 | 3 | 0.5 | 1 | 1.5 |
| 54 | 0.4 | 12 | 0.5 | 1 | 1 |
| 55 | 0.2 | 1.6 | 0.13 | 0.3 | 0.6 |
| 56 | 0.2 | 3.4 | 0.2 | 0.6 | 1 |
| 57 | 0.4 | 12 | 0.5 | 1 | 1 |
| 58 | 0.15 | 1.6 | 0.15 | 0.45 | 1 |
| 59 | 0.5 | 5.7 | 1 | 3 | 3 |
| 60 | 0.4 | 3.5 | 0.5 | 1.5 | 2 |
| 61 | 0.3 | 3 | 0.4 | 1 | 1.5 |
| 62 | 7 | 48 | 9 | 21.5 | 30 |
| 63 | 0.3 | 3.3 | 0.3 | 1 | 1 |
| 64 | 0.3 | 4 | 0.2 | 0.6 | 0.7 |
| 65 | 3 | 21 | 3.5 | 9.5 | 10.6 |
| 66 | 105 | 793 | 106 | 139 | 369 |
| 67 | 0.4 | 4 | 0.4 | 1 | 1.4 |
| 68 | 1 | 8 | 1 | 3 | 4 |
| 69 | 0.4 | 2 | 0.4 | 1.6 | 1.6 |
| 70 | 110 | 790 | 160 | 219 | 420 |
| 71 | 1 | 4.5 | 1 | 2 | 3 |
| 72 | 0.4 | 3 | 0.45 | 1 | 1.5 |

Kinome Selectivity Assay Procedure

A compound of the present disclosure was screened at 10× its enzyme IC50 for FGFR2 against 394 kinases using the KinSight Quantitative Kinome Profiling Service at AssayQuant, which is performed at cellular ATP concentrations of 1 mM. The compound showed 78% inhibition of FGFR2 and only 2 other kinases were inhibited more than 50% (FGFR3, ROS1).

TABLE 4 p-FGFR inhibition cell $IC_{50}$ data or fold shift from FGFR2 WT IC50

| Assay | IC50 or Fold Shift from FGFR2 WT |
|---|---|
| FGFR2 WT | 2 nM* |
| FGFR1 WT | 140× |
| FGFR2 N549K | 4× |
| FGFR2-V564I | 4× |
| FGFR2-V564F | 3× |
| FGFR2-V564L | 1.5× |

*Denotes FBS shifted IC50 value

A compound of the invention showed 140× selective for FGFR2 over FGFR1, exhibits low nM potency on FGFR2 WT and retains activity across FGFR2 mutations.

Figure 2:
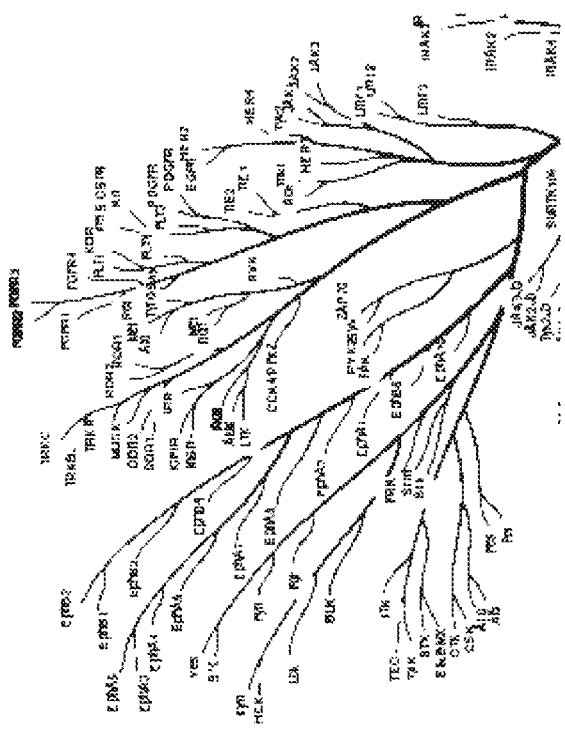
FIG. 2 illustrates a kinome tree showing inhibition of 3 kinases by a compound of the invention.

A compound of the invention was profiled at 10× the enzyme IC50 for FGFR2 against a panel of 371 kinases. FGFR2, FGFR3, and ROS1 where the only kinases that showed >50% target inhibition. Partial kinome tree shown in FIG. 2.

Pharmacokinetics of a Compound of the Invention in Animals

The absorption and pharmacokinetics of a compound in the invention was investigated in bioavailability studies in mice, rats, dogs, and monkeys. CD1 Mice and Sprague-Dawley Rats were dosed at 3 mpk IV while Beagle Dogs and Cynomolgus Monkeys were dosed at 1 mg/kg IV. CD1 Mice, Sprague-Dawley Rats, Beagle Dogs and Cynomolgus Monkeys were dosed at 10 mg/kg Oral Administration. Blood samples were taken at various time points and processed for plasma. The plasma samples were further processed using the procedure below for analysis.

General Sample Processing Procedure for Pharmacokinetic and Efficacy Studies

Protein precipitation (PPT) operations were done for all collected plasma samples. An aliquot of calibration standard, quality control (if any), dilution quality control (if any), single blank and double blank samples were added to a 96-well plate respectively. Each sample (except the double blank, quenched with blank crash solution) was quenched with internal standard spiked crash solution and the mixture vortex-mixed for 5 min and centrifuged for 10 min. All unknown samples were quenched with internal standard spiked crash solution and the mixture vortex-mixed.

An aliquot of supernatant was transferred to a clean 96-well plate containing diluent and the plated samples injected for LC-MS/MS analysis. Plasma concentration versus time data was analyzed by non-compartmental approaches using appropriate PK modeling software. Related PK parameters were calculated according to dosing route for all routes.

TABLE 5

A summary of PK of a compound of the invention dosed in mouse, rat, dog, and cynomolgus monkey

| PK | Mouse | Rat | Dog | Cyno |
|---|---|---|---|---|
| Time (h) with $C_{plasma\,free}$ > Cell $IC_{50}$ | >24 | >24 | >24 | >24 |
| $t_{1/2}$ (hr) | 5.2 | 3.3 | 22 | 21 |
| F (%) | >100 | 81 | >100 | 94 |
| CL (mL/min/kg) | 3.6 | 5.1 | 5.3 | 0.8 |
| $VD_{ss}$ (L/kg) | 1.2 | 1.3 | 2.2 | 1.0 |

Figure 3:
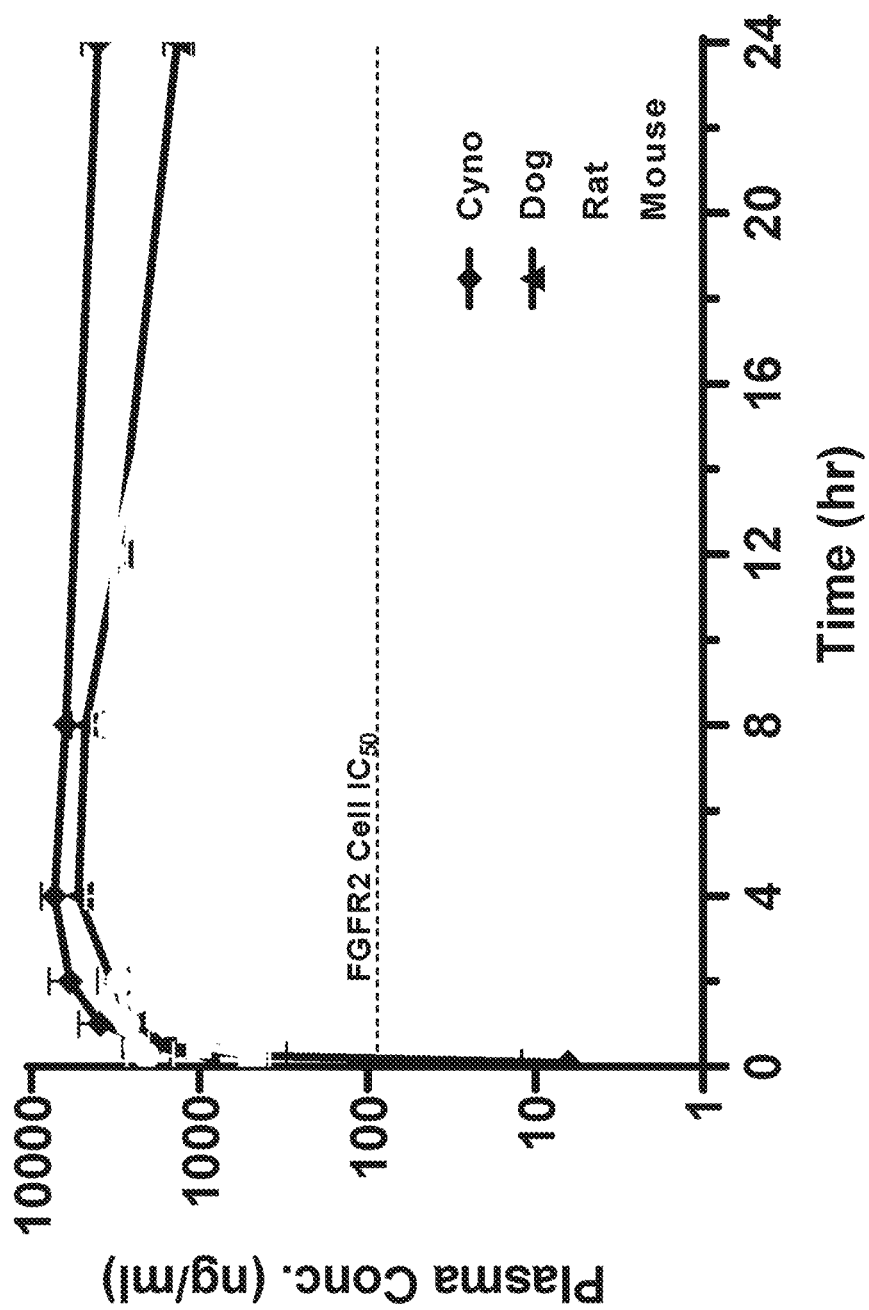
FIG. 3 shows a graph of PK of a compound of the invention dosed in mouse, rat, dog, and cynomolgus monkey.

A compound of the invention was used to study bioavailability across species including mouse, rat, dog, and cynomolgus monkey. PK studies of a compound of the invention dosed in mouse, rat, dog, and cynomolgus monkey at 1 or 3 mg/kg IV and 10 mg/kg PO were conducted and the results are summarized in FIG. 3. A compound of the invention showed 24-hour coverage of the free fraction adjusted WT FGFR2 cellular IC50 across species. PK studies across species showed a compound of the invention to be a low clearance compound with high oral bioavailability.

Figure 4:
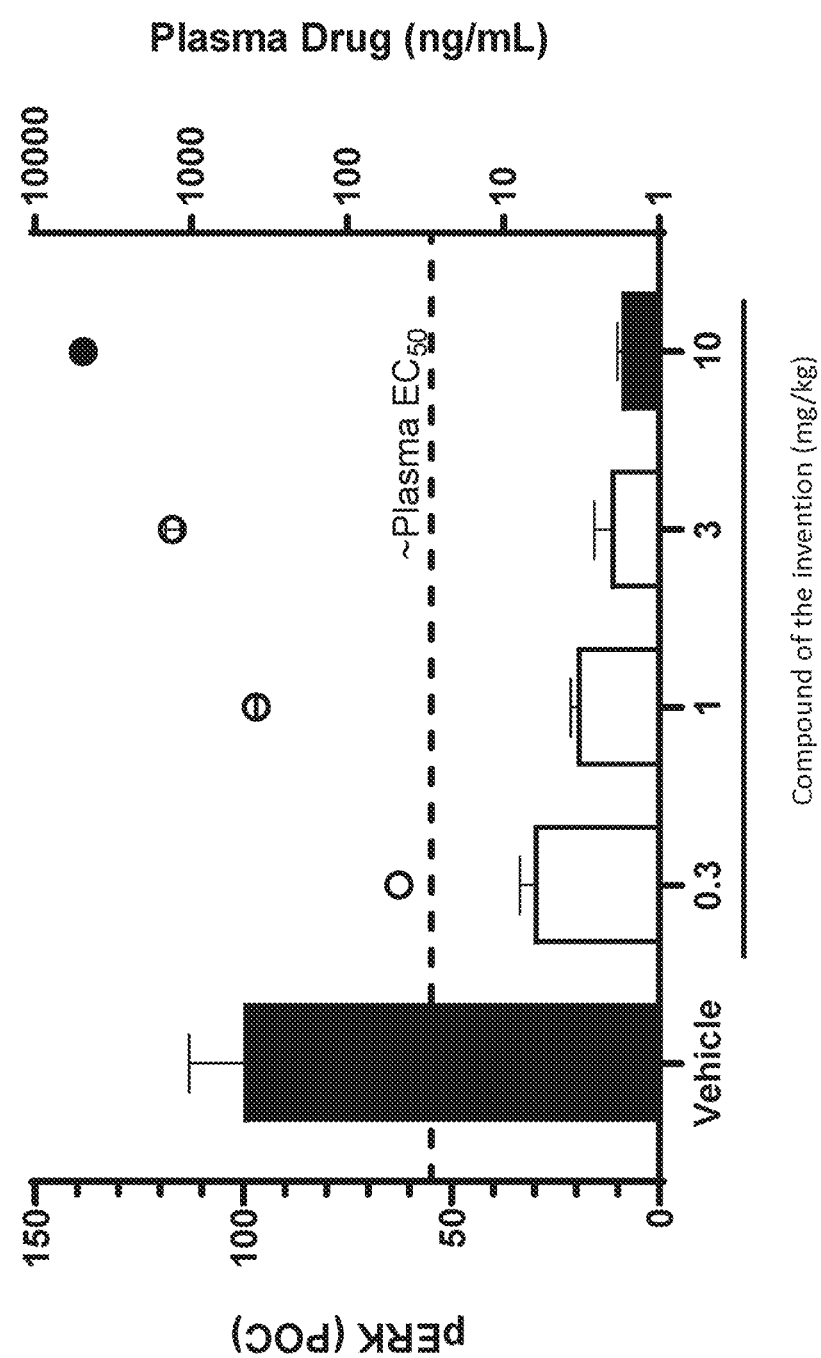
FIG. 4 shows a graph of inhibition of pERK with various dosages of a compound of the invention.
Figure 5:
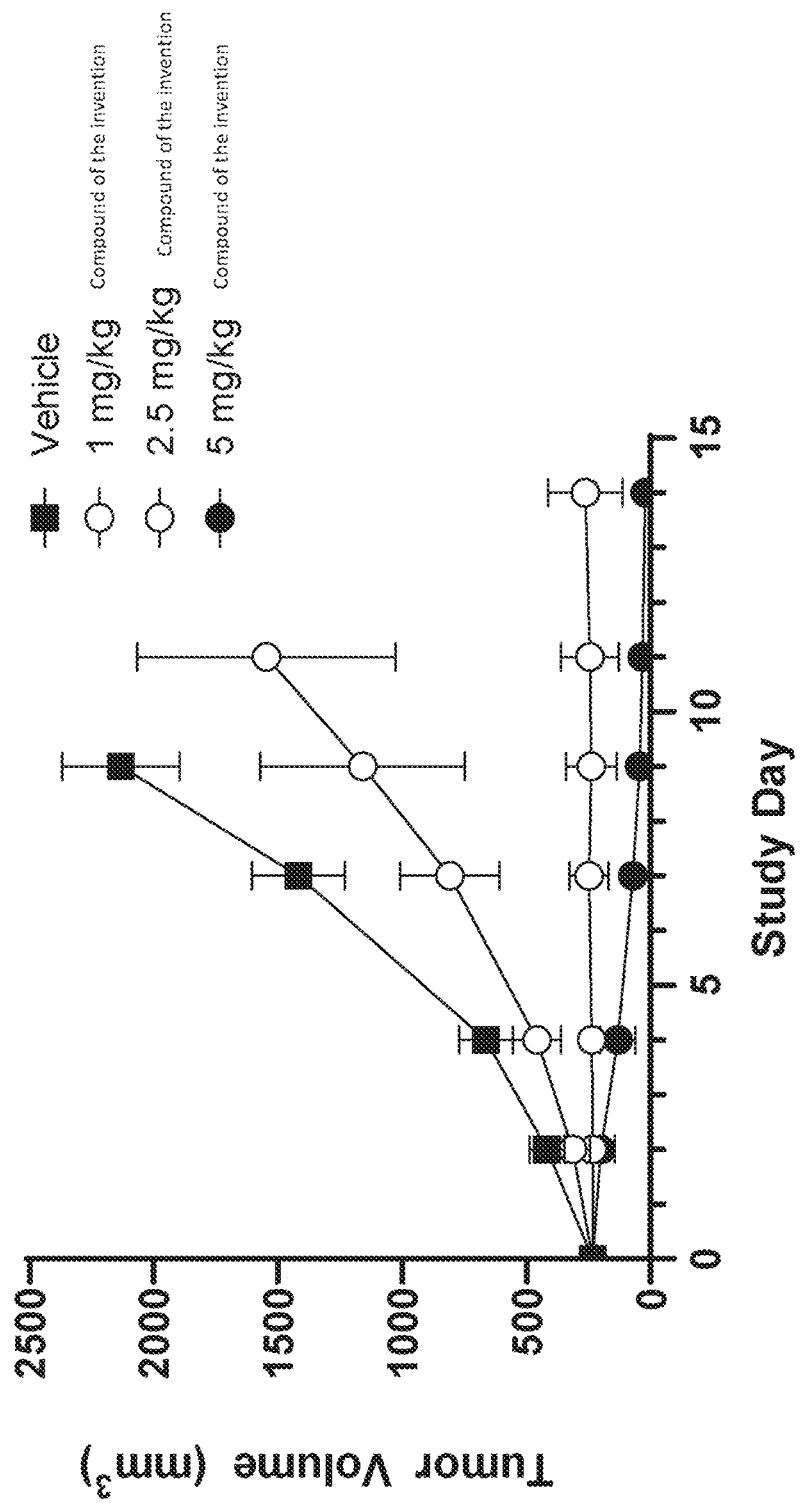
FIG. 5 shows a graph of tumor growth inhibition with various doses of a compound of the invention.

A compound of the invention was dosed by oral gavage at 0.3, 1, 3, or 10 mg/kg in AN3 CA (K310R/N549K) tumor-bearing mice. Dose-related effects were observed on the inhibition of ERK phosphorylation (4 hr post dose administration). A compound of the invention showed that more than 88% inhibition of pERK was observed when dosed at or above 3 mg/kg PO. FIG. 4 shows Inhibition of pERK with various dosages of a compound of the invention.

In one embodiment method of treating a disease associated with mutations in FGFR2 comprises providing a therapeutically effective amount of the compound or the pharmaceutical composition of the present disclosure in the amount of about 1-10 mg/kg per day intravenously or orally. In some embodiments, the therapeutically effective amount is about 1-5 mg/kg per day. In some certain embodiments, the therapeutically effective amount is about 1-3 mg/kg per day.

In one embodiment, a method of treating a cancer comprises providing a therapeutically effective amount of the compound or the pharmaceutical composition of the present disclosure in the amount of about 1-10 mg/kg per day intravenously or orally. In some embodiments, the therapeutically effective amount is about 1-5 mg/kg per day intravenously or orally. In some certain embodiments, the therapeutically effective amount of the compound or the pharmaceutical composition achieves a complete tumor regression.

AN3CA TGI Study Design

Female NCr nu/nu mice (7-8 weeks) were subcutaneously implanted with 5×106 AN3 CA cells (1:1, PBS: Matrigel). Following randomization by tumor volume, animals were dosed with a compound in the invention at 0-5 mg/kg PO, QD for two weeks. Tumor volumes were measured three times per week and groups reaching an average tumor volume ≥2000 mm3 were euthanized.

AN3CA PK/PD Study Design

Female NCr nu/nu mice (7-8 weeks) were subcutaneously implanted with 5×106 AN3 CA cells (1:1, PBS: Matrigel). Following randomization by tumor volume, animals were administered a single oral dose of a compound in the invention (0-10 mg/kg) and tumors and plasma were harvested 4 hours post dose. Plasma was analyzed for drug concentrations; tumors were homogenized and evaluated for

The invention claimed is:

1. A compound having the following structure of Formula (IV):

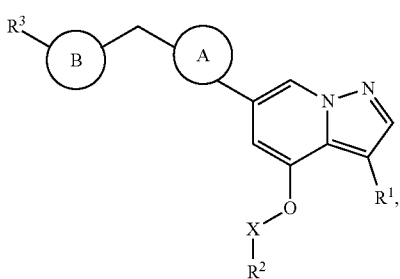

(IV)

or a stereoisomer of the compound, salt or tautomer of the compound thereof, wherein:
$R^2$ is 5-6 membered heteroaryl optionally substituted with halo;
$R^3$ is selected from the group consisting of H, —OH, halo, $C_1$-$C_6$ alkyl, —C(=O) $R^4$, =$NR^5$, —$NR^5R^6$, —$NR^5$C(=O) $R^4$, oxo, CN, and phosphate, wherein the $C_1$-$C_6$ alkyl is optionally substituted with one or more-OH;
$R^4$ is selected from the group consisting of —$C_1$-$C_6$ alkyl, $C_1$-$C_6$ heteroalkyl, $C_4$-$C_6$ cycloalkyl, and $C_4$-$C_6$ heterocycloalkyl, wherein the $C_1$-$C_6$ alkyl or $C_4$-$C_6$ cycloalkyl is optionally substituted with one or more —OH or —$N^5SR^6$;
$R^5$ and $R^6$ are, each independently, H, or $C_1$-$C_6$ alkyl;
X is —(CHCH$_3$)$_n$—, —(CHCF$_3$)$_n$—, —(CHCH$_2$OH)$_n$— and —(CHCH$_2$CH$_3$)$_n$—;
n is an integer between 1 and 4;
A is 5-6 membered heteroarylene having at most of two nitrogen atoms, wherein the 5-6 membered heteroarylene is optionally substituted with one or more $C_1$-$C_6$ alkyl, halo, —CN, -NH$_2$, or —($C_1$-$C_6$ alkylene)-($C_1$-$C_6$ alkoxy); and
B is $C_3$-$C_8$ cycloalkylene optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol.

2. The compound of claim 1, wherein $R^2$ is pyridinyl optionally substituted with halo.

3. The compound of claim 1, wherein $R^2$ is pyridinyl optionally substituted with F.

4. The compound of claim 1, wherein $R^2$ is selected from the group consisting of:

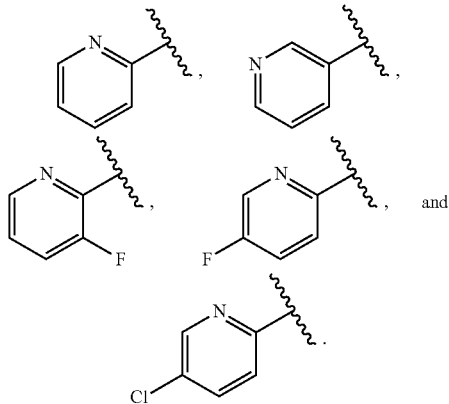

5. The compound of claim 1, wherein $R^3$ is selected from the group consisting of: H, —OH, halo, $C_1$-$C_6$ alkyl, —C(=O) $R^4$, =$NR^5$, —$NR^5R^6$, —$NR^5$C(=O) $R^4$, oxo, and CN, wherein the $C_1$-$C_6$ alkyl is optionally substituted with one or more —OH.

6. The compound of claim 1, wherein $R^3$ is selected from the group consisting of: H, —OH, halo, $C_1$-$C_6$ alkyl, —C(=O) $R^4$, =$NR^5$, —$NR^5R^6$, —$NR^5$C(=O) $R^4$, and oxo, wherein the $C_1$-$C_6$ alkyl is optionally substituted with one or more-OH.

7. The compound of claim 1, wherein $R^3$ is selected from the group consisting of: —OH, halo, $C_1$-$C_6$ alkyl, —C(=O) $R^4$, =$NR^5$, —$NR^5R^6$, —$NR^5$C(=O) $R^4$, and oxo, wherein the $C_1$-$C_6$ alkyl is optionally substituted with one or more-OH.

8. The compound of claim 1, wherein $R^3$ is selected from the group consisting of: H, OH, $C_1$-$C_6$ alkyl, and —C(=O) $R^4$, wherein the $C_1$-$C_6$ alkyl is optionally substituted with one or more-OH.

9. The compound of claim 1, wherein $R^3$ is selected from the group consisting of: OH, $C_1$-$C_6$ alkyl, and —C(=O) $R^4$, wherein the $C_1$-$C_6$ alkyl is optionally substituted with one or more —OH.

10. The compound of claim 1, wherein $R^3$ is $C_1$-$C_6$ alkyl optionally substituted with 1, 2, or 3-OH.

11. The compound of claim 1, wherein $R^4$ is —CH$_3$, —CH$_2$OH, —CH(CH$_3$)OH, —C(CH$_3$)$_2$OH, —CH(CH(CH$_3$)$_2$) NH$_2$, and $C_4$-$C_6$ cycloalkyl, wherein the $C_4$-$C_6$ cycloalkyl is optionally substituted with —OH or —$NR^5R^6$.

12. The compound of claim 1, wherein $R^4$ is —CH$_3$ or -CH(CH$_3$)OH.

13. The compound of claim 1, wherein $R^5$ and $R^6$ are, each independently, H or —CH$_3$.

14. The compound of claim 1, wherein $R^5$ and $R^6$ are H.

15. The compound of claim 1, wherein X is —(CHCH$_3$)$_n$—.

16. The compound of claim 1, wherein n is 1.

17. The compound of claim 1, wherein A is pyrazolylene optionally substituted with one or more $C_1$-$C_6$ alkyl, halo, —CN, -NH$_2$, or —($C_1$-$C_6$ alkylene)-($C_1$-$C_6$ alkoxy).

18. The compound of claim 1, wherein A is 5-6 membered heteroarylene is selected from the group consisting of:

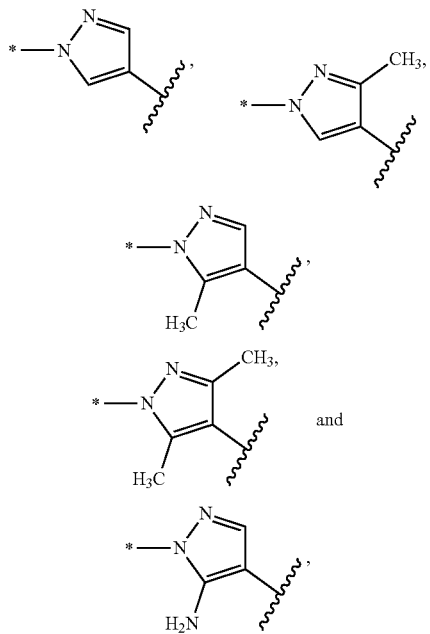

wherein * indicates a location of a bond to B, and ⁄ indicates a location of a bond to the pyrazolopyrimidine core.

19. The compound of claim 1, wherein B is $C_6$ cycloalkylene optionally substituted with one or more substituents each independently selected from the group consisting of $C_1$-$C_6$ alkyl, —OH, oxo, $C_1$-$C_6$ alkoxy, halo, $C_1$-$C_6$ haloalkyl, and $C_1$-$C_6$ alkyl alcohol.

20. The compound of claim 1, wherein B is $C_3$-$C_8$ cycloalkylene, wherein the $C_3$-$C_8$ cycloalkylene is optionally substituted with $C_1$-$C_6$ alkyl or —OH.

21. The compound of claim 1, wherein the compound has one of the following structures:

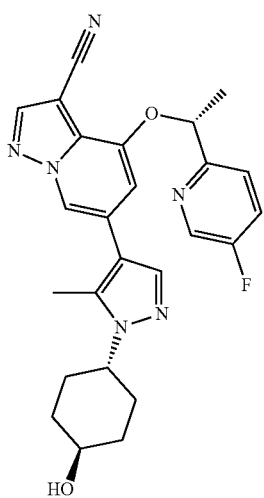

-continued

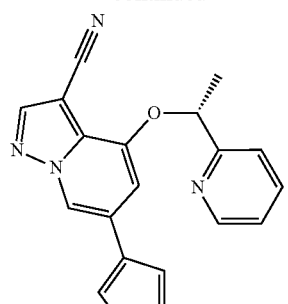

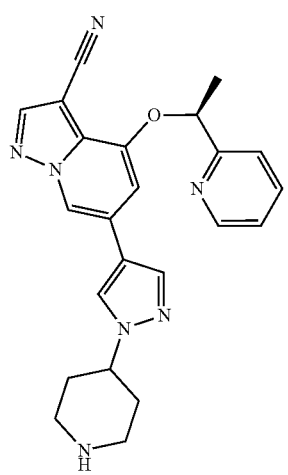

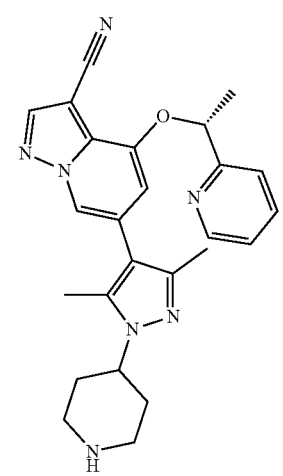

,

293
-continued
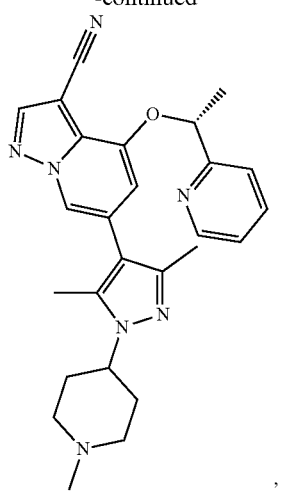
,
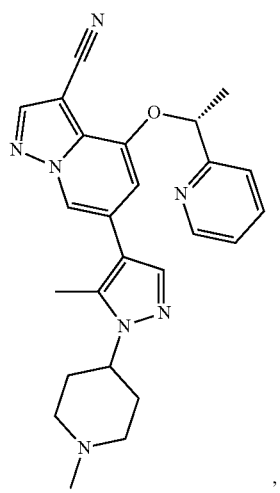
,
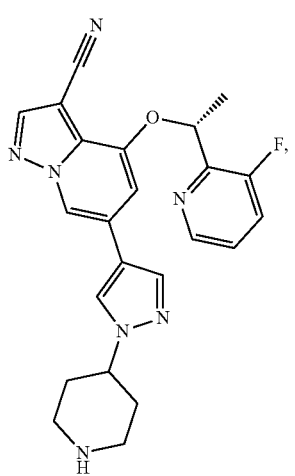
,
294
-continued
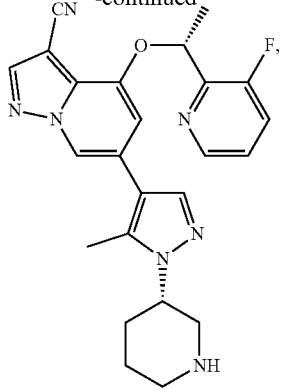
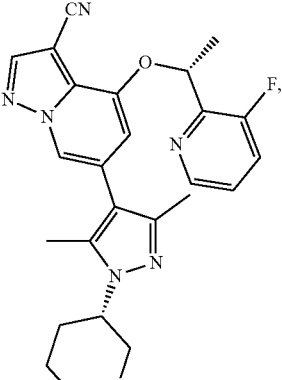
,
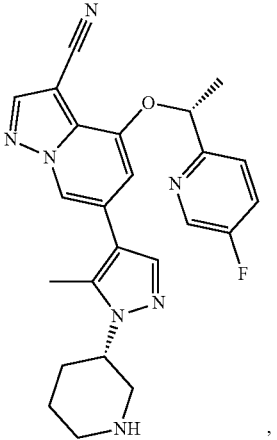
,
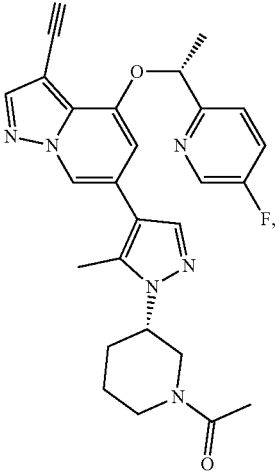

295
-continued
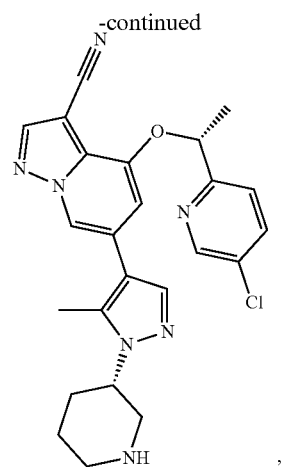
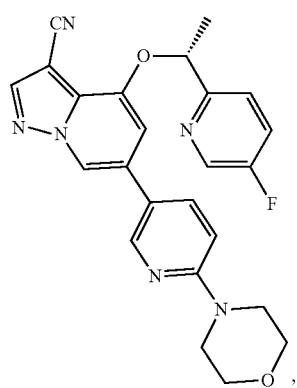
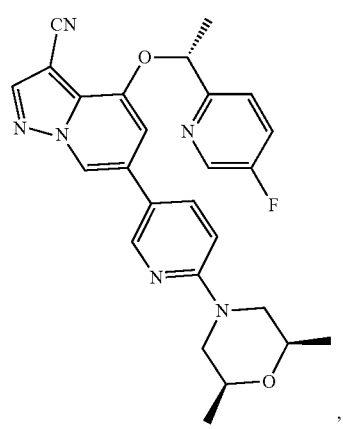
296
-continued
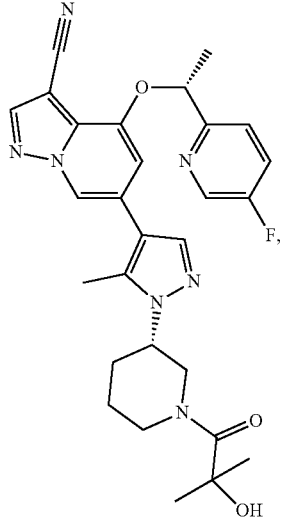
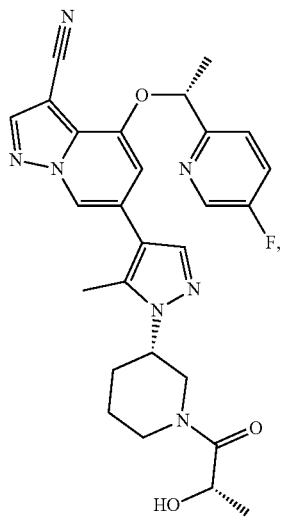
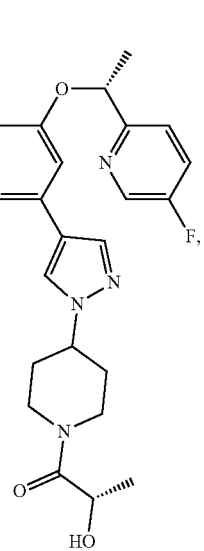

297
-continued
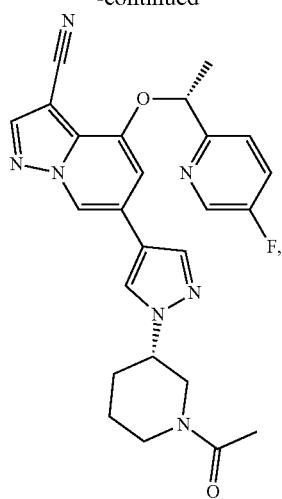
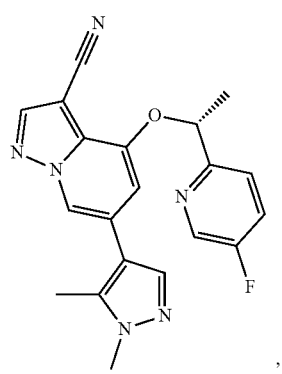
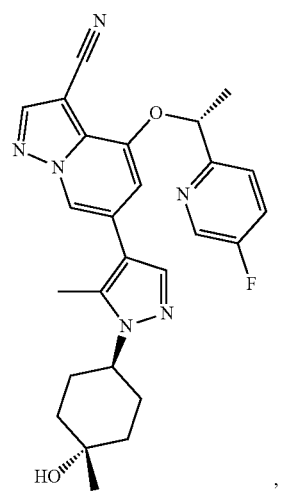
298
-continued
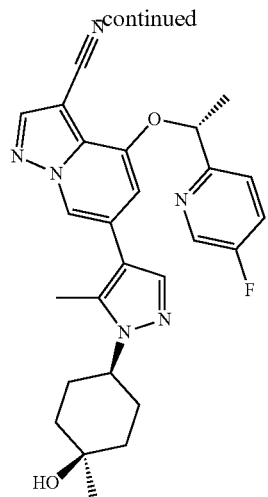
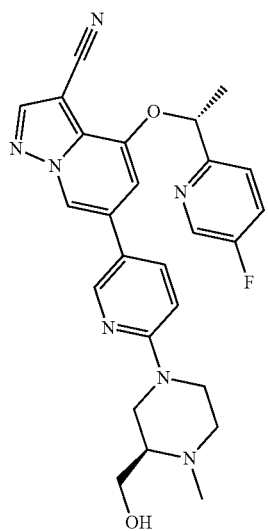
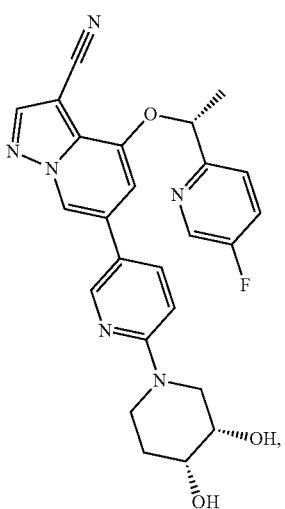

-continued
299
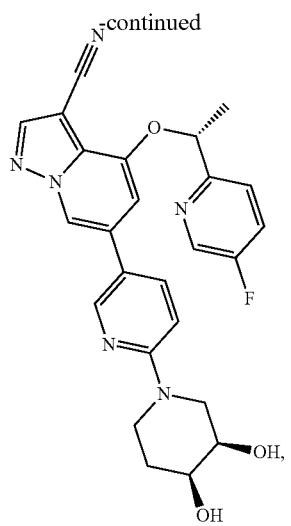
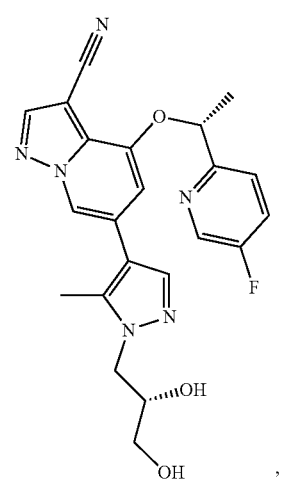
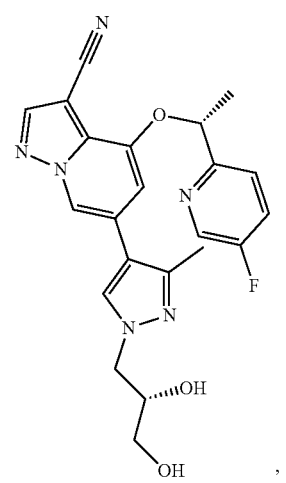
-continued
300
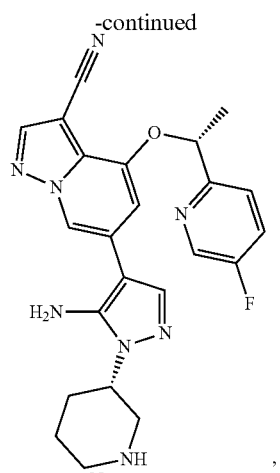
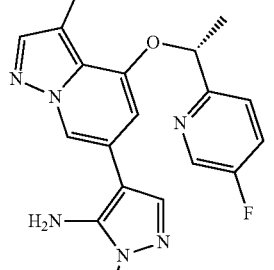
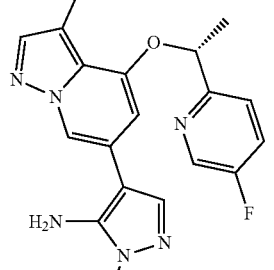
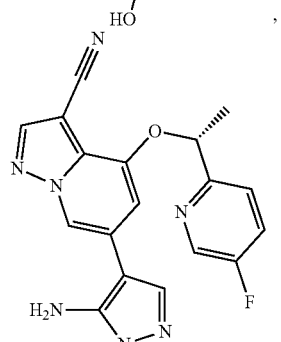
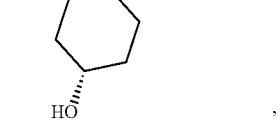

-continued
301
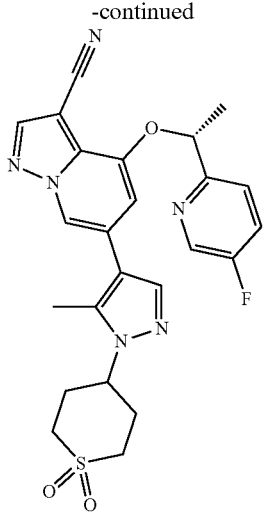
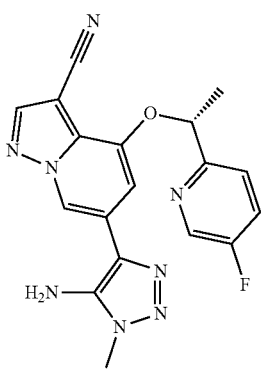
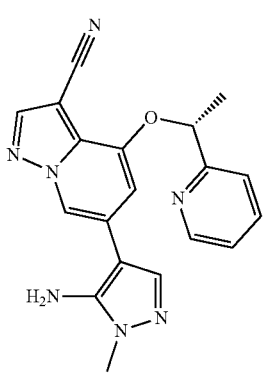
302
-continued
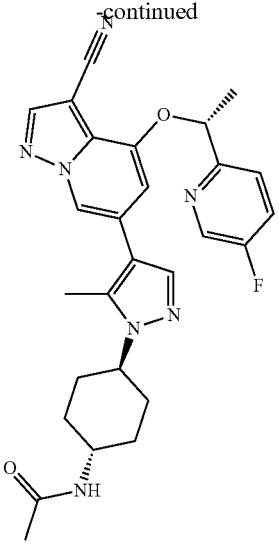
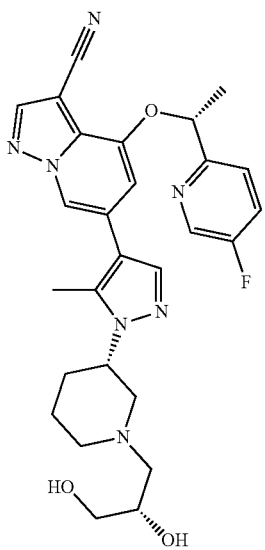
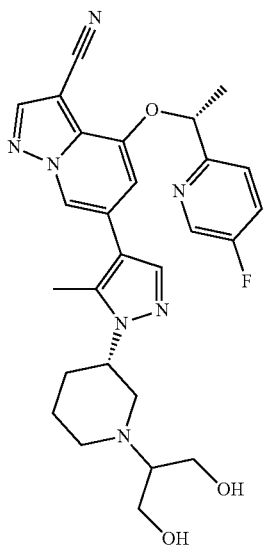

| 303 -continued | 304 -continued |
|---|---|
| 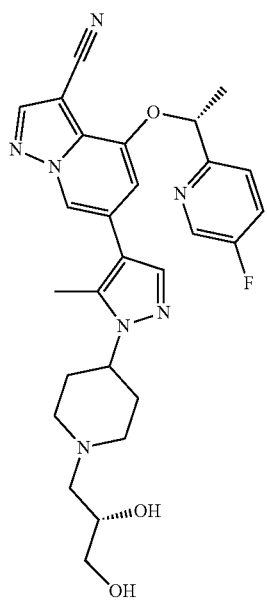 | 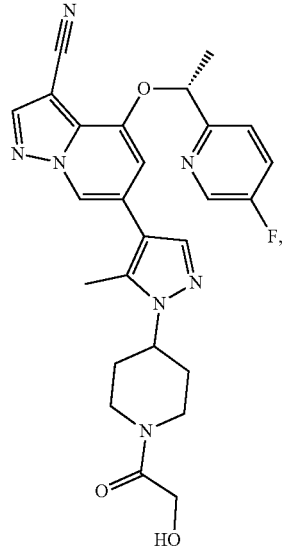 |
| 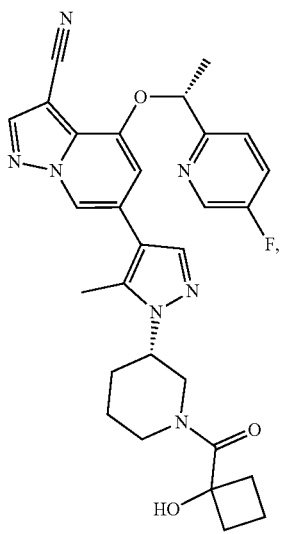 | 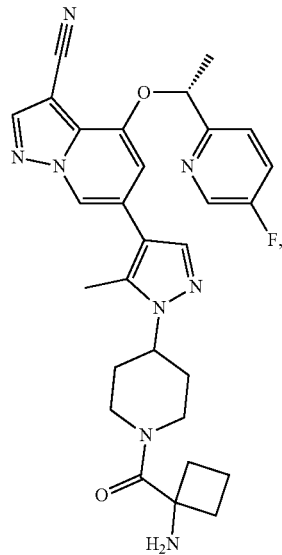 |
| 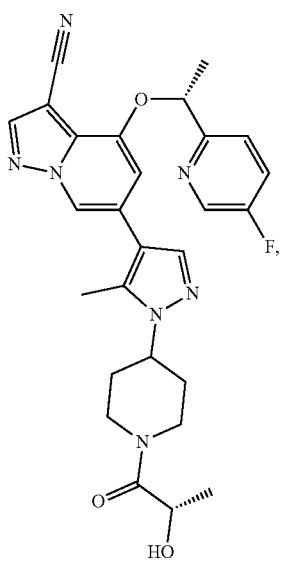 | 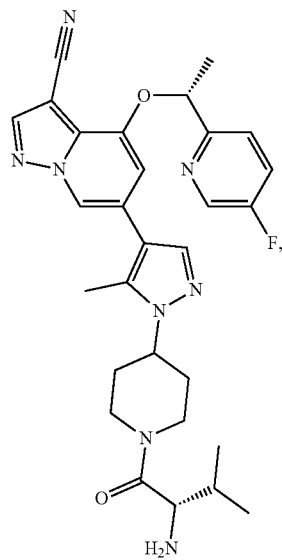 |

-continued
305
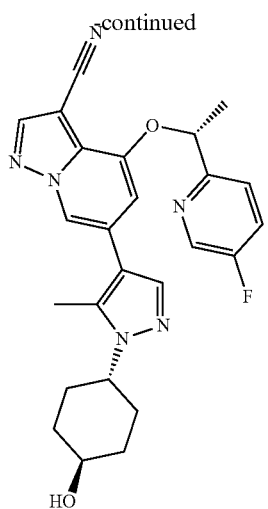
,
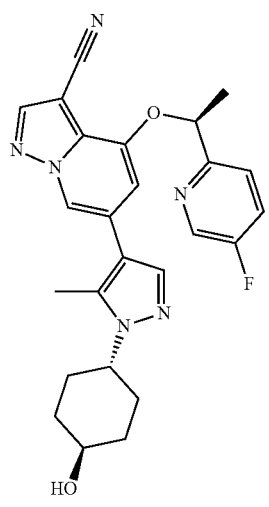
,
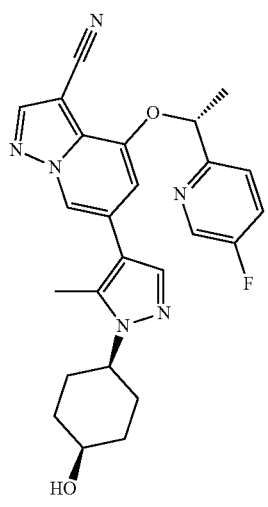
,
-continued
306
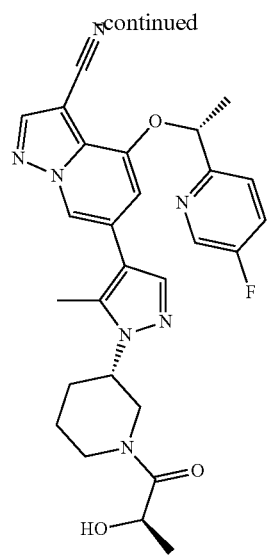
,
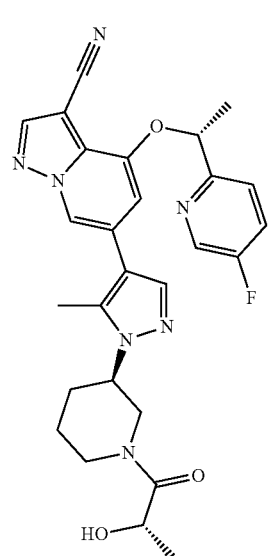
,
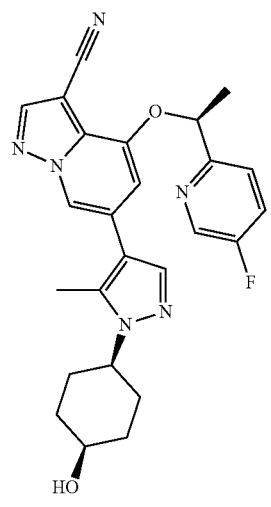
, 307
-continued
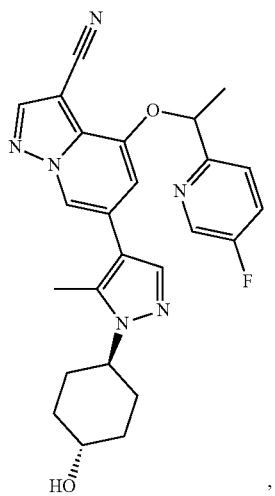
,
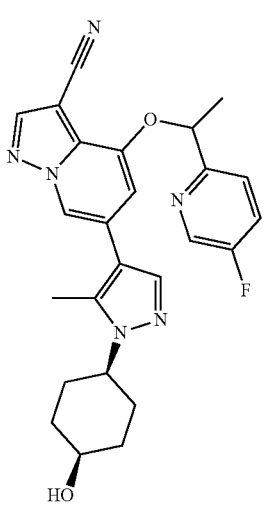
,
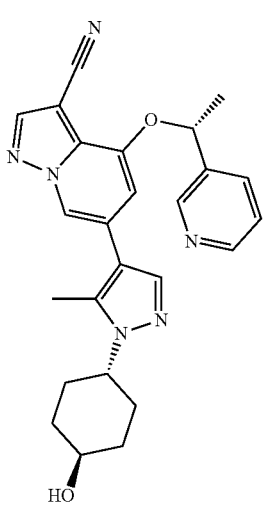
,
308
-continued
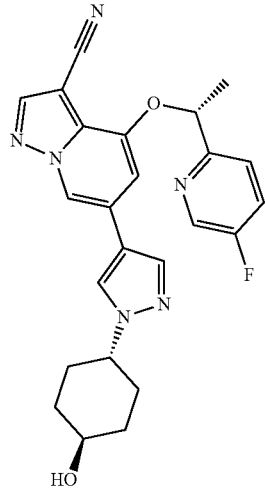
,
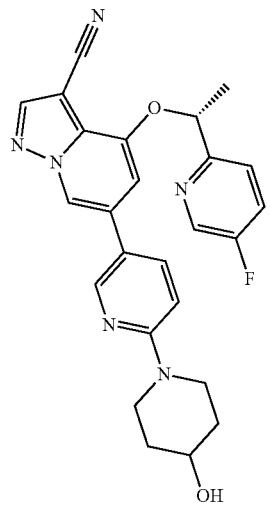
,
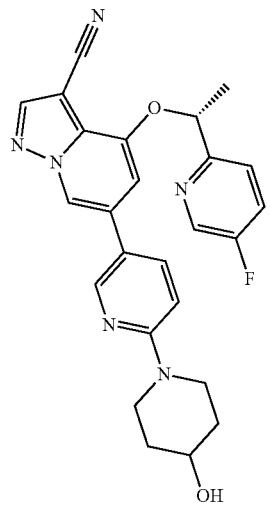
,

309
-continued
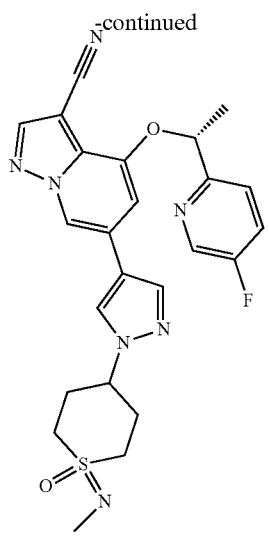
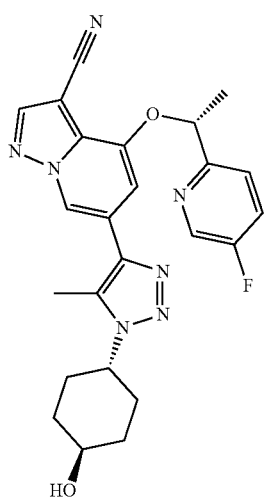
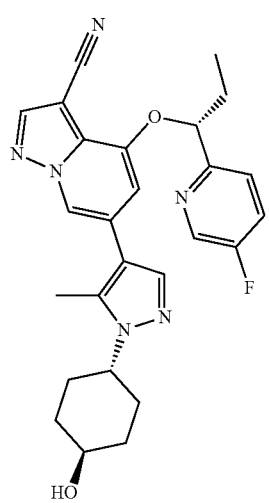
310
-continued
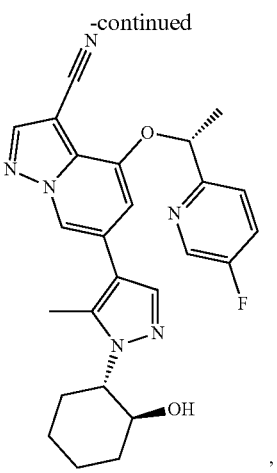
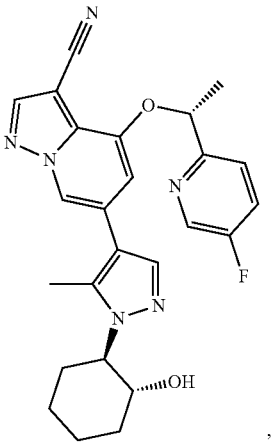
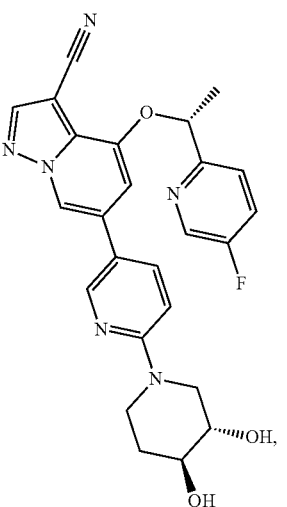

311
-continued
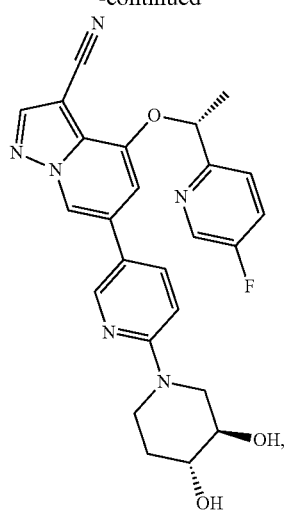
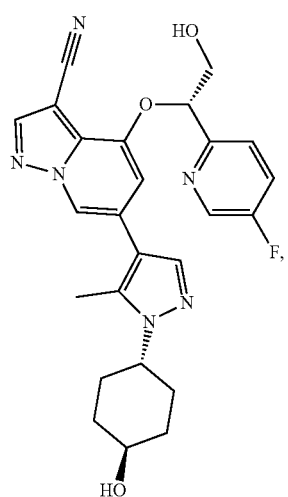
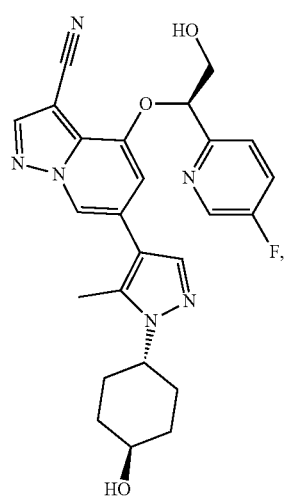
312
-continued
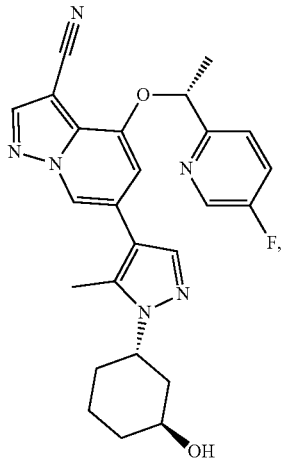
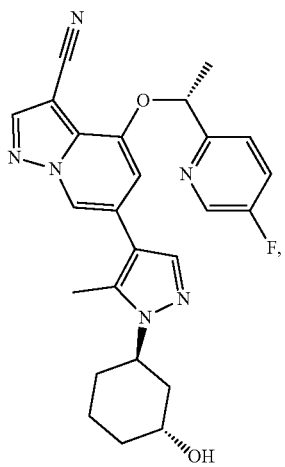
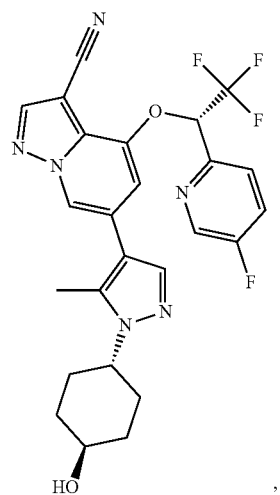

-continued

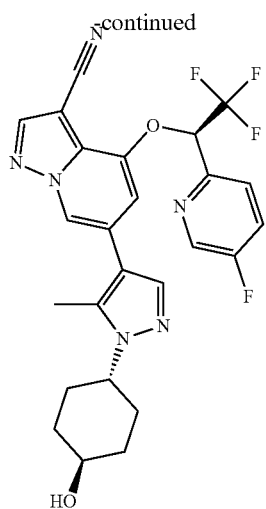

,

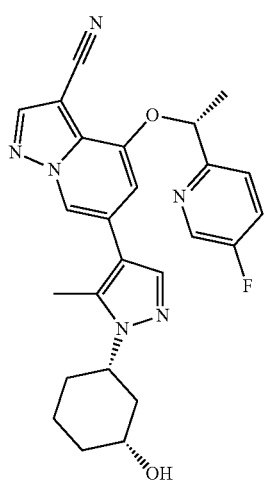 [SMILES: Cc1c(-c2cc(O[C@H](C)c3ccc(F)cn3)c3c(C#N)cnn3c2)cnn1[C@H]1CCC[C@@H](O)C1]

,

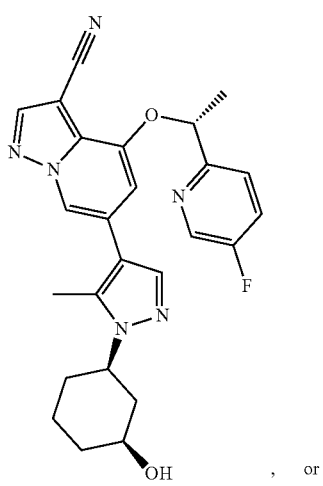

, or

-continued

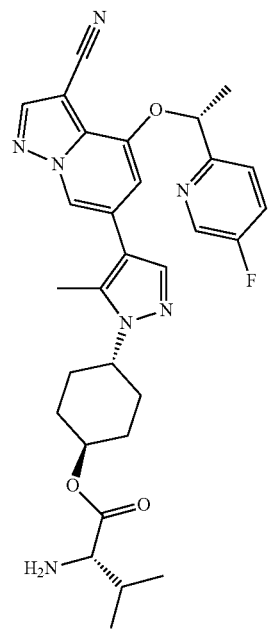

.

22. The compound of claim 1, wherein the salt is a pharmaceutically acceptable salt.

23. A pharmaceutical composition comprising the compound of claim 1 or a pharmaceutically acceptable salt thereof and a pharmaceutically acceptable excipient.

24. The compound of claim 1, wherein B is

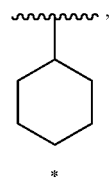

wherein * indicates the location of a bond to $R^3$, and $R^3$ is selected from the group consisting of: H, OH, $C_1$-$C_6$ alkyl, and —C(=O) $R^4$, wherein the $C_1$-$C_6$ alkyl is optionally substituted with one or more -OH.

25. The compound or a pharmaceutically acceptable salt thereof of claim 1, wherein the compound has the following structure:

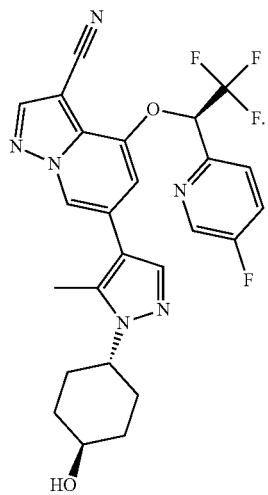 [SMILES: Cc1c(-c2cc(O[C@H](c3ccc(F)cn3)C(F)(F)F)c3c(C#N)cnn3c2)cnn1[C@H]1CC[C@H](O)CC1]

26. The compound or a pharmaceutically acceptable salt thereof of claim 1, wherein the compound has the following structure;

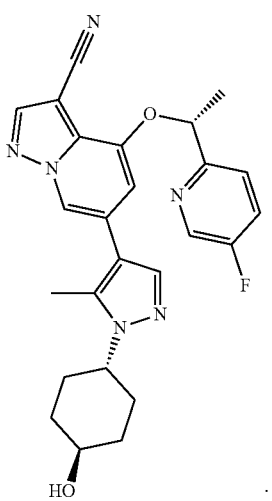 [SMILES: Cc1c(-c2cc(O[C@H](C)c3ccc(F)cn3)c3c(C#N)cnn3c2)cnn1[C@H]1CC[C@H](O)CC1]

27. The compound or a pharmaceutically acceptable salt thereof of claim 1, wherein the compound has the following structure;

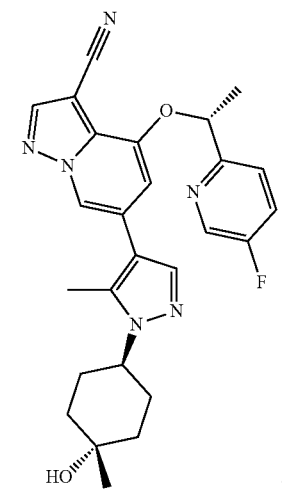

28. The compound or a pharmaceutically acceptable salt thereof of claim 1, wherein the compound has the following structure:

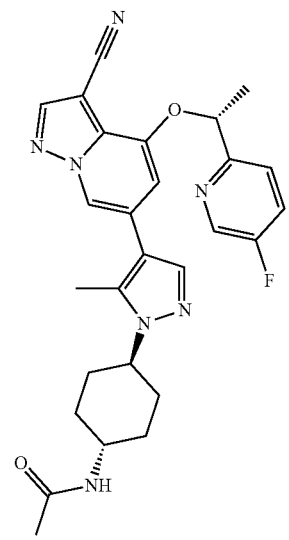

29. The compound or a pharmaceutically acceptable salt thereof of claim 1, wherein the compound has the following structure:
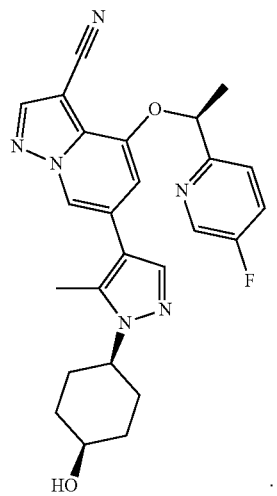 [SMILES: Cc1c(-c2cc(O[C@@H](C)c3ccc(F)cn3)c3c(C#N)cnn3c2)cnn1[C@H]1CC[C@@H](O)CC1]
30. The compound or a pharmaceutically acceptable salt thereof of claim 1, wherein the compound has the following structure:
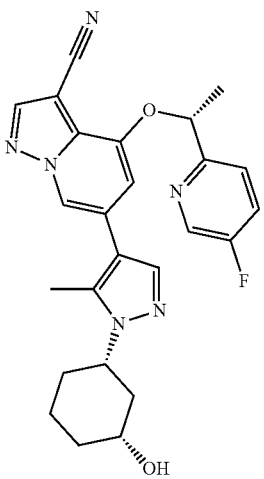
* * * * *